(12) United States Patent
Lu et al.

(10) Patent No.: US 8,173,654 B2
(45) Date of Patent: May 8, 2012

(54) TRIAZOLOPYRIDAZINE COMPOUNDS

(75) Inventors: Tianbao Lu, Churchville, PA (US); Richard Alexander, Newark, DE (US); Richard W. Connors, Harleysville, PA (US); Maxwell D. Cummings, Wayne, PA (US); Robert A. Galemmo, Paoli, PA (US); Heather Rae Hufnagel, Glenmoore, PA (US); Dana L. Johnson, Upper Black Eddy, PA (US); Ehab Khalil, West Chester, PA (US); Kristi A. Leonard, Flourtown, PA (US); Thomas P. Markotan, Morgantown, PA (US); Anna C. Maroney, Media, PA (US); Jan L. Sechler, Doylestown, PA (US); Jeremy M. Travins, Downingtown, PA (US); Robert W. Tuman, Chalfont, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 101 days.

(21) Appl. No.: 12/187,524

(22) Filed: Aug. 7, 2008

(65) Prior Publication Data

US 2009/0098181 A1 Apr. 16, 2009

Related U.S. Application Data

(63) Continuation of application No. 11/612,020, filed on Dec. 18, 2006, now Pat. No. 8,030,305.

(60) Provisional application No. 60/752,634, filed on Dec. 21, 2005.

(51) Int. Cl.
*A61K 31/4985* (2006.01)
*C07D 487/04* (2006.01)
*A61P 3/10* (2006.01)
*A61P 17/06* (2006.01)
*A61P 25/18* (2006.01)
*A61P 19/02* (2006.01)
*A61P 9/10* (2006.01)
*A61P 9/00* (2006.01)
*A61P 35/00* (2006.01)

(52) U.S. Cl. ........................ 514/248; 544/236
(58) Field of Classification Search ................... 514/349; 546/297
See application file for complete search history.

(56) References Cited

U.S. PATENT DOCUMENTS

| 3,483,193 | A | 12/1969 | Gall et al. |
| 3,506,656 | A | 4/1970 | Berger et al. |
| 3,823,137 | A | 7/1974 | Berger et al. |
| 3,919,200 | A | 11/1975 | Berger et al. |
| 4,260,755 | A | 4/1981 | Moran et al. |
| 4,810,705 | A | 3/1989 | Bourguignon et al. |
| 5,278,161 | A | 1/1994 | Branca et al. |
| 5,474,765 | A | 12/1995 | Thorpe et al. |
| 5,498,774 | A | 3/1996 | Mitsudera et al. |
| 5,762,918 | A | 6/1998 | Thorpe et al. |
| 5,855,866 | A | 1/1999 | Thorpe et al. |
| 6,297,235 | B1 | 10/2001 | Ladduwahetty et al. |
| 6,342,219 | B1 | 1/2002 | Thorpe et al. |
| 6,355,798 | B1 | 3/2002 | Madin et al. |
| 6,444,666 | B1 | 9/2002 | Ladduwahetty et al. |
| 6,776,796 | B2 | 8/2004 | Falotico et al. |
| 7,173,033 | B2 | 2/2007 | Igarashi et al. |
| 7,186,720 | B2 | 3/2007 | Baroni et al. |
| 7,250,518 | B2 | 7/2007 | Magee et al. |
| 2002/0016625 | A1 | 2/2002 | Falotico et al. |
| 2002/0111495 | A1 | 8/2002 | Magee et al. |
| 2003/0181455 | A1 | 9/2003 | Yuan et al. |
| 2004/0138264 | A1 | 7/2004 | Baroni et al. |
| 2004/0147568 | A1 | 7/2004 | Yu et al. |
| 2004/0171798 | A1 | 9/2004 | Magee et al. |
| 2004/0192696 | A1 | 9/2004 | Green et al. |
| 2005/0096322 | A1 | 5/2005 | Igarasi et al. |
| 2005/0261297 | A1 | 11/2005 | Igarashsi et al. |
| 2006/0173009 | A1 | 8/2006 | Kanoh et al. |

FOREIGN PATENT DOCUMENTS

| CA | 2158994 | 9/1994 |
| CA | 2132489 | 3/1995 |
| DE | 1545598 A1 | 11/1969 |
| DE | 1670160 A1 | 11/1970 |
| DE | 2030581 A1 | 12/1971 |

(Continued)

OTHER PUBLICATIONS

Wikipedia, Conjugated, http://en.wikipedia.org/wiki/Conjugated, downloaded Dec. 1, 2010.*

(Continued)

*Primary Examiner* — James O Wilson
*Assistant Examiner* — Cecilia M Jaisle
(74) *Attorney, Agent, or Firm* — Rajiv S. Shah

(57) ABSTRACT

The invention is directed to triazolopyridazine compounds of Formula I:

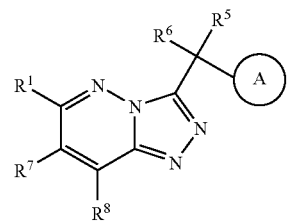

where $R^1$, $R^5$, $R^6$, $R^7$, $R^8$, and A are as defined herein, the use of such compounds as protein tyrosine kinase modulators, particularly inhibitors of c-Met, and the use of such compounds to reduce or inhibit kinase activity of c-Met in a cell or a subject, and modulate c-Met expression in a cell or subject, and the use of such compounds for preventing or treating in a subject a cell proliferative disorder and/or disorders related to c-Met. The present invention is further directed to pharmaceutical compositions comprising the compounds of the present invention and to methods for treating conditions such as cancers and other cell proliferative disorders.

15 Claims, 4 Drawing Sheets

FOREIGN PATENT DOCUMENTS

| | | |
|---|---|---|
| DE | 2113438 A1 | 9/1972 |
| DE | 2147013 A1 | 3/1973 |
| DE | 2161587 A1 | 6/1973 |
| DE | 2222834 A1 | 11/1973 |
| DE | 4309285 A1 | 9/1994 |
| EP | 156734 A1 | 10/1985 |
| EP | 404190 A1 | 12/1990 |
| EP | 464572 A2 | 1/1992 |
| EP | 464572 A3 | 10/1992 |
| EP | 404190 B1 | 10/1995 |
| EP | 1229034 A1 | 8/2002 |
| EP | 1481977 A1 | 12/2004 |
| GB | 1324060 | 12/1971 |
| JP | 56012390 * | 2/1981 |
| JP | 63199347 A | 8/1988 |
| JP | 6331089 A1 | 12/1988 |
| WO | WO 9421616 | 9/1994 |
| WO | WO 9632907 A1 | 10/1996 |
| WO | WO 9937303 A1 | 7/1999 |
| WO | WO 0006566 A1 | 2/2000 |
| WO | WO 0134603 A2 | 5/2001 |
| WO | WO 0134603 A3 | 1/2002 |
| WO | WO 0212236 A1 | 2/2002 |
| WO | WO 02085888 | 10/2002 |
| WO | WO 03032916 A2 | 4/2003 |
| WO | WO 03074525 A1 | 9/2003 |
| WO | WO 03032916 A3 | 3/2004 |
| WO | WO 2004017950 A2 | 3/2004 |
| WO | WO 2004021984 A2 | 3/2004 |
| WO | WO 2004021984 A3 | 3/2004 |
| WO | WO 2004017950 A3 | 5/2004 |
| WO | WO 2004058769 A2 | 7/2004 |
| WO | WO 2004058769 A3 | 9/2004 |
| WO | WO 2005/002590 A1 | 1/2005 |
| WO | WO 2005004607 A1 | 1/2005 |
| WO | WO 2005004808 A3 | 1/2005 |
| WO | WO 2005010005 A1 | 2/2005 |
| WO | WO 2006135667 A1 | 12/2006 |
| WO | WO 2007064797 | 6/2007 |
| WO | WO 2007138472 | 12/2007 |
| WO | WO 2008/008539 A2 | 1/2008 |

OTHER PUBLICATIONS

Wikipedia, Vascular-targeting agent, http://en.wikipedia.org/wiki/Vascular-targeting_agent, downloaded Nov. 27, 2010.*
Albright, J.D. et al., "Synthesis and Anxiolytic Activity of 6-(Substituted-phenyl)-1,2,4-triazolo[4,3-b]pyridazines", Journal of Medicinal Chemistry, 1981, vol. 24, No. 5, pp. 592-600.
Amer, Adel et al., "Dehydration of 2-(2-Arylethyl)-2-hydroxy-4-oxopentanoic Acids and Their Hydrazones to Form Heterocycles [1]", Journal fur praktische Chemie Chemiker-Zeitung, 339, 1997, pp. 20-25.
Arnon, R., et al. "Monoclonal Antibodies for Immunotargeting of Drugs in Cancer Therapy", Monoclonal Antibodies and Cancer Therapy, (1985) p. 243-256.
Berge, S., et al. "Pharmaceutical Salts", Journal of Pharmaceutical Sciences, (1977), vol. 66,No. 1, p. 1.
Bieche, Ivan et al., Infrequent Mutations of the MET gene in spordic breast tumours, Int. J. Cancer: vol. 82, pp. 908-910, 1999.
Bratusek, Urska et al., "Synthesis and Reactivity of (Z)-3-Benzoylamino-4-Dimethylamino-2-OXYO-3-Butene, Preparation of 1-Aryl- and 1-Heteroaryl-substituted 4-Benzoylamino-5-Methyl-1H-Pyrazoles", Heerocycles, vol. 57, No. 11, 2002, pp. 2045-2064.
Bratusek, Urska, "Transformation of 4-(1-Dimethylaminoethylidene)-2-phenyl-5(4H)-oxazolone into Methyl 2-Benzoylamino-3-oxobutanoate. The Synthesis of 1-Substituted 4-Benzoylamino-3-methyl-5(2H)-pyrazolones", J. Heterocyclic Chem., vol. 35, pp. 1281-1284, 1998.
Bratusek, Urska et al., "The synthesis of N-phthaloyl-azatryptophan derivatives," Acta Chimica Slovenica (1996), 43(2), 105-117.
Bundgaard,.S, Design of Prodrugs, Table of contents, 1985.
Camp, Robert L. et al., "Met Expression Is Associated with Poor Outcome in Patients with Axillary Lymph Node Negative Breast Carcinoma", American Cancer Society, Dec. 1, 1999, vol. 86, No. 11, pp. 2259-2265.
Chu, D., et al. "Synthesis and Structure-Activity Relationships of New Arylfluoronaphthyridine Antibacterial Agents", J. Med. Chem. (1986), vol. 22, p. 2363-2369.
Cucek, Karmen et al., "Synthesis of novel [1,2,4]triazolo[4,3-b]pyridazines", Faculty of Chemistry and Chemical Technology, University of Ljubljana, Askerceva 5, 1000, Ljubljana, Arkivoc, 2001, pp. 79-86.
Danishefsky, S., et al. J. Org. Chem. vol. 42, No. 10, (1977), p. 1821.
Di Renzo, M.F. et al., "Overexpression of the c-MET/HGF receptor in human thyroid carcinomas derived from the follicular epithelium", J. Endocrinol. Invest. vol. 18: 1995, pp. 134-139.
Di Renzo, M.F. et al., "Overexpression of the MET/HGF Receptor in Ovarian Cancer", Int. J. Cancer: vol. 58, 1994, pp. 658-662.
Di Renzo, M.F. et al., "Somatic mutations of the MET oncogene are selected during metastic spread of human HNSC carcinomas", Oncogene, vol. 19, 2000, pp. 1547-1555.
Dunn, James P. et al., "Analgetic and Antiinflammatory 7-aroylbenzofuran-5-ylacetic Acids and 7-Aroylbenzothiophene-5-ylacetic Acids", J. Med. Chem, vol. 29, 1986, pp. 2326-2329.
Ebert, Matthias et al., "Coexpression of the c-met Proto-oncogene and Hepatocyte Growth Factor in Human Pancreatic Cancer", Cancer Research, vol. 54, Nov. 15, 1994, pp. 4775-5778.
Ferracini, Riccardo et al., "The Met/HGF receptor is over-expressed in human osteosarcomas and is activated by either a paracrine or an autocrine circuit", Oncogene, vol. 10, 1995, pp. 739-749.
Fischer, Joachim et al., "Duplication and overexpression of the mutant allele of the MET proto-oncogene in multiple hereditary papillary renal cell tumours", Oncogene, vol. 17, 1998, pp. 733-739.
Gohji, Kazuo et al., "Independent Prognostic Value of Serum hepatocyte Growth Factor in Bladder Cancer", Journal of Clinical Oncology, vol. 18, No. 16, Aug. 2000, pp. 2963-2971.
Gould, P., "Salt Selection for Basic Drugs", International Journal of Pharmaceutics, (1986), 33 p. 201-217.
Hansel, D., et al. "Met Proto-Oncogene and Insulin-Like Growth Factor Binding Protein 3 Overexpression Correlates with Metastic Ability in Well-Differentiated Pancreatic Endocrine Neoplasms", Clinical Cancer Reserch, vol. 10, (Sep. 15, 2004) p. 6152-6158.
Hennessy, E., et al. "A General and Mild Copper-Catalyzed Arylation of Diethyl Malonate", Organic Letters, vol. 4, No. 2, (2002) p. 269-272.
Herrera, Luis J. et al., "The HGF Receptor c-Met is Overexpressed in Esophageal Adenocarcinoma", Neoplasia, vol. 7, No. 1, Jan. 2005, pp. 75-84.
Hjertner, Oyvind et al, "Hepatocye Growth Factor (HGF) INduces Interleukin-11 Secretion From Osteoblasts: A Possible Role for HGF in Myeloma-Associaed Osteolytic Bone Disease", Blood, vol. 94, No. 11, Dec. 1, 1999, pp. 3883-3888.
How, Pow-Yui et al., Thermal Cyclisation of Pyridazinylhydrazones to give s-Triazolo[4,3-b]-pyridazines and Pyridazino[2,3-a] benzimidazole, J.C.S. Perkin I, pp. 1363-1366, 1975.
Humphrey, Peter A., "Hepatocyte Growth Factor and Its Receptor (cMET) in Prostatic Carcinoma", American Journal of Pathology, vol. 147, No. 2, Aug. 1995, pp. 386-396.
Ichimura, Eiji et al., "Expression of c-met/HGF Receptor in Human Non-small Cell Lung Carcinomas in vitro and in vivo and Its Prognostic Significance", Jpn. J. Cancer Res., vol. 87, Oct. 1996, pp. 1063-1069.
Jiang, Wen G. et al., "Hepatocyte growth factor, its receptor, and their potential value in cancer therapies", Critical Reviews in Oncology/Hematology, vol. 53, 2005, pp. 35-69.
Johnson, Wynoma M.P. et al., "Synthesis and Relative Sterochemistry of 2-Monohalo DDT Pyrethroid Structures: 2-Halo-1-(4-ethoxyphenyl)cyclopropane-1-methanols and Cyclopropane-1-carboxylic Acids and Esters", Aust. J. Chem., vol. 39, 1986, pp. 271-280.
Jucker, Manfred et al., "The Met/Hepatocyte Growth Factor Receptor (HGFR) Gene is Overexpressed in Some Cases of Human Leukemia and Lymphoma", Leukemia Research, vol. 18, No. 1, 1994, pp. 7-16.
Juillerat, M., et al. "A New Reagent for the Cleavage of NPS-Amino Protecting Groups in Peptide Synthesis", Helvetica Chimica Acta vol. 59, No. 3 (1976) p. 855.

Kawano, R. et al., "Prognostic significance of hepatocyte growth factor and c-MET expression in patients with diffuse large B-cell lymphoma", British Journal of Haematology, vol. 127, Aug. 20, 2004, pp. 305-307.

Kirmse, Wolfgang et al., "Zerfall von 1-Arylcyclopropandiazonium-Ionen", Chem. Ber. 119, 1986, pp. 3694-3703.

Klominek, Julius et al., "Hepatocyte Growth Factor/Scatter Factor Stimulates Chemotaxis and Growth of Malignant Mesothelioma Cells Through c-met Receptor", Int. J. Cancer, vol. 76, 1998, pp. 240-249.

Knudsen, Beatrice S. et al., "Prostate Cancer and the Met Hepatocyte Growth Factor Receptor", Advances in Cancer Research, 2004, pp. 31-67.

Kocienski, P.Thieme Medical Publishers (2000) "Protecting Groups in Organic Syunthesis", $3^{rd}$ Ed. Wiley Interscience.

Kosary, J. et al., "Preparation of New [1,2,4]Triazolo[4,3-b]pyridazines", Pharmazie, vol. 38, 1983, pp. 369-371.

Kosary J., et al. "Studies in the Field of Pyridazine Compounds, II", Acta Chimica Academiae Scientarum Hungaricae, Tomus 103 (4) p. 405-413 (1980).

Kuniyasu, Hiroki et al., "Aberrant Expression of c-met mRNA in Human Gastric Carcinomas", Int. J. Cancer, vol. 55, 1993, pp. 72-75.

Kuniyasu, H., et al. "Frequent amplification of the c-met gene in scirrhous type stomach cancer". Biochem. Biophys. Res. Commun. 189 (1992), pp. 227-232.

Lee, Jae-Ho et al., "A novel germ line juxtamembrane Met mutation in human gastric cancer", Oncogene, vol. 19, 2000, pp. 4947-4953.

Legraverend, Michel et al., Synthesis of s-Triazolo[4,3-*b*]pyridazine C-Nucleosides (1), J. Heterocyclic Chem., vol. 18, 1981, pp. 893-898.

Lengyel, Ernst et al., "c-Met overexpression in node-positive breast cancer identifies patients with poor clinical outcome independent of Her2/neu", Int. J. Cancer: vol. 113, 2005, pp. 678-682.

Liu, Chi et al., "Overexpression of c-*met* proto-oncogene but not epidermal growth factor receptor or c-*erb*B-2 in primary human colorectal carcinomas", Oncogene, vol. 7, 1992, pp. 181-185.

Liu, Chi et al., "In Vitro and in Vivo Expressions of Transforming Growth Factor-a and Tyrosine Kinase Receptors in Human Non-Small-Cell Lung Carcinomas", American Journal of Pathology, vol. 142, No. 4, Apr. 1993, pp. 1155-1162.

Lundina, I. B.; Frolova, N. N.; Postovskii, I. Ya.; Bedrin, A. V.; Vereshchagina, N. N., "Synthesis and study of the antitubercular activity of 2-(5-nitro-2-furyl)vinyl derivatives of pyridazine and s-triazolo[4,3-b]pyridazine," Khimiko-Farmatsevticheskii Zhurnal (1972), 6(4), 13-17.

Massry, Abdel Moneim El et al., "Synthesis of New s-Triazolo[4,3-b]Pyridazines", Heterocycles, vol. 29, No. 10, 1989, pp. 1907-1914.

Masuya, D. et al., "The tumour-stromal interaction between intratumoral c-Met and stromal hepatocyte growth factor associated with tumour growth and prognosis in non-small-cell lung cancer patients", British Journal of Cancer, vol. 90, 2004, pp. 1555-1562.

Maulik, Gautam et al., "Role of the hepatocyte growth factor receptor, c-Met, in oncogenesis and potential for therapeutic inhibition", Cytokine & Growth Factor Reviews, vol. 13, 2002, pp. 41-59.

Mederski, Werner W.K.R. et al., "2, Endothelin Antagonists: Evaluation of 2,1,3-Benzolthiadiazole as a Methylendioxyphenyl bioisoster", Bioorangic & Medicinal Chemistry Letters, vol. 8, 1998, pp. 17-22.

Meyer, Michael D. et al., "Structure-Activity Studies for a Novel Series of N-(Arylethyl)-N-(1,2,3,4-tetrahydronaphthalen-1-ylmethyl)-N-methylamines Possessing Dual 5-HT Uptake Inhibiting and $a_2$-Antagonistic Activities", Journal of Medicinal Chemistry, vol. 40, No. 7, Mar. 28, 1997, pp. 1049-1062.

Mitchieli, Paolo et al., "Targeting the tumor and its microenvironment by a dual-function decoy Met receptor", Cancel Cell, vol. 6, Jul. 2004, pp. 61-73.

Miyaura, Norio et al., "Palladium-Catalyzed Cross-Coupling Reactions of Organoboron Compounds", Chem. Rev., vol. 95, 1995, pp. 2457-2483.

Moon, Young-Wan, M.D., et al., "Missense Mutation of the *MET* Gene Detected in Human Glioma",The United States and Canadian Academy of Pathology, Inc., vol. 13, No. 9, 2000, pp. 973-977.

Morishita, Ryuichi et al., "Hepatocyte Growth Factor as Cardiovascular Hormone: Role of HGF in the Pathogenesis of Cardiovascular Disease", Endocrine Journal, vol. 49 (3), 2002, pp. 273-284.

Moriyama, T., et al., "Concomitant expression of hepatocyte growth factor (HGF), HGF activator and c-met genes in human glioma cells in vitro", FEBS Letters, vol. 372, 1995, pp. 78-82.

Naegeli, C., et al. Abbaustudien an Hochmolekularen, UngestattigtenSauren Der Abbau der Chaulmoograsaure zum Homohydnocarpylamin. Ein Modifizierter Curtius Scher Abbau, Taabelle 8. Helvitica Chemica Acta, 1928, 11, 609-656.

Nakopoulou, L. et al., "c-met tyrosine kinase receptor expression is associated with abnormal β-catenin expression and favourable prognostic factors in invasive breast carcinoma", Histopathology, vol. 36, 2000, pp. 313-315.

Natali, P.G. et al., "Expression of the c-Met/HGF receptor in human melanocytic neoplasms: demonstration of the relationship to malignant melanoma tumor progression", Br. J. Cancer, vol. 68, 1993, pp. 746-750.

Nomenclature of Organic Chemistry, Sections A, B, C, D, E, F and H, (Pergamon Press, Oxford, 1979, Copyright 1979 IUPAC).

Nomenclature of Organic Chemistry, Section E: Pure Appl. Chem., 1976, 45:13-30.

Oda, Yoshinao et al., "Expression of Hepatocyte Growth Factor (HGF)/Scatter Factor and Its Receptor c-MET Correlates with Poor Prognosis in Synovial Sarcoma", pp. 185-192, 2000.

Olivero, Martina et al., "Novel Mutation in the ATP-Binding Site of the *MET* Oncogene Tyrosine Kinase in a HPRCC Family", Int. J. Cancer, vol. 82, 1999, pp. 640-643.

Olivero, M. et al., "Overexpression and activation of hepatocyte growth factor/scatter factor in human non-small-cell lung carcinomas", British Journal of Cancer, vol. 74, 1996, pp. 1862-1868.

Organ(O'Brien) et al. "Easily Prepared Air- and Moisture-Stable Pd-NHC = N-Heterocyclic Carbene) Complexes: A Reliable, User-Friendly, Highly Active Palladium Precatalyst for the Suzuki-Miyaura Reaction", Chem. Eur. J. vol. 12, 2006, pp. 4743-4748.

Park, Morag et al., "Sequence of *MET* protooncogene cDNA has features characteristic of the tyrosine kinase family of growth-factor receptors", Proc. Natl. Acad. Sci. USA, vol. 84, Sep. 1987, pp. 6379-6383.

Park, Won Sang et al., "Absence of mutations in the kinase domain of the *Met* gene and frequent expression of Met and HGF/SF protein in primary gastric carcinomas", APMIS, vol. 108, 2000, pp. 195-200.

Park, Won Sang et al., "Somatic Mutations in the Kinase Domain of the *Met*/Hepatocyte Growth Factor Receptor Gene in Childhood Hepatocellular Carcinomas", Cancer Research, vol. 59, Jan. 15, 1999, pp. 307-310.

Pisters, Louis L. et al., "C-Met Proto-Oncogene Expression in Benign and Malignant Human Prostate Tissues", The Journal of Urology, vol. 154, Jul. 1995, pp. 293-296.

Poissonnet, Guillaume, "A Simple and Convenient Synthesis of 1,2-Benzoxazoles via Intramolecular Mitsunobu Reaction From Salicylaldoximes and Orthohydroxyarylketoximes", Synthetic Communications, vol. 27 (22), 1997, pp. 3839-3846.

Ries, Uwe J. et al., "Heterocyclic Thrombin Inhibitors. Part 1: Design and Synthesis of amidino-Phenoxy Quinline Derivatives", Biooranic & Medicinal Chemistry Letters, vol. 13, 2003, pp. 2291-2295.

Rygaard, K. et al., "Expression of the proto-oncogenes c-*met* and c-*kit* and their ligands, hepatocyte growth factor/scatter factor and stem cell factor, in SCLC cell lines and xenografts", Br. J. Cancer, vol. 67, 1993, pp. 37-46.

Sala, Martin et al., "Synthesis of 3-(a- and β-D-arabinofuranosyl)-6-chloro-1,2,4-triazolo[4,3-*b*]pyridazine", Carbohydrate Research, vol. 338, 2003, pp. 2057-2066.

Schiele, Thomas M. et al., "Vascular restenosis—striving for therapy", Expert Opin. Pharmacother. vol. 5 (11), 2004, pp. 2221-2232.

Schmidt, Laura et al., Two North American Families with Hereditary Papillary Renal Carcinoma and Identical Novel Mutations in the MET Proto-Oncogene, Cancer Research, vol. 58, Apr. 15, 1998, pp. 1719-1722.

Schmidt, Laura et al., "Novel mutations of the MET proto-oncogene in papillary renal carcinomas", Oncogene, vol. 18, 1999, pp. 2343-2350.

Searcey, Mark et al., "A mild procedure for the production of secondary amines from oximes and benzisoxazoles", Tetrahedron Letters, vol. 44, 2003, pp. 6745-6747.

Siegfried, Jill M. et al., "The Clinical Significance of Hepatocyte Growth Factor for Non-Small Cell Lung Cancer", The Society of Thoracic Surgeons, vol. 55, 1998, pp. 1915-1918.

Simpson, William G., "The Calcium Channel Blocker Verapamil and Cancer Chemotherapy", Cell Calcium, vol. 6, 1985, pp. 449-467.

Sircar, Ila, "Synthesis of New 1,2,4-Triazolo[4,3-b]pyridazines and Related Compounds", J. Heterocyclic Chem., vol. 22, 1985, pp. 1045-1048.

Sowter, Heidi et al., "Hepatocyte Growth Factor (HGF) in Ovarian Epithelial Tumour Fluids Stimulates the Migration of Ovarian Carcinoma Cells", Int. J. Cancer: vol. 83, 1999, pp. 476-480.

Stille, John K., "The Palladium-Catalyzed Cross-Coupling Reactions of Organotin Reagents with Organic Electrophiles", Angew Chem. Int. Ed. Engl., vol. 25, 1986, pp. 508-524.

Sun, Li-Qiang et al., "Synthesis and structure-activity relationship of novel benzoxazole derivatives as melatonin receptor agonists", Bioorganic & Medicinal Chemistry Letters, vol. 14, 2004, pp. 3799-3802.

Suzuki, Kunio et al., "Expression of the c-*met* Protooncogene in Human Hepatocellular Carcinoma", pp. 1231-1236, 1994.

Svete, Jurij et al., "A Simple One Pot Synthesis of 1-(s-Triazolo[4,3-x]azinyl-3)-substituted Polyols", pp. 1115-1121, 1997.

Taher, Taher E.I. et al., "Hepatocyte growth factor triggers signaling cascades mediating vascular smooth muscle cell migration", Biochemical and Biophysical Research Communications, vol. 298, 2002, pp. 80-86.

Takanami, F. Tanana, T. Hashizume et al., Hepatocyte growth factor and c-Met/hepatocyte growth factor receptor in pulmonary adenocarcinomas: an evaluation of their expression as prognostic markers. Oncology 53 (1996), pp. 392-397.

Thirkettle, I. et al., "Immunoreactivity for cadherins, HGF/SF, met, and erbB-2 in pleural malignant mesotheliomas", Histopathology 2000, vol. 36, pp. 522-528.

Thorpe, "Antibody Carriers of Cytotoxic Agents in Cancer Therapy: A Review", in Monoclonal Antibodies '84: Biological and Clinical Applications, Pinchera et al. (eds.), pp. 475-506 (1985).

Tokunou, Masahide et al., "c-MET Expression in Myofibroblasts Role in Autocrine Activation and Prognostic Significance in Lung Adenocarcinoma", American Journal of Pathology, vol. 158, No. 4, Apr. 2001, pp. 1451-1463.

Tolnay, Edina et al., "Hepatocyte growth factor/scatter factor and its receptor c-Met are overexpressed and associated with an increased microvessel density in malignant pleural mesothelioma", J. Cancer Es. Clin Oncol, vol. 124, 1998, pp. 291-296.

Tsukinoki, Keiichi et al., "Hepatocyte growth factor and c-Met immunoreactivity are associated with metastasis in high grade salivery gland carcinoma", Oncology Reports, vol. 12, 2004, pp. 1017-1021.

Umeki, Kensuke et al., "Clinical Significance of c-met Oncogene Alterations in Human Colorectal Cancer", Oncology, vol. 56, 1999, pp. 314-321.

Vinot, Nicole et al., "Étude de l'acide y-benzimidazobutyrique", Laboratoire de Chimie Orgaique II, Faculte des Sciences, vol. 45, pp. 245-247, 1963.

Vranicar, Lidija et al., "2H-Pyran-2-ones as Synthons for (E)-a, β-Didehydroamino Acid Derivatives", Tetrahedron, vol. 55, 1999, pp. 271-278.

Vranicar, Lidija et al., "Transformation of N-(5-Acetyl-6-Methyl-2-Oxo-2H-Pyran-3-YL)Benzamide with Hydrazines in the Presence of an Acidic Catalyst", Heterocycles, vol. 61, 2003, pp. 105-112.

Wang, You-Chu, "First Enantioselective Total Synthesis of (−)-Tejedine", Organic Letters, vol. 4, No. 16, 2002, pp. 2675-2678.

Yuedong,H., et al.. [Expression and correlation of c-Met and estrogen receptor in endometrial carcinomas] Sichuan Da Xue Xue Bao Yi Xue Ban. Jan. 2003;34(1):78-9, 88 (English Abstract Only).

Zeng, Zhaoshi et al., "Immunoblot analysis of c-Met expression in human colorectal cancer: Overexpression is associated with advanced stage cancer", Clinical & Experimental Metastasis, vol. 21, 2004, pp. 409-417.

Zhuang, Zhengping et al., "Trisomy 7-harbouring non-random duplication of the mutant *MET* allele in hereditary papillary renal carcinomas", Nature America Inc., pp. 66-69, 1998.

European Search Report issued on corresponding application No. PCT/US2006/048241 dated May 11, 2007.

* cited by examiner

TRIAZOLOPYRIDAZINE COMPOUNDS

CROSS REFERENCE TO RELATED APPLICATIONS

This application is a continuation of U.S. application Ser. No. 11/612,020, filed Dec. 18, 2006, now U.S. Pat. No. 8,030, 305 which in turn claims priority to U.S. Provisional Application for Patent No. 60/752,634, filed Dec. 21, 2005, the entire disclosures of which are hereby incorporated herein in their entirety.

FIELD OF THE INVENTION

The invention relates to novel compounds that function as protein tyrosine kinase modulators. More particularly, the invention relates to novel compounds that function as inhibitors of c-Met.

BACKGROUND OF THE INVENTION

The present invention relates to triazolopyridazines as inhibitors of tyrosine kinases, including c-Met. Triazolopyridazines have been reported with useful therapeutic properties: U.S. Pat. No. 5,278,161 and US 2003181455 report triazolopyridazines as renin inhibitors; U.S. Pat. No. 6,355, 798 reports triazolopyridazines as GABA inhibitors and GABAA receptor ligands respectively; WO 2005002590 and US 2005096322 report triazolopyridazines as mediating increases in bone mass; US 2004192696 reports triazolopyridazines as useful for treating or lessening the severity of a disease or condition. Academic laboratories have reported experiments with triazolopyridazines in the following: Science of Synthesis (2002), 12, 15-225, Heterocycles (2003), 61, 105-112, Heterocycles (2002), 57(11), 2045-2064, Journal of Heterocyclic Chemistry (1998), 35(6), 1281-1284, and Tetrahedron (1999), 55(1), 271-278.

Also of note are U.S. Pat. No. 4,810,705; DE 2222834 (equivalent U.S. Pat. No. 3,823,137); DE 2147013 (equivalent, U.S. Pat. No. 3,919,200); DE 2113438; DE 2030581 (equivalent U.S. Pat. No. 3,823,137); DE 1670160 (U.S. Pat. No. 3,506,656); DE 1545598 (equivalent U.S. Pat. No. 3,483, 193); DE 2161587; DE 4309285; WO 2004021984; US 2004147568; JP 63199347; WO 1999037303; U.S. Pat. No. 6,297,235; U.S. Pat. No. 6,444,666; WO 2001034603; WO 2004017950; CA 2132489; WO 2004058769; US 2004192696 WO 2003074525; WO 2003032916; Japanese Patent Application Number 62-147775; U.S. Pat. No. 4,260, 755; WO 2002012236; EP 464572; EP 404190; EP 156734; WO 2005002590; WO 2003074525; JP 63310891 and El Massry, Abdel Moneim; Amer, Adel, "Synthesis of new s-triazolo[4,3-b]pyridazines," Heterocycles (1989), 29(10), 1907-14; Amer, Adel; El Massry, Abdel Moneim; Badawi, Mohamed; Abdel-Rahman, Mohamed, M.; El Sayed, Safaa A. F., "Synthetic reactions and structural studies of heterocycles containing nitrogen. Part 14. Dehydration of 2-(2-arylethyl)-2-hydroxy-4-oxopentanoic acids and their hydrazones to form heterocycles," Journal fuer Praktische Chemie/Chemiker-Zeitung (1997), 339(1), 20-25; Legraverend, Michel; Bisagni, Emile; Lhoste, Jean Marc, "Synthesis of s-triazolo[4,3-b]pyridazine C-nucleosides (1)," Journal of Heterocyclic Chemistry (1981), 18(5), 893-8; Albright, J. D.; Moran, D. B.; Wright, W. B., Jr.; Collins, J. B.; Beer, B.; Lippa, A. S.; Greenblatt, E. N., "Synthesis and anxiolytic activity of 6-(substituted-phenyl)-1,2,4-triazolo[4,3-b]pyridazines," Journal of Medicinal Chemistry (1981), 24(5), 592-600; How, Pow-Yui; Parrick, John, "Thermal cyclization of pyridazinylhydrazones to give s-triazolo[4,3-b]pyridazines and pyridazino[2,3-a]benzimidazole," Journal of the Chemical Society, Perkin Transactions 1: Organic and Bio-Organic Chemistry (1972-1999) (1976), (13), 1363-6; Lundina, I. B.; Frolova, N. N.; Postovskii, I. Ya.; Bedrin, A. V.; Vereshchagina, N. N., "Synthesis and study of the antitubercular activity of 2-(5-nitro-2-furyl)vinyl derivatives of pyridazine and s-triazolo[4,3-b]pyridazine," Khimiko-Farmatsevticheskii Zhurnal (1972), 6(4), 13-17; Sircar, IIa, "Synthesis of new 1,2,4-triazolo[4,3-b]pyridazines and related compounds," Journal of Heterocyclic Chemistry (1985), 22(4), 1045-8; Bratusek, Urska et al., "The synthesis of N-phthaloyl-azatryptophan derivatives," Acta Chimica Slovenica (1996), 43(2), 105-117; Sala, Martin et al., "Synthesis of 3-(a- and b-D-arabinofuranosyl)-6-chloro-1,2,4-triazolo[4,3-b]pyridazine," Carbohydrate Research (2003), 338(20), 2057-2066; Cucek, Karmen et al., "Synthesis of novel [1,2,4]triazolo[4,3-b]pyridazines," ARKIVOC (Gainesville, Fla., United States) [online computer file] (2001), (5), 79-86, URL: http://www.arkat-usa.org/ark/journal/Volume2/Part3/Tisler/MT-161/MT-161.pdf; Svete, Jurij et al., "A simple one pot synthesis of 1-(s-triazolo[4,3-x]azinyl-3)-substituted polyols," Journal of Heterocyclic Chemistry (1997), 34(4), 1115-1121; Kosary, Judit et al., "Preparation of new [1,2,4]triazolo[4,3-b]pyridazines. Part 12: Studies in the field of pyridazine compounds," Pharmazie (1983), 38(6), 369-71; Kosary, J. et al., "Studies in the field of pyridazine compounds. II. Derivatives of [1,2,4]triazolo[4,3-b]pyridazine-3-carboxylic acid," Acta Chimica Academiae Scientiarum Hungaricae (1980), 103(4), 405-13; Stanovnik, B. et al., "Product class 1: pyrazoles, "Science of Synthesis (2002), 12, 15-225; Vranicar, Lidija et al., "Transformation of N-(5-acetyl-6-methyl-2-oxo-2H-pyran-3-yl)benzamide with hydrazines in the presence of an acidic catalyst, "Heterocycles (2003), 61, 105-112; Bratusek, Urska et al., "Synthesis and reactivity of (Z)-3-benzoylamino-4-dimethylamino-2-oxo-3-butene. Preparation of 1-aryl- and 1-heteroaryl-substituted 4-benzoylamino-5-methyl-1H-pyrazoles, "Heterocycles (2002), 57(11), 2045-2064; Bratusek, Urska et al., "Transformation of 4-[1-(dimethylamino)ethylidene]-2-phenyl-5(4H)-oxazolone into methyl 2-(benzoylamino)-3-oxobutanoate. The synthesis of 1-substituted 4-(benzoylamino)-3-methyl-5(2H)-pyrazolones, "Journal of Heterocyclic Chemistry (1998), 35(6), 1281-1284; Vranicar, Lidija et al., "2H-Pyran-2-ones as synthons for (E)-α,β-didehydroamino acid derivatives, "Tetrahedron (1999), 55(1), 271-278.

Protein kinases are enzymatic components of the signal transduction pathways that catalyze the transfer of the terminal phosphate from ATP to the hydroxy group of tyrosine, serine and/or threonine residues of proteins. Thus, compounds that inhibit protein kinase functions are valuable tools for assessing the physiological consequences of protein kinase activation. The overexpression or inappropriate expression of normal or mutant protein kinases in mammals has been a topic of extensive study and has been demonstrated to play a significant role in the development of many diseases, including diabetes, angiogenesis, psoriasis, restenosis, ocular diseases, schizophrenia, rheumatoid arthritis, atherosclerosis, cardiovascular disease and cancer. The cardiotonic benefit of kinase inhibition has also been studied. In sum, inhibitors of protein kinases have particular utility in the treatment of human and animal disease.

The hepatocyte growth factor (HGF) (also known as scatter factor) receptor, c-Met, is a receptor tyrosine kinase that regulates cell proliferation, morphogenesis, and motility. The c-Met gene is translated into a 170 kD protein that is processed into a cell surface receptor composed of a 140 kD β transmembrane subunit and 50 kD glycosylated extra cellular α subunit.

Mutations in c-Met, over-expression of c-Met and/or HGF/SF, expression of c-Met and HGF/SF by the same cell, and overexpression and/or aberrant c-Met signaling is present in a variety of human solid tumors and is believed to participate in angiogenesis, tumor development, invasion, and metastasis.

Cell lines with uncontrolled c-Met activation, for example, are both highly invasive and metastatic. A notable difference between normal and transformed cells expressing c-Met receptor is that phosphorylation of the tyrosine kinase domain in tumor cells is often independent of the presence of ligand.

C-Met mutations/alterations have been identified in a number of human diseases, including tumors and cancers—for instance, hereditary and sporadic human papillary renal carcinomas, breast cancer, colorectal cancer, gastric carcinoma, glioma, ovarian cancer, hepatocellular carcinoma, head and neck squamous cell carcinomas, testicular carcinoma, basal cell carcinoma, liver carcinoma, sarcoma, malignant pleural mesothelioma, melanoma, multiple myeloma, osteosarcoma, pancreatic cancer, prostate cancer, synovial sarcoma, thyroid carcinoma, non-small cell lung cancer (NSCLC) and small cell lung cancer, transitional cell carcinoma of urinary bladder, testicular carcinoma, basal cell carcinoma, liver carcinoma—and leukemias, lymphomas, and myelomas—for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM), myeloid sarcoma, non-Hodgkin's lymphoma and Hodgkin's disease (also called Hodgkin's lymphoma). See Maulik G, Shrikhande A, Kijima T, Ma P C, Morrison P T, Salgia R., Role of the hepatocyte growth factor receptor, c-Met, in oncogenesis and potential for therapeutic inhibition. *Cytokine Growth Factor Rev.* 2002 February; 13(1):41-59, and cites therein: Bieche, M. H. Champeme and R. Lidereau, Infrequent mutations of the MET gene in sporadic breast tumours (letter). *Int. J. Cancer* 82 (1999), pp. 908-910; R. L. Camp, E. B. Rimm and D. L. Rimm, Met expression is associated with poor outcome in patients with axillary lymph node negative breast carcinoma. *Cancer* 86 (1999), pp. 2259-2265; L. Nakopoulou, H. Gakiopoulou, A. Keramopoulos et al., c-met tyrosine kinase receptor expression is associated with abnormal beta-catenin expression and favourable prognostic factors in invasive breast carcinoma. *Histopathology* 36 (2000), pp. 313-325; C. Liu, M. Park and M. S. Tsao, Over-expression of c-met proto-oncogene but not epidermal growth factor receptor or c-erbB-2 in primary human colorectal carcinomas. *Oncogene*. 7 (1992), pp. 181-185; K. Umeki, G. Shiota and H. Kawasaki, Clinical significance of c-met oncogene alterations in human colorectal cancer. *Oncology* 56 (1999), pp. 314-321; H. Kuniyasu, W. Yasui, Y. Kitadai et al., Frequent amplification of the c-met gene in scirrhous type stomach cancer. *Biochem. Biophys. Res. Commun.* 189 (1992), pp. 227-232; H. Kuniyasu, W. Yasui, H. Yokozaki et al., Aberrant expression of c-met mRNA in human gastric carcinomas. *Int. J. Cancer* 55 (1993), pp. 72-75; W. S. Park, R. R. Oh, Y. S. Kim et al., Absence of mutations in the kinase domain of the Met gene and frequent expression of Met and HGF/SF protein in primary gastric carcinomas. Apmis 108 (2000), pp. 195-200; J. H. Lee, S. U. Han, H. Cho et al., A novel germ line juxtamembrane Met mutation in human gastric cancer. *Oncogene* 19 (2000), pp. 4947-4953; T. Moriyama, H. Kataoka, H. Tsubouchi et al., Concomitant expression of hepatocyte growth factor (HGF), HGF activator and c-met genes in human glioma cells in vitro. *FEBS Lett.* 372 (1995), pp. 78-82; Y. W. Moon, R. J. Weil, S. D. Pack et al., Missense mutation of the MET gene detected in human glioma. *Mod. Pathol.* 13 (2000), pp. 973-977; M. Di Renzo, M. Olivero, T. Martone et al., Somatic mutations of the met oncogene are selected during metastatic spread of human HNSC carcinomas. *Oncogene* 19 (2000), pp. 1547-1555; K. Suzuki, N. Hayashi, Y. Yamada et al., Expression of the c-met proto-oncogene in human hepatocellular carcinoma. *Hepatology* 20 (1994), pp. 1231-1236; W. S. Park, S. M. Dong, S. Y. Kim et al., Somatic mutations in the kinase domain of the Met/hepatocyte growth factor receptor gene in childhood hepatocellular carcinomas. Cancer Res. 59 (1999), pp. 307-310; L. Schmidt, K. Junker, G. Weirich et al., Two North American families with hereditary papillary renal carcinoma and identical novel mutations in the MET proto-oncogene. *Cancer Res.* 58 (1998), pp. 1719-1722; J. Fischer, G. Palmedo, R. von Knobloch et al., Duplication and over-expression of the mutant allele of the MET proto-oncogene in multiple hereditary papillary renal cell tumours. *Oncogene.* 17 (1998), pp. 733-739; Z. Zhuang, W. S. Park, S. Pack et al., Trisomy 7-harbouring non-random duplication of the mutant MET allele in hereditary papillary renal carcinomas. *Nat Genet.* 20 (1998), pp. 66-69; M. Olivero, G. Valente, A. Bardelli et al., Novel mutation in the ATP-binding site of the MET oncogene tyrosine kinase in a HPRCC family. *Int. J. Cancer* 82 (1999), pp. 640-643; L. Schmidt, K. Junker, N. Nakaigawa et al., Novel mutations of the MET proto-oncogene in papillary renal carcinomas. *Oncogene* 18 (1999), pp. 2343-2350; M. Jucker, A. Gunther, G. Gradl et al., The Met/hepatocyte growth factor receptor (HGFR) gene is over-expressed in some cases of human leukemia and lymphoma. *Leuk. Res.* 18 (1994), pp. 7-16; E. Tolnay, C. Kuhnen, T. Wiethege et al., Hepatocyte growth factor/scatter factor and its receptor c-Met are over-expressed and associated with an increased microvessel density in malignant pleural mesothelioma. *J. Cancer Res. Clin. Oncol.* 124 (1998), pp. 291-296; J. Klominek, B. Baskin, Z. Liu et al., Hepatocyte growth factor/scatter factor stimulates chemotaxis and growth of malignant mesothelioma cells through c-met receptor. *Int. J. Cancer* 76 (1998), pp. 240-249; Thirkettle, P. Harvey, P. S. Hasleton et al., Immunoreactivity for cadherins, HGF/SF, met, and erbB-2 in pleural malignant mesotheliomas. *Histopathology* 36 (2000), pp. 522-528; P. G. Natali, M. R. Nicotra, M. F. Di Renzo et al., Expression of the c-Met/HGF receptor in human melanocytic neoplasms: demonstration of the relationship to malignant melanoma tumour progression. *Br. J. Cancer* 68 (1993), pp. 746-750; O. Hjertner, M. L. Torgersen, C. Seidel et al., Hepatocyte growth factor (HGF) induces interleukin-11 secretion from osteoblasts: a possible role for HGF in myeloma-associated osteolytic bone disease. *Blood* 94 (1999), pp. 3883-3888; C. Liu and M. S. Tsao, In vitro and in vivo expression of transforming growth factor-alpha and tyrosine kinase receptors in human non-small-cell lung carcinomas. *Am. J. Pathol.* 142 (1993), pp. 1155-1162; M. Olivero, M. Rizzo, R. Madeddu et al., Over-expression and activation of hepatocyte growth factor/scatter factor in human non-small-cell lung carcinomas. *Br J. Cancer* 74 (1996), pp. 1862-1868; E. Ichimura, A. Maeshima, T. Nakajima et al., Expression of c-met/HGF receptor in human non-small cell lung carcinomas in vitro and in vivo and its prognostic significance. *Jpn. J. Cancer Res.* 87 (1996), pp. 1063-1069;

Takanami, F. Tanana, T. Hashizume et al., Hepatocyte growth factor and c-Met/hepatocyte growth factor receptor in pulmonary adenocarcinomas: an evaluation of their expression as prognostic markers. *Oncology* 53 (1996), pp. 392-397; J. M. Siegfried, L. A. Weissfeld, J. D. Luketich et al., The clinical significance of hepatocyte growth factor for non-small cell lung cancer. *Ann Thorac. Surg.* 66 (1998), pp. 1915-1918; M. Tokunou, T. Niki, K. Eguchi et al., c-MET expression in myofibroblasts: role in autocrine activation and prognostic significance in lung adenocarcinoma. *Am J. Pathol.* 158 (2001), pp. 1451-1463; R. Ferracini, M. F. Di Renzo, K. Scotlandi et al., The Met/HGF receptor is over-expressed in human osteosarcomas and is activated by either a paracrine or an autocrine circuit. *Oncogene* 10 (1995), pp. 739-749; M. F. Di Renzo, M. Olivero, D. Katsaros et al., Over-expression of the Met/HGF receptor in ovarian cancer. *Int. J. Cancer* 58 (1994), pp. 658-662; H. M. Sowter, A. N. Corps and S. K. Smith, Hepatocyte growth factor (HGF) in ovarian epithelial tumour fluids stimulates the migration of ovarian carcinoma cells. *Int. J. Cancer* 83 (1999), pp. 476-480; M. Ebert, M. Yokoyama, H. Friess et al., Co-expression of the c-met proto-oncogene and hepatocyte growth factor in human pancreatic cancer. *Cancer Res.* 54 (1994), pp. 5775-5778; L. L. Pisters, P. Troncoso, H. E. Zhau et al., c-met proto-oncogene expression in benign and malignant human prostate tissues. *J. Urol.* 154 (1995), pp. 293-298; P. A. Humphrey, X. Zhu, R. Zarnegar et al., Hepatocyte growth factor and its receptor (c-MET) in prostatic carcinoma. *Am J. Pathol.* 147 (1995), pp. 386-396; K. Rygaard, T. Nakamura, M. Spang-Thomsen et al., Expression of the proto-oncogenes c-met and c-kit and their ligands, hepatocyte growth factor/scatter factor and stem cell factor, in SCLC cell lines and xenografts. *Br. J. Cancer* 67 (1993), pp. 37-46; Y. Oda, A. Sakamoto, T. Saito et al., Expression of hepatocyte growth factor (HGF)/scatter factor and its receptor c-MET correlates with poor prognosis in synovial sarcoma. *Hum. Pathol.* 31 (2000), pp. 185-192; M. F. Di Renzo, M. Olivero, G. Serini et al., Over-expression of the c-MET/HGF receptor in human thyroid carcinomas derived from the follicular epithelium. *J. Endocrinol. Invest* 18 (1995), pp. 134-139; K. Gohji, M. Nomi, Y. Niitani et al., Independent prognostic value of serum hepatocyte growth factor in bladder cancer. *J. Clin. Oncol.* 18 (2000), pp. 2963-2971.

Because of the role of aberrant HGF/SF-Met signaling in the pathogenesis of various human cancers, inhibitiors of c-Met receptor tyrosine kinase have broad applications in the treatment of cancers in which Met activity contributes to the invasive/metastatic phenotype, including those in which c-Met is not overexpressed or otherwise altered. Inhibitors of c-Met also inhibit angiogenesis and therefore are believed to have utility in the treatment of diseases associated with the formation of new vasculature, such as rheumatoid, arthritis, retinopathy. See, Michieli P, Mazzone M, Basilico C, Cavassa S, Sottile A, Naldini L, Comoglio P M. Targeting the tumor and its microenvironment by a dual-function decoy Met receptor. Cancer Cell. 2004 July; 6(1):61-73.

Over-expression of c-Met is also believed to be a potentially useful predictor for the prognosis of certain diseases, such as, for example, breast cancer, non-small cell lung carcinoma, pancreatic endocrine neoplasms, prostate cancer, esophageal adenocarcinoma, colorectal cancer, salivary gland carcinoma, diffuse large B-cell lymphoma and endometrial carcinoma.

See Herrera L J, El-Hefnawy T, Queiroz de Oliveira P E, Raja S, Finkelstein S, Gooding W, Luketich J D, Godfrey T E, Hughes S J., The HGF Receptor c-Met Is Overexpressed in Esophageal Adenocarcinoma. *Neoplasia.* 2005 January; 7(1):75-84; Zeng Z, Weiser M R, D'Alessio M, Grace A, Shia J, Paty P B., Immunoblot analysis of c-Met expression in human colorectal cancer: overexpression is associated with advanced stage cancer. *Clin Exp Metastasis.* 2004; 21(5): 409-17; He Y, Peng Z, Pan X, Wang H, Ouyang Y. [Expression and correlation of c-Met and estrogen receptor in endometrial carcinomas] *Sichuan Da Xue Xue Bao Yi Xue Ban.* 2003 January; 34(1):78-9, 88 (English Abstract Only); Tsukinoki K, Yasuda M, Mori Y, Asano S, Naito H, Ota Y, Osamura R Y, Watanabe Y. Hepatocyte growth factor and c-Met immunoreactivity are associated with metastasis in high grade salivary gland carcinoma. *Oncol Rep.* 2004 November; 12(5):1017-21; Kawano R, Ohshima K, Karube K, Yamaguchi T, Kohno S, Suzumiya J, Kikuchi M, Tamura K. Prognostic significance of hepatocyte growth factor and c-MET expression in patients with diffuse large B-cell lymphoma. *Br J Haematol.* 2004 November; 127(3):305-7; Lengyel E, Prechtel D, Resau J H, Gauger K, Welk A, Lindemann K, Salanti G, Richter T, Knudsen B, Vande Woude G F, Harbeck N. C-Met overexpression in node-positive breast cancer identifies patients with poor clinical outcome independent of Her2/neu. *Int J Cancer.* 2005 Feb. 10; 113(4):678-82; Hansel D E, Rahman A, House M, Ashfaq R, Berg K, Yeo C J, Maitra A. Met proto-oncogene and insulin-like growth factor binding protein 3 overexpression correlates with metastatic ability in well-differentiated pancreatic endocrine neoplasms. *Clin Cancer Res.* 2004 Sep. 15; 10(18 Pt 1):6152-8; Knudsen B S, Edlund M. Prostate cancer and the met hepatocyte growth factor receptor. *Adv Cancer Res.* 2004; 91:31-67; D Masuya, C Huang, D Liu, T Nakashima, et al., The tumour-stromal interaction between intratumoral c-Met and stromal hepatocyte growth factor associated with tumour growth and prognosis in non-small-cell lung cancer patients. *British Journal of Cancer.* 2004; 90:1552-1562; Ernst Lengyel, Dieter Prechtel, James H. Resau, Katja Gauger, et al. C-Met overexpression in node-positive breast cancer identifies patients with poor clinical outcome independent of Her2/neu. Int. J. Cancer 2005; 113: 678-682.

Many strategies have been devised to attenuate aberrant Met signaling in human tumors. Some of these strategies include the use of HGF antagonists and small-molecule inhibitors. For instance, there are a number of HGF/SF antagonists or inhibitors currently in clinical development, such as Abbott (ABT-510), EntreMed (angiostatin), Kosan Biosciences (17-AAG), Amgen (AMG-102), Exelixis (XL-880 and XL-184), Pfizer (PNU-145156E), and ArQule (ARQ 197).

SUMMARY OF THE INVENTION

The present invention provides novel triazolopyridazines (the compounds of Formula I) as protein tyrosine kinase modulators, particularly inhibitors of c-Met, and the use of such compounds to reduce or inhibit kinase activity of c-Met in a cell or a subject, and modulate c-Met expression in a cell or subject, and the use of such compounds for preventing or treating in a subject a cell proliferative disorder and/or disorders related to c-Met.

Illustrative of the invention is a pharmaceutical composition comprising a compound of Formula I and a pharmaceutically acceptable carrier. Another illustration of the present invention is a pharmaceutical composition prepared by mixing any of the compounds of Formula I and a pharmaceutically acceptable carrier.

Other features and advantages of the invention will be apparent from the following detailed description of the invention and from the claims.

DETAILED DESCRIPTION OF THE INVENTION

Definitions

Figure 1:
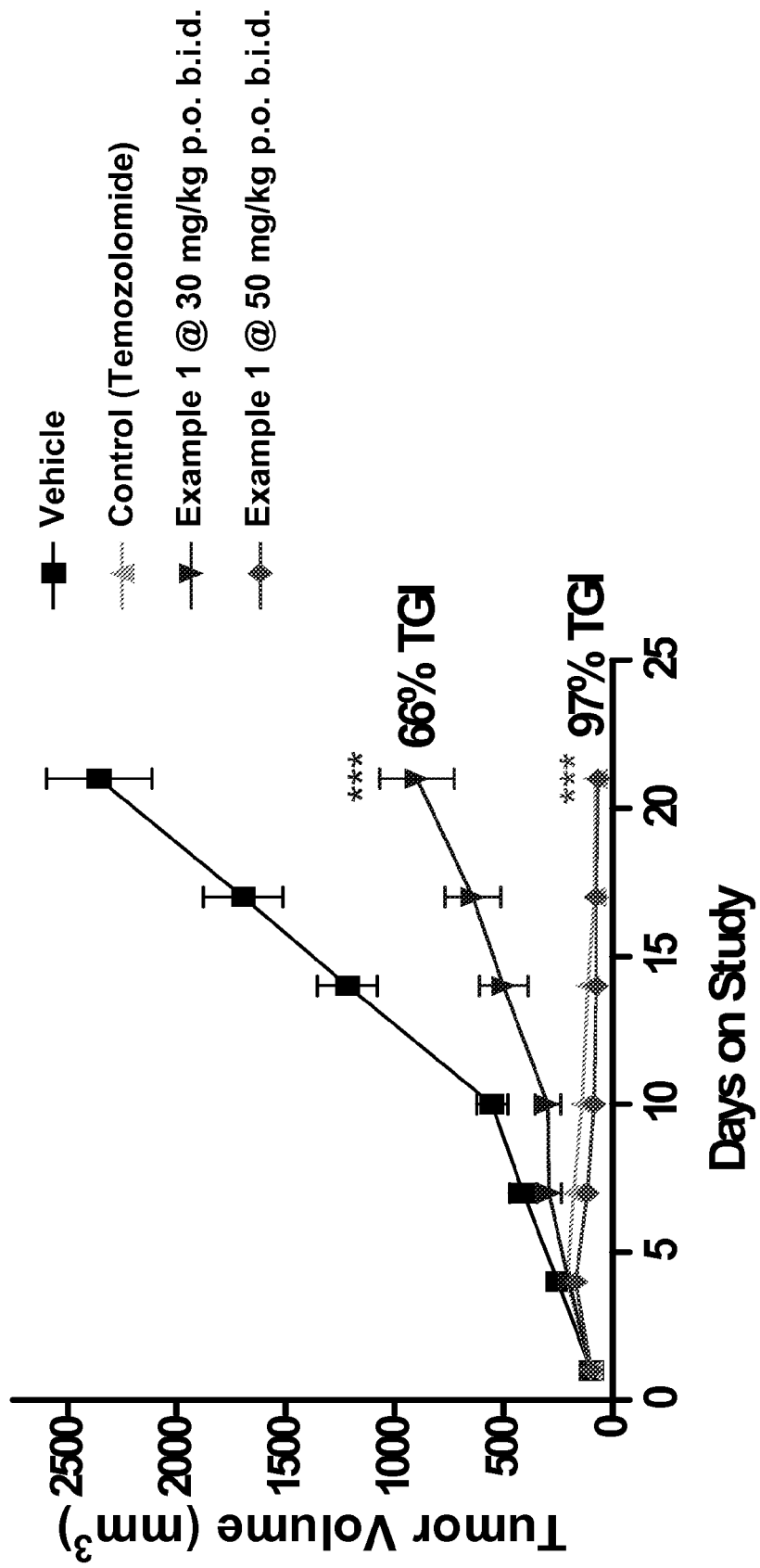
FIG. 1 shows the effects of oral administration of compounds of the present invention (Example Compound No. 1) on tumor growth inhibition (TGI) in U87MG glioblastoma tumors in nude mice. All treatments began on Day 1 in mice bearing established subcutaneous U87MG tumors. Tumor growth is plotted as the median tumor volume ($mm^3$), versus time (Days), for each group in the study. At the end of the 21-day study, final TGI % was calculated from the difference between the median tumor volumes of vehicle-treated and drug-treated mice, expressed as a percentage of the median tumor volume of the vehicle-treated control group. (*=$p<0.05$, =$p<0.01$, *=$p<0.001$)

As used herein, the following terms are intended to have the following meanings (additional definitions are provided where needed throughout the Specification):

The term "alkenyl," whether used alone or as part of a substituent group, for example, "$C_{1-4}$alkenyl(aryl)," refers to a partially unsaturated branched or straight chain monovalent hydrocarbon radical having at least one carbon-carbon double bond, whereby the double bond is derived by the removal of one hydrogen atom from each of two adjacent carbon atoms of a parent alkyl molecule and the radical is derived by the removal of one hydrogen atom from a single carbon atom. Atoms may be oriented about the double bond in either the cis (Z) or trans (E) conformation. Typical alkenyl radicals include, but are not limited to, ethenyl, propenyl, allyl (2-propenyl), butenyl and the like. Examples include $C_{2-8}$alkenyl or $C_{2-4}$alkenyl groups.

The term "$C_{a-b}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{1-4}$ denotes a radical containing 1, 2, 3 or 4 carbon atoms.

The term "alkyl," whether used alone or as part of a substituent group, refers to a saturated branched or straight chain monovalent hydrocarbon radical, wherein the radical is derived by the removal of one hydrogen atom from a single carbon atom. Unless specifically indicated (e.g. by the use of a limiting term such as "terminal carbon atom"), substituent variables may be placed on any carbon chain atom. Typical alkyl radicals include, but are not limited to, methyl, ethyl, propyl, isopropyl and the like. Examples include $C_{1-8}$alkyl, $C_{1-6}$alkyl and $C_{1-4}$alkyl groups.

The term "alkylamino" refers to a radical formed by the removal of one hydrogen atom from the nitrogen of an alkylamine, such as butylamine, and the term "dialkylamino" refers to a radical formed by the removal of one hydrogen atom from the nitrogen of a secondary amine, such as dibutylamine. In both cases it is expected that the point of attachment to the rest of the molecule is the nitrogen atom.

The term "alkynyl," whether used alone or as part of a substituent group, refers to a partially unsaturated branched or straight chain monovalent hydrocarbon radical having at least one carbon-carbon triple bond, whereby the triple bond is derived by the removal of two hydrogen atoms from each of two adjacent carbon atoms of a parent alkyl molecule and the radical is derived by the removal of one hydrogen atom from a single carbon atom. Typical alkynyl radicals include ethynyl, propynyl, butynyl and the like. Examples include $C_{2-8}$alkynyl or $C_{2-4}$alkynyl groups.

The term "alkoxy" refers to a saturated or partially unsaturated branched or straight chain monovalent hydrocarbon alcohol radical derived by the removal of the hydrogen atom from the hydroxide oxygen substituent on a parent alkane, alkene or alkyne. Where specific levels of saturation are intended, the nomenclature "alkoxy", "alkenyloxy" and "alkynyloxy" are used consistent with the definitions of alkyl, alkenyl and alkynyl. Examples include $C_{1-8}$alkoxy or $C_{1-4}$alkoxy groups.

The term "aromatic" refers to a cyclic hydrocarbon ring system having an unsaturated, conjugated π electron system.

The term "benzo-fused heterocyclyl" refers to a bicyclic fused ring system radical wherein one of the rings is benzene and the other is a heterocyclyl ring. Typical benzo-fused heterocyclyl radicals include 1,3-benzodioxolyl (also known as 1,3-methylenedioxyphenyl), 2,3-dihydro-1,4-benzodioxinyl (also known as 1,4-ethylenedioxyphenyl), benzo-dihydro-furyl, benzo-tetrahydro-pyranyl, benzo-dihydro-thienyl and the like.

The term "cycloalkyl" refers to a saturated or partially unsaturated monocyclic or bicyclic hydrocarbon ring radical derived by the removal of one hydrogen atom from a single ring carbon atom. Typical cycloalkyl radicals include cyclopropyl, cyclobutyl, cyclopentyl, cyclopentenyl, cyclohexyl, cyclohexenyl, cycloheptyl and cyclooctyl. Additional examples include $C_{3-8}$cycloalkyl, $C_{5-8}$cycloalkyl, $C_{3-12}$cycloalkyl, $C_{3-20}$cycloalkyl, decahydronaphthalenyl, and 2,3,4,5,6,7-hexahydro-1H-indenyl.

The term "fused ring system" refers to a bicyclic molecule in which two adjacent atoms are present in each of the two cyclic moieties. Heteroatoms may optionally be present. Examples include benzothiazole, 1,3-benzodioxole and decahydronaphthalene.

The term "hetero" used as a prefix for a ring system refers to the replacement of at least one ring carbon atom with one or more atoms independently selected from N, S, O or P. Examples include rings wherein 1, 2, 3 or 4 ring members are a nitrogen atom; or, 0, 1, 2 or 3 ring members are nitrogen atoms and 1 member is an oxygen or sulfur atom.

The term "heteroaryl" refers to a radical derived by the removal of one hydrogen atom from a ring carbon atom of a heteroaromatic ring system. Typical heteroaryl radicals include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolizinyl, indolyl, isoindolyl, benzo[b]furyl, benzo[b]thienyl, indazolyl, benzimidazolyl, benzthiazolyl, purinyl, 4H-quinolizinyl, quinolinyl, isoquinolinyl, cinnolinyl, phthalzinyl, quinazolinyl, quinoxalinyl, 1,8-naphthyridinyl, pteridinyl and the like.

The term "heterocyclyl" refers to a saturated or partially unsaturated monocyclic ring radical derived by the removal of one hydrogen atom from a single carbon or nitrogen ring atom. Typical heterocyclyl radicals include 2H-pyrrole, 2-pyrrolinyl or 3-pyrrolinyl), pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, piperidinyl, 1,4-dioxanyl, morpholinyl, 1,4-dithianyl, thiomorpholinyl, piperazinyl, azepanyl, hexahydro-1,4-diazepinyl and the like.

The term "substituted," refers to a core molecule on which one or more hydrogen atoms have been replaced with one or more functional radical moieties. Substitution is not limited to a core molecule, but may also occur on a substituent radical, whereby the substituent radical becomes a linking group.

The term "independently selected" refers to one or more substituents selected from a group of substituents, wherein the substituents may be the same or different.

The substituent nomenclature used in the disclosure of the present invention was derived by first indicating the atom having the point of attachment, followed by the linking group atoms toward the terminal chain atom from left to right, substantially as in:

or by first indicating the terminal chain atom, followed by the linking group atoms toward the atom having the point of attachment, substantially as in:

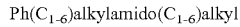

either of which refers to a radical of the Formula:

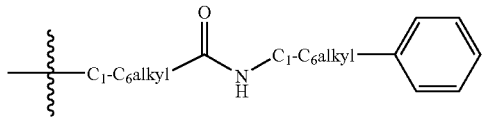

Lines drawn into ring systems from substituents indicate that the bond may be attached to any of the suitable ring atoms.

When any variable (e.g. $R_4$) occurs more than one time in any embodiment of Formula I, each definition is intended to be independent.

The terms "comprising", "including", and "containing" are used herein in their open, non-limited sense.

Nomenclature

Except where indicated, compound names were derived using nomenclature rules well known to those skilled in the art, by either standard IUPAC nomenclature references, such as *Nomenclature of Organic Chemistry, Sections A, B, C, D, E, F and H*, (Pergamon Press, Oxford, 1979, Copyright 1979 IUPAC) and *A Guide to IUPAC Nomenclature of Organic Compounds* (*Recommendations* 1993), (Blackwell Scientific Publications, 1993, Copyright 1993 IUPAC), or commercially available software packages such as Autonom (brand of nomenclature software provided in the ChemDraw Ultra® office suite marketed by CambridgeSoft.com) and ACD/Index Name™ (brand of commercial nomenclature software marketed by Advanced Chemistry Development, Inc., Toronto, Ontario). It is well known in the art that the radical form of certain heterocycles, such as pyridine and quinoline, may be named according to different conventions without referring to different radicals. For example: either pyridyl or pyridinyl refer to a radical of pyridine, and either quinolyl or quinolinyl refer to a radical of quinoline.

Abbreviations

As used herein, the following abbreviations are intended to have the following meanings (additional abbreviations are provided where needed throughout the Specification):
$^1$H NMR Proton Nuclear Magnetic Resonance
AcOH Acetic Acid
aq Aqueous
CD$_3$OD Deuterated Methanol
CDCl$_3$ Deuterated Chloroform
CH$_2$Cl$_2$ Methylene Chloride
CH$_3$CN Acetonitrile
Cs$_2$CO$_3$ Cesium Carbonate
DAST (Dimethylamino)sulfur trifluoride
DCM Dichloromethane
DIEA Diisopropylethyl amine
DMAP 4-Dimethylaminopyridine
DMSO Dimethylsulfoxide
EDC N-(3-dimethylaminopropyl)-N'-ethyl-carbodiimide
ESI-MS Electrospray ionization mass spectroscopy
Et$_2$O Diethyl ether
Et$_3$N Triethylamine
EtOAc Ethyl Acetate
EtOAc Ethyl acetate
EtOH Ethanol
g Grams
h Hour
H$_2$O Water
HATU O-(7-Azabenzotriazol-1-yl)-N,N,N',N'-tetramethyluronium hexafluorophosphate
HBTU O-benzotriazol-1-yl-N,N,N',N'-tetramethyluronium
HCl Hydrochloric Acid
Hex Hexanes hexafluorophosphate
HOBT 1-Hydroxybenzotriazole hydrate
HPLC High Pressure Liquid Chromotography
K$_2$CO$_3$ Potassium Carbonate
KOtBu Potassium tert-butoxide
LCMS Liquid Chromatography Mass Spectrophometry
MeOH Methanol
mg Milligrams
MgSO$_4$ Magnesium Sulfate
min minute
mL Milliliters
mmol millimole
mol mole
MW Molecular weight Na$_2$CO$_3$ Sodium Carbonate
Na$_2$SO$_4$ Sodium Sulfite
NaHCO$_3$ Sodium hydrogen carbonate
NaOH Sodium Hydroxide
NaOH Sodium hydroxide
NaOH Sodium Hydroxide
NBS n-Bromosuccinimide
NH$_4$Cl Ammonium chloride
Pd(PPh$_3$)$_4$ Tetrakistriphenylphosphine palladium (0)
Peppsi-iPr Pyridine-Enhanced Precatalyst Preparation Stabilization and Initiation (trademark of Sigma-Aldrich)
ppt Precipitate
RP-HPLC Reverse Phase High Pressure Liquid Chromotography
rt Room Temperature
SiO$_2$ Silicon Dioxide
TFA Trifluoroacetic acid
THF Tetrahydrofuran
TLC Thin layer chromatography
µL Microliters
Formula I The present invention comprises compounds of Formula I:

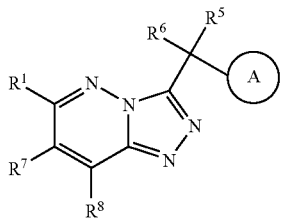

Formula I and N-oxides, prodrugs, pharmaceutically acceptable salts, solvates, and stereochemical isomers thereof, wherein:

R$^1$ is mono or bicyclic heteroaryl (preferably pyridyl, thiophenyl, thiazolyl, pyrazolyl, furanyl, imidazolyl, oxazolyl, pyrrolyl, indolyl, isothiazolyl, triazolyl, benzothiophenyl, benzothiazolyl, benzoimidazolyl, benzoxazolyl, quinolyl, benzofuranyl, quinazolinyl, or quinoxalinyl), or pyridin-2-on-yl (preferably pyridin-2-on-5-yl), wherein said heteroaryl is optionally substituted with -one, two or three R$_a$ substituents;

wherein R$_a$ is —NH$_2$, halogen (preferably F, Cl or Br), alkoxy (preferably C$_{1-6}$ alkoxy), alkylether (preferably —C$_{(1-6)}$alkyl-O—C$_{(1-6)}$alkyl), alkylthio (preferably C$_{1-6}$ alkylthio), alkylsulfonyl (preferably C$_{1-6}$ alkylsulfonyl), phenylsulfonyl, heteroarylsulfonyl (wherein the heteroaryl portion of said heteroarylsulfonyl is preferably pyridyl, thiophenyl, thiazolyl, pyrazolyl, furanyl, imidazolyl, oxazolyl, pyrrolyl, indolyl, isothiazolyl, triazolyl, benzothiophenyl, benzothiazolyl, benzoimidazolyl, benzoxazolyl, quinolyl, benzofuranyl, quinazolinyl, or quinoxalinyl), heterocyclylsulfonyl (wherein the heterocyclyl portion of said heterocyclylsulfonyl is preferably pyrrolidinyl, tetrahydrofuranyl, tetrahydrothiophenyl, imidazolidinyl, thiazolidinyl, oxazolidinyl, tetrahydropyranyl, tetrahydrothiopyranyl, piperidinyl, thiomorpholinyl, thiomorpholinyl 1,1-dioxide, morpholinyl, or piperazinyl), —SO$_2$NH$_2$, alkylsulfonamide (preferably C$_{1-6}$ alkylsulfonamide), alkyl (preferably C$_{1-6}$ alkyl), aminoalkyl (preferably methylamine), alkylamino (preferably C$_{1-6}$ alkylamino), phenyl, heteroaryl (preferably pyridyl, thiophenyl, thiazolyl, pyrazolyl, furanyl, imidazolyl, oxazolyl, pyrrolyl, indolyl, isothiazolyl, triazolyl, benzothiophenyl, benzothiazolyl, benzoimidazolyl, benzoxazolyl, quinolyl, benzofuranyl, quinazolinyl, or quinoxalinyl), cyano, alkenyl (preferably C$_{1-6}$ alkenyl), alkynyl (preferably C$_{1-6}$ alkynyl), cycloalkyl (preferably cyclopropyl, cyclobutyl, cyclopentyl, cyclohexyl or cycloheptyl), heterocyclyl (preferably pyrrolidinyl, tetrahydrofuranyl, tetrahydrothiophenyl, imidazolidinyl, thiazolidinyl, oxazolidinyl, tetrahydropyranyl, tetrahydrothiopyranyl, piperidinyl, thiomorpholinyl, thiomorpholinyl 1,1-dioxide, morpholinyl, or piperazinyl), —CO$_2$-alkyl (preferably —CO$_2$—CH$_2$CH$_3$), —C(O)—R$_b$, —C$_{(1-4)}$alkyl-morpholinyl, —C$_{(1-4)}$alkyl-piperidinyl, —C$_{(1-4)}$alkyl-piperazinyl, —C$_{(1-4)}$alkyl-N'-methyl piperazinyl, —C$_{(1-4)}$alkyl-R$_b$, —C(O)NH—C$_{(1-4)}$alkyl-R$_b$, or —C(O)NR$_c$R$_d$;

wherein R$_b$ is heterocyclyl (preferably pyrrolidinyl, tetrahydrofuranyl, tetrahydrothiophenyl, imidazolidinyl, thiazolidinyl, oxazolidinyl, tetrahydropyranyl, tetrahydrothiopyranyl, piperidinyl, thiomorpholinyl, thiomorpholinyl 1,1-dioxide, morpholinyl, or piperazinyl), alkylsulfonyl (preferably C$_{1-6}$ alkylsulfonyl), —SO$_2$NH$_2$, alkylsulfonamide (preferably C$_{1-6}$ alkylsulfonamide), —OH, —Oalkyl (preferably —OC$_{1-6}$ alkyl), —NH$_2$, —NHalkyl (preferably —NHC$_{1-6}$ alkyl), or —N(alkyl)$_2$ (preferably —N(C$_{1-6}$ alkyl)$_2$);

R$_c$ and R$_d$ are independently selected from: H, phenyl, heteroaryl, or C$_{1-6}$ alkyl, wherein said C$_{1-6}$alkyl may optionally be substituted with one substituent selected from: —N(CH$_3$)$_2$, morpholinyl, piperidinyl, piperazinyl, N-methyl piperazinyl, alkylsulfonyl (preferably C$_{1-6}$ alkylsulfonyl), —SO$_2$NH$_2$, alkylsulfonamide (preferably C$_{1-6}$ alkylsulfonamide), hydroxyl, and alkoxy;

or R$_c$ and R$_d$ together may form a 5 to 7 membered heterocyclic ring, optionally containing a second heteromoiety selected from O, NH, N(alkyl), SO, SO$_2$, or S, (said R$_c$-R$_d$ heterocyclic ring preferably selected from the group consisting of:

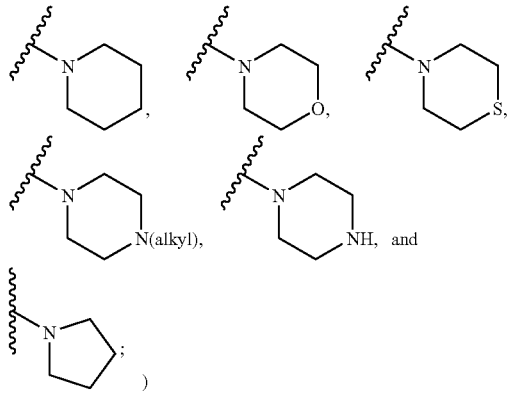

wherein said R$_c$-R$_d$ heterocyclic ring is optionally substituted with alkyl (preferably —C$_{(1-6)}$alkyl), —SO$_2$alkyl (preferably —SO$_2$C$_{(1-6)}$alkyl), or —C(O)alkyl (preferably —C(O)C$_{(1-6)}$alkyl);

A is a ring selected from the group consisting of: phenyl, mono or bicyclic heteroaryl (preferably pyridyl, benzoxazolyl, benzothiazolyl, quinolinyl, quinolin-6-yl-N-oxide, quinazolinyl, quinoxalinyl, benzimidazolyl, benzothiophenyl, benzofuranyl, or [1,2,4]triazolo[1,5-o]pyridinyl), quinazolin-4-on-yl (preferably quinazolin-4-on-6-yl, or 3-(4-Methoxy-benzyl)-3H-quinazolin-4-on-6-yl), and benzo-fused heterocyclyl (preferably benzo[1,3]dioxolyl, or 2,3-dihydro-benzofuranyl); wherein said phenyl, heteroaryl, or benzo-fused heterocyclyl are optionally substituted with one, two or three substituents independently selected from the group consisting of: —OH, alkyl, phenyl, heteroaryl, alkoxy, —CN, halogen, nitro, —$NH_2$, —$N(CH_3)_2$, —$NHC(O)NHC_{1-6}$alkyl, and —$NHC(O)C_{1-6}$alkyl;

$R^5$ and $R^6$ are independently selected from: H, F, $C_{1-6}$ alkyl, —OH, —$OC_{1-6}$alkyl, —$NHC_{1-6}$alkyl, or —$N(C_{1-6}$alkyl$)_2$; or $R^5$ and $R^6$ can together form a $C_{3-5}$ cycloalkyl ring, an aziridinyl ring, or, an epoxidyl ring; and $R^7$ and $R^8$ are H, halogen or $C_{1-6}$ alkyl.

As used hereafter, the terms "compound of Formula I" and "compounds of Formula I" are meant to include also the pharmaceutically acceptable salts, N-oxides, solvates and stereochemical isomers thereof Embodiments of Formula I Preferred embodiments of the invention are compounds of Formula I wherein one or more of the following limitations are present:

$R^1$ is mono or bicyclic heteroaryl, or pyridin-2-on-5-yl, wherein said heteroaryl is optionally substituted with one, two or three $R_a$ substituents;
  wherein $R_a$ is —$NH_2$, halogen, alkoxy, alkylether, alkylthio, alkylsulfonyl, phenylsulfonyl, heteroarylsulfonyl, heterocyclylsulfonyl, —$SO_2NH_2$, alkylsulfonamide, alkyl, aminoalkyl, alkylamino, phenyl, heteroaryl, cyano, alkenyl, alkynyl, cycloalkyl, heterocyclyl, —$CO_2$-alkyl, —C(O)—$R_b$, —$C_{(1-4)}$alkyl-morpholinyl, —$C_{(1-4)}$alkyl-piperidinyl, —$C_{(1-4)}$alkyl-piperazinyl, —$C_{(1-4)}$alkyl-N'-methyl piperazinyl, —$C_{(1-4)}$alkyl-$R_b$, —C(O)NH—$C_{(1-4)}$alkyl-$R_b$, or —C(O)$NR_cR_d$;
    wherein $R_b$ is heterocyclyl, alkylsulfonyl, —$SO_2NH_2$, alkylsulfonamide, —OH, —Oalkyl, —$NH_2$, —NHalkyl, or —N(alkyl)$_2$;
    $R_c$ and $R_d$ are independently selected from: H, phenyl, heteroaryl, or $C_{1-6}$ alkyl, wherein said $C_{1-6}$alkyl may optionally be substituted with one substituent selected from: —$N(CH_3)_2$, morpholinyl, piperidinyl, piperazinyl, N-methyl piperazinyl, alkylsulfonyl, —$SO_2NH_2$, alkylsulfonamide, hydroxyl, and alkoxy;
    or $R_c$ and $R_d$ together may form a 5 to 7 membered heterocyclic ring, optionally containing a second heteromoiety selected from O, NH, N(alkyl), SO, $SO_2$, or S, wherein said $R_c$-$R_d$ heterocyclic ring is optionally substituted with alkyl, —$SO_2$alkyl, or —C(O)alkyl;

A is a ring selected from the group consisting of: phenyl, mono or bicyclic heteroaryl, 3-(4-methoxy-benzyl)-3H-quinazolin-4-on-6-yl, quinazolin-4-on-6-yl, and benzo-fused heterocyclyl; wherein said phenyl, heteroaryl, or benzo-fused heterocyclyl are optionally substituted with one to three substituents independently selected from the group consisting of: —OH, alkyl, phenyl, heteroaryl, alkoxy, —CN, halogen, nitro, —$NH_2$, —$N(CH_3)_2$, —$NHC(O)NHC_{1-6}$alkyl, and —$NHC(O)C_{1-6}$alkyl;

$R^5$ and $R^6$ are independently selected from: H, F, $C_{1-6}$ alkyl, —OH, —$OC_{1-6}$alkyl, —$NHC_{1-6}$alkyl, or —$N(C_{1-6}$alkyl$)_2$; or $R^5$ and $R^6$ can together form a $C_{3-5}$ cycloalkyl ring, an aziridinyl ring, or, an epoxidyl ring; and $R^7$ and $R^8$ are H.

Other preferred embodiments of the invention are compounds of Formula I wherein one or more of the following limitations are present:

$R^1$ is mono or bicyclic heteroaryl, or pyridin-2-on-5-yl, wherein said heteroaryl is optionally substituted with one, two or three $R_a$ substituents;
  wherein $R_a$ is —$NH_2$, halogen, alkoxy, alkylether, alkylthio, alkylsulfonyl, phenylsulfonyl, heteroarylsulfonyl, heterocyclylsulfonyl, —$SO_2NH_2$, alkylsulfonamide, alkyl, aminoalkyl, alkylamino, phenyl, heteroaryl, cyano, alkenyl, alkynyl, cycloalkyl, heterocyclyl, —$CO_2$-alkyl, —C(O)—$R_b$, —$C_{(1-4)}$alkyl-morpholinyl, —$C_{(1-4)}$alkyl-piperidinyl, —$C_{(1-4)}$alkyl-piperazinyl, —$C_{(1-4)}$alkyl-N'-methyl piperazinyl, —$C_{(1-4)}$alkyl-$R_b$, —C(O)NH—$C_{(1-4)}$alkyl-$R_b$, or —C(O)$NR_cR_d$;
    wherein $R_b$ is heterocyclyl, alkylsulfonyl, —$SO_2NH_2$, alkylsulfonamide, —OH, —Oalkyl, —$NH_2$, —NHalkyl, or —N(alkyl)$_2$;
    $R_c$ and $R_d$ are independently selected from: H, phenyl, heteroaryl, or $C_{1-6}$ alkyl, wherein said $C_{1-6}$alkyl may optionally be substituted with one substituent selected from: —$N(CH_3)_2$, morpholinyl, piperidinyl, piperazinyl, N-methyl piperazinyl, alkylsulfonyl, —$SO_2NH_2$, alkylsulfonamide, hydroxyl, and alkoxy;
    or $R_c$ and $R_d$ together may form a 5 to 7 membered heterocyclic ring selected from the group consisting of: piperidinyl, morpholinyl, and piperazinyl, wherein said piperazinyl is optionally substituted with alkyl, —$SO_2$alkyl, or —C(O)alkyl;

A is a ring selected from the group consisting of: phenyl, mono or bicyclic heteroaryl, 3-(4-methoxy-benzyl)-3H-quinazolin-4-on-6-yl, quinazolin-4-on-6-yl, and benzo-fused heterocyclyl; wherein said phenyl, heteroaryl, or benzo-fused heterocyclyl are optionally substituted with one to three substituents independently selected from the group consisting of: —OH, alkyl, phenyl, heteroaryl, alkoxy, —CN, halogen, nitro, —$NH_2$, —$N(CH_3)_2$, —$NHC(O)NHC_{1-6}$alkyl, and —$NHC(O)C_{1-6}$alkyl;

$R^5$ and $R^6$ are independently selected from: H, F, $C_{1-6}$ alkyl, —OH, —$OC_{1-6}$alkyl, —$NHC_{1-6}$alkyl, or —$N(C_{1-6}$alkyl$)_2$; or $R^5$ and $R^6$ can together form a $C_{3-5}$ cycloalkyl ring, an aziridinyl ring, or, an epoxidyl ring; and $R^7$ and $R^8$ are H.

Other preferred embodiments of the invention are compounds of Formula I wherein one or more of the following limitations are present:

$R^1$ is mono or bicyclic heteroaryl, or pyridin-2-on-5-yl, wherein said heteroaryl is optionally substituted with one, two or three $R_a$ substituents;
  wherein $R_a$ is —$NH_2$, halogen, alkoxy, alkylether, alkylthio, alkylsulfonyl, phenylsulfonyl, heteroarylsulfonyl, heterocyclylsulfonyl, —$SO_2NH_2$, alkylsulfonamide, alkyl, aminoalkyl, alkylamino, phenyl, heteroaryl, cyano, alkenyl, alkynyl, cycloalkyl, heterocyclyl, —$CO_2$-alkyl, —C(O)—$R_b$, —$C_{(1-4)}$alkyl-morpholinyl, —$C_{(1-4)}$alkyl-piperidinyl, —$C_{(1-4)}$alkyl-piperazinyl, —$C_{(1-4)}$alkyl-N'-methyl piperazinyl, —$C_{(1-4)}$alkyl-$R_b$, —C(O)NH—$C_{(1-4)}$alkyl-$R_b$, or —C(O)$NR_cR_d$;
    wherein $R_b$ is heterocyclyl, alkylsulfonyl, —$SO_2NH_2$, alkylsulfonamide, —OH, —Oalkyl, —$NH_2$, —NHalkyl, or —N(alkyl)$_2$;
    $R_c$ and $R_d$ are independently selected from: H, phenyl, heteroaryl, or $C_{1-6}$ alkyl, wherein said $C_{1-6}$alkyl may optionally be substituted with one substituent selected from: —$N(CH_3)_2$, morpholinyl, piperidinyl, piperazinyl, N-methyl piperazinyl, alkylsulfonyl, —$SO_2NH_2$, alkylsulfonamide, hydroxyl, and alkoxy;
    or $R_c$ and $R_d$ together may form a 5 to 7 membered heterocyclic ring selected from the group consisting of: piperidinyl, morpholinyl, and piperazinyl, wherein said piperazinyl is optionally substituted with alkyl, —SO$_2$alkyl, or —C(O)alkyl;

A is a ring selected from the group consisting of: phenyl, mono or bicyclic heteroaryl, 3-(4-methoxy-benzyl)-3H-quinazolin-4-on-6-yl, quinazolin-4-on-6-yl, and benzo-fused heterocyclyl; wherein said phenyl, heteroaryl, or benzo-fused heterocyclyl are optionally substituted with one to three substituents independently selected from the group consisting of: —OH, alkyl, phenyl, heteroaryl, alkoxy, —CN, halogen, nitro, —NH$_2$, —N(CH$_3$)$_2$, —NHC(O)NHC$_{1-6}$alkyl, and —NHC(O)C$_{1-6}$alkyl;

$R^5$ and $R^6$ are independently selected from: H, F, or —CH$_3$; or $R^5$ and $R^6$ can together form a cyclopropyl ring; and $R^7$ and $R^8$ are H.

Other preferred embodiments of the invention are compounds of Formula I wherein one or more of the following limitations are present:

$R^1$ is mono or bicyclic heteroaryl, or pyridin-2-on-5-yl, wherein said heteroaryl is optionally substituted with one, two or three $R_a$ substituents;
  wherein $R_a$ is —NH$_2$, halogen, alkoxy, alkylether, alkylthio, alkylsulfonyl, phenylsulfonyl, heteroarylsulfonyl, heterocyclylsulfonyl, —SO$_2$NH$_2$, alkylsulfonamide, alkyl, aminoalkyl, alkylamino, phenyl, heteroaryl, cyano, alkenyl, alkynyl, cycloalkyl, heterocyclyl, —CO$_2$-alkyl, —C(O)—R$_b$, —C$_{(1-4)}$alkyl-morpholinyl, —C$_{(1-4)}$alkyl-piperidinyl, —C$_{(1-4)}$alkyl-piperazinyl, —C$_{(1-4)}$alkyl-N'-methyl piperazinyl, —C$_{(1-4)}$alkyl-R$_b$, —C(O)NH—C$_{(1-4)}$alkyl-R$_b$, or —C(O)NR$_c$R$_d$;
  wherein R$_b$ is heterocyclyl, alkylsulfonyl, —SO$_2$NH$_2$, alkylsulfonamide, —OH, —Oalkyl, —NH$_2$, —NHalkyl, or —N(alkyl)$_2$;
  R$_c$ and R$_d$ are independently selected from: H, phenyl, heteroaryl, or C$_{1-6}$ alkyl, wherein said C$_{1-6}$alkyl may optionally be substituted with one substituent selected from: —N(CH$_3$)$_2$, morpholinyl, piperidinyl, piperazinyl, N-methyl piperazinyl, alkylsulfonyl, —SO$_2$NH$_2$, alkylsulfonamide, hydroxyl, and alkoxy;
  or R$_c$ and R$_d$ together may form a 5 to 7 membered heterocyclic ring selected from the group consisting of: piperidinyl, morpholinyl, and piperazinyl, wherein said piperazinyl is optionally substituted with alkyl, —SO$_2$alkyl, or —C(O)alkyl;

A is a ring selected from the group consisting of: phenyl, mono or bicyclic heteroaryl, 3-(4-methoxy-benzyl)-3H-quinazolin-4-on-6-yl, quinazolin-4-on-6-yl, and benzo-fused heterocyclyl; wherein said phenyl, heteroaryl, or benzo-fused heterocyclyl are optionally substituted with one substituent independently selected from the group consisting of: —OH, alkyl, phenyl, heteroaryl, alkoxy, —CN, halogen, nitro, —NH$_2$, —N(CH$_3$)$_2$, —NHC(O)NHC$_{1-6}$alkyl, and —NHC(O)C$_{1-6}$alkyl;

$R^5$ and $R^6$ are independently selected from: H, F, or —CH$_3$; or $R^5$ and $R^6$ can together form a cyclopropyl ring; and $R^7$ and $R^8$ are H.

Other preferred embodiments of the invention are compounds of Formula I wherein one or more of the following limitations are present:

$R^1$ is mono or bicyclic heteroaryl, or pyridin-2-on-5-yl, wherein said heteroaryl is optionally substituted with one, two or three $R_a$ substituents;
  wherein $R_a$ is —NH$_2$, halogen, alkoxy, alkylether, alkylthio, alkylsulfonyl, phenylsulfonyl, heteroarylsulfonyl, heterocyclylsulfonyl, —SO$_2$NH$_2$, alkylsulfonamide, alkyl, aminoalkyl, alkylamino, phenyl, heteroaryl, cyano, alkenyl, alkynyl, cycloalkyl, heterocyclyl, —CO$_2$-alkyl, —C(O)—R$_b$, —C$_{(1-4)}$alkyl-morpholinyl, —C$_{(1-4)}$alkyl-piperidinyl, —C$_{(1-4)}$alkyl-piperazinyl, —C$_{(1-4)}$alkyl-N'-methyl piperazinyl, —C$_{(1-4)}$alkyl-R$_b$, —C(O)NH—C$_{(1-4)}$alkyl-R$_b$, or —C(O)NR$_c$R$_d$;
  wherein R$_b$ is heterocyclyl, alkylsulfonyl, —SO$_2$NH$_2$, alkylsulfonamide, —OH, —Oalkyl, —NH$_2$, —NHalkyl, or —N(alkyl)$_2$;
  R$_c$ and R$_d$ are independently selected from: H, phenyl, heteroaryl, or C$_{1-6}$ alkyl, wherein said C$_{1-6}$alkyl may optionally be substituted with one substituent selected from: —N(CH$_3$)$_2$, morpholinyl, piperidinyl, piperazinyl, N-methyl piperazinyl, alkylsulfonyl, —SO$_2$NH$_2$, alkylsulfonamide, hydroxyl, and alkoxy;
  or R$_c$ and R$_d$ together may form a 5 to 7 membered heterocyclic ring selected from the group consisting of: piperidinyl, morpholinyl, and piperazinyl, wherein said piperazinyl is optionally substituted with alkyl, —SO$_2$alkyl, or —C(O)alkyl;

A is a ring selected from the group consisting of: 2,3 dihydrobenzofuran-5-yl, quinolin-6-yl, quinolin-6-yl-N-oxide, 2-amino benzothiazol-6-yl, 4-methoxyphenyl, 3-(4-methoxy-benzyl)-3H-quinazolin-4-on-6-yl, quinazolin-4-on-6-yl, 2-dimethyl-amino benzothiazol-6-yl, and 4-hydroxy phenyl;

$R^5$ and $R^6$ are independently selected from: H, F, or —CH$_3$; or $R^5$ and $R^6$ can together form a cyclopropyl ring; and $R^7$ and $R^8$ are H.

Other preferred embodiments of the invention are compounds of Formula I wherein one or more of the following limitations are present:

$R^1$ is mono or bicyclic heteroaryl, or pyridin-2-on-5-yl, wherein said heteroaryl is optionally substituted with one $R_a$ substituent;
  wherein $R_a$ is —NH$_2$, halogen, alkoxy, alkylether, alkylthio, alkylsulfonyl, phenylsulfonyl, heteroarylsulfonyl, heterocyclylsulfonyl, —SO$_2$NH$_2$, alkylsulfonamide, alkyl, aminoalkyl, alkylamino, phenyl, heteroaryl, cyano, alkenyl, alkynyl, cycloalkyl, heterocyclyl, —CO$_2$-alkyl, —C(O)—R$_b$, —C$_{(1-4)}$alkyl-morpholinyl, —C$_{(1-4)}$alkyl-piperidinyl, —C$_{(1-4)}$alkyl-piperazinyl, —C$_{(1-4)}$alkyl-N'-methyl piperazinyl, —C$_{(1-4)}$alkyl-R$_b$, —C(O)NH—C$_{(1-4)}$alkyl-R$_b$, or —C(O)NR$_c$R$_d$;
  wherein R$_b$ is heterocyclyl, alkylsulfonyl, —SO$_2$NH$_2$, alkylsulfonamide, —OH, —Oalkyl, —NH$_2$, —NHalkyl, or —N(alkyl)$_2$;
  R$_c$ and R$_d$ are independently selected from: H, phenyl, heteroaryl, or C$_{1-6}$ alkyl, wherein said C$_{1-6}$alkyl may optionally be substituted with one substituent selected from: —N(CH$_3$)$_2$, morpholinyl, piperidinyl, piperazinyl, N-methyl piperazinyl, alkylsulfonyl, —SO$_2$NH$_2$, alkylsulfonamide, hydroxyl, and alkoxy;
  or R$_c$ and R$_d$ together may form a 5 to 7 membered heterocyclic ring selected from the group consisting of: piperidinyl, morpholinyl, and piperazinyl, wherein said piperazinyl is optionally substituted with alkyl, —SO$_2$alkyl, or —C(O)alkyl;

A is a ring selected from the group consisting of: 2,3 dihydrobenzofuran-5-yl, quinolin-6-yl, quinolin-6-yl-N-oxide, 2-amino benzothiazol-6-yl, 4-methoxyphenyl, 3-(4-methoxy-benzyl)-3H-quinazolin-4-on-6-yl, quinazolin-4-on-6-yl, 2-dimethyl-amino benzothiazol-6-yl, and 4-hydroxy phenyl;

$R^5$ and $R^6$ are independently selected from: H, F, or —CH$_3$; or $R^5$ and $R^6$ can together form a cyclopropyl ring; and $R^7$ and $R^8$ are H.

Other preferred embodiments of the invention are compounds of Formula I wherein one or more of the following limitations are present:

$R^1$ is thiophen-2-yl, thiazol-2-yl, pyrazolyl, imidazolyl, pyridin-2-on-5-yl, or pyridyl, wherein said thiophen-2-yl, thiazol-2-yl, pyrazolyl, imidazolyl, and pyridyl may be optionally substituted with one $R_a$ substituent;

wherein $R_a$ is —$NH_2$, halogen, alkoxy, alkylether, alkylthio, alkylsulfonyl, phenylsulfonyl, heteroarylsulfonyl, heterocyclylsulfonyl, —$SO_2NH_2$, alkylsulfonamide, alkyl, aminoalkyl, alkylamino, phenyl, heteroaryl, cyano, alkenyl, alkynyl, cycloalkyl, heterocyclyl, —$CO_2$-alkyl, —C(O)—$R_b$, —$C_{(1-4)}$alkyl-morpholinyl, —$C_{(1-4)}$alkyl-piperidinyl, —$C_{(1-4)}$alkyl-piperazinyl, —$C_{(1-4)}$alkyl-N'-methyl piperazinyl, —$C_{(1-4)}$alkyl-$R_b$, —C(O)NH—$C_{(1-4)}$alkyl-$R_b$, or —C(O)$NR_cR_d$;

wherein $R_b$ is heterocyclyl, alkylsulfonyl, —$SO_2NH_2$, alkylsulfonamide, —OH, —Oalkyl, —$NH_2$, —NHalkyl, or —N(alkyl)$_2$;

$R_c$ and $R_d$ are independently selected from: H, phenyl, heteroaryl, or $C_{1-6}$ alkyl, wherein said $C_{1-6}$alkyl may optionally be substituted with one substituent selected from: —N(CH$_3$)$_2$, morpholinyl, piperidinyl, piperazinyl, N-methyl piperazinyl, alkylsulfonyl, —$SO_2NH_2$, alkylsulfonamide, hydroxyl, and alkoxy;

or $R_c$ and $R_d$ together may form a 5 to 7 membered heterocyclic ring selected from the group consisting of: piperidinyl, morpholinyl, and piperazinyl, wherein said piperazinyl is optionally substituted with alkyl, —$SO_2$alkyl, or —C(O)alkyl;

A is a ring selected from the group consisting of: 2,3 dihydrobenzofuran-5-yl, quinolin-6-yl, quinolin-6-yl-N-oxide, 2-amino benzothiazol-6-yl, 4-methoxyphenyl, 3-(4-methoxy-benzyl)-3H-quinazolin-4-on-6-yl, quinazolin-4-on-6-yl, 2-dimethyl-amino benzothiazol-6-yl, and 4-hydroxy phenyl;

$R^5$ and $R^6$ are independently selected from: H, F, or —CH$_3$; or $R^5$ and $R^6$ can together form a cyclopropyl ring; and $R^7$ and $R^8$ are H.

Other preferred embodiments of the invention are compounds of Formula I wherein one or more of the following limitations are present:

$R^1$ is thiophen-2-yl, thiazol-2-yl, pyrazolyl, imidazolyl, pyridin-2-on-5-yl, or pyridyl, wherein said thiophen-2-yl, thiazol-2-yl, pyrazolyl, imidazolyl, and pyridyl may be optionally substituted with one $R_a$ substituent;

wherein $R_a$ is —$NH_2$, halogen, alkoxy, alkylether, alkylthio, alkylsulfonyl, phenylsulfonyl, heteroarylsulfonyl, heterocyclylsulfonyl, —$SO_2NH_2$, alkylsulfonamide, alkyl, aminoalkyl, alkylamino, phenyl, heteroaryl, cyano, alkenyl, alkynyl, cycloalkyl, heterocyclyl, —$CO_2$-alkyl, —C(O)—$R_b$, —$C_{(1-4)}$alkyl-morpholinyl, —$C_{(1-4)}$alkyl-piperidinyl, —$C_{(1-4)}$alkyl-piperazinyl, —$C_{(1-4)}$alkyl-N'-methyl piperazinyl, —$C_{(1-4)}$alkyl-$R_b$, —C(O)NH—$C_{(1-4)}$alkyl-$R_b$, or —C(O)$NR_cR_d$;

wherein $R_b$ is heterocyclyl, alkylsulfonyl, —$SO_2NH_2$, alkylsulfonamide, —OH, —Oalkyl, —$NH_2$, —NHalkyl, or —N(alkyl)$_2$;

$R_c$ and $R_d$ are independently selected from: H, phenyl, heteroaryl, or $C_{1-6}$ alkyl, wherein said $C_{1-6}$alkyl may optionally be substituted with one substituent selected from: —N(CH$_3$)$_2$, morpholinyl, piperidinyl, piperazinyl, N-methyl piperazinyl, alkylsulfonyl, —$SO_2NH_2$, alkylsulfonamide, hydroxyl, and alkoxy;

or $R_c$ and $R_d$ together may form a 5 to 7 membered heterocyclic ring selected from the group consisting of: piperidinyl, morpholinyl, and piperazinyl, wherein said piperazinyl is optionally substituted with alkyl, —$SO_2$alkyl, or —C(O)alkyl;

A is a ring selected from the group consisting of: 2,3 dihydrobenzofuran-5-yl, quinolin-6-yl, quinolin-6-yl-N-oxide, 2-amino benzothiazol-6-yl, 4-methoxyphenyl, 3-(4-methoxy-benzyl)-3H-quinazolin-4-on-6-yl, quinazolin-4-on-6-yl, 2-dimethylamino benzothiazol-6-yl, and 4-hydroxy phenyl;

$R^5$ and $R^6$ are independently selected from: H or F; and $R^7$ and $R^8$ are H.

Other embodiments of the invention are compounds of Formula I wherein one or more of the following limitations are present:

$R^1$ is mono or bicyclic heteroaryl (preferably pyridyl, thiophenyl, thiazolyl, pyrazolyl, furanyl, imidazolyl, oxazolyl, pyrrolyl, indolyl, isothiazolyl, triazolyl, benzothiophenyl, benzothiazolyl, benzoimidazolyl, benzoxazolyl, quinolyl, benzofuranyl, quinazolinyl, or quinoxalinyl), wherein said heteroaryl is optionally substituted with -one, two or three $R_a$ substituents;

wherein $R_a$ is halogen (preferably F, Cl or Br), alkoxy (preferably $C_{1-6}$ alkoxy), alkylether (preferably —$C_{(1-6)}$alkyl-O—$C_{(1-6)}$alkyl), alkylthio (preferably $C_{1-6}$ alkylthio), alkylsulfonyl (preferably $C_{1-6}$ alkylsulfonyl), phenylsulfonyl, heteroarylsulfonyl (wherein the heteroaryl portion of said heteroarylsulfonyl is preferably pyridyl, thiophenyl, thiazolyl, pyrazolyl, furanyl, imidazolyl, oxazolyl, pyrrolyl, indolyl, isothiazolyl, triazolyl, benzothiophenyl, benzothiazolyl, benzoimidazolyl, benzoxazolyl, quinolyl, benzofuranyl, quinazolinyl, or quinoxalinyl), heterocyclylsulfonyl (wherein the heterocyclyl portion of said heterocyclylsulfonyl is preferably pyrrolidinyl, tetrahydrofuranyl, tetrahydrothiophenyl, imidazolidinyl, thiazolidinyl, oxazolidinyl, tetrahydropyranyl, tetrahydrothiopyranyl, piperidinyl, thiomorpholinyl, thiomorpholinyl 1,1-dioxide, morpholinyl, or piperazinyl), —$SO_2NH_2$, alkylsulfonamide (preferably $C_{1-6}$ alkylsulfonamide), alkyl (preferably $C_{1-6}$ alkyl), aminoalkyl (preferably methylamine), alkylamino (preferably $C_{1-6}$ alkylamino), phenyl, heteroaryl (preferably pyridyl, thiophenyl, thiazolyl, pyrazolyl, furanyl, imidazolyl, oxazolyl, pyrrolyl, indolyl, isothiazolyl, triazolyl, benzothiophenyl, benzothiazolyl, benzoimidazolyl, benzoxazolyl, quinolyl, benzofuranyl, quinazolinyl, or quinoxalinyl), cyano, alkenyl (preferably $C_{1-6}$ alkenyl), alkynyl (preferably $C_{1-6}$ alkynyl), cycloalkyl (preferably cyclopropyl, cyclobutyl, cyclopentyl, cyclohexyl or cycloheptyl), heterocyclyl (preferably pyrrolidinyl, tetrahydrofuranyl, tetrahydrothiophenyl, imidazolidinyl, thiazolidinyl, oxazolidinyl, tetrahydropyranyl, tetrahydrothiopyranyl, piperidinyl, thiomorpholinyl, thiomorpholinyl 1,1-dioxide, morpholinyl, or piperazinyl), —$CO_2$-alkyl (preferably —$CO_2$—$CH_2CH_3$), —C(O)—$R_b$, —$C_{(1-4)}$alkyl-morpholinyl, —$C_{(1-4)}$alkyl-piperidinyl, —$C_{(1-4)}$alkyl-piperazinyl, —$C_{(1-4)}$alkyl-N'-methyl piperazinyl, —$C_{(1-4)}$alkyl-$R_b$, —C(O)NH—$C_{(1-4)}$alkyl-$R_b$, or —C(O)$NR_cR_d$;

wherein $R_b$ is heterocyclyl (preferably pyrrolidinyl, tetrahydrofuranyl, tetrahydrothiophenyl, imidazolidinyl, thiazolidinyl, oxazolidinyl, tetrahydropyranyl, tetrahydrothiopyranyl, piperidinyl, thiomorpholinyl, thiomorpholinyl 1,1-dioxide, morpholinyl, or piperazinyl), alkylsulfonyl (preferably $C_{1-6}$ alkylsulfonyl), —$SO_2NH_2$, alkylsulfonamide (preferably $C_{1-6}$ alkylsulfonamide), —OH, —Oalkyl (preferably —$OC_{1-6}$ alkyl), —$NH_2$, —NHalkyl (preferably —NH$C_{1-6}$ alkyl), or —N(alkyl)$_2$ (preferably —N($C_{1-6}$ alkyl)$_2$);

$R_c$ and $R_d$ are independently selected from: H, phenyl, heteroaryl, or $C_{1-6}$ alkyl, wherein said $C_{1-6}$alkyl may optionally be substituted with one substituent selected from: —N(CH$_3$)$_2$, morpholinyl, piperidinyl, piperazinyl, N-methyl piperazinyl, alkylsulfonyl (preferably $C_{1-6}$ alkylsulfonyl), —SO$_2$NH$_2$, alkylsulfonamide (preferably $C_{1-6}$ alkylsulfonamide), hydroxyl, and alkoxy;

or $R_c$ and $R_d$ together may form a 5 to 7 membered heterocyclic ring, optionally containing a second heteromoiety selected from O, NH, N(alkyl), SO, SO$_2$, or S, (said $R_c$-$R_d$ heterocyclic ring preferably selected from the group consisting of:

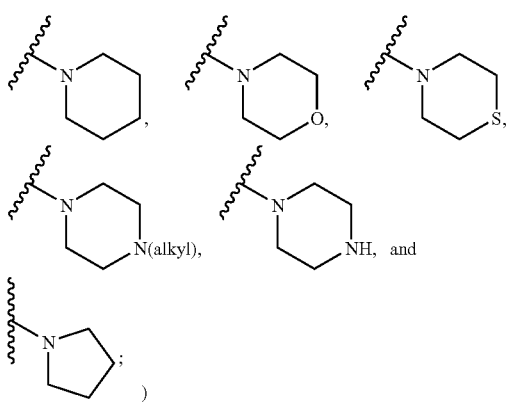

)

wherein said $R_c$-$R_d$ heterocyclic ring is optionally substituted with alkyl (preferably —C$_{(1-6)}$alkyl), —SO$_2$alkyl (preferably —SO$_2$C$_{(1-6)}$alkyl), or —C(O)alkyl (preferably —C(O)C$_{(1-6)}$alkyl);

A is a ring selected from the group consisting of: phenyl, mono or bicyclic heteroaryl (preferably pyridyl, benzooxazolyl, benzothiazolyl, quinolinyl, quinazolinyl, quinoxalinyl, benzimidazolyl, benzothiophenyl, benzofuranyl, or [1,2,4]triazolo[1,5-o]pyridinyl), and benzo-fused heterocyclyl (preferably benzo[1,3]dioxolyl, or 2,3-dihydro-benzofuranyl); wherein said phenyl, heteroaryl, or benzo-fused heterocyclyl are optionally substituted with one, two or three substituents independently selected from the group consisting of: —OH, alkyl, phenyl, heteroaryl, alkoxy, —CN, halogen, nitro, —NH$_2$, —NHC(O)NHC$_{1-6}$alkyl, and —NHC(O)C$_{1-6}$alkyl;

$R^5$ and $R^6$ are independently selected from: H, F, $C_{1-6}$ alkyl, —OH, —OC$_{1-6}$alkyl, —NHC$_{1-6}$alkyl, or —N(C$_{1-6}$alkyl)$_2$;

or $R^5$ and $R^6$ can together form a $C_{3-5}$ cycloalkyl ring, an aziridinyl ring, or, an epoxidyl ring; and $R^7$ and $R^8$ are H, halogen or $C_{1-6}$ alkyl.

Another embodiment of the invention includes:

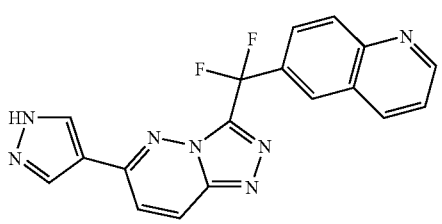

Pharmaceutically Acceptably Salts

The compounds of the present invention may also be present in the form of pharmaceutically acceptable salts.

For use in medicines, the salts of the compounds of this invention refer to non-toxic "pharmaceutically acceptable salts." FDA approved pharmaceutically acceptable salt forms (Ref International J. Pharm. 1986, 33, 201-217; J. Pharm. Sci., 1977, January, 66(1), p 1) include pharmaceutically acceptable acidic/anionic or basic/cationic salts.

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), benzathine, t-butylamine, calcium, calcium gluconate, calcium hydroxide, chloroprocaine, choline, choline bicarbonate, choline chloride, cyclohexylamine, diethylamine, ethylenediamine, lithium, LiOMe, L-lysine, magnesium, meglumine, NH$_3$, NH$_4$OH, N-methyl-D-glucamine, piperidine, potassium, potassium-t-butoxide, potassium hydroxide (aqueous), procaine, quinine, sodium, sodium carbonate, sodium-2-ethylhexanoate (SEH), sodium hydroxide, triethylamine (TEA) or zinc.

Prodrugs

The present invention includes within its scope prodrugs of the compounds of the invention. In general, such prodrugs will be functional derivatives of the compounds that are readily convertible in vivo into an active compound. Thus, in the methods of treatment of the present invention, the term "administering" shall encompass the means for treating, ameliorating or preventing a syndrome, disorder or disease described herein with a compound specifically disclosed or a compound, or prodrug thereof, which would obviously be included within the scope of the invention albeit not specifically disclosed for certain of the instant compounds. Conventional procedures for the selection and preparation of suitable prodrug derivatives are described in, for example, "Design of Prodrugs", ed. H. Bundgaard, Elsevier, 1985.

Stereochemically Isomeric Forms

One skilled in the art will recognize that the compounds of Formula I may have one or more asymmetric carbon atoms in their structure. It is intended that the present invention include within its scope single enantiomer forms of the compounds, racemic mixtures, and mixtures of enantiomers in which an enantiomeric excess is present.

The term "single enantiomer" as used herein defines all the possible homochiral forms which the compounds of Formula I and their N-oxides, addition salts, quaternary amines or physiologically functional derivatives may possess.

Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereoselective reactions.

The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (enantiomers).

The term "stereoisomer" refers to isomers of identical constitution that differ in the arrangement of their atoms in space. Enantiomers and diastereomers are stereoisomers wherein an asymmetrically substituted carbon atom acts as a chiral center.

The term "chiral" refers to the structural characteristic of a molecule that makes it impossible to superimpose it on its mirror image.

The term "enantiomer" refers to one of a pair of molecular species that are mirror images of each other and are not superimposable.

The term "diastereomer" refers to stereoisomers that are not mirror images.

The symbols "R" and "S" represent the configuration of substituents around a chiral carbon atom(s).

The term "racemate" or "racemic mixture" refers to a composition composed of equimolar quantities of two enantiomeric species, wherein the composition is devoid of optical activity.

The term "homochiral" refers to a state of enantiomeric purity

The term "optical activity" refers to the degree to which a homochiral molecule or nonracemic mixture of chiral molecules rotates a plane of polarized light.

The term "geometric isomer" refers to isomers that differ in the orientation of substituent atoms in relationship to a carbon-carbon double bond, to a cycloalkyl ring or to a bridged bicyclic system. Substituent atoms (other than H) on each side of a carbon-carbon double bond may be in an E or Z configuration. In the "E" (opposite sided) configuration, the substituents are on opposite sides in relationship to the carbon-carbon double bond; in the "Z" (same sided) configuration, the substituents are oriented on the same side in relationship to the carbon-carbon double bond. Substituent atoms (other than H) attached to a carbocyclic ring may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

It is to be understood that the various substituent stereoisomers, geometric isomers and mixtures thereof used to prepare compounds of the present invention are either commercially available, can be prepared synthetically from commercially available starting materials or can be prepared as isomeric mixtures and then obtained as resolved isomers using techniques well-known to those of ordinary skill in the art.

The isomeric descriptors "R," "S," "E," "Z," "cis," and "trans" are used as described herein for indicating atom configuration(s) relative to a core molecule and are intended to be used as defined in the literature (IUPAC Recommendations for Fundamental Stereochemistry (Section E), *Pure Appl Chem.*, 1976, 45:13-30).

The compounds of the present invention may be prepared as individual isomers by either isomer-specific synthesis or resolved from an isomeric mixture. Conventional resolution techniques include forming the free base of each isomer of an isomeric pair using an optically active salt (followed by fractional crystallization and regeneration of the free base), forming an ester or amide of each of the isomers of an isomeric pair (followed by chromatographic separation and removal of the chiral auxiliary) or resolving an isomeric mixture of either a starting material or a final product using preparative TLC (thin layer chromatography) or a chiral HPLC column.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope solvates of the compounds of the present invention. Thus, in the methods of treatment of the present invention, the term "administering" shall encompass the means for treating, ameliorating or preventing a syndrome, disorder or disease described herein with the compounds of the present invention or a solvate thereof, which would obviously be included within the scope of the invention albeit not specifically disclosed.

Tautomeric Forms

Some of the compounds of Formula I may also exist in their tautomeric forms. Such forms although not explicitly indicated in the present application are intended to be included within the scope of the present invention.

Preparation of Compounds of the Present Invention

During any of the processes for preparation of the compounds of the present invention, it may be necessary and/or desirable to protect sensitive or reactive groups on any of the molecules concerned. This may be achieved by means of conventional protecting groups, such as those described in *Protecting Groups*, P. Kocienski, Thieme Medical Publishers, 2000; and T. W. Greene & P. G. M. Wuts, *Protective Groups in Organic Synthesis*, 3$^{rd}$ ed. Wiley Interscience, 1999. The protecting groups may be removed at a convenient subsequent stage using methods known in the art.

General Reaction Scheme

Compounds of Formula I can be prepared by methods known to those who are skilled in the art. The following reaction schemes are only meant to represent examples of the invention and are in no way meant to be a limit of the invention.

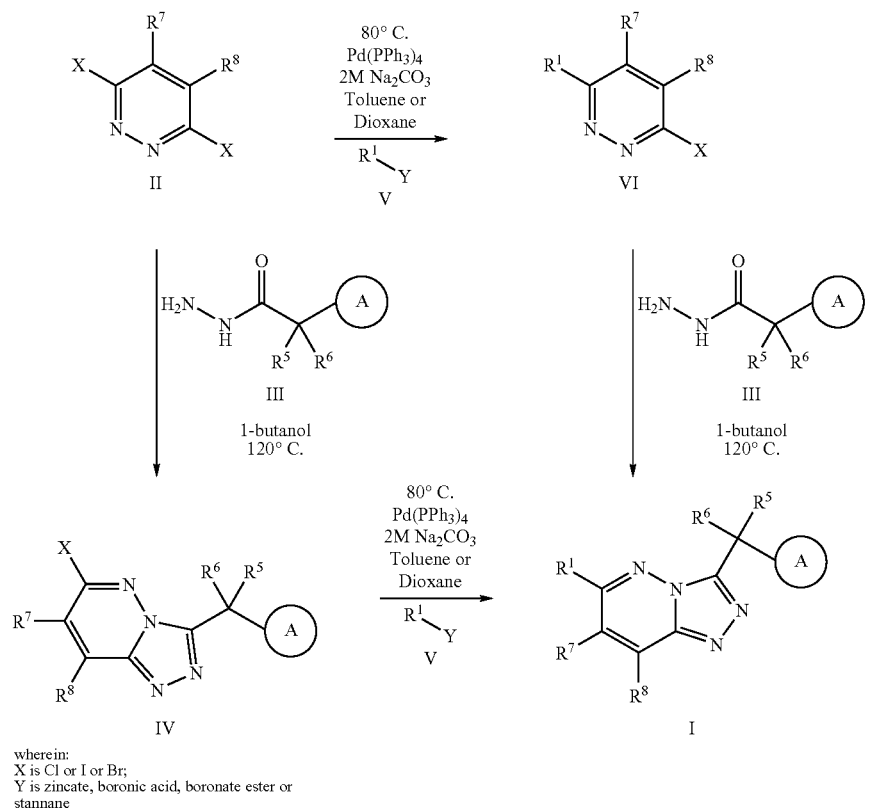

wherein:
X is Cl or I or Br;
Y is zincate, boronic acid, boronate ester or stannane Scheme 1 illustrates the dual synthetic routes leading to compounds of Formula I, wherein A, $R^1$, $R^5$, $R^6$, $R^7$, and $R^8$ are as defined in Formula I. Starting with the dihalopyridazine II and following the path to the right, a transition-metal catalyzed cross-coupling reaction can take place using an appropriately substituted boronic acid, boronate ester, zincate or stanne V under Suzuki (Miyaura, N., Suzuki, A., Chem. Rev. 95:2457 (1995)), Negishi (Negishi, E., et. al., J. Org. Chem. 42:1821 (1977)), or Stille conditions (Stille, J. K., Agnew. Chem., Int. Ed. Engl., 25: 508 (1986) and references therein). The resulting pyridazine VI may be converted to triazolopyridazine I by the reaction of 3-halopyridazine with a variety of acylhydrazines III in refluxing 1-butanol (Albright, J. D., et. al., J. Med. Chem., 1981, 24, 592-600). Alternately, following the path down, reaction of the 3,6-dihalopyridazine II with a variety of acylhydrazines III, followed by the transition—metal cross-coupling reaction with IV generates triazolopyridazine I. This route lends itself to generate a library of compounds from the triazolopyridazine core scaffold via cross coupling reactions with the halogenated scaffold.

The aforementioned cross-coupling reactions of aryl halides with arylboronic acid, arylzincate or arylstanne are generally performed in an inert environment mediated by a catalyst such as palladium tetrakis-triphenylphosphine. These reactions can occur at temperatures ranging from 60° C. to 150° C. in polar aprotic solvents or biphasic solutions. In most cases where the arylboronic acid, arylzincate or arylstanne is not commercially available it can be synthesized from the corresponding aryl halide or direct metallation/transmetallation procedures. Alternatively, the Peppsi-iPr catalyst may be used in place of Pd(PPh$_3$)$_4$, see M. G. Organ et al, Chemistry—A European Journal, Volume 12, Issue 18, Jun. 14, 2006, pp: 4743-4748, and references therein

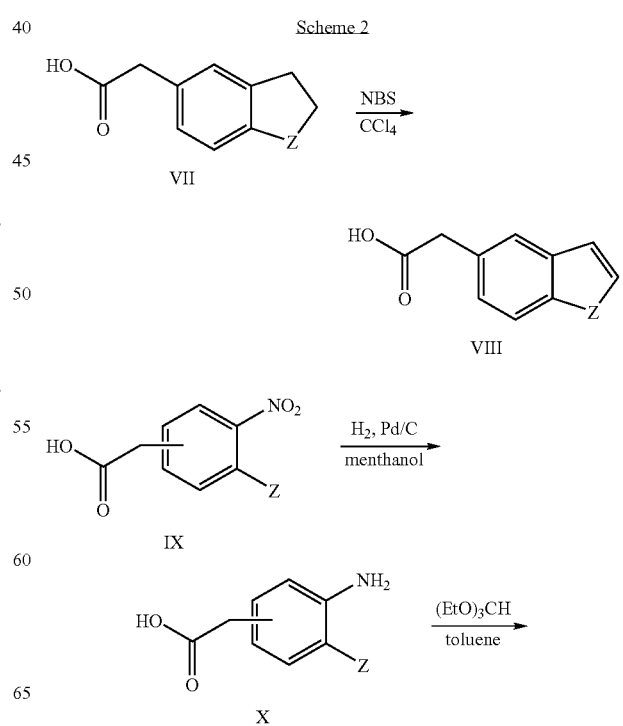

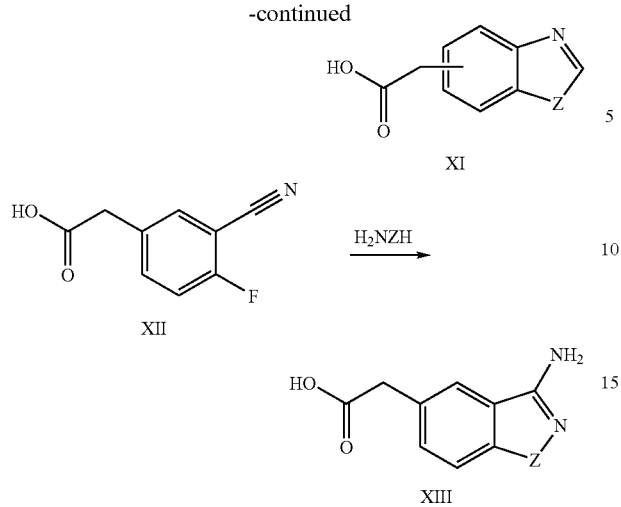

wherein Z is NH, O or S.

Aryl and heteroaryl acetic acids can be accessed by methods known in the art (Journal of Medicinal Chemistry, 1986, 29 (11), 2326-2329; Bioorganic and Medicinal Chemistry Letters, 2004, 14(14), 3799-3802; EP 1229034 A1 20020807; Tetrahedron Letters, 2003, 44 (35), 6745-6747; Synthetic Communications, 1997, 27 (22), 3839-3846). Several examples of aryl acetic acid synthesis are illustrated in Scheme 2. Benzofused heterocyclic compound VII, (Journal of Medicinal Chemistry, 1996, 29 (11), 2362-2369; Journal of Medicinal Chemistry, 1997, 40(7), 1049-1062), is treated with N-bromosuccinimide in carbon tetrachloride to give compound VIII. Nitrophenylacetic acid IX, (Bioorganic and Medicinal Chemistry Letters, 1998, 8 (1), 17-22; Organic Letters, 2002, 4 (16), 2675-2678; WO 00/06566, Helvitica Chemica Acta, 1976, 59 (3), 855-866) is reduced with conditions such as hydrogenation in the presence of palladium on activated carbon in a solvent such as methanol to give compound X, which is then treated with triethyl orthoformate in toluene to give XI. Compound XII can be treated with an appropriate amine to give Compound XIII.

The following compounds can be synthesized by methods known in the art:

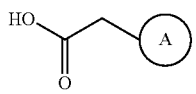

where A is selected from:

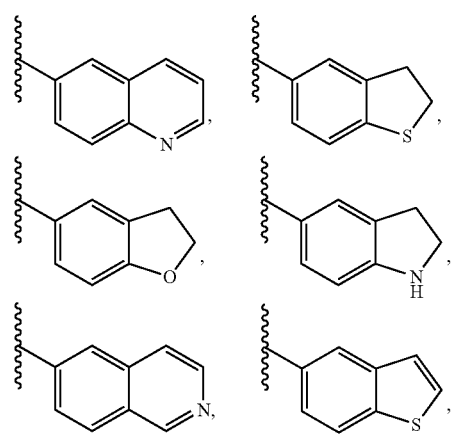

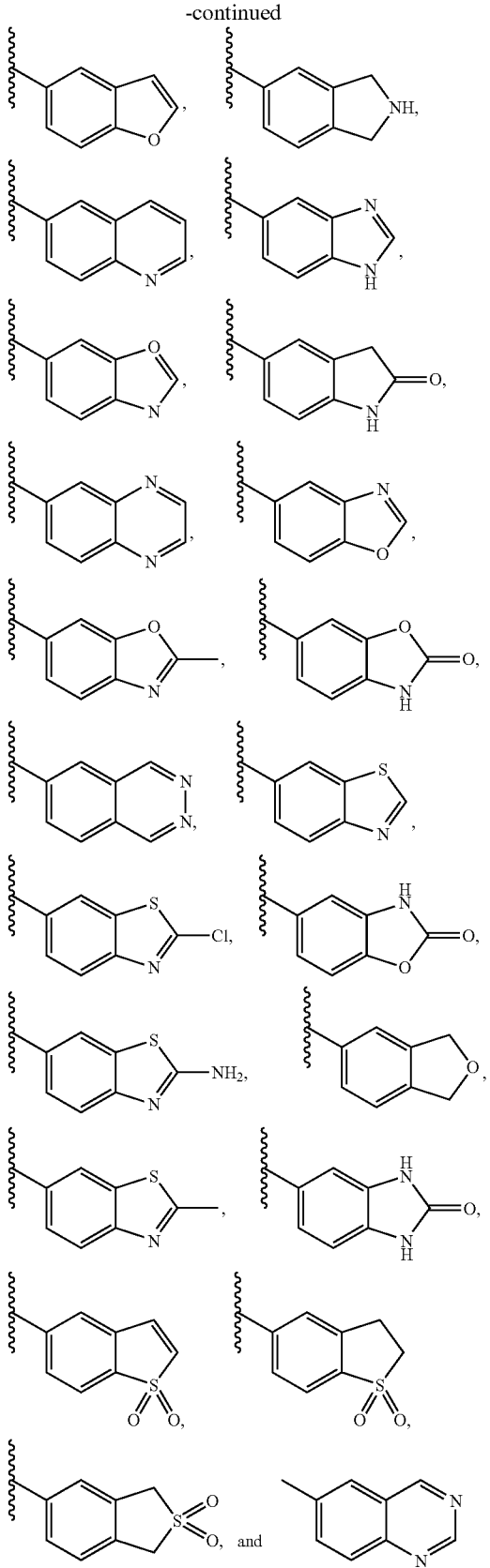

See, e.g., Journal of Medicinal Chemistry, 1997, 40 (7), 1049-1058, and references therein; and WO 2002085888.

Scheme 3

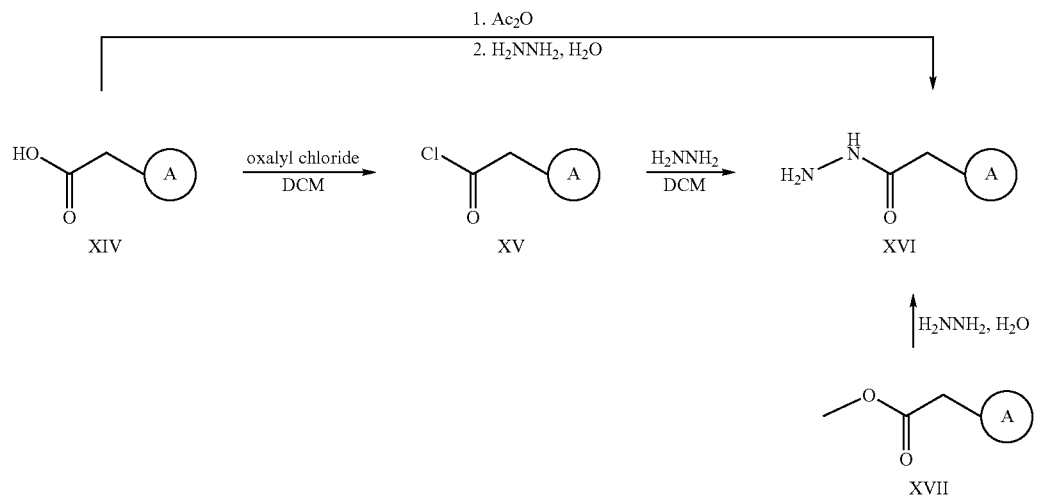

Synthesis of aryl and heteroaryl acetyl chlorides and aryl and heteroaryl acetic acid hydrazides can also be accessed by methods known in the art (see, Bulletin de la Societe Chimique de France, 1964, 2, 245-247; and Helvitica Chemica Acta, 1928, 11, 609-656). Compound XIV, where A is as defined in Formula I is treated with oxalyl chloride in DCM to give Compound XV, which is treated with anhydrous hydrazine in DCM to give hydrazide XVI. Alternatively, Compound XIV can be treated with acetic anhydride, followed by hydrazine in water to give Compound XVI. Acetic acid methyl ester XVII can be treated with aqueous hydrazine in ethanol to give Compound XVI.

Scheme 4a

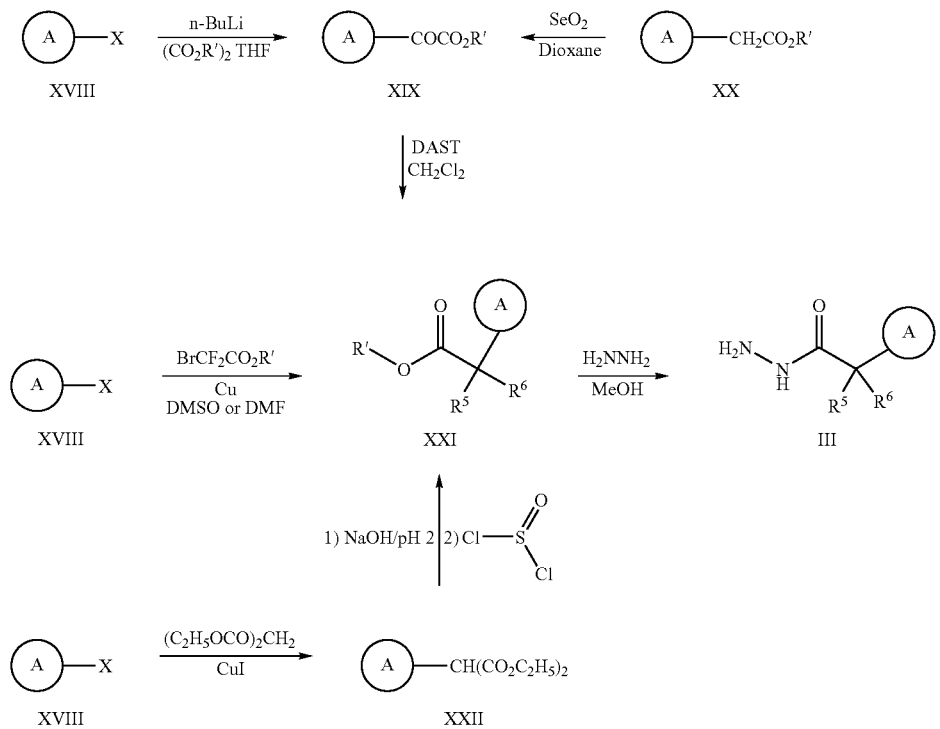

wherein
X is Br or I
R' is CH₃ or C₂H₅.

Scheme 4a illustrates the routes taken to obtain compounds of Formula III wherein $R^5$ and $R^6$ are both F or H, and A is as defined in Formula I. The first route to generate the acylhydrazide involves the metal-halogen exchange of an appropriate arylhalide XVIII with an organometallic like n-butyllythium followed by acetylation with dialkyl oxalate. The acetyl alkylester XIX formed is then fluorinated with DAST ((dimethylamino)sulfur trifluoride) in a solvent like methylene chloride to form the difluoroalkylester XXI, followed by treatment with hydrazine to form the difluoroacylhydrazide III. The second route involves a copper mediated cross coupling of the arylhalide XVIII with a halogenated difluoroester generating the difluoroalkylester XXI intermediate followed by treatment with hydrazine to form the difluoroacylhydrazide III. The third route involves the oxidation of an arylacetic ester XX to an aryl ketoester XIX followed by fluorination with DAST generating the difluoroalkylester XXI intermediate and then treatment with hydrazine to form the difluoroacylhydrazide III. The fourth route involves the copper mediated cross coupling of the aryl halide XVIII with a malonate diester to form the alkyldiester XXII. Saponification and then treatment with thionyl chloride in alcohol or alternately reflux with alcohol in the presence of acid yields the alkylester XXI. Treatment with hydrazine results in acylhydrazide III, wherein both $R^5$ and $R^6$ are H.

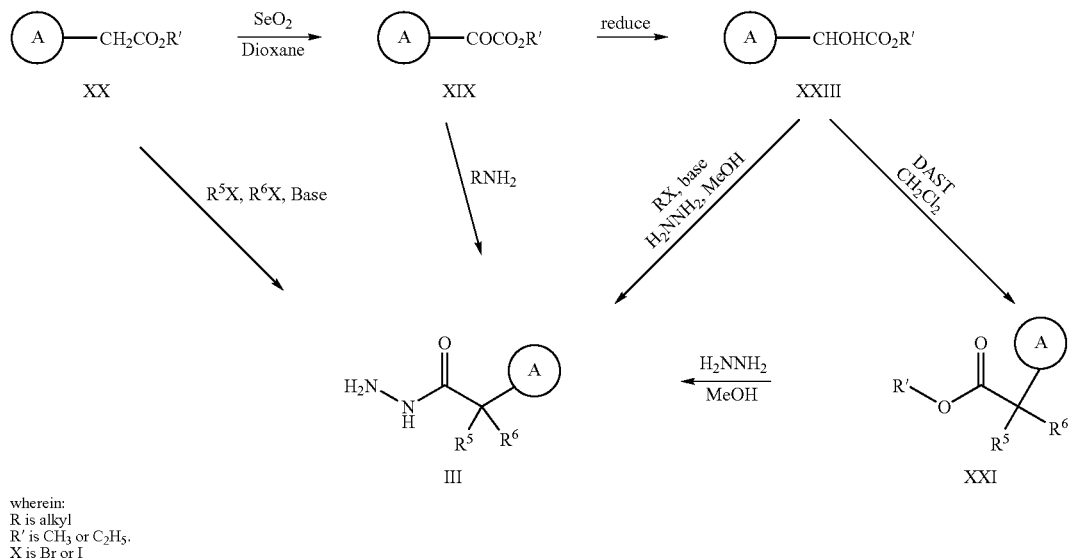

Scheme 4b wherein:
R is alkyl
R' is $CH_3$ or $C_2H_5$.
X is Br or I

Scheme 4b illustrates a route taken to obtain compounds of Formula III wherein $R^5$ and $R^6$ are H, F, alkyl, OH, Oalkyl, NHalkyl, or N(alkyl)$_2$, and A is as defined in Formula I. This route involves the oxidation of an aryl ester XX to an acetyl alkylester XIX followed by reduction to the alcohol XXIII followed by fluorination with DAST generating the monofluoroalkylester XXI intermediate and then treatment with hydrazine to form III. Alternatively compound XXIII can directly convert into III by treatment with hydrazine in a solvent such as methanol or reacted XXIII with alkyl halide in the presence of strong base such as sodium hydride followed by treatment with hydrazine in a solvent such as methanol to give III. Compound XX can be convert to III by treatment with alkyl halide in the present of base such as sodium hydride followed by treatment with hydrazine in a solvent such as methanol. Conversion of compound XIX to III can be achieved by reduction amination followed by treatment with hydrazine in a solvent such as methanol.

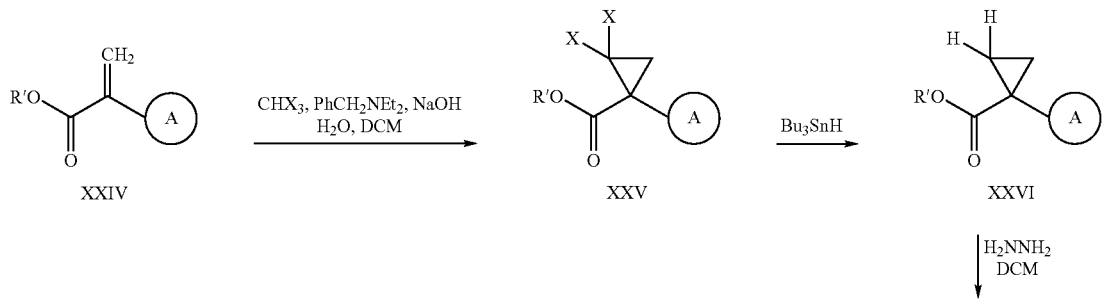

Scheme 4c

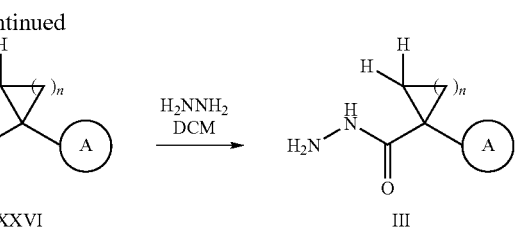

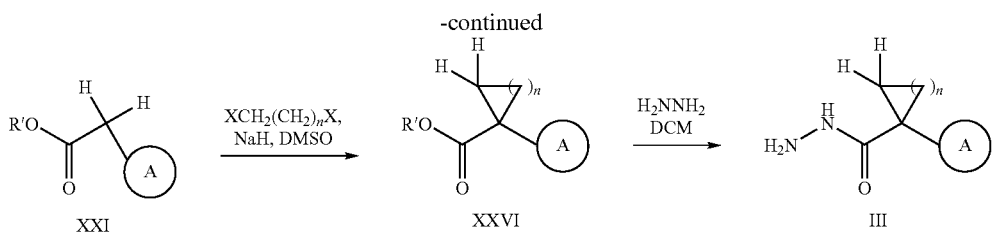

Where:
R' is methyl or ethyl
n is 1-5

The synthesis of compounds of Formula III where $R^5$ and $R^6$ join together to form a ring, and A is as defined in Formula I, can be accomplished by methods known in the arts (Chemische Berichte, 119(12), 3694-703; 1986, Australian Journal of Chemistry, 39(2) 271-80; 1986, Bioorganic and Medicinal Chemistry Letters 13(14), 2291-2295; 2003). Scheme 4c illustrates two alternate routes to obtain the acyl hydrazide III. Starting with the commercially available acrylic ester XXIV followed by treatment with the trihalo methane resulting in the formation of a dihalo cycyl XXV, which is then treated with organo tin, followed by treatment with hydrazine to form III. The second route involves the direct addition of a dihaloalkyl to the commercially available starting material XXI followed by hydrazine formation resulting in the acyl hydrazine III.

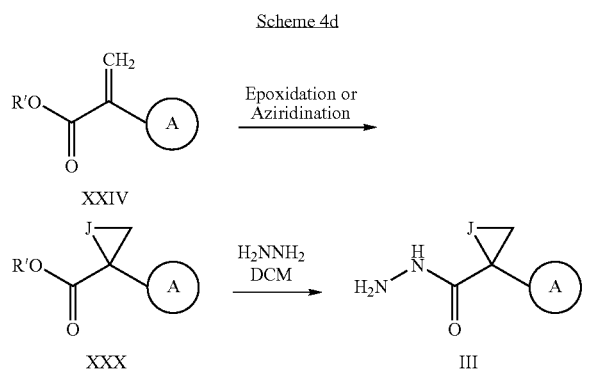

Where:
R' is methyl or ethyl
J is N or O

The synthesis of compounds of Formula III where $R^5$ and $R^6$ join together to form an aziridine or epoxide, and A is as defined in Formula I, can also be accessed by methods known in the art. Scheme 4d illustrates the route by which the heterocyclic acyl hydrazide III is formed starting with the commercially available acrylic ester XXIV followed by treatment with hydrazine.

Schemes 5a-5e illustrate routes to functionalize heteroaryl groups on compounds of Formula I such as thiophene, pyrazole, and furan. The composition of $R_1$ is not limited to the described text contained below but also including commercially available substituted mono or bicyclic heteroaryl starting materials. These materials can also be obtained by methods described in prior art, see (Miyaura, N., Suzuki, A., *Chem. Rev.* 95:2457 (1995)), (Negishi, E., et. al., *J. Org. Chem.* 42:1821 (1977)), (Stille, J. K., Agnew. Chem., Int. Ed. Engl., 25: 508 (1986).

Scheme 5a

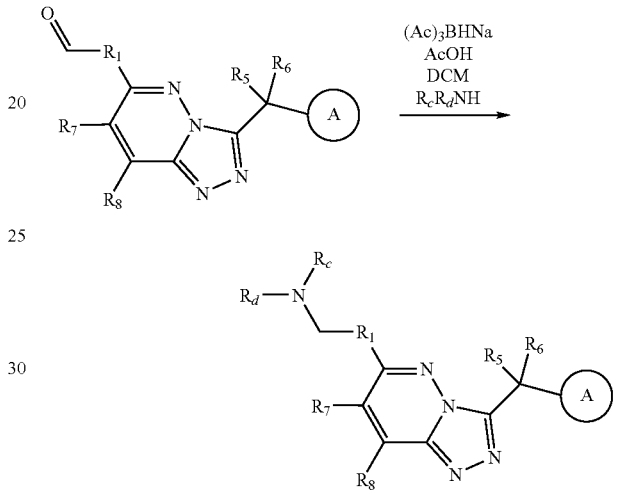

Scheme 5a illustrates the use of reductive amination to introduce amines to the triazolopyridazine series. This chemistry begins with compounds of Formula I wherein $R^1$ is a 2,5 substituted-thiophene or a 2,5 substituted-furan, and $R^5$, $R^6$, $R^7$, $R^8$, and A are as defined in Formula I. Treatment with sodium triacetoxyborohydride and a secondary amine in acidic methanol gives the corresponding amine substituted furan or thiophene.

Scheme 5b

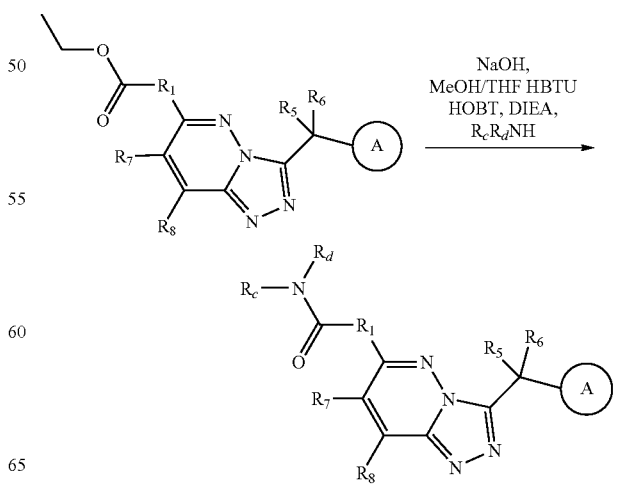

Scheme 5b illustrates the use of saponification followed by coupling with secondary amines to introduce amides to the triazolopyridazine series. This two step reaction begins with compounds of Formula I wherein $R^1$ is mono or bicyclic heteroaryl, and $R^5$, $R^6$, $R^7$, $R^8$, and A are as defined in Formula I. Treatment with sodium hydroxide (NaOH) and 2-(1H-benzotriazole-1-yl)-1,1,3,3-tetramethyluronium hexafluorophosphate (HBTU) in methanol and tetrahydrofuran followed by 1-hydroxybenzotriazole (HOBT), Hunig's base (DIEA) and the desired secondary amine resulting in compounds of Formula I wherein $R^1$ is an amide substituted thiophene. Compounds of Formula I in which $R_a$ is —C(O)NH—$C_{(1-4)}$alkyl-$R_b$ are made in an analogous manner.

Scheme 5c

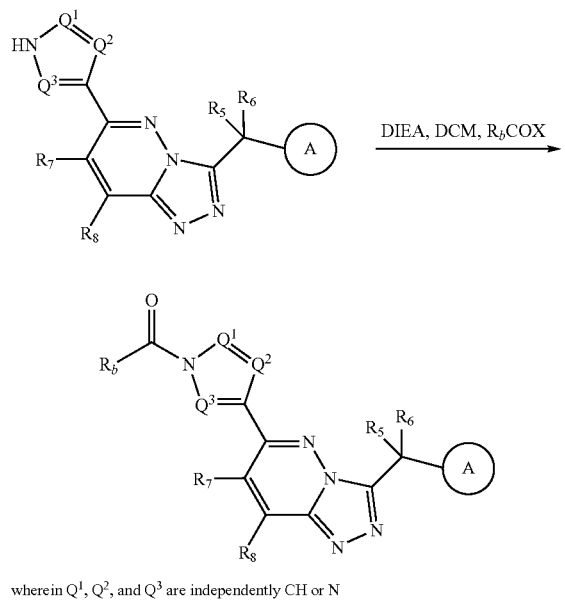

wherein $Q^1$, $Q^2$, and $Q^3$ are independently CH or N

Scheme 5c illustrates the use of acetylation to introduce an acyl group to $R^1$ where $R^1$ is a nitrogen containing heteroaryl (for example pyrazole), and $R^5$, $R^6$, $R^7$, $R^8$, and A are as defined in Formula I. This chemistry utilizes an acyl group appropriately substituted with a leaving group, preferably a halogen, in a solvent like DCM with a scavenger base like DIEA resulting in the acetylation of $R^1$.

Scheme 5d

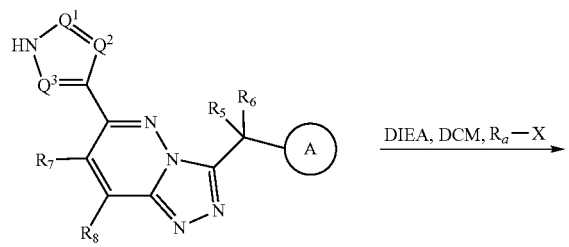

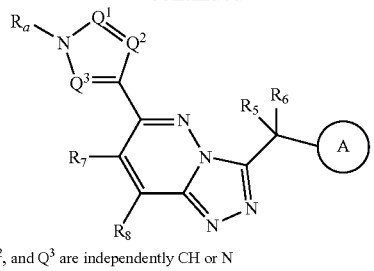

wherein $Q^1$, $Q^2$, and $Q^3$ are independently CH or N

Scheme 5d illustrates the use of sulfoxylation to introduce an sulfoxyl group to $R^1$ where $R^1$ is a nitrogen containing heteroaryl (for example pyrazole) and $R_a$ is a sulfonyl or sulfonamide, and $R^5$, $R^6$, $R^7$, $R^8$, and A are as defined in Formula I. This chemistry utilizes a sulfoxyl group appropriately substituted with a leaving group, preferably a halogen, in a solvent like DCM with a scavenger base like DIEA resulting in the sulfoxylation of $R^1$.

Scheme 5e

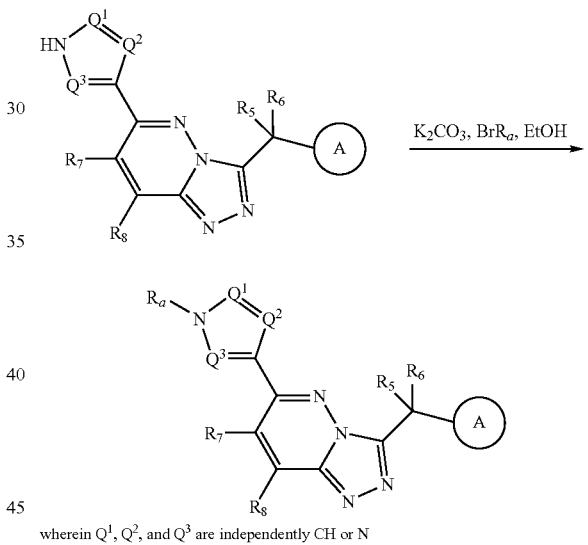

wherein $Q^1$, $Q^2$, and $Q^3$ are independently CH or N

Scheme 5e illustrates the substitution of $R^1$ with $R_a$ where $R^1$ is a nitrogen containing heteroaryl (for example pyrazole), $R_a$ is alkyl, aminoalkyl, or $C_{(1-4)}$alkyl-$R_b$, and $R^5$, $R^6$, $R^7$, $R^8$ and A are as defined in Formula I. The chemistry utilizes an alkyl group appropriately substituted with a leaving group, preferably a halogen, in a solvent like ethanol and a base like potassium carbonate resulting in the alkylation of $R^1$.

Representative Compounds

Representative compounds of the present invention synthesized by the aforementioned methods are presented below. Examples of the synthesis of specific compounds are presented thereafter. Preferred compounds are numbers 17, 20, 22, 38, 39, 47, 51, 54, 55, 57, 59, 60, 61, 65, 66, 72, 73, 74, 77, 86, 87, 97, 98, 99, 100, 100b, 101, 102, 103 and 104; more preferred compounds are numbers 39, 47, 55, 60, 61, 65, 72, 73, 74, 77, 97, and 98. More preferred compounds are numbers 60, 61, 97, and 98.

| Example # | Structure |
|---|---|
| 1 | 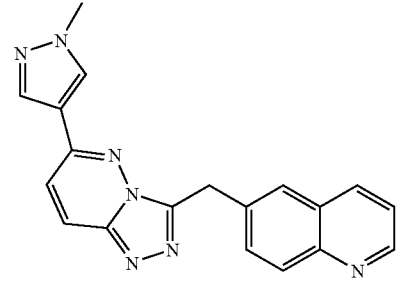 |
| 2 | 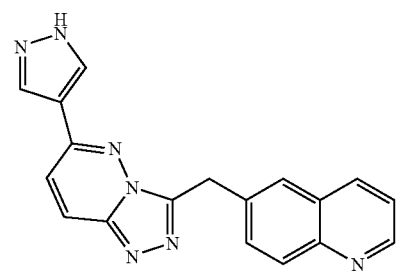 |
| 3 | 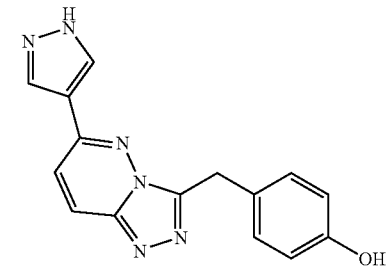 |
| 4 | 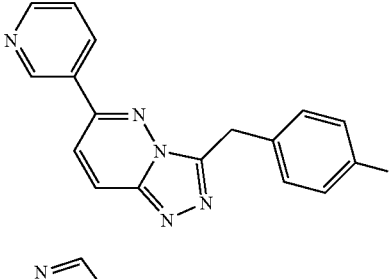 |
| 5 | 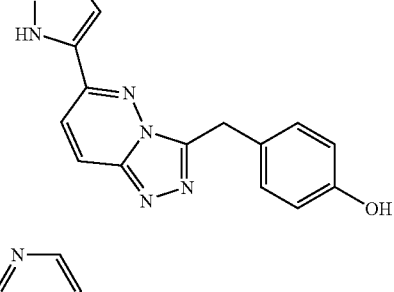 |
| 6 | 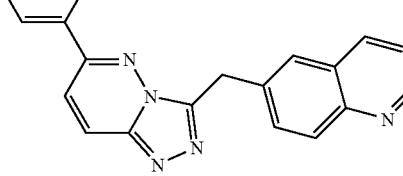 |

| Example # | Structure |
|---|---|
| 7 | 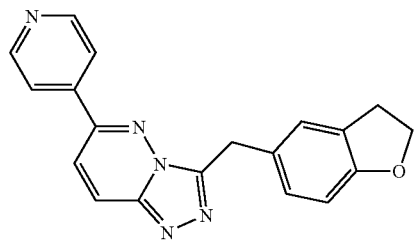 |
| 8 | 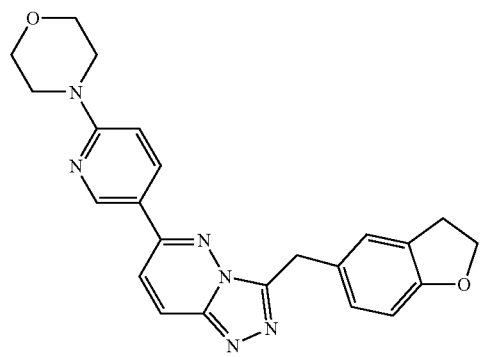 |
| 9 | 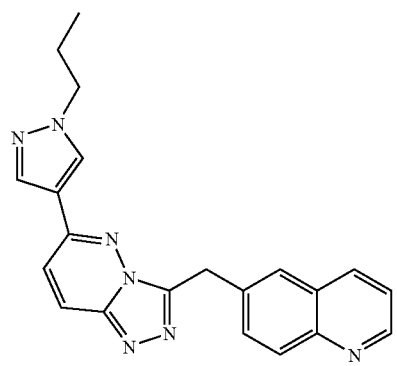 |
| 10 | 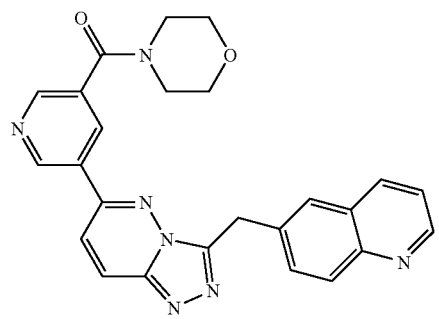 |
| 11 | 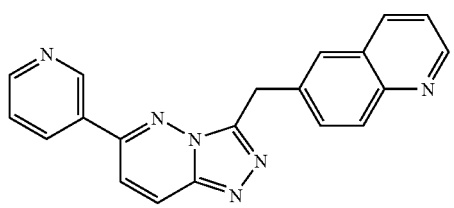 |

-continued
| Example # | Structure |
|---|---|
| 12 | 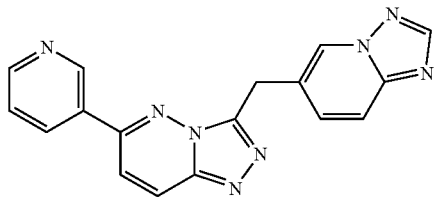 |
| 13 | 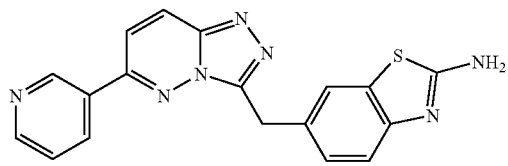 |
| 14 | 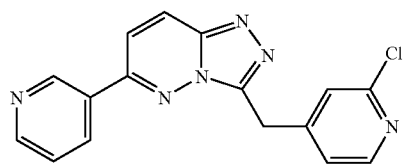 |
| 15 | 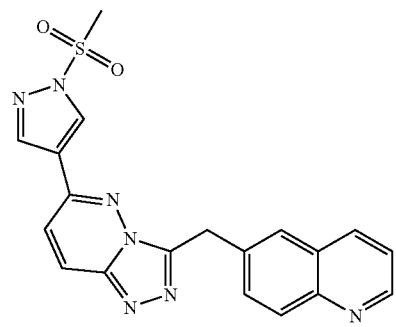 |
| 16 | 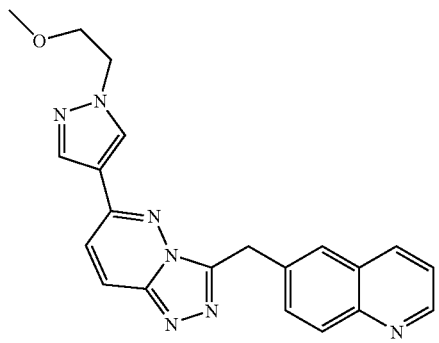 |
| 17 | 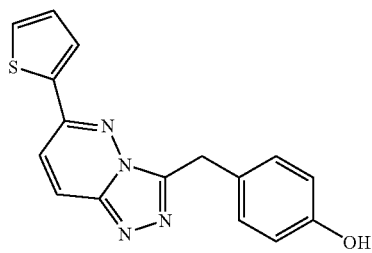 |

| Example # | Structure |
|---|---|
| 18 | 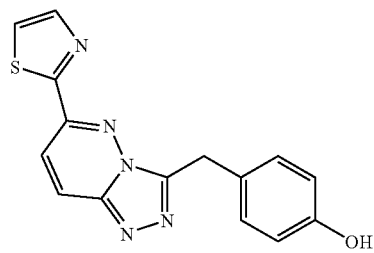 |
| 19 | 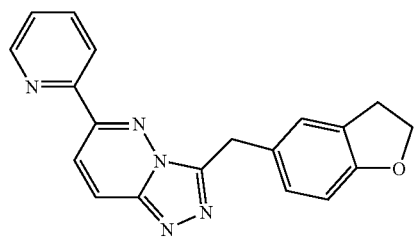 |
| 20 | 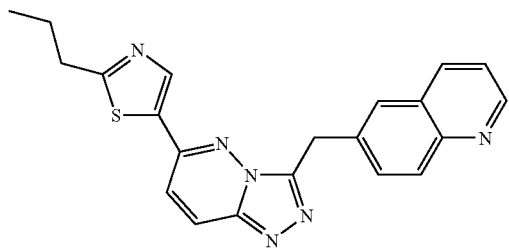 |
| 21 | 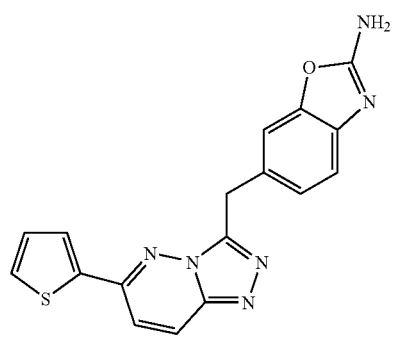 |
| 22 | 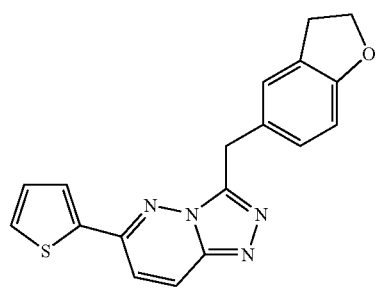 |

-continued
| Example # | Structure |
|---|---|
| 23 | 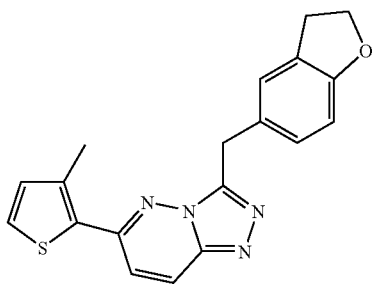 |
| 24 | 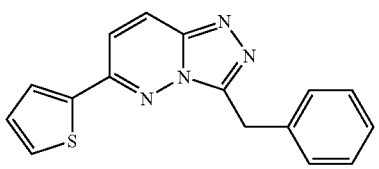 |
| 25 | 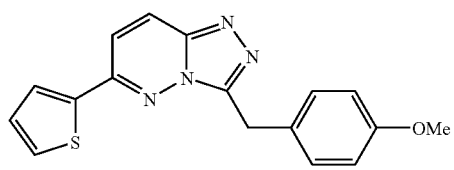 |
| 26 | 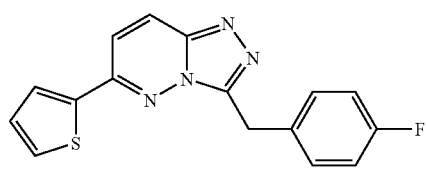 |
| 27 | 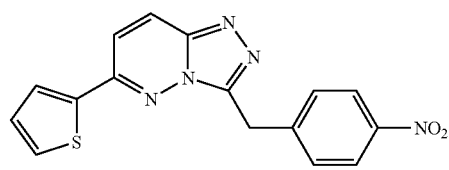 |
| 28 | 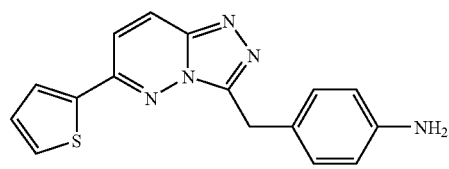 |
| 29 | 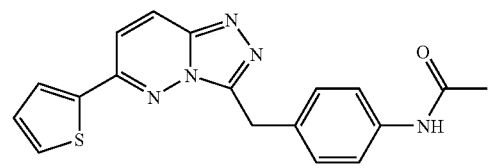 |
| 30 | 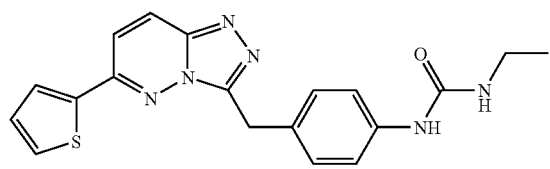 |

-continued
| Example # | Structure |
|---|---|
| 31 | 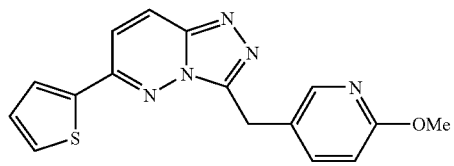 |
| 32 | 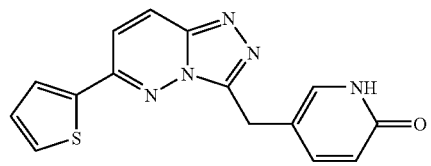 |
| 33 | 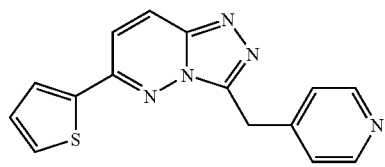 |
| 34 | 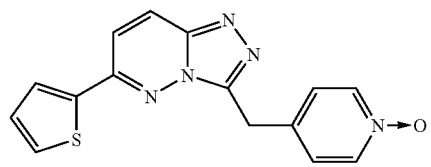 |
| 35 | 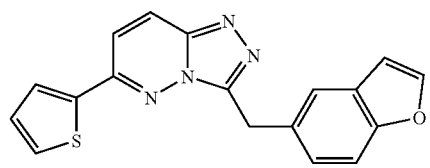 |
| 36 | 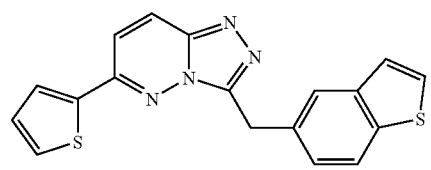 |
| 37 | 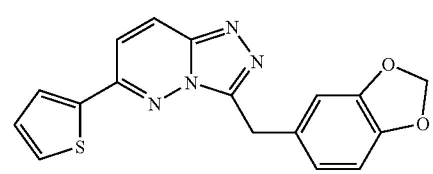 |
| 38 | 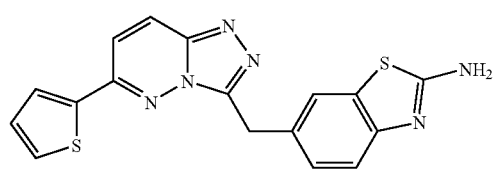 |

US 8,173,654 B2
47                                   48
-continued
| Example # | Structure |
|---|---|
| 39 | 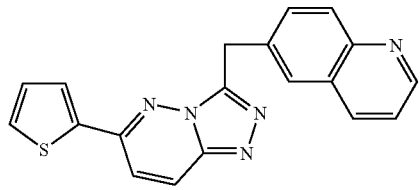 |
| 40 | 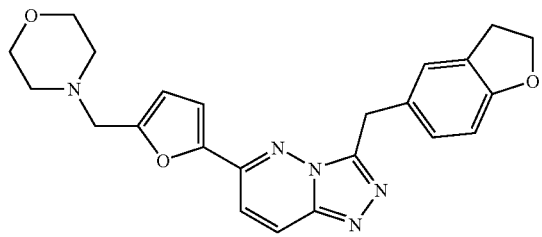 |
| 41 | 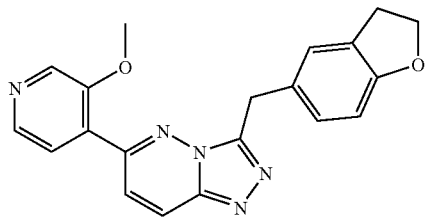 |
| 42 | 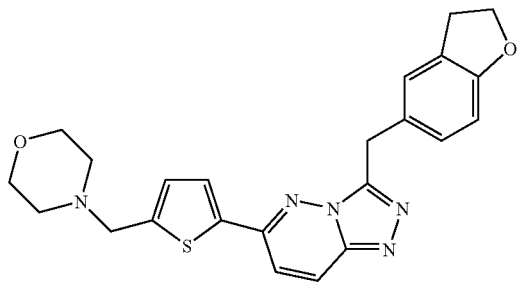 |
| 43 | 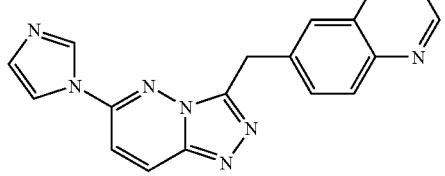 |
| 44 | 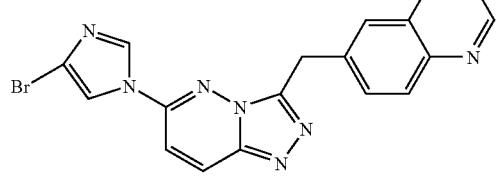 |
| 45 | 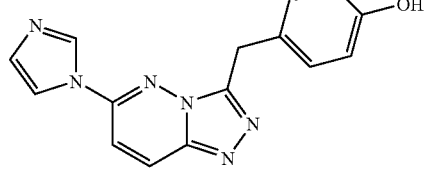 |

-continued
| Example # | Structure |
|---|---|
| 46 | 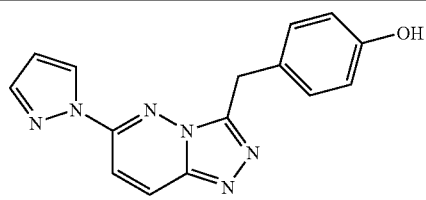 |
| 47 | 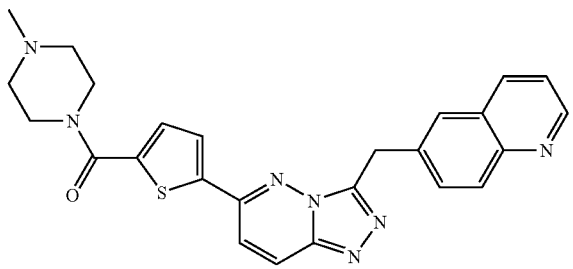 |
| 48 | 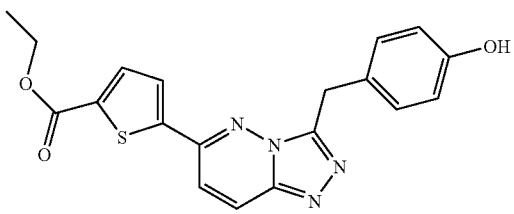 |
| 49 | 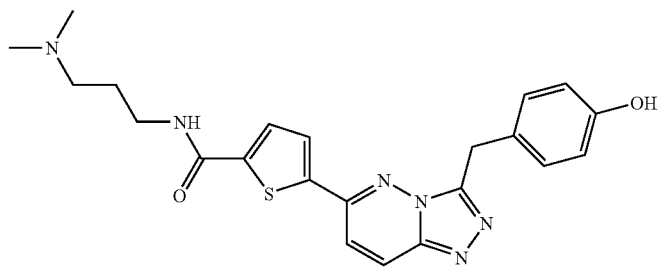 |
| 50 | 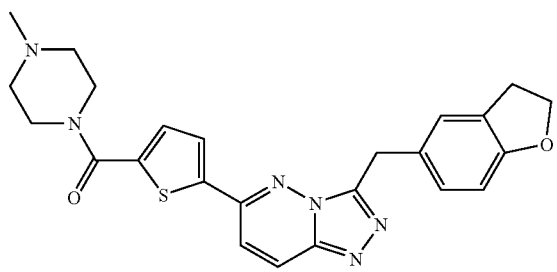 |
| 51 | 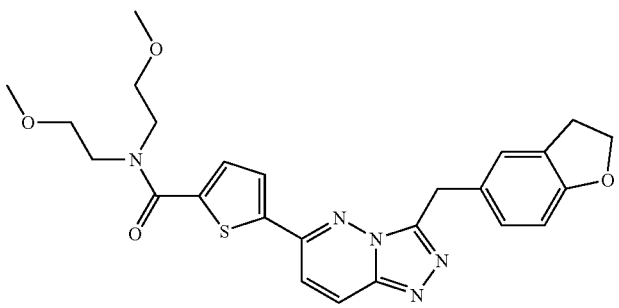 |

| Example # | Structure |
|---|---|
| 52 | 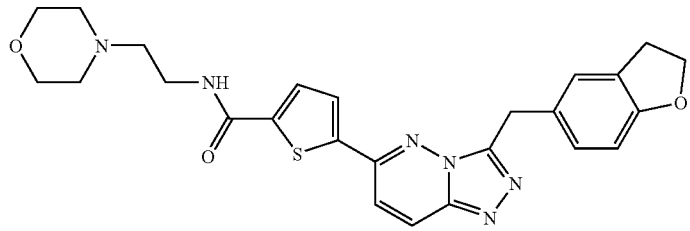 |
| 53 | 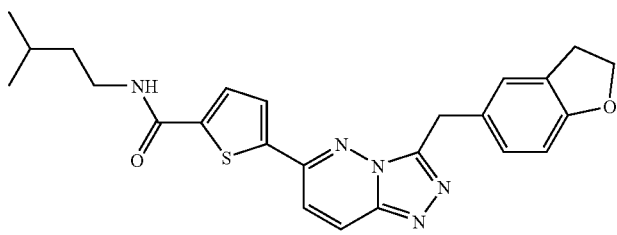 |
| 54 | 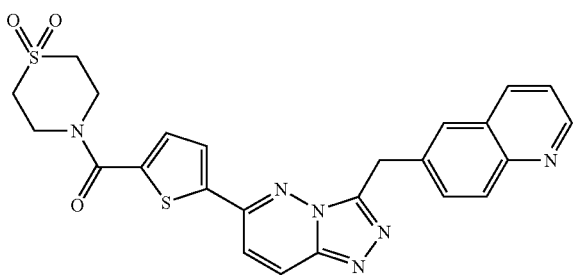 |
| 55 | 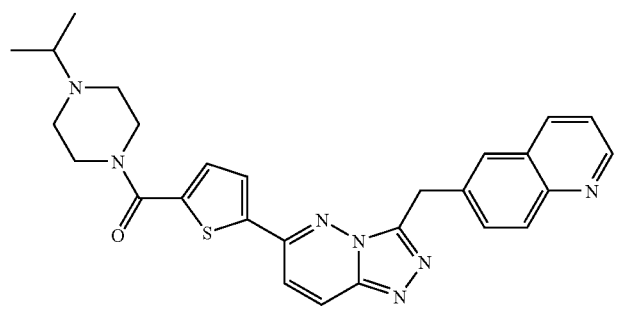 |
| 56 | 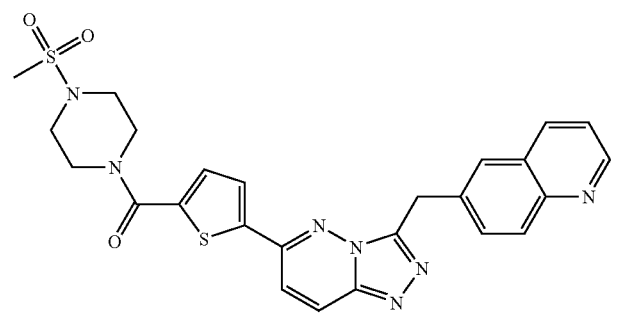 |

-continued
| Example # | Structure |
|---|---|
| 57 | 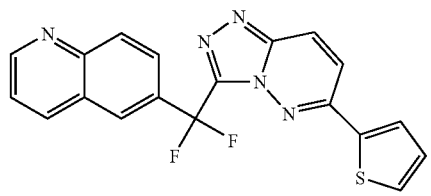 |
| 58 | 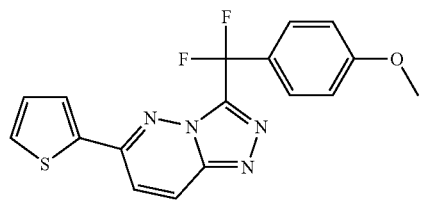 |
| 59 | 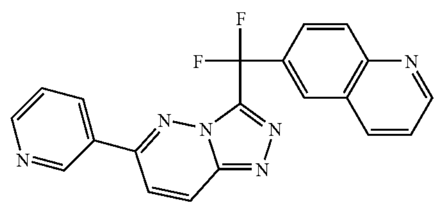 |
| 60 | 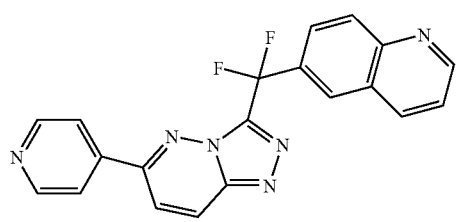 |
| 61 | 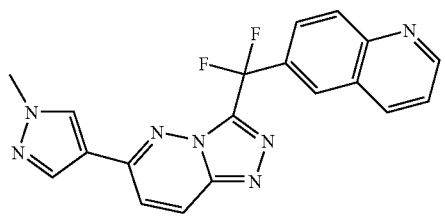 |
| 62 | 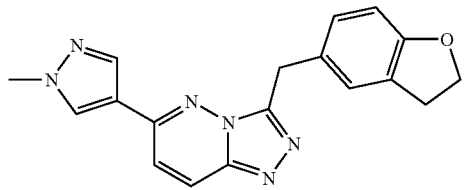 |
| 63 | 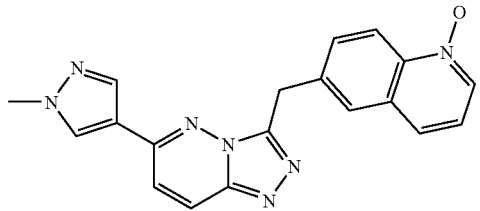 |

| Example # | Structure |
|---|---|
| 64 | 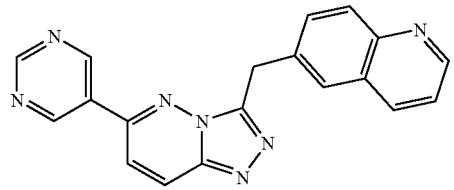 |
| 65 | 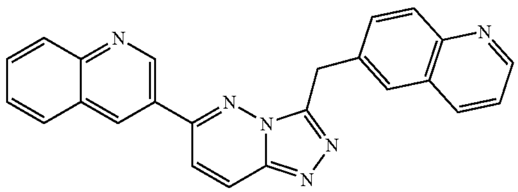 |
| 66 | 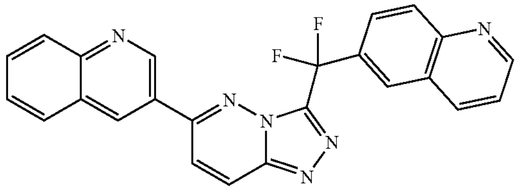 |
| 67 | 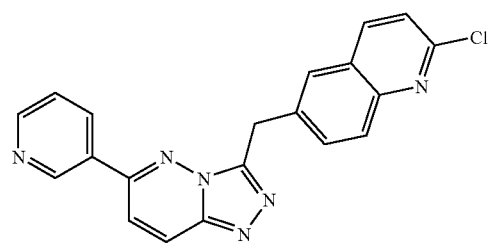 |
| 68 | 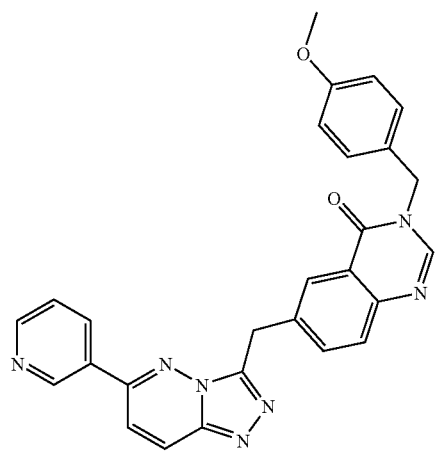 |
| 69 | 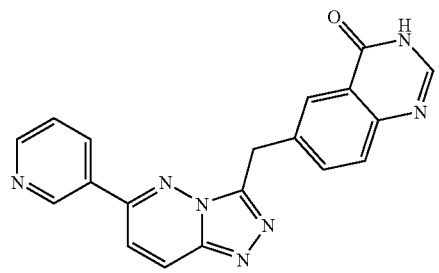 |

-continued
| Example # | Structure |
|---|---|
| 70 | 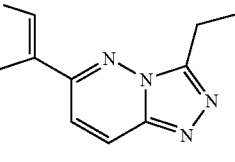 |
| 71 | 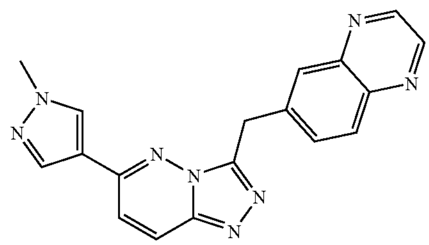 |
| 72 | 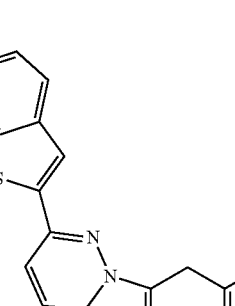 |
| 73 | 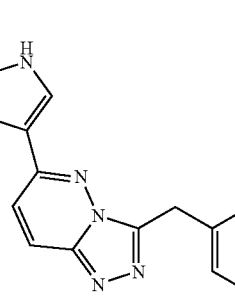 |
| 74 | 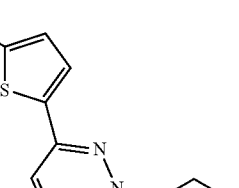 |

-continued
| Example # | Structure |
|---|---|
| 75 | 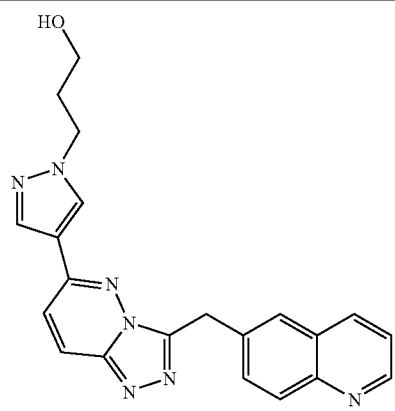 |
| 76 | 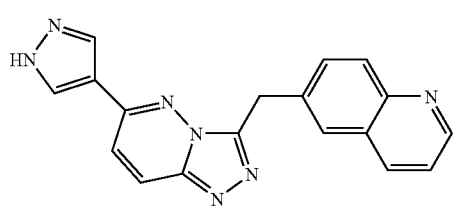 |
| 77 | 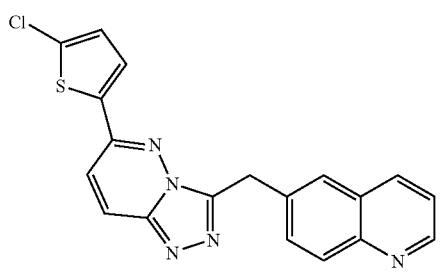 |
| 78 | 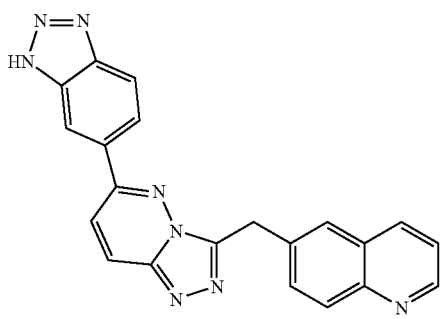 |
| 79 | 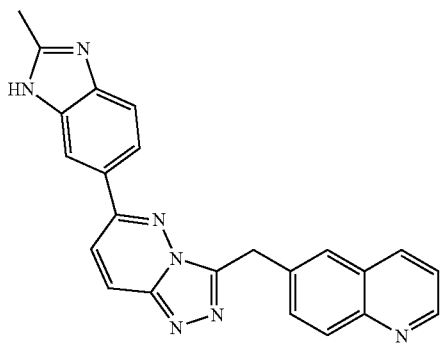 |

| Example # | Structure |
|---|---|
| 80 | 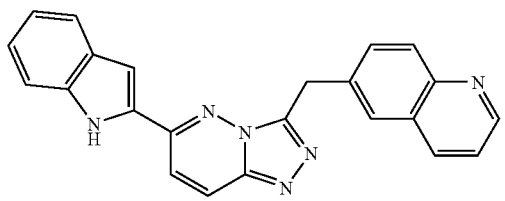 |
| 81 | 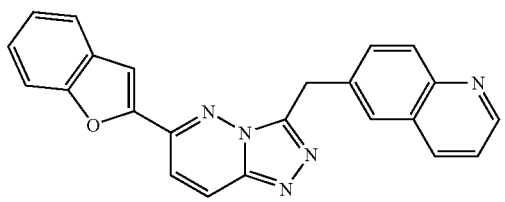 |
| 82 | 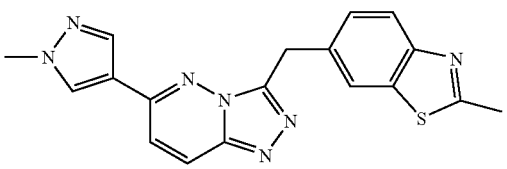 |
| 83 | 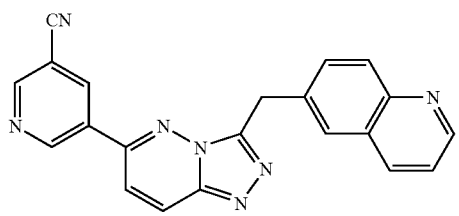 |
| 84 | 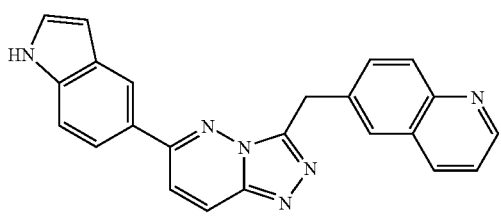 |
| 85 | 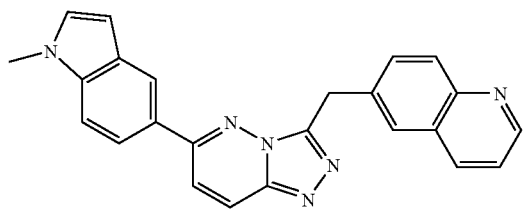 |
| 86 | 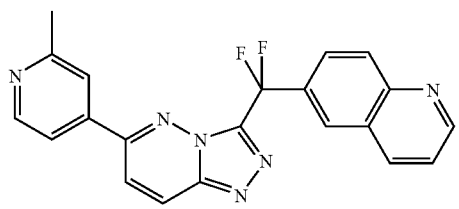 |

-continued
| Example # | Structure |
|---|---|
| 87 | 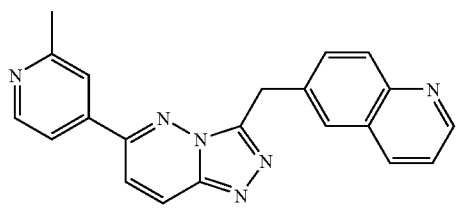 |
| 88 | 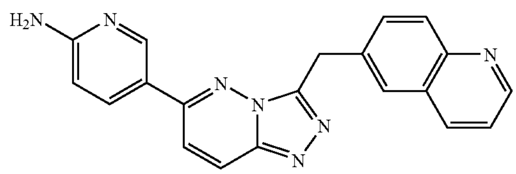 |
| 89 | 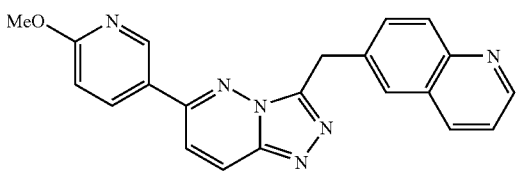 |
| 90 | 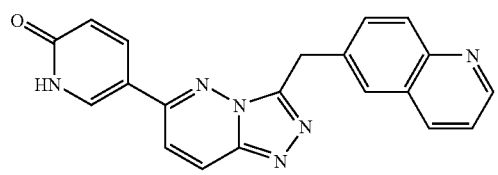 |
| 91 | 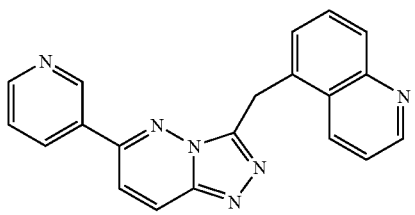 |
| 92 | 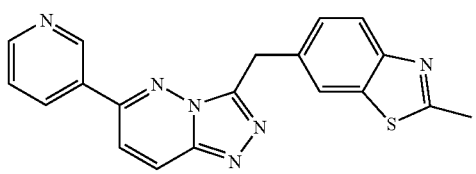 |
| 93 | 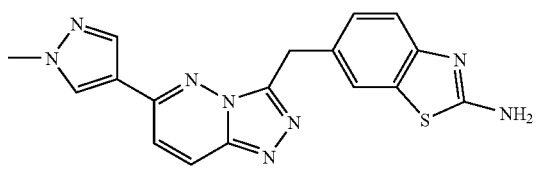 |
| 94 | 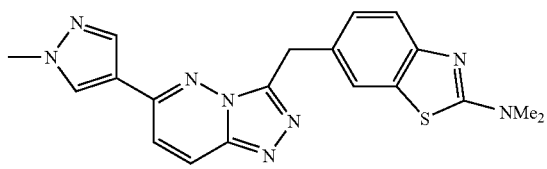 |

| Example # | Structure |
|---|---|
| 95 | 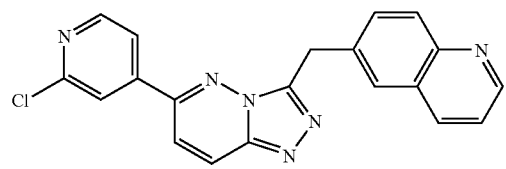 |
| 96 | 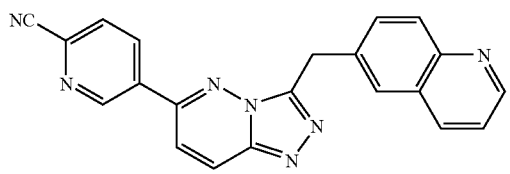 |
| 97 | 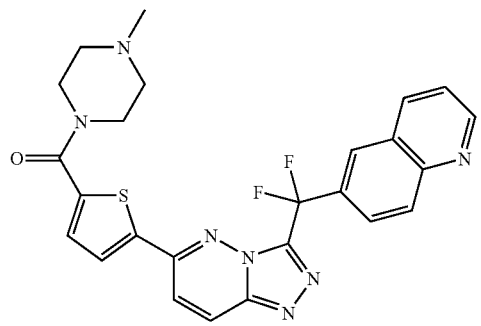 |
| 98 | 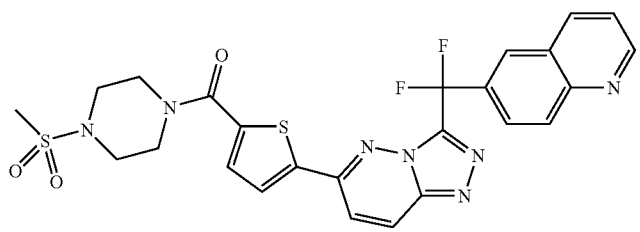 |
| 99 | 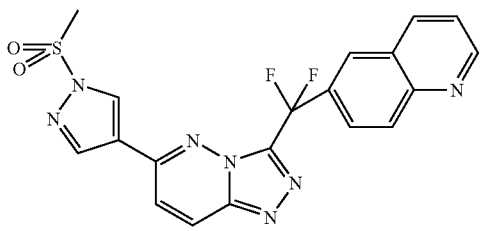 |
| 100 | 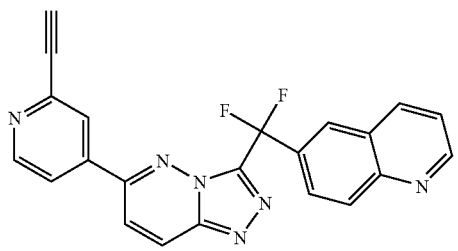 |

| Example # | Structure |
|---|---|
| 100b | 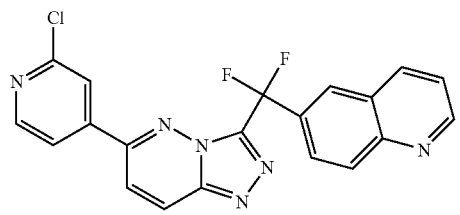 |
| 101 | 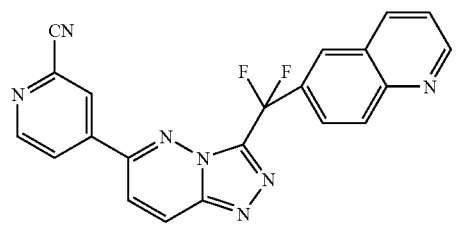 |
| 102 | 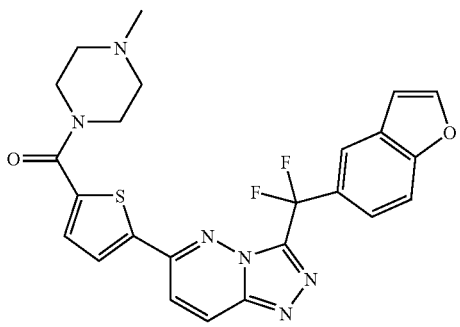 |
| 103 | 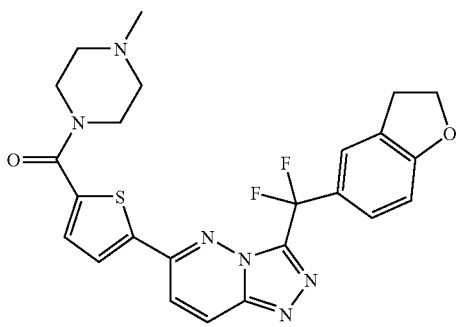 |
| 104 | 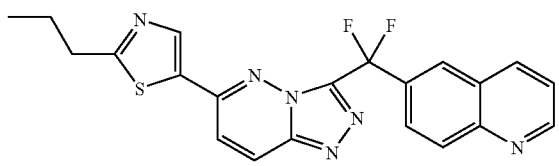 |

Examples of individual compound syntheses are shown below.

EXAMPLE 1

6-[6-(1-Methyl-1H-pyrazol-4-yl)-[1,2,4]triazolo[4,3-b]pyridazin-3-ylmethyl]-quinoline

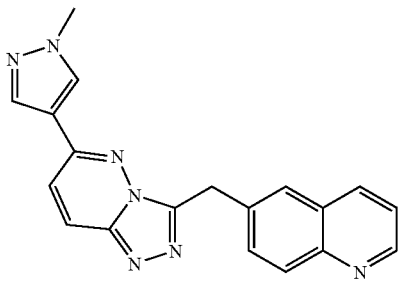

EXAMPLE 1

Step a

3-Chloro-6-(1-methyl-1H-pyrazol-4-yl)-pyridazine

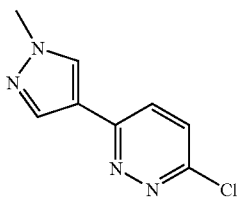

A flask was charged with 3,6-dichloropyridzine (Aldrich, 297 mg, 2.0 mmol), 1-Methyl-4-(4,4,5,5-tetramethyl-[1,3,2]dioxaborolan-2-yl)-1H-pyrazole (499 mg, 2.4 mmol), 2 M $Na_2CO_3$ (4 mL) and dioxane (4 mL). Argon was bubbled through the reaction for 60 seconds followed by the addition of Tetrakis(triphenylphosphine)palladium (0) (231 mg, 0.2 mmol). The reaction was heated to 80° C. overnight followed by aqueous work up using EtOAc and brine. The organic layer was dried ($MgSO_4$) and concentrated in vacuo followed by column chromatography purification (20% Ethyl Acetate in Hexanes) resulting in the title compound as a white solid (183 mg, 47%). $^1$H-NMR ($CD_3OD$): δ 8.23 (1H, s), 8.08 (1H, s), 7.84 (1H, br s), 7.34 (1H, br s), 4.00 (3H, s).

EXAMPLE 1

Step b

6-[6-(1-Methyl-1H-pyrazol-4-yl)-[1,2,4]triazolo[4,3-b]pyridazin-3-ylmethyl]-quinoline

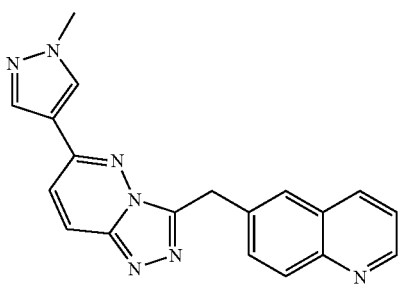

Quinolin-6-yl-acetic acid hydrazide (188 mg, 0.93 mmol) and 3-Chloro-6-(1-methyl-1H-pyrazol-4-yl)-pyridazine (202 mg, 0.93 mmol, Example 1: step a) were dissolved in butanol (120 mL). The reaction mixture was heated to 120° C. overnight fitted with water cooled refluxing condenser and argon line. The reaction was concentrated in vacuo followed by HPLC purification (5-65% $CH_3CN$ over 40 min) resulting in the title compound as a tan solid (201.6 mg, 65%). $^1$H-NMR ($CD_3OD$): δ 9.08-9.04 (2H, m), 8.30-8.29 (2H, m), 8.21-8.06 (4H, m), 7.99-7.95 (1H, q, J=5.3, 3.0 Hz), 7.68-7.65 (1H, d, J=9.8), 4.85 (2H, s), 3.89 (3H, s), 4.96 (2H, s). ESI-MS (m/z): Calcd. For $C_{19}H_{15}N_7$: 341.37; found: 342.3 (M+H).

EXAMPLE 2

6-[6-(1H-Pyrazol-4-yl)-[1,2,4]triazolo[4,3-b]pyridazin-3-ylmethyl]-quinoline

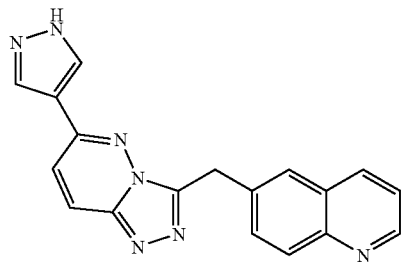

The title compound was prepared as described in Example 1. $^1$H-NMR ($CD_3OD$): δ 9.08-9.05 (2H, m), 8.30 (1H, s), 8.26 (1H, m), 8.21-8.19 (2H, m), 8.15-8.12 (2H, m), 7.99-7.90 (1H, m), 7.75-7.65 (1H, m), 4.86 (2H, s). ESI-MS (m/z): Calcd. For $C_{18}H_{13}N_7$: 327.12; found: 328.2 (M+H).

EXAMPLE 3

4-[6-(1H-Pyrazol-4-yl)-[1,2,4]triazolo[4,3-b]pyridazin-3-ylmethyl]-phenol

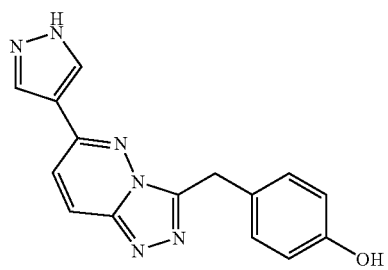

The title compound was prepared as described in Example 1. $^1$H-NMR ($CD_3OD$): δ 9.33 (1H, s), 8.67 (1H, s), 8.38-8.35 (1H, d, J=9.6 Hz), 8.26 (1H, s), 7.79-7.76 (1H, d, J=9.6 Hz), 7.28-7.26 (1H, d, J=8.6 Hz), 6.75-6.73 (1H, d, J=8.5 Hz), 4.45 (2H, s), 3.24-3.22 (2H, d, J=5.3). ESI-MS (m/z): Calcd. For $C_{15}H_{12}N_6O$: 292.11; found: 293.2 (M+H).

EXAMPLE 4

4(6-Pyridin-3-yl-[1,2,4]triazolo[4,3-b]pyridazin-3-ylmethyl)-phenol

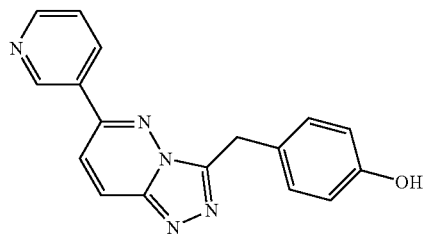

The title compound was prepared as described in Example 1. $^1$H-NMR ($CD_3OD$): δ 9.41 (1H, s), 8.93-8.91 (2H, d, J=9.34 Hz), 8.42-8.40 (1H, d, J=9.6 Hz), 8.07-8.04 (1H, d, J=9.6 Hz), 8.01-7.98 (1H, t, J=7.57 Hz), 7.27-7.25 (2H, d, J=8.8 Hz), 6.75-6.73 (2H, d, J=8.5 Hz), 4.59 (2H, s). ESI-MS (m/z): Calcd. For $C_{17}H_{13}N_5O$: 303.11; found: 304.2 (M+H).

EXAMPLE 5

4-[6-(2H-Pyrazol-3-yl)-[1,2,4]triazolo[4,3-b]pyridazin-3-ylmethyl]-phenol

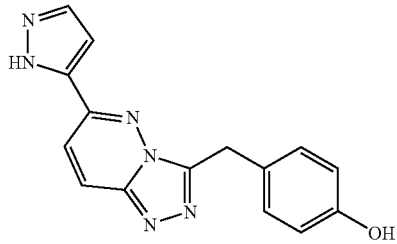

The title compound was prepared as described in Example 1. $^1$H-NMR (CD$_3$OD/CDCl$_3$): δ 8.56-8.53 (1H, d, J=2.2 Hz), 8.32-8.29 (1H, d, J=10.1 Hz), 8.17-8.19 (1H, d, J=10.1 Hz), 7.87 (1H, m), 7.26-7.24 (2H, d, J=8.5 Hz), 6.75-6.72 (2H, d, J=8.5 Hz), 6.67-6.65 (1H, m), 4.49 (2H, s). ESI-MS (m/z): Calcd. For $C_{15}H_{12}N_6O$: 292.11; found: 293.2 (M+H).

EXAMPLE 6

6-(6-Pyridin-4-yl-[1,2,4]triazolo[4,3-b]pyridazin-3-ylmethyl)-quinoline

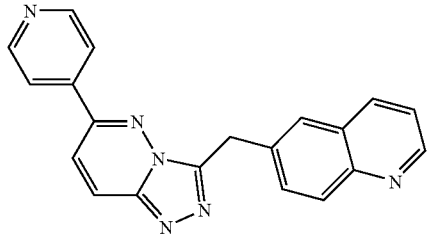

The title compound was prepared as described in Example 1. $^1$H-NMR (CD$_3$OD): δ 9.20-9.18 (1H, d, J=5.3 Hz), 9.15-9.13 (1H, d, J=8.3 Hz), 9.00-8.99 (2H, d, J=6.5 Hz), 8.58-8.56 (2H, d, J=6.5 Hz), 8.52-8.49 (1H, d, J=9.8 Hz), 8.42 (1H, s), 8.32-8.26 (2H, d, J=8.8, 10.3 Hz), 8.16-8.14 (1H, d, J=8.9 Hz), 8.09-8.06 (1H, m), 5.07 (2H, br s). ESI-MS (m/z): Calcd. For $C_{20}H_{14}N_6$: 338.37; found: 339.3 (M+H).

EXAMPLE 7

3-(2,3-Dihydro-benzofuran-5-ylmethyl)-6-pyridin-4-yl-[1,2,4]triazolo[4,3-b]pyridazine

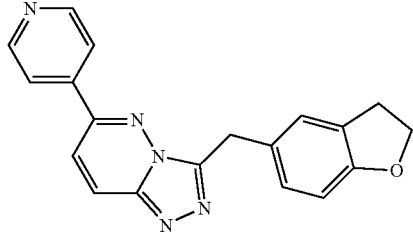

The title compound was prepared as described in Example 1. $^1$H-NMR (CD$_3$OD): δ 8.91-8.88 (2H, d, J=6.5 Hz), 8.48-8.47 (2H, d, J=6.8 Hz), 8.34-8.31 (1H, d, J=9.6 Hz), 8.00-7.89 (1H, d, J=9.8 Hz), 7.15 (1H, s), 7.07-7.04 (1H, d, J=8.0 Hz), 6.55-6.53 (1H, d, J=8.3 Hz), 4.49 (2H, s), 4.38-4.34 (2H, t, J=8.8 Hz), 3.04-3.00 (2H, d, J=8.5 Hz). ESI-MS (m/z): Calcd. For $C_{19}H_{15}N_5O$: 329.13; found: 330.2 (M+H).

EXAMPLE 8

3-(2,3-Dihydro-benzofuran-5-ylmethyl)-6-(6-morpholin-4-yl-pyridin-3-yl)-[1,2,4]triazolo[4,3-b]pyridazine

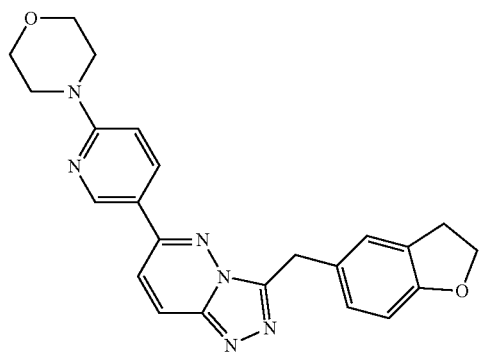

The title compound was prepared as described in Example 1. $^1$H-NMR (CD$_3$OD): δ 8.52-8.51 (1H, d, J=2.5 Hz), 8.26-8.23 (1H, dd, J=2.2, 9.3 Hz), 8.06-8.03 (1H, d, J=9.8 Hz), 7.74-7.72 (1H, d, J=9.8 Hz), 7.05-7.01 (2H, m), 6.94-6.92 (1H, d, J=9.3 Hz), 6.45-6.42 (1H, d, J=8.0 Hz), 4.33 (2H, s), 4.28-4.24 (2H, t, J=8.5 Hz), 3.64-6.32 (4H, m), 3.52-3.50 (4H, m), 2.93-2.89 (2H, t, J=8.8 Hz). ESI-MS (m/z): Calcd. For $C_{23}H_{22}N_6O_2$: 414.18; found: 415.3 (M+H).

EXAMPLE 9

6-[6-(1-Propyl-1H-pyrazol-4-yl)-[1,2,4]triazolo[4,3-b]pyridazin-3-ylmethyl]-quinoline

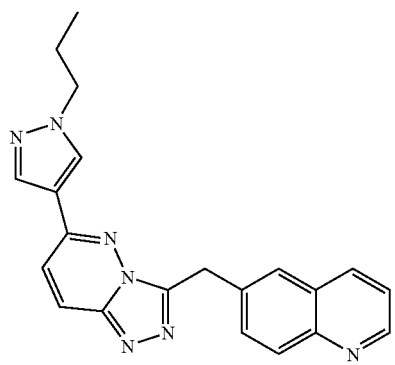

The title compound was prepared as described in Example 1. $^1$H-NMR (CD$_3$OD): δ 9.18-9.16 (1H, dd, J=1.5, 5.5 Hz), 9.14-9.12 (1H, d, J=7.5 Hz), 8.46 (1H, s), 8.39 (1H, s), 8.30-8.19 (4H, m), 8.07-8.04 (1H, q, J=3.0, 5.3 Hz), 7.78-7.76 (1H, d, J=9.6 Hz), 4.96 (2H, s), 4.24-4.20 (2H, t, J=6.8 Hz), 1.99-1.90 (2H, m), 0.91-0.93 (3H, t, J=7.3 Hz). ESI-MS (m/z): Calcd. For $C_{21}H_{19}N_7$: 369.17; found: 370.3 (M+H).

EXAMPLE 10

Morpholin-4-yl-[5-(3-quinolin-6-ylmethyl-[1,2,4]triazolo[4,3-b]pyridazin-6-yl)-pyridin-3-yl]-methanone

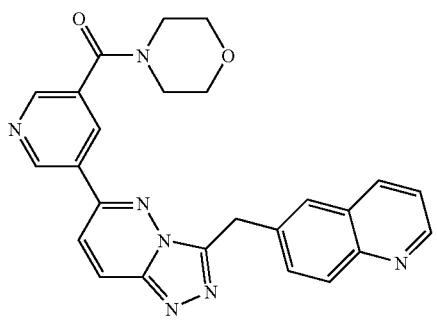

The title compound was prepared as described in Example 1. $^1$H-NMR (CD$_3$OD): δ 9.22-9.20 (1H, d, J=2.2 Hz), 8.72-8.70 (2H, m), 8.41-8.40 (1H, t, J=2.2 Hz), 8.28-8.23 (2H, m), 7.91-7.89 (2H, m), 7.77-7.74 (1H, dd, J=2.0, 8.8 Hz), 7.44-7.41 (1H, q, J=4.2), 4.55 (2H, s), 3.73 (4H, br s), 3.51 (2H, br s), 3.38 (2H, br s). ESI-MS (m/z): Calcd. For C$_{25}$H$_{21}$N$_7$O$_2$: 451.18; found: 452.4 (M+H).

EXAMPLE 11

6-(6-Pyridin-3-yl-[1,2,4]triazolo[4,3-b]pyridazin-3-ylmethyl)-quinoline

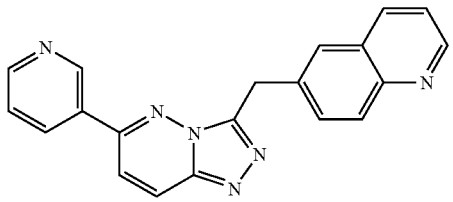

EXAMPLE 11

Step a

3-Chloro-6-pyridin-3-yl-pyridazine

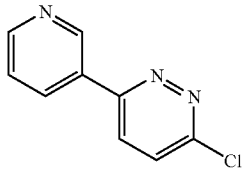

The title compound was prepared as described in Example 1: step a. $^1$H-NMR (CDCl$_3$): δ 9.21 (1H, dd, J=1.0, 2.5 Hz), 8.77 (1H, dd, J=1.8, 4.8 Hz), 8.46 (1H, ddd, J=1.8, 2.5, 8.1 Hz), 7.89 (1H, d, J=8.8 Hz), 7.64 (1H, d, J=8.8 Hz), (1H, ddd, J=1.0, 4.8, 8.1 Hz). ESI-MS (m/z): Calcd. for C$_9$H$_6$ClN$_3$: 191.0/192.0 found: 192.2/194.4 (M+H/M+2+H).

EXAMPLE 11

Step b 6-(6-Pyridin-3-yl-[1,2,4]triazolo[4,3-b]pyridazin-3-ylmethyl)-quinoline

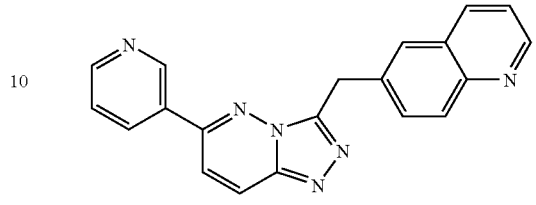

The title compound was prepared as described in Example 1: step b. $^1$H-NMR (CD$_3$OD): δ 9.81 (1H, m), 9.50 (1H, m), 9.27 (1H, m), 9.25 (1H, dd, J=1.5, 5.3 Hz), 9.16 (1H, m), 8.86 (1H, d, J=9.9 Hz), 8.71 (1H, d, J=9.6 Hz), 8.58 (1H, m), 8.42 (1H, m), 8.40 (1H, m), 8.36 (1H, m), 8.14 (1H, dd, J=5.3, 8.3 Hz), 5.22 (2H, s). ESI-MS (m/z): Calcd. for C$_{20}$H$_{16}$N$_6$: 338.1; found: 339.3 (M+H).

EXAMPLE 12

6-Pyridin-3-yl-3-[1,2,4]triazolo[1,5-a]pyridin-6-ylmethyl-[1,2,4]triazolo[4,3-b]pyridazine

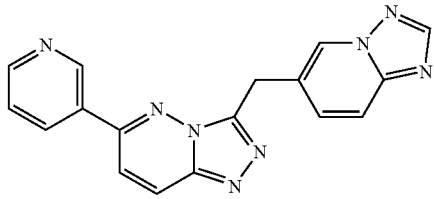

EXAMPLE 12

Step a

2-[1,2,4]Triazolo[1,5-a]pyridin-6-yl-malonic acid diethyl ester

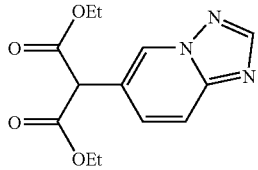

Diethyl malonate (400 µL) was added to a mixture of 6-iodo-[1,2,4]triazolo[1,5-a]pyridine (245 mg, 1 mmol), copper iodide (19 mg, 0.1 mmol), biphenyl-2-ol (34 mg, 0.2 mmol), and Cs$_2$CO$_3$ in THF (5 mL). The heterogeneous solution was stirred for 16 h at 70° C. After cooling, the mixture was partitioned between chloroform (40 mL) and aq NH$_4$Cl (20 mL). The organic layer was washed with NH$_4$Cl (3×15 mL), NaHCO$_3$ (20 mL), and brine (20 mL) then was dried over Na$_2$SO$_4$. Concentration of the solution followed by SiO$_2$ flash chromatography purification yielded the product (170 mg, 61%) as a colorless glass. $^1$H-NMR (CDCl$_3$): δ 8.77 (1H, m), 8.37 (1H, s), 7.78 (1H, dd, J=0.9, 9.1 Hz), 7.69 (1H, dd, J=1.8, 9.3 Hz), 4.76 (1H, s), 4.27 (4H, m), 1.30 (6H, t, J=7.3 Hz). ESI-MS (m/z): Calcd. for C$_{13}$H$_{15}$N$_3$O$_4$: 277.1; found: 278.2 (M+H).

EXAMPLE 12

Step b

[1,2,4]Triazolo[1,5-a]pyridin-6-yl-acetic acid hydrazide

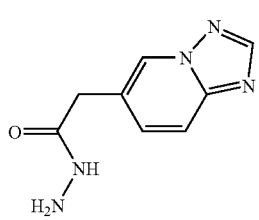

To a solution of 2-[1,2,4]Triazolo[1,5-a]pyridin-6-yl-malonic acid diethyl ester as prepared in Example 12: step a (170 mg, 0.6 mmol) in Dioxane (4 mL) and MeOH (6 mL) was added 2N NaOH (1.2 mL, 2.4 mmol). The reaction was stirred for 4 h at rt, then the solution was adjusted to pH~2 with 0.5N HCl. The solution was stirred for 1 h (decarboxylation occurs) and the volatiles were removed in vacuo. The residue was dissolved in dry MeOH (15 mL), cooled on an ice bath, and thionyl chloride (500 µL, 6.8 mmol) was added dropwise. The solution was stirred for 4 h at rt, filtered, and the volatile components were removed in vacuo. $^1$H-NMR (CD$_3$OD/CDCl$_3$): δ 9.23 (1H, s), 9.15 (1H, s), 8.26 (1H, d, J=8.6 Hz), 8.15 (1H, d, J=8.6 Hz), 4.02 (2H, s), 3.77 (3H, s). The residue was dissolved in EtOH (10 mL) and hydrazine (50 µL) was added. The solution was heated at 70° C. for 14 h and the volatiles removed in vacuo. The residue was thrice re-dissolved in EtOH and concentrated in vacuo to remove excess hydrazine. The material was used without further purification. $^1$H-NMR (DMSO-d$_6$): δ 9.34 (1H, br s), 8.81 (1H, s), 8.46 (1H, s), 7.79 (1H, d, J=9.0 Hz), 7.56 (1H, dd, J=1.5, 9.0 Hz), 3.45 (2H, s, masked by H$_2$O peak).

EXAMPLE 12

Step c

6-Pyridin-3-yl-3-[1,2,4]triazolo[1,5-a]pyridin-6-ylmethyl-[1,2,4]triazolo[4,3-b]pyridazine

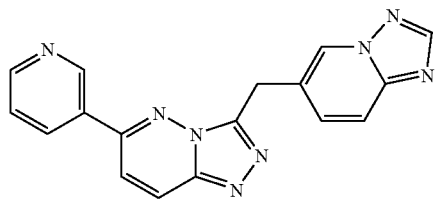

The title compound was prepared as described in Example 1: step b. $^1$H-NMR (CD$_3$OD): δ 9.48 (1H, s), 9.09 (1H, s), 8.96 (1H, ddd, J=1.5, 2.0, 8.1 Hz), 8.94 (1H, d, J=5.0 Hz), 8.57 (1H, s), 8.46 (1H, d, J=9.6 Hz), 8.06 (1H, d, J=9.6 Hz), 8.03 (1H, m, J=5.3, 8.1 Hz), 7.85 (1H, d, J=9.4 Hz), 4.89 (2H, s). ESI-MS (m/z): Calcd. for C$_{17}$H$_{12}$N$_8$: 328.1; found: 329.3 (M+H).

EXAMPLE 13

6-(6-Pyridin-3-yl-[1,2,4]triazolo[4,3-b]pyridazin-3-ylmethyl)-benzothiazol-2-ylamine

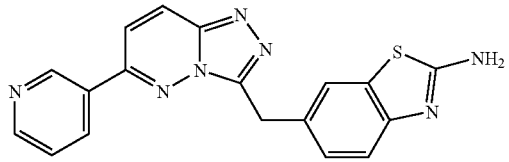

The title compound was prepared as described in Example 1 from (2-amino-benzothiazol-6-yl)-acetic acid hydrazide (0.65 mmol) and 3-chloro-6-pyridin-3-yl-pyridazine (0.34 mmol) to afford a yellow solid. $^1$H NMR (DMSO-d$_6$) δ 9.30 (1H, d, J=1.6 Hz), 8.78 (1H, dd, J=4.8 Hz, 1.7 Hz), 8.50 (1H, m), 8.49 (1H, d, J=9.5 Hz), 8.01 (1H, d, J=9.6 Hz), 7.69 (1H, s), 7.64 (1H, ddd, J=8.1 Hz, 4.8 Hz, 1.0 Hz), 7.42 (2H, s), 7.26 (2H, s), 4.61 (2H, s). ESI-MS (m/z): Calcd for C$_{18}$H$_{13}$N$_7$S: 359.1; found 360.3 (M+H).

EXAMPLE 14

3-(2-Chloro-pyridin-4-ylmethyl)-6-pyridin-3-yl-[1,2,4]triazolo[4,3-b]pyridazine

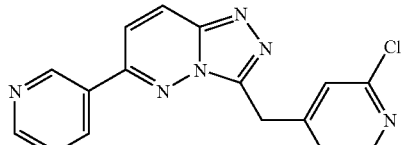

EXAMPLE 14

Step a 2-(2-Chloro-pyridin-4-yl)-malonic acid diethyl ester

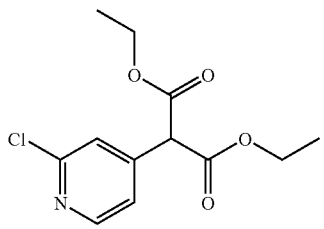

The title compound was prepared as a colorless oil from 2-chloro-4-iodopyridine (4.18 mmol) by the method of Hennessy and Buchwald (*Org. Lett.* 2002, 4, 269). $^1$H NMR (CDCl$_3$) δ 8.37 (1H, dd, J=21 Hz, 5.2 Hz), 7.35 (1H, dd, J=49 Hz, 1.4 Hz), 7.24 (1H, ddd, J=55 Hz, 5.2 Hz, 1.5 Hz), 4.23 (4H, m), 3.61 (1H, s), 1.28 (6H, m). ESI-MS (m/z): Calcd for C$_{12}$H$_{14}$NO$_4$Cl: 271.1; found 272.1 (M+H).

EXAMPLE 14

Step b (2-Chloro-pyridin-4-yl)-acetic acid

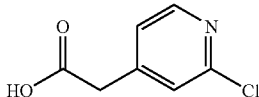

The product of the preceding step (2.43 mmol) was dissolved in methanol (20 mL), treated with 2N aqueous NaOH (4.0 mL), and stirred at ambient temperature for 5 h. The reaction was treated with 2N aqueous HCl (4.0 mL), concentrated to dryness in vacuo, dissolved in methanol, and filtered. Concentration of the filtrate in vacuo gave the title compound as a hygroscopic yellow solid. $^1$H NMR (DMSO-d$_6$) δ 8.32 (1H, d, J=5.1 Hz), 7.43 (1H, s), 7.32 (1H, dd, J=5.1 Hz, 1.5 Hz), 3.64 (2H, s). ESI-MS (m/z): Calcd for $C_7H_6NO_2Cl$: 171.0; found 172.1 (M+H).

EXAMPLE 14

Step c (2-Chloro-pyridin-4-yl)-acetic acid hydrazide

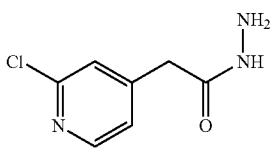

The title compound was prepared as a light yellow solid from the product of the preceding step (2.43 mmol) by the method of Example 17: step b. $^1$H NMR (400 MHz, CDCl$_3$/CD$_3$OD) δ 8.30 (d, J=5.0 Hz, 1H), 7.34 (m, 1H), 7.22 (dd, J=5.1 Hz, 1.5 Hz, 1H), 3.48 (s, 2H).

EXAMPLE 14

Step d 3-(2-Chloro-pyridin-4-ylmethyl)-6-pyridin-3-yl-[1,2,4]triazolo[4,3-b]pyridazine

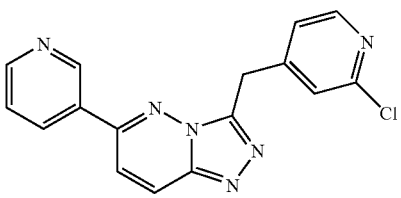

The title compound was prepared as described in Example 1 as a pale orange solid from (2-Chloro-pyridin-4-yl)-acetic acid hydrazide (0.61 mmol) and 3-chloro-6-pyridin-3-yl-pyridazine (0.33 mmol). $^1$H NMR (CDCl$_3$/CD$_3$OD) δ 9.17 (1H, d, J=2.6 Hz), 8.79 (1H, dd, J=4.9 Hz, 1.6 Hz), 8.32 (1H, d, J=4.6 Hz), 8.30 (1H, d, J=9.5 Hz), 8.28 (1H, ddd, J=8.0 Hz, 2.4 Hz, 1.6 Hz), 7.70 (1H, d, J=9.6 Hz), 7.58 (1H, m), 7.47 (1H, s), 7.34 (1H, m), 4.67 (2H, s). ESI-MS (m/z): Calcd for $C_{16}H_{11}N_6Cl$: 322.1; found 323.3 (M+H).

EXAMPLE 15

6-[6-(1-Methanesulfonyl-1H-pyrazol-4-yl)-[1,2,4]triazolo[4,3-b]pyridazin-3-ylmethyl]-quinoline

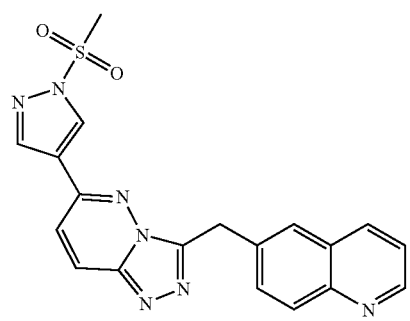

To a solution of 6-[6-(1H-Pyrazol-4-yl)-[1,2,4]triazolo[4,3-b]pyridazin-3-ylmethyl]-quinoline as prepared in Example 3 (10 mg, 0.03 mmol) and DIEA (9 μL, 0.05 mmol) in DCM (2 mL) was added methane sulfonylchloride (4 μL, 0.05 mmol). The reaction was stirred at rt overnight. The reaction was concentrated in vacuo followed by purification by HPLC (5-65% CH$_3$CN over 35 min) resulting in the title compound (3.1 mg, 31%) as a white solid. $^1$H-NMR (CD$_3$OD): δ 9.06-9.00 (2H, q, J=5.3, 7.0 Hz), 8.89 (1H, s), 8.44 (1H, s), 8.29-8.10 (4H, m), 7.96-7.92 (1H, q, J=5.3, 3.0), 7.75-7.73 (1H, d, J=9.8 Hz), 4.87 (2H, s), 3.42 (3H, s). ESI-MS (m/z): Calcd. For $C_{19}H_{15}N_7O_2S$: 405.10; found: 406.1 (M+H).

EXAMPLE 16

6-{6-[1-(2-Methoxy-ethyl)-1H-pyrazol-4-yl]-[1,2,4]triazolo[4,3-b]pyridazin-3-yl methyl}-quinoline

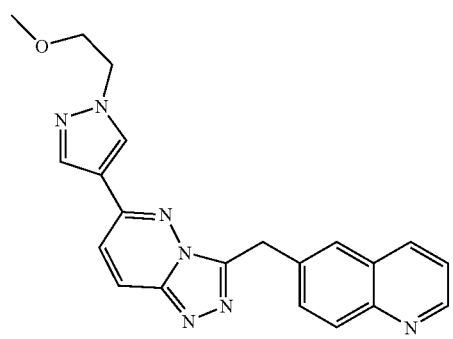

To a solution of 6-[6-(1H-Pyrazol-4-yl)-[1,2,4]triazolo[4,3-b]pyridazin-3-ylmethyl]-quinoline as prepared in Example 3 (19 mg, 0.06 mmol) and K$_2$CO$_3$ (12 mg, 0.09 mmol) in EtOH (2 mL) was added 2-bromoethyl methyl ether (8 μL, 0.09 mmol). The reaction was stirred at rt overnight. The reaction was concentrated in vacuo followed by purification by HPLC (5-65% CH$_3$CN over 35 min) resulting in the title compound (2.8 mg, 15%) as a clear glass. $^1$H-NMR (CD$_3$OD): δ 9.05-9.03 (1H, dd, J=3.7, 5.3 Hz), 9.02-8.99 (1H, d, J=7.8 Hz), 8.32 (1H, s), 8.27 (1H, s), 8.18-8.08 (4H, m), 7.95-7.91 (1H, q, J=3.0, 5.5 Hz), 7.66-7.63 (1H, d, J=9.8 Hz), 4.84 (2H, s), 4.30-4.28 (2H, t, 4.8 Hz), 3.70-3.76 (2H, t, J=5.3 Hz), 3.23 (2H, br s). ESI-MS (m/z): Calcd. For $C_{21}H_{19}N_7O$: 385.17; found: 386.2 (M+H).

EXAMPLE 17

4(6-Thiophen-2-yl-[1,2,4]triazolo[4,3-b]pyridazin-3-ylmethyl)-phenol

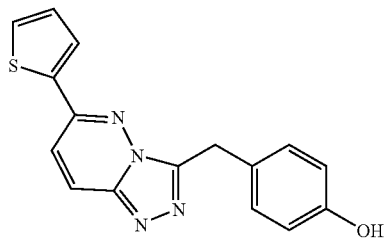

EXAMPLE 17

Step a

3-Chloro-6-thiophene-2-yl-pyridazine

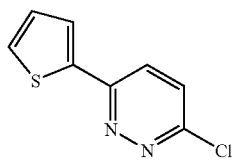

3,6-dichloropyridizine (149.9 mg, 1 mmol) and 2-zinc bromide-thiophene (Aldrich, 0.5 M, 1 mL, 0.5 mmol) were combined with THF (2 mL) and bubbled with argon for 60 seconds. To the reaction mixture was added Tetrakis (triphenylphosphine)palladium (0) (12 mg, 0.01 mmol). The reaction was heated to 65° C. overnight. The reaction was concentrated in vacuo, adsorbed to silica followed by column chromatography purification (20% Ethyl Acetate in Hexanes) resulting in the title compound as a white solid. $^1$H-NMR (CD$_3$OD): δ 7.75-7.73 (1H, d, J=9.0 Hz), 7.67-7.66 (1H, dd, J=1.2, 3.7 Hz), 7.53-7.52 (1H, d, J=5.0 Hz), 7.50-7.48 (1H, d, J=8.5 Hz), 7.18-7.16 (1H, t, J=5.3 Hz). ESI-MS (m/z): Calcd. For $C_8H_5ClN_2S$: 195.98; found: 197.2 (M+H).

EXAMPLE 17

Step b (4-Hydroxy-phenyl)-acetic acid hydrazide

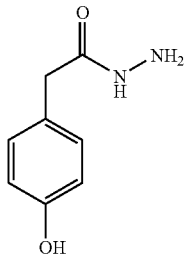

To a solution of (4-Hydroxy-phenyl)-acetic acid methyl ester (5 g, 30.08 mmol) in MeOH (20 mL, anhydrous) was added hydrazine (3.77 mL, 120.35 mmol) and then heated to 55° C. for 1 hour. A white precipitate formed during heating. The reaction was then cooled to rt and stirred for an additional hour to facilitate precipitation of solid. The reaction was filtered and the solid was washed with MeOH and dried resulting in the desired product (4.3 g, 86%) as a white solid. $^1$H-NMR (DMSO): δ 9.20 (1H, s), 9.10 (1H, s), 7.04-7.02 (2H, d, J=8.6 Hz), 6.67-6.65 (2H, d, J=8.6 Hz), 4.17-4.16 (2H, s), 4.11-4.09 (1H, q, J=5.0, 5.5 Hz).

EXAMPLE 17

Step c 4-(6-Thiophen-2-yl-[1,2,4]triazolo[4,3-b]pyridazin-3-ylmethyl)-phenol

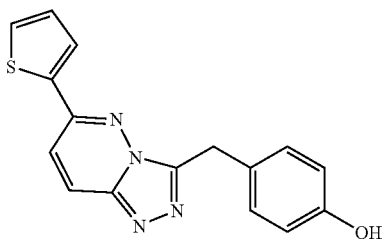

A solution containing 3-Chloro-6-thiophene-2-yl-pyridazine (58 mg, 0.29 mmol) Example 17: step a and (4-Hydroxy-phenyl)-acetic acid hydrazide (120 mg, 0.58 mmol) in butanol (5 mL) was heated to reflux overnight. The reaction was cooled to rt and the solids were filtered and washed with MeOH. The solid was recrystallized from MeOH to yield the title compound as a tan solid. $^1$H-NMR (CD$_3$OD/CDCl$_3$): δ 8.12-8.10 (1H, d, J=9.34 Hz), 7.83-7.82 (1H, d, J=3.7 Hz), 7.78-7.76 (1H, d, J=9.8 Hz), 7.67-7.65 (1H, d, J=5.0 Hz), 7.34-7.32 (2H, d, J=6.5 Hz), 7.22-7.21 (1H, m), 6.77-6.75 (2H, d, J=8.3 Hz), 4.49 (2H, s). ESI-MS (m/z): Calcd. For $C_{16}H_{12}N_4OS$: 308.07; found: 309.2 (M+H).

EXAMPLE 18

4-(6-Thiazol-2-yl-[1,2,4]triazolo[4,3-b]pyridazin-3-ylmethyl)-phenol

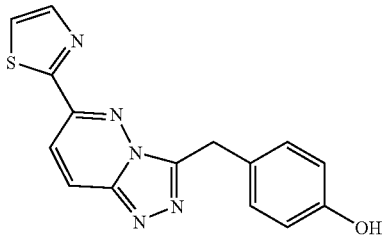

EXAMPLE 18

Step a

3-Chloro-6-thiazol-2-yl-pyridazine

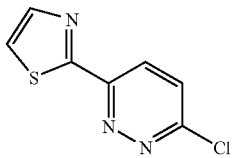

3,6-dichloropyridizine (149.9 mg, 1 mmol) and 2-zinc bromide-thiazole (0.5 M Aldrich, 2.4 mL, 1.2 mmol) were dissolved into THF (2 mL) and bubbled with argon for 60 seconds. To the reaction mixture was added Tetrakis (triphenylphosphine)palladium (0) (57 mg, 0.05 mmol). The reaction was heated to 65° C. overnight. Analysis by LCMS showed conversion to product at 60%-ESI-MS (m/z): Calcd. For $C_7H_4ClN_3S$: 196.98; found: 198.2. Therefore another portion of 2-zinc bromide-thiazole (0.5 M Aldrich, 2.4 mL, 1.2 mmol) and Tetrakis(triphenylphosphine)palladium (0) (57 mg, 0.05 mmol) were added and heating continued for 4 hours until reaction was complete. The reaction was concentrated in vacuo, adsorbed to silica followed by column chromatography purification (20% Ethyl Acetate in Hexanes) resulting in the title compound as a white solid. $^1$H-NMR (CD$_3$OD): δ 8.32-8.30 (1H, d, J=9.0 Hz), 7.95-7.94 (1H, d, J=3.0 Hz), 7.84-7.81 (1H, d, J=9.09 Hz), 7.73-7.72 (1H, d, J=3.2 Hz).

EXAMPLE 18

Step b 4-(6-Thiazol-2-yl-[1,2,4]triazolo[4,3-b]pyridazin-3-ylmethyl)-phenol

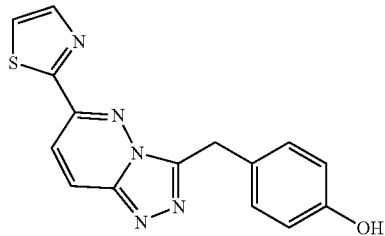

3-Chloro-6-thiazol-2-yl-pyridazine (20 mg, 0.10 mmol) and (4-Hydroxy-phenyl)-acetic acid hydrazide (20 mg, 0.12 mmol) were combined in butanol (5 mL), fitted with water filled condenser and heated to 120° C. overnight. The reaction was concentrated in vacuo followed by purification by HPLC (10-80% CH$_3$CN over 25 min) resulting in the title compound (11.5 mg, 37%) as a white solid. $^1$H-NMR (CD$_3$OD/CDCl$_3$): δ 8.26-8.24 (1H, d, J=9.6 Hz), 8.17-8.15 (1H, d, J=9.6 Hz), 8.05-8.04 (1H, d, J=3.2 Hz), 7.82-7.81 (1H, d, J=3.0 Hz), 7.32-7.30 (2H, t, J=8.6 Hz), 6.77-6.74 (2H, d, J=8.3 Hz), 4.53 (2H, s). ESI-MS (m/z): Calcd. For $C_{15}H_{11}N_5OS$: 309.07; found: 310.2 (M+H).

EXAMPLE 19

3-(2,3-Dihydro-benzofuran-5-ylmethyl)-6-pyridin-2-yl-[1,2,4]triazolo[4,3-b]pyridazine

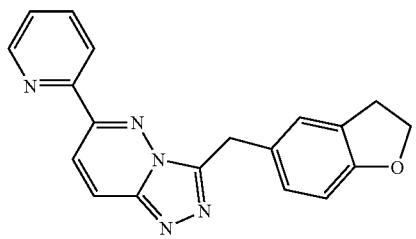

The title compound was prepared as described in Example 17. $^1$H-NMR (CD$_3$OD/CDCl$_3$): δ 8.78-8.77 (1H, d, J=7.5 Hz), 8.43-8.41 (1H, d, J=9.6 Hz), 8.38-8.36 (1H, d, J=7.8 Hz), 8.24-8.21 (1H, d, J=9.8 Hz), 8.09-8.05 (1H, t, J=9.6 Hz), 7.62-7.58 (1H, m), 7.26 (1H, s), 7.16-7.14 (1H, d, J=6.3 Hz), 6.69-6.67 (1H, d, J=8.0 Hz), 4.51 (2H, s), 4.47-4.43 (2H, t, J=8.8 Hz), 3.13-3.08 (2H, t, J=8.6 Hz). ESI-MS (m/z): Calcd. For $C_{19}H_{15}N_5O$: 329.13; found: 330.3 (M+H).

EXAMPLE 20

6-[6-(2-Propyl-thiazol-5-yl)-[1,2,4]triazolo[4,3-b]pyridazin-3-ylmethyl]-quinoline

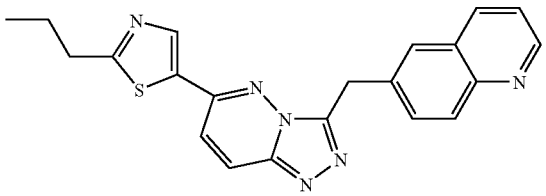

EXAMPLE 20

Step a

3-Chloro-6-(2-propyl-thiazol-5-yl)-pyridazine

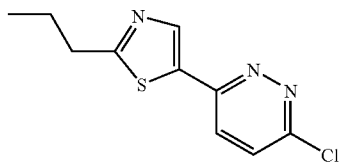

N-butyllithium (2.5M in Hexanes, 1.3 mL, 3.3 mmol) was added dropwise over 2 min to a −78° C. solution of 2-propylthiazole (380 mg, 3 mmol) in THF (8 mL). After stirring for 45 min at −78° C., a solution of zinc chloride (0.5M in THF, 7 mL, 3.5 mmol) was added. The solution was stirred for 1 h, during which it warmed to rt. Tetrakis-triphenylphosphine (172 mg, 0.15 mmol) and 3,6-dichloropyridazine were added and the reaction was heated to 68° C. for 16 h. After cooling to rt, methanol (3 mL) and 2N HCl (2 mL) were added. The pH was adjusted to ~8 with Na$_2$CO$_3$ and the mixture was partitioned between EtOAc (50 mL) and water (30 mL). The organic layer was washed with water (2×10 mL) and brine (20 mL) and was dried over Na$_2$SO$_4$. Concentration of the solution in vacuo followed by SiO$_2$ flash chromatography yielded the product as an off-white solid (200 mg, 28%). $^1$H-NMR (CDCl$_3$): δ 8.16 (1H, s), 7.77 (1H, d, J=8.8 Hz), 7.53 (1H, d, J=8.8 Hz), 3.04 (2H, t, J=7.6 Hz), 1.89 (2H, sextet, J=7.6 Hz), 1.06 (2H, t, J=7.6 Hz). ESI-MS (m/z): Calcd. for $C_{10}H_{10}ClN_3S$: 239.0/241.0; found: 240.2/242.2 (M+H; M+2+H).

EXAMPLE 20

Step b

6-[6-(2-Propyl-thiazol-5-yl)-[1,2,4]triazolo[4,3-b]pyridazin-3-ylmethyl]-quinoline

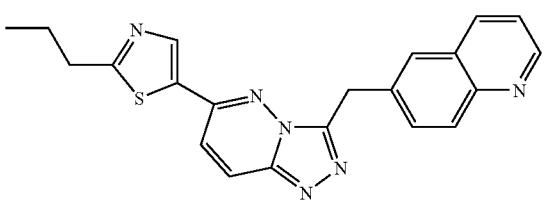

The title compound was prepared as described in Example 17: step b. $^1$H-NMR (CD$_3$OD): δ 9.29 (1H, d, J=8.3), 9.26 (1H, d, J=4.8 Hz), 8.97 (1H, s), 8.72 (d, 1H, J=9.9 Hz), 8.60 (1H, d, J=9.9 Hz), 8.55 (1H, s), 8.37 (2H, s), 8.15 (1H, dd, J=5.6, 8.3 Hz), 5.11 (2H, s), 7.98 (d, 1H, J=9.9 Hz), 3.26 (1H, t, J=7.6 Hz), 1.94 (2H, sextet, J=7.3 Hz), 1.06 (2H, t, J=7.3 Hz). ESI-MS (m/z): Calcd. for C$_{21}$H$_{18}$N$_6$S: 386.1; found: 387.3 (M+H).

EXAMPLE 21

6-(6-Thiophen-2-yl-[1,2,4]triazolo[4,3-b]pyridazin-3-ylmethyl)-benzooxazol-2-ylamine

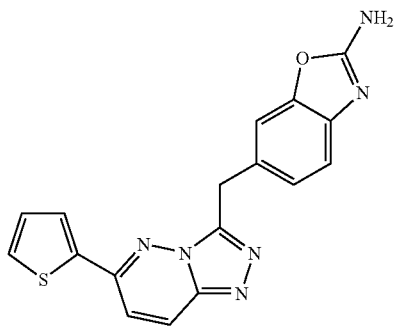

The title compound was prepared as described in Example 17. $^1$H-NMR (CDCl$_3$): δ 8.05-8.03 (1H, d, J=9.6 Hz), 7.66-7.65 (1H, dd J=1.2, 3.6 Hz), 7.46-7.44 (1H, d, J=9.8 Hz), 7.23-7.15 (2H, m), 4.64 (2H, s), 3.49 (2H, s). ESI-MS (m/z): Calcd. For C$_{17}$H$_{12}$N$_6$OS: 348.08; found: 349.3 (M+H).

EXAMPLE 22

3-(2,3-Dihydro-benzofuran-5-ylmethyl)-6-thiophen-2-yl-[1,2,4]triazolo[4,3-b]pyridazine

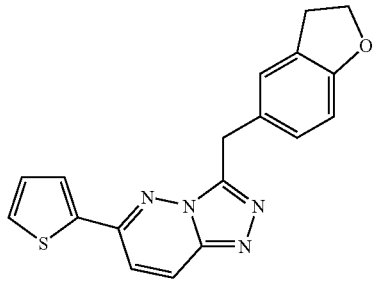

The title compound was prepared as described in Example 17. $^1$H-NMR (CDCl$_3$): δ 8.05-8.03 (1H, d, J=9.8 Hz), 7.67-7.66 (1H, dd, J=1.0, 3.7 Hz), 7.56-7.55 (1H, d, J=1.0, 5.0 Hz), 7.47-7.44 (1H, d, J=9.8 Hz), 7.35 (1H, s), 7.29-7.27 (1H, m), 7.19-7.16 (1H, q, J=3.7 Hz), 6.72-6.70 (1H, d, J=8.0 Hz), 4.53-4.49 (4H, m), 3.18-3.13 (2H, t, J=8.8 Hz). ESI-MS (m/z): Calcd. For C$_{18}$H$_{14}$N$_4$OS: 334.09; found: 335.2 (M+H).

EXAMPLE 23

3-(2,3-Dihydro-benzofuran-5-ylmethyl)-6-(3-methyl-thiophen-2-yl)-[1,2,4]triazolo[4,3-b]pyridazine

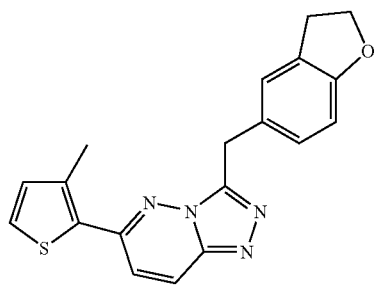

The title compound was prepared as described in Example 17. $^1$H-NMR (CDCl$_3$): δ 8.06-8.04 (1H, d, J=9.8 Hz), 7.42-7.41 (1H, d, J=5.0 Hz), 7.40-7.37 (1H, d, J=9.6 Hz), 7.28 (1H, s), 7.20-7.18 (1H, d, J=6.82 Hz), 7.02-7.00 (1H, d, J=5.0 Hz), 6.71-6.69 (1H, d, J=8.0 Hz), 4.56-4.49 (4H, m), 3.17-3.12 (2H, d, J=8.5 Hz), 2.55 (3H, s). ESI-MS (m/z): Calcd. For C$_{19}$H$_{16}$N$_4$OS: 348.10; found: 349.2 (M+H).

EXAMPLE 24

3-Benzyl-6-thiophen-2-yl-[1,2,4]triazolo[4,3-b]pyridazine

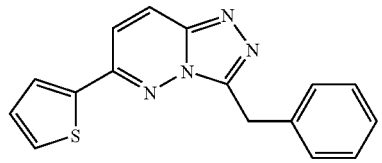

The title compound was prepared as described in Example 17 from phenylacetic acid hydrazide (0.67 mmol) and 3-chloro-6-thiophen-2-yl-pyridazine (0.21 mmol). $^1$H NMR (400 MHz, CDCl$_3$) δ 8.05 (1H, d, J=9.8 Hz), 7.66 (1H, dd, J=3.8 Hz, 1.3 Hz), 7.55 (1H, dd, J=5.0 Hz, 1.0 Hz), 7.53 (2H, m), 7.46 (1H, d, J=9.9 Hz), 7.31 (2H, m), 7.24 (1H, t, J=7.5 Hz), 7.17 (1H, dd, J=5.0 Hz, 3.8 Hz), 4.60 (2H, s). ESI-MS (m/z): Calcd for C$_{16}$H$_{12}$N$_4$S: 292.1; found 293.2 (M+H).

EXAMPLE 25

3-(4-Methoxy-benzyl)-6-thiophen-2-yl-[1,2,4]triazolo[4,3-b]pyridazine

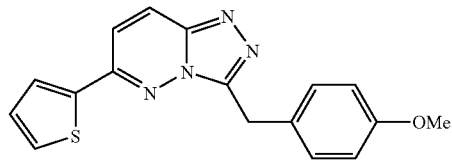

The title compound was prepared as described in Example 17 from 4-methoxy-phenylacetic acid hydrazide (1.39 mmol) and 3-chloro-6-thiophen-2-yl-pyridazine (0.32 mmol) as a pale orange solid. $^1$H NMR (CD$_3$OD) δ 8.17 (1H, d, J=9.8 Hz), 7.92 (1H, dd, J=3.8 Hz, 1.2 Hz), 7.88 (1H, d, J=9.9 Hz), 7.74 (1H, dd, J=5.0 Hz, 1.0 Hz), 7.40 (2H, d, J=8.8 Hz), 7.23 (1H, dd, J=5.0 Hz, 3.8 Hz), 6.88 (2H, d, J=8.9 Hz,), 4.51 (s, 2H), 3.75 (3H, s). ESI-MS (m/z): Calcd for C$_{17}$H$_{14}$N$_4$OS: 322.1; found 323.2 (M+H).

EXAMPLE 26

3-(4-Fluoro-benzyl)-6-thiophen-2-yl-[1,2,4]triazolo[4,3-b]pyridazine

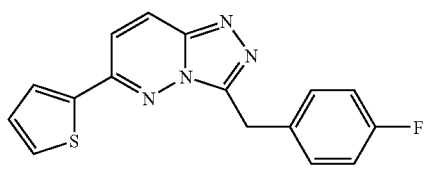

The title compound was prepared as described in Example 17 from 4-fluorophenylacetic acid hydrazide (1.04 mmol) and 3-chloro-6-thiophen-2-yl-pyridazine (0.52 mmol) as a pale beige solid. $^1$H NMR (CD$_3$OD) δ 8.19 (1H, d, J=9.9 Hz), 7.93 (1H, dd, J=3.8 Hz, 0.9 Hz), 7.90 (1H, d, J=9.9 Hz), 7.75 (1H, dd, J=5.0 Hz, 1.0 Hz), 7.50 (2H, dd, J=9.0 Hz, 5.3 Hz), 7.24 (1H, dd, J=5.3 Hz, 3.8 Hz), 7.06 (2H, t, J=8.8 Hz), 4.59 (2H, s). ESI-MS (m/z): Calcd for C$_{16}$H$_{11}$FN$_4$S: 310.1; found 311.2 (M+H).

EXAMPLE 27

3-(4-Nitro-benzyl)-6-thiophen-2-yl-[1,2,4]triazolo[4,3-b]pyridazine

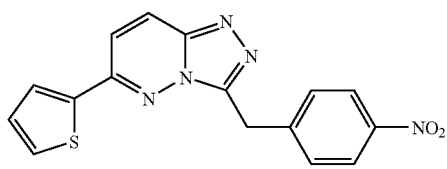

EXAMPLE 27

Step a

4-Nitrophenylacetic acid hydrazide

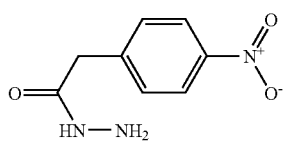

A solution of 4-nitrophenylacetic acid (2.81 mmol) in dry dichloromethane (10 mL) was treated with a 2N solution of oxalyl chloride (3.0 mL) and DMF (0.02 mL) via syringe, and the reaction stirred at ambient temperature for 1 h. The reaction was concentrated to dryness in vacuo and the crude product was dissolved in dry dichloro-methane (20 mL), treated with anhydrous hydrazine (11.1 mmol) via syringe, and stirred at ambient temperature for 18 h. The resulting suspension was filtered, solids rinsed with dichloromethane, dissolved in MeOH/CH$_2$Cl$_2$, filtered, and filtrate concentrated in vacuo giving the title compound as an orange solid. $^1$H NMR (DMSO-d$_6$) δ 8.17 (2H, d, J=8.8 Hz,), 7.54 (2H, d, J=8.8 Hz), 3.54 (2H, s).

EXAMPLE 27

Step b 3-(4-Nitro-benzyl)-6-thiophen-2-yl-[1,2,4]triazolo[4,3-b]pyridazine

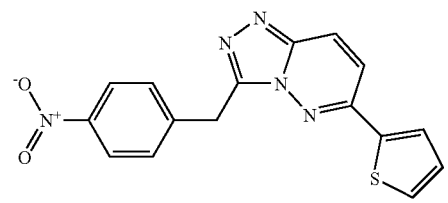

The title compound was prepared as a pale tan solid from the product of the preceding step (0.52 mmol) and 3-chloro-6-thiophen-2-yl-pyridazine (0.27 mmol), as prepared in Example 17: step a by the method of Example 16: step b. $^1$H NMR (CDCl$_3$) δ 8.18 (2H, d, J=8.8 Hz,), 8.09 (1H, d, J=9.7 Hz,), 7.67 (3H, m), 7.58 (1H, dd, J=5.0 Hz, 1.0 Hz), 7.51 (1H, d, J=9.8 Hz), 7.19 (1H, dd, J=5.1 Hz, 3.7 Hz), 4.70 (2H, s). ESI-MS (m/z): Calcd for C$_{16}$H$_{11}$N$_5$O$_2$S: 337.1; found 338.2 (M+H).

EXAMPLE 28

4(6-Thiophen-2-yl-[1,2,4]triazolo[4,3-b]pyridazin-3-ylmethyl)-phenylamine

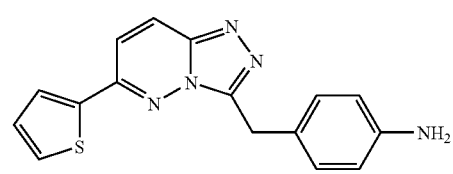

The product of the preceding example (0.20 mmol) was hydrogenated over 10 wt. % palladium (0) on carbon (9 mg) in 2:1 EtOH/THF (12 mL) at ambient temperature and pressure for 2 days, filtered over Celite 521, concentrated, and purified twice by preparative TLC (10% MeOH/CH$_2$Cl$_2$ on silica) giving the title compound as a pale yellow solid. $^1$H NMR (CDCl$_3$/CD$_3$OD) δ 8.08 (1H, d, J=10.0 Hz), 7.78 (1H, dd, J=3.8 Hz, 1.0 Hz), 7.67 (1H, d, J=9.9 Hz), 7.63 (1H, dd, J=5.0 Hz, 1.0 Hz), 7.29 (2H, d, J=8.6 Hz), 7.21 (1H, dd, J=5.0 Hz, 3.8 Hz), 6.69 (2H, d, J=8.6 Hz), 4.03 (2H, s). ESI-MS (m/z): Calcd for C$_{16}$H$_{13}$N$_5$S: 307.1; found 308.2 (M+H).

EXAMPLE 29

N-[4(6-Thiophen-2-yl-[1,2,4]triazolo[4,3-b]pyridazin-3-ylmethyl)-phenyl]-acetamide

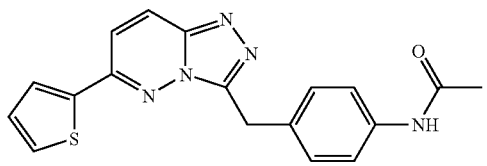

The product of the preceding example (0.09 mmol) was treated with acetyl chloride (0.14 mmol) and triethylamine (1.43 mmol) in anhydrous $CH_2Cl_2$ (5 mL) at ambient temperature for 24 h, concentrated, and purified by preparative TLC (10% MeOH/$CH_2Cl_2$ on silica) giving the title compound as a pale yellow solid. $^1$H NMR ($CD_3OD$) δ 8.18 (1H, d, J=9.7 Hz), 7.93 (1H, m), 7.90 (1H, d, J=9.7 Hz), 7.75 (1H, dd, J=5.1 Hz, 1.1 Hz), 7.52 (2H, m), 7.42 (2H, m), 7.24 (1H, dd, J=5.1 Hz, 3.8 Hz), 4.56 (2H, s), 2.10 (3H, s). ESI-MS (m/z): Calcd for $C_{18}H_{15}N_5OS$: 349.1; found 350.3 (M+H).

EXAMPLE 30

1-Ethyl-3-[4-(6-thiophen-2-yl-[1,2,4]triazolo[4,3-b]pyridazin-3-ylmethyl)-phenyl]-urea

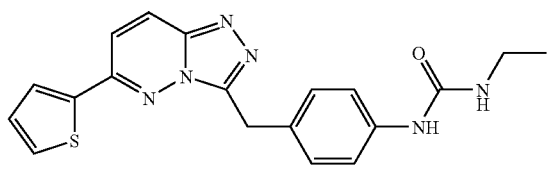

The product of Example 32 (0.12 mmol) was treated with ethyl isocyanate (0.19 mmol) and triethylamine (0.72 mmol) in anhydrous $CH_2Cl_2$ (5 mL) at ambient temperature for 18 h, concentrated, and purified twice by preparative TLC (10% MeOH/$CH_2Cl_2$ then 7.5% MeOH/$CH_2Cl_2$ on silica) giving the title compound as a yellow solid. $^1$H NMR ($CDCl_3$/$CD_3OD$) δ 8.05 (1H, d, J=9.9 Hz), 7.70 (1H, dd, J=3.8 Hz, 1.2 Hz), 7.59 (1H, dd, J=5.0 Hz, 1.0 Hz), 7.55 (1H, d, J=9.7 Hz), 7.40 (2H, d, J=8.5 Hz), 7.28 (2H, d, J=8.7 Hz), 7.18 (1H dd, J=5.0 Hz, 3.8 Hz), 4.51 (2H s,), 3.21 (2H, q, J=7.3 Hz), 1.11 (3H, t, J=7.3 Hz). ESI-MS (m/z): Calcd for $C_{19}H_{18}N_6OS$: 378.1; found 379.2 (M+H).

EXAMPLE 31

3-(6-Methoxy-pyridin-3-ylmethyl)-6-thiophen-2-yl-[1,2,4]triazolo[4,3-b]pyridazine

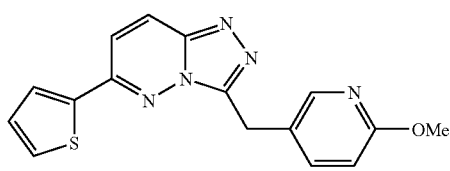

EXAMPLE 31

Step a (6-Methoxy-pyridin-3-yl)-methanol

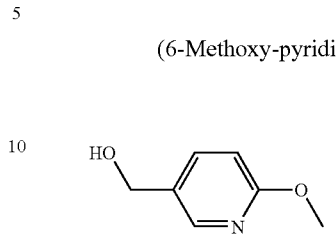

A solution of methyl 6-methoxy-nicotinate (50 mmol) in anhydrous methanol (60 mL) was treated with sodium borohydride (122 mmol) at 0° C., warmed to ambient temperature for 18 h, then heated to reflux for 6 h. The incomplete reaction product was concentrated to dryness in vacuo, dissolved in anhydrous 1,4-dioxane (70 mL), treated with more sodium borohydride (122 mmol), and heated to reflux for 18 h. After cooling to ambient temperature, the reaction was quenched with methanol, filtered over a coarse glass frit, solids washed with methanol, and the filtrate concentrated. The residue was repeatedly dissolved in methanol, filtered, and concentrated in vacuo until no solids remained, then triturated with 10% MeOH/$CH_2Cl_2$, filtered, and concentrated. The impure product was then adsorbed onto silica gel, poured onto a 9.5×5.5 cm plug of silica gel, and eluted with a gradient of 0 to 15% MeOH/$CHCl_3$, and the pure fractions concentrated in vacuo giving the title compound as a pale yellow oil. $^1$H NMR ($CDCl_3$) δ 8.08 (1H, d, J=2.5 Hz), 7.61 (1H, dd, J=8.5 Hz, 2.4 Hz), 6.74 (1H, d, J=8.5 Hz), 4.60 (2H, s), 3.92 (3H, s).

EXAMPLE 31

Step b

Sulfuric acid 6-methoxy-pyridin-3-ylmethyl ester methyl ester

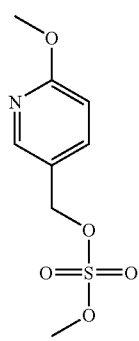

The product of the preceding step (31.3 mmol) was dissolved in anhydrous dichloromethane (30 mL) and triethylamine (6.5 mL), treated dropwise with methanesulfonyl chloride (38.7 mmol) at ambient temperature, and the reaction stirred for 2 d. The reaction was washed with water, the aqueous layer extracted 3 times with $CH_2Cl_2$, combined organic layers washed with brine, dried over $Na_2SO_4$, filtered, and the filtrate was concentrated in vacuo giving the title compound as a yellow oil. $^1$H NMR ($CDCl_3$) δ 8.09 (1H, d, J=2.3 Hz), 7.65 (1H, dd, J=8.5 Hz, 2.4 Hz), 6.77 (1H d, J=8.5 Hz), 4.57 (2H, s), 3.93 (3H, s), 3.41 (3H, s).

EXAMPLE 31

Step c (6-Methoxy-pyridin-3-yl)-acetonitrile

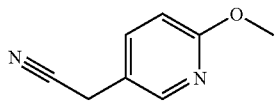

The product of the preceding step (17.0 mmol) was dissolved in anhydrous acetonitrile (35 mL), treated with sodium cyanide (41.6 mmol), and heated to reflux for 2 d. The reaction was concentrated to dryness in vacuo, the crude product purified by flash chromatography on silica gel (gradient elution, 0 to 30% EtOAc/CHCl$_3$), and the pure column fractions concentrated in vacuo giving the title compound as a white solid. $^1$H NMR (CDCl$_3$) δ 8.10 (1H, d, J=1.6 Hz), 7.56 (1H, dd, J=8.5 Hz, 2.3 Hz), 6.78 (1H, d, J=8.6 Hz), 3.94 (3H, s), 3.67 (2H, s).

EXAMPLE 31

Step d (6-Methoxy-pyridin-3-yl)-acetic acid

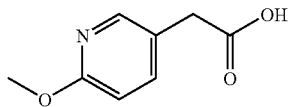

The product of the preceding step (14.2 mmol) was dissolved in reagent ethanol (35 mL), treated with a solution of potassium hydroxide (56.7 mmol) in water (35 mL), and heated to reflux for 20 h. The reaction was concentrated to dryness in vacuo, the residue dissolved in water, acidified to pH 5 with aqueous 10% v/v HCl, and again concentrated to dryness in vacuo. The crude product was triturated with 10% MeOH/CHCl$_3$, filtered, and the filtrate concentrated and dried in vacuo overnight giving the title compound as a very hygroscopic pale yellow solid. $^1$H NMR (400 MHz, DMSO-d$_6$) δ 7.91 (1H, s), 7.57 (1H, dd, J=8.5 Hz, 1.8 Hz), 6.65 (1H, d, J=8.6 Hz), 3.79 (3H, s), 3.51 (1H, bs), 3.13 (2H, s). ESI-MS (m/z): Calcd for C$_8$H$_9$NO$_3$: 167.1; found 168.2 (M+H).

EXAMPLE 31

Step e (6-Methoxy-pyridin-3-yl)-acetic acid methyl ester

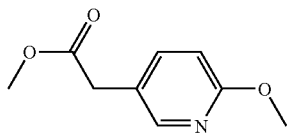

The product of the preceding step (7.88 mmol) was dissolved in dry methanol under argon, cooled to −10° C., and treated with thionyl chloride (20.5 mmol) via syringe. After warming to ambient temperature and stirring overnight, the reaction was concentrated in vacuo, and the residue dissolved in CH$_2$Cl$_2$. The solution was washed with saturated aqueous NaHCO$_3$ and brine, dried over Na$_2$SO$_4$, filtered, and the filtrate concentrated in vacuo giving the title compound as a light yellow oil. $^1$H NMR (CDCl$_3$) δ 8.04 (1H, d, J=2.4 Hz), 7.53 (1H, dd, J=8.5 Hz, 2.5 Hz), 6.73 (1H, d, J=8.6 Hz), 3.92 (3H, s), 3.70 (3H, s), 3.55 (2H, s).

EXAMPLE 31

Step f (6-Methoxy-pyridin-3-yl)-acetic acid hydrazide

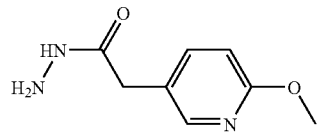

The title compound was prepared as a white solid from the product of the preceding step (5.34 mmol) by the method of Example 17: step b. $^1$H NMR (400 MHz, DMSO-d$_6$) δ 9.20 (bs, 1H), 8.00 (d, J=2.6 Hz, 1H), 7.58 (dd, J=8.4 Hz, 2.5 Hz, 1H), 6.75 (d, J=8.3 Hz, 1H), 4.21 (bs, 2H), 3.81 (s, 3H), 3.29 (s, 2H). ESI-MS (m/z): Calcd for C$_8$H$_{11}$N$_3$O$_2$: 181.1; found 182.1 (M+H).

EXAMPLE 31

Step g 3-(6-Methoxy-pyridin-3-ylmethyl)-6-thiophen-2-yl-[1,2,4]triazolo[4,3-b]pyridazine

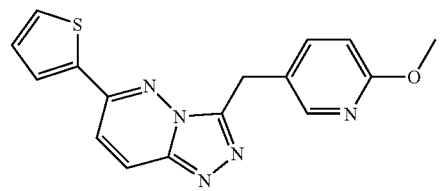

The title compound was prepared as described in Example 17 from the product of the preceding step (1.40 mmol) and 3-chloro-6-thiophen-2-yl-pyridazine (0.58 mmol) as pale yellow solid. $^1$H NMR (CD$_3$OD) δ 8.29 (1H, d, J=2.5 Hz), 8.19 (1H, d, J=9.9 Hz), 7.93 (1H, dd, J=3.8 Hz, 1.3 Hz), 7.90 (1H, d, J=9.9 Hz), 7.78 (1H, dd, J=8.6 Hz, 2.5 Hz), 7.75 (1H, dd, J=5.1 Hz, 1.1 Hz), 7.24 (1H, dd, J=5.1 Hz, 3.8 Hz), 6.78 (1H, d, J=8.6 Hz), 4.54 (2H, s), 3.88 (3H, s). ESI-MS (m/z): Calcd for C$_{16}$H$_{13}$N$_5$OS: 323.1; found 324.2 (M+H).

EXAMPLE 32

5-(6-Thiophen-2-yl-[1,2,4]triazolo[4,3-b]pyridazin-3-ylmethyl)-1H-pyridin-2-one

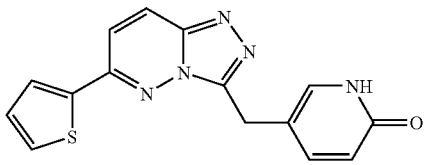

The product of the preceding example (0.23 mmol) was dissolved in anhydrous dichloromethane (10 mL), treated with a 1N solution of boron tribromide (4.0 mL) in $CH_2Cl_2$, and heated to reflux for 2 d. The reaction was concentrated to dryness in vacuo, dissolved in EtOAc, and extracted with aqueous $NaHCO_3$ and NaCl. The combined aqueous layers were concentrated to dryness in vacuo and triturated with 10% $MeOH/CH_2Cl_2$, filtered, and the evaporated filtrate purified by preparative TLC (15% $MeOH/CH_2Cl_2$ on silica) giving the title compound as a pale yellow solid. $^1$H NMR ($CD_3OD$) δ 8.21 (1H, d, J=9.9 Hz), 7.96 (1H, m), 7.93 (1H, d, J=9.8 Hz), 7.76 (1H, m), 7.73 (1H, dd, J=9.4 Hz, 2.5 Hz), 7.62 (1H, m), 7.26 (1H, dd, J=5.3 Hz, 3.8 Hz), 6.54 (1H, d, J=9.6 Hz), 4.42 (2H, s). ESI-MS (m/z): Calcd for $C_{15}H_{11}N_5OS$: 309.1; found 310.3 (M+H).

EXAMPLE 33

3-Pyridin-4-ylmethyl-6-thiophen-2-yl-[1,2,4]triazolo[4,3-b]pyridazine

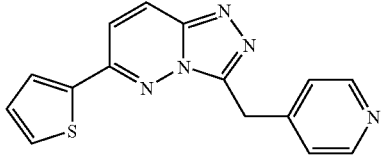

The title compound was prepared as described in Example 17 from 4-pyridineacetic acid hydrazide (1.81 mmol) and 3-chloro-6-thiophen-2-yl-pyridazine (0.58 mmol) as a pale yellow solid. $^1$H NMR ($CD_3OD$) δ 8.50 (2H dd, J=4.6 Hz, 1.4 Hz), 8.22 (1H d, J=9.6 Hz), 7.94 (1H, dd, J=3.8 Hz, 1.2 Hz), 7.93 (1H, d, J=9.8 Hz), 7.74 (1H, dd, J=5.0 Hz, 1.0 Hz), 7.52 (2H, m), 7.23 (1H, dd, J=5.3 Hz, 3.8 Hz), 4.69 (2H, s). ESI-MS (m/z): Calcd for $C_{15}H_{11}N_5S$: 293.1; found 294.2 (M+H).

EXAMPLE 34

3-(1-Oxy-pyridin-4-ylmethyl)-6-thiophen-2-yl-[1,2,4]triazolo[4,3-b]pyridazine

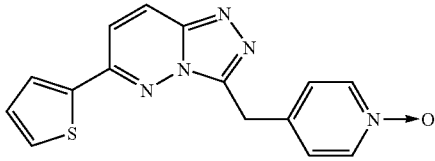

The product of the preceding example (0.20 mmol) was treated with 3-chloroperoxybenzoic acid (0.26 mmol) in $CHCl_3$ at 0° C., warmed to ambient temperature over 5 h, washed with aqueous $NaHCO_3$, water, and brine, and the combined aqueous layers extracted with $CH_2Cl_2$. The combined organic layers were dried over $Na_2SO_4$, filtered, and the evaporated filtrate purified by preparative TLC (10% MeOH/$CH_2Cl_2$ on silica) giving the title compound as a pale yellow solid. $^1$H NMR ($CD_3OD$) δ 8.32 (2H, m), 8.24 (1H, d, J=9.9 Hz), 7.95 (1H, dd, J=3.8 Hz, 1.1 Hz), 7.94 (1H, d, J=9.8 Hz), 7.75 (1H, dd, J=5.1 Hz, 1.1 Hz), 7.65 (2H, d, J=7.1 Hz), 7.24 (1H, dd, J=5.1 Hz, 3.8 Hz), 4.72 (2H, s). ESI-MS (m/z): Calcd for $C_{15}H_{11}N_5OS$: 309.1; found 310.3 (M+H).

EXAMPLE 35

3-Benzofuran-5-ylmethyl-6-thiophen-2-yl-[1,2,4]triazolo[4,3-b]pyridazine

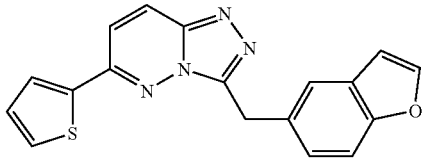

EXAMPLE 35

Step a

5-Bromomethyl-benzofuran

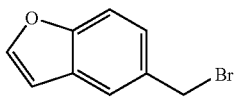

N-bromosuccinimide (5.0 mmol) was added to a solution of 2,3-dihydrobenzofuran-5-ylacetic acid (5.0 mmol) and benzoyl peroxide (10 mg) in carbon tetrachloride (100 mL) and refluxed for 3 h. The mixture was cooled to room temperature, filtered and concentrated. The product was recrystallized from ethyl acetate:hexane (2:1) to giving the title compound as a white solid. $^1$H NMR ($CD_3OD$) δ 7.62 (1H, d, J=2.4 Hz), 7.52 (1H, d, J=0.8 Hz), 7.46 (1H, d, J=8.4 Hz), 7.21 (1H, dd, J=1.6, 8.4 Hz), 6.74 (1H, d, J=3.2 Hz), 3.74 (2H, s).

EXAMPLE 35

Step b

Benzofuran-5-yl-acetic acid

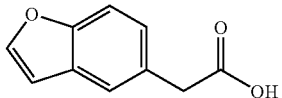

N-bromosuccinimide (0.89 g, 5.0 mmol) was added to a solution of 2,3-dihydrobenzofuran-5-ylacetic acid (0.89 g, 5.0 mmol) and benzoyl peroxide (10 mg) in carbon tetrachloride (100 mL) and refluxed for 3 hours. The mixture was cooled to room temperature, filtered and concentrated. The product was recrystallized from ethyl acetate:hexane (2:1) to give a 0.39 g (44%) of white solid. $^1$H NMR ($CD_3OD$) δ 7.62

(1H, d, J=2.4 Hz), 7.52 (1H, d, J=0.8 Hz), 7.46 (1H, d, J=8.4 Hz), 7.21 (1H, dd, J=1.6, 8.4 Hz), 6.74 (1H, d, J=3.2 Hz), 3.74 (2H, s).

EXAMPLE 35

Step c

Benzofuran-5-yl-acetic acid hydrazide

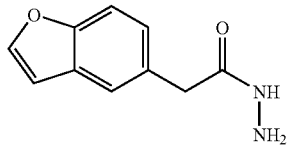

The title compound was prepared as a yellow solid from the product of the preceding step (1.15 mmol) by the method of Example 17: step b. $^1$H NMR (400 MHz, DMSO-$d_6$) δ 9.22 (1H, bs), 7.96 (1H, d, J=2.2 Hz), 7.53 (1H, d, J=1.5 Hz), 7.50 (1H d, J=8.6 Hz), 7.20 (1H, dd, J=8.4 Hz, 2.0 Hz), 6.93 (1H, dd, J=2.2 Hz, 1.0 Hz), 4.24 (2H, bs), 3.43 (2H, s).

EXAMPLE 35

Step d

3-Benzofuran-5-ylmethyl-6-thiophen-2-yl-[1,2,4]triazolo[4,3-b]pyridazine

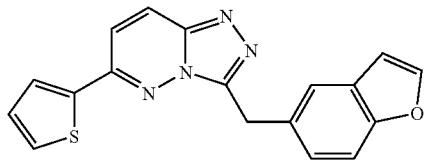

The title compound was prepared as described in Example 17 from the product of the preceding step (0.63 mmol) and 3-chloro-6-thiophen-2-yl-pyridazine (0.34 mmol) as a pale yellow solid. $^1$H NMR (400 MHz, CDCl$_3$) δ 8.04 (1H, d, J=9.9 Hz), 7.75 (1H, d, J=1.3 Hz), 7.66 (1H, dd, J=3.8 Hz, 1.1 Hz), 7.58 (1H, d, J=2.3 Hz), 7.56 (1H, dd, J=5.2 Hz, 1.1 Hz), 7.46 (3H, m), 7.17 (1H, dd, J=5.0 Hz, 3.8 Hz), 6.72 (1H, m), 4.69 (2H, s). ESI-MS (m/z): Calcd for C$_{18}$H$_{12}$N$_4$OS: 332.1; found 333.3 (M+H).

EXAMPLE 36

3-Benzo[b]thiophen-5-ylmethyl-6-thiophen-2-yl-[1,2,4]triazolo[4,3-b]pyridazine

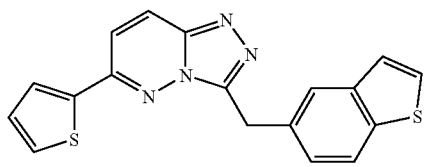

EXAMPLE 36

Step a

Benzo[b]thiophen-5-yl-acetic acid

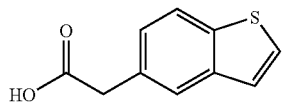

The title compound was made by treated 5-methylbenzothiophene with NBS in carbon tetrachloride, followed by the treatment with sodium cyanide in DMF and then refluxed with aqueous sodium hydroxide in ethanol. $^1$H NMR (CD$_3$OD) δ 8.02-8.00 (1H, d, J=8.2 Hz), 7.84-7.83 (1H, m), 7.82 (1H, s), 7.51-7.50 (1H, d, J=5.0 Hz), 7.35-7.33 (1H, d, J=9.7 Hz), 3.76 (2H, s).

EXAMPLE 36

Step b

Benzo[b]thiophen-5-yl-acetic acid hydrazide

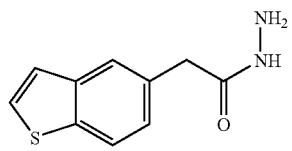

The title compound was prepared as a yellow solid from the product of the preceding step (1.08 mmol) by the method of Example 17: step b. $^1$H NMR (400 MHz, DMSO-$d_6$) δ 9.24 (1H, bs), 7.91 (1H, d, J=8.3 Hz), 7.75 (1H, d, J=1.0 Hz), 7.73 (1H, d, J=5.8 Hz), 7.42 (1H, d, J=5.3 Hz), 7.26 (1H, dd, J=8.3 Hz, 1.8 Hz), 4.21 (2H, bs), 3.46 (2H, s). ESI-MS (m/z): Calcd for C$_{10}$H$_{10}$N$_2$OS: 206.1; found 207.1 (M+H).

EXAMPLE 36

Step c

3-Benzo[b]thiophen-5-ylmethyl-6-thiophen-2-yl-[1,2,4]triazolo[4,3-b]pyridazine

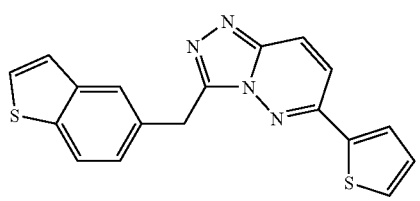

The title compound was prepared as described in Example 17 from the product of the preceding step (0.53 mmol) and 3-chloro-6-thiophen-2-yl-pyridazine (0.26 mmol) as a pale yellow solid. $^1$H NMR (CD$_3$OD) δ 8.17 (1H, d, J=9.9 Hz), 7.98 (1H, m), 7.90 (1H, dd, J=3.8 Hz, 1.0 Hz), 7.86 (1H, d, J=9.8 Hz), 7.85 (1H, d, J=8.4 Hz), 7.74 (1H, dd, J=5.0 Hz, 1.3 Hz), 7.55 (1H, d, J=5.5 Hz), 7.46 (1H, dd, J=8.3 Hz, 1.7 Hz), 7.34 (1H, d, J=5.6 Hz), 7.22 (1H, dd, J=5.0 Hz, 3.8 Hz), 4.71 (2H, s). ESI-MS (m/z): Calcd for $C_{18}H_{12}N_4S_2$: 348.1; found 349.2 (M+H).

EXAMPLE 37

3-Benzo[1,3]dioxol-5-ylmethyl-6-thiophen-2-yl-[1,2,4]triazolo[4,3-b]pyridazine

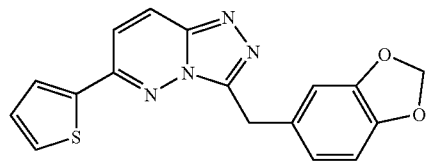

EXAMPLE 37

Step a

Benzo[1,3]dioxol-5-yl-acetic acid hydrazide

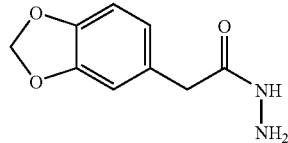

The title compound was prepared as a pale pink solid from 3,4-(methylenedioxy)-phenylacetic acid (1.74 mmol) by the method of Example 17: step b. $^1$H NMR (DMSO-d$_6$) δ 9.13 (1H, bs), 6.82 (1H, d, J=5.3 Hz), 6.81 (1H, d, J=4.4 Hz), 6.69 (1H, dd, J=7.9 Hz, 1.6 Hz), 5.96 (2H, s), 4.18 (1H, d, J=4.3 Hz), 3.24 (2H, s).

EXAMPLE 37

Step b

3-Benzo[1,3]dioxol-5-ylmethyl-6-thiophen-2-yl-[1,2,4]triazolo[4,3-b]pyridazine

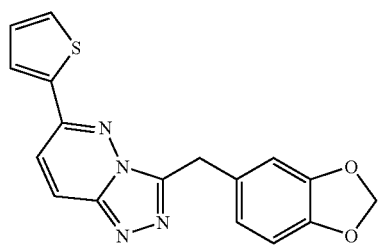

The title compound was prepared as described in Example 17 from the product of the preceding step (0.39 mmol) and 3-chloro-6-thiophen-2-yl-pyridazine (0.21 mmol) as a white solid. $^1$H NMR (CDCl$_3$) δ 8.05 (1H, d, J=9.8 Hz), 7.67 (1H, dd, J=3.8 Hz, 1.2 Hz), 7.56 (1H, dd, J=5.1 Hz, 1.1 Hz), 7.46 (1H, d, J=9.8 Hz), 7.18 (1H, dd, J=5.0 Hz, 3.8 Hz), 7.00 (m, 2H), 6.75 (1H, d, J=7.8 Hz), 5.90 (2H, s), 4.51 (2H, s).
ESI-MS (m/z): Calcd for $C_{18}H_{12}N_4OS$: 336.1; found 337.2 (M+H).

EXAMPLE 38

6-(6-Thiophen-2-yl-[1,2,4]triazolo[4,3-b]pyridazin-3-ylmethyl)-benzothiazol-2-ylamine

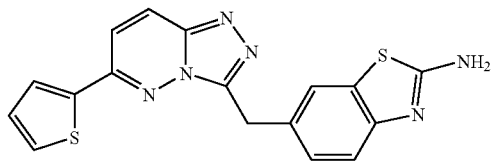

EXAMPLE 38

Step a (2-Amino-benzothiazol-6-yl)-acetic acid ethyl ester

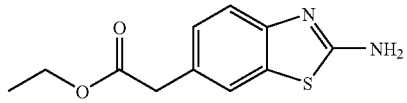

A solution of (2-amino-benzothiazol-6-yl)-acetic acid (0.61 mmol, as prepared by Meyer et al. in *J. Med. Chem.* 1997, 40, 1060) in absolute ethanol (10 mL) was treated with 3 drops of concentrated H$_2$SO$_4$ and ca. 1 g of dry 4A molecular sieves, and heated to reflux for 3 d. The reaction was concentrated to dryness in vacuo, partitioned between CH$_2$Cl$_2$ and saturated aqueous NaHCO$_3$, filtered, and phases separated. The aqueous layer was extracted with CH$_2$Cl$_2$, and the combined organic layers were washed with water and brine, dried over Na$_2$SO$_4$, filtered, and the filtrate concentrated in vacuo giving the title compound as a yellow solid. $^1$H NMR (CDCl$_3$) δ 7.50 (1H, m), 7.41 (1H, d, J=8.3 Hz), 7.20 (1H, dd, J=8.2 Hz, 1.9 Hz), 4.15 (2H, q, J=7.2 Hz), 3.65 (2H, s), 3.42 (4H, s [NH$_2$+H$_2$O]), 1.26 (3H, t, J=7.1 Hz).
ESI-MS (m/z): Calcd for $C_{11}H_{12}N_2O_2S$: 236.1; found 237.1 (M+H).

EXAMPLE 38

Step b (2-Amino-benzothiazol-6-yl)-acetic acid hydrazide

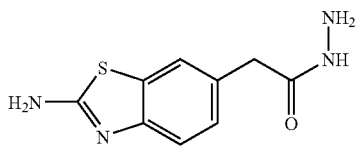

The title compound was prepared as a yellow solid from the product of the preceding step (0.40 mmol) by the method of Example 17: step b. $^1$H NMR (400 MHz, DMSO-d$_6$) δ 9.18 (bs, 1H), 7.51 (d, J=1.5 Hz, 1H), 7.40 (bs, 2H), 7.24 (d, J=8.1

Hz, 1H), 7.08 (dd, J=8.1 Hz, 1.8 Hz, 1H), 4.25 (bs, 2H). Mass spectrum (LCMS, ESI pos.): Calcd for $C_9H_{10}N_4OS$: 222.1; found 223.1 (M+H).

EXAMPLE 38

Step c 6-(6-Thiophen-2-yl-[1,2,4]triazolo[4,3-b]pyridazin-3-ylmethyl)-benzothiazol-2-ylamine

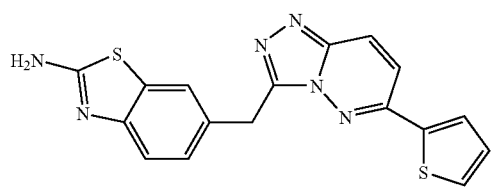

The title compound was prepared as described in Example 17 from the product of the preceding step (0.36 mmol) and 3-chloro-6-thiophen-2-yl-pyridazine (0.22 mmol) as a yellow solid. $^1$H NMR (DMSO-d$_6$) δ 8.36 (1H, d, J=9.8 Hz), 8.08 (1H, dd, J=3.8 Hz, 1.2 Hz), 7.94 (1H, d, J=9.6 Hz), 7.87 (1H dd, J=5.1 Hz, 1.4 Hz), 7.68 (1H, s), 7.41 (2H, m), 7.26 (3H, m), 4.51 (2H, s). ESI-MS (m/z): Calcd for $C_{17}H_{12}N_6S_2$: 364.1; found 365.3 (M+H).

EXAMPLE 39

6-(6-Thiophen-2-yl-[1,2,4]triazolo[4,3-b]pyridazin-3-ylmethyl)-quinoline

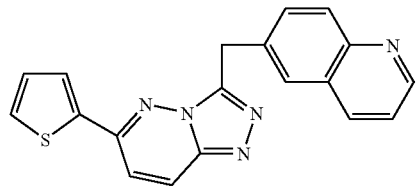

The title compound was prepared as described in Example 17. $^1$H-NMR (CDCl$_3$): δ 8.13-8.11 (1H, d, J=8.5 Hz), 8.08-8.05 (2H, m), 7.96-7.95 (1H, d, J=1.7 Hz), 7.90-7.87 (1H, dd, J=2.0, 2.0 Hz), 7.66-7.65 (1H, dd, J=1.0, 1.0 Hz), 7.57-7.56 (1H, dd, J=1.3, 1.3 Hz), 7.48-7.46 (1H, d, J=9.8 Hz), 7.38-7.35 (1H, q, J=4.2 Hz), 7.18-7.16 (1H, dd, J=3.7 Hz), 4.79 (2H, s). ESI-MS (m/z): Calcd. For $C_{19}H_{13}N_5S$: 343.04; found: 344.3 (M+H).

EXAMPLE 40

3-(2,3-Dihydro-benzofuran-5-ylmethyl)-6-(5-morpholin-4-ylmethyl-furan-2-yl)-[1,2,4]triazolo[4,3-b]pyridazine

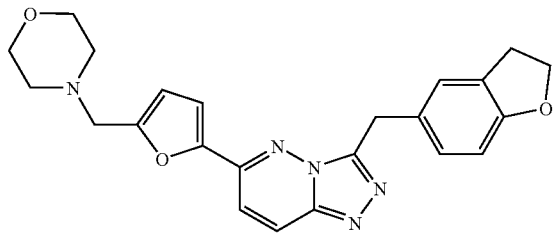

EXAMPLE 40

Step a

6-Chloro-3-(2,3-dihydro-benzofuran-5-ylmethyl)-[1,2,4]triazolo[4,3-b]pyridazine

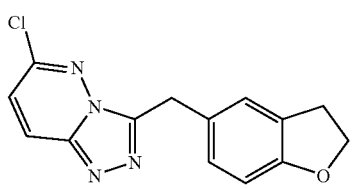

(2,3-Dihydro-benzofuran-5-yl)-acetic acid hydrazide (633 mg, 3.3 mmol) and 3,6-dichloropyridizine (Aldrich, 447 mg, 3.0 mmol) were combined and dissolved in butanol (120 mL). The reaction mixture was heated to 120° C. overnight. The reaction mixture turned yellow and cloudy. After cooling to rt the reaction was filtered and washed with MeOH yielding the desired product (816 mg, 95%) as a tan solid. $^1$H-NMR (CD$_3$OD): δ 8.06-8.03 (1H, d, J=9.6 Hz), 7.27 (1H, s), 7.08-7.06 (1H, d, J=9.6 Hz), 6.72-6.70 (1H, d, J=8.6 Hz), 4.55-4.50 (2H, t, J=8.8 Hz), 4.46 (2H, s), 3.18-3.14 (2H, t, J=8.58 Hz).

EXAMPLE 40

Step b

5-[3-(2,3-Dihydro-benzofuran-5-ylmethyl)-[1,2,4]triazolo[4,3-b]pyridazin-6-yl]-furan-2-carbaldehyde

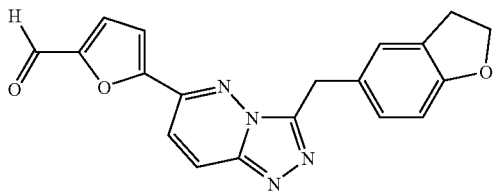

The general procedure for Suzuki cross coupling as described in Example 1 was followed using 2-carbaldehyde-furan-5-boronic acid (24 mg, 0.7 mmol) and 6-Chloro-3-(2,3-dihydro-benzofuran-5-ylmethyl)-[1,2,4]triazolo[4,3-b]pyridazine (41 mg, 0.14 mmol). ESI-MS (m/z): Calcd. For $C_{19}H_{14}N_4O_3$: 347.2; found: 346.11 (M+H).

EXAMPLE 40

Step c 3-(2,3-Dihydro-benzofuran-5-ylmethyl)-6-(5-morpholin-4-ylmethyl-furan-2-yl)-[1,2,4]triazolo[4,3-b]pyridazine

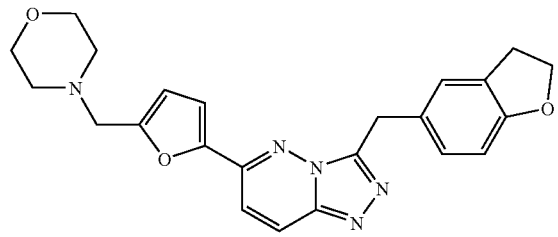

5-[3-(2,3-Dihydro-benzofuran-5-ylmethyl)-[1,2,4]triazolo[4,3-b]pyridazin-6-yl]-furan-2-carbaldehyde (21.6 mg, 0.06 mmol), morpholine (6.5 μL, 0.07 mmol) and AcOH (2 drops) were combined in DCM (1 mL). To this was added sodium triacetoxyborohydride (19 mg, 0.09 mmol) and the reaction was stirred at rt for 2 hours. The reaction was concentrated in vacuo followed by purification by HPLC (5-65% CH$_3$CN over 35 min) resulting in the title compound (5.9 mg, 27%) as a solid. $^1$H-NMR (CD$_3$OD/CDCl$_3$): δ 8.23-8.21 (1H, d, J=9.6 Hz), 7.81-7.78 (1H, d, J=9.8 Hz), 7.42-7.41 (1H, d, J=3.5 Hz), 7.22 (1H, s), 7.17-7.15 (1H, d, J=9.6 Hz), 6.99-6.98 (1H, d, J=3.5 Hz), 6.67-6.65 (1H, d, J=8.3 Hz), 4.57 (2H, s), 4.45-4.38 (4H, m), 3.94 (4H, br s), 3.40-3.33 (4H, m), 3.17-3.13 (2H, t, J=8.8 Hz). ESI-MS (m/z): Calcd. For C$_{23}$H$_{23}$N$_5$O$_3$: 417.18; found: 418.3 (M+H).

EXAMPLE 41

3-(2,3-Dihydro-benzofuran-5-ylmethyl)-6-(3-methoxy-pyridin-4-yl)-[1,2,4]triazolo[4,3-b]pyridazine

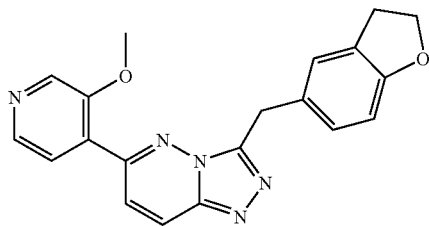

The title compound was prepared as described in Example 40. $^1$H-NMR (CD$_3$OD): δ 8.63 (1H, s), 8.44-8.43 (1H, d, J=5.3 Hz), 8.20-8.17 (1H, d, J=9.8 Hz), 7.88-7.87 (1H, d, J=5.3 Hz), 7.80-7.77 (1H, d, J=9.6 Hz), 7.12 (1H, s), 7.02-7.00 (1H, d, J=8.0 Hz), 6.56-6.54 (1H, d, J=8.3 Hz), 4.44 (2H, s), 4.41-4.37 (2H, t, J=8.3 Hz), 4.00 (3H, s), 3.06-3.01 (2H, t, J=8.3 Hz). ESI-MS (m/z): Calcd. For C$_{20}$H$_{17}$N$_5$O$_2$: 359.14; found: 360.3 (M+H).

EXAMPLE 42

3-(2,3-Dihydro-benzofuran-5-ylmethyl)-6-(5-morpholin-4-ylmethyl-thiophen-2-yl)-[1,2,4]triazolo[4,3-b]pyridazine

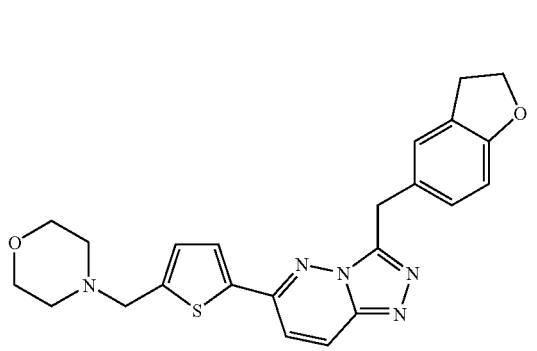

The title compound was prepared as described in Example 40. $^1$H-NMR (CD$_3$OD): δ 8.14-8.12 (1H, d, 9.8 Hz), 7.85- 7.84 (1H, d, J=3.7 Hz), 7.81-7.79 (1H, d, J=9.8 Hz), 7.35-7.34 (1H, d, J=3.7 Hz), 7.13 (1H, s), 7.08-7.06 (1H, d, J=8.8 Hz), 6.56-6.54 (1H, d, J=8.0 Hz), 4.60 (2H, s), 4.40-4.36 (4H, m), 3.84 (2H, br s), 3.29 (2H, br s), 3.21 (2H, m), 3.05-3.01 (2H, t, J=8.8 Hz). ESI-MS (m/z): Calcd. For C$_{23}$H$_{23}$N$_5$O$_2$S: 433.16; found: 434.3 (M+H).

EXAMPLE 43

6-(6-Imidazol-1-yl-[1,2,4]triazolo[4,3-b]pyridazin-3-ylmethyl)-quinoline

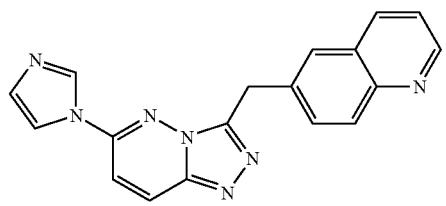

A mixture of 6-(6-Chloro-[1,2,4]triazolo[4,3-b]pyridazin-3-ylmethyl)-quinoline, imidazole, and potassium carbonate were stirred in DMF (3 mL) for 8 h at 100° C. Aqueous HCl (0.5 N) was added and the volatiles were removed in vacuo. Purification by HPLC (5-35% B over 45 min) yielded the product as a TFA salt. The residue was dissolved in aq 1N HCl (5 mL) and the volatiles removed in vacuo. After two repetitions, the product-dihydrochloride was dried under high vacuum to yield a glassy solid (53 mg, 44% yield). $^1$H-NMR (CD$_3$OD): δ 9.60 (1H, s), 9.17 (1H, dd, J=1.5, 5.3 Hz), 9.10 (1H, m), 8.58 (1H, d, J=9.9 Hz), 8.38 (1H, m), 8.36 (1H, m), 8.27 (1H, m), 8.23 (1H, m), 8.05 (1H, dd, J=5.3, 8.3 Hz), 7.98 (1H, d, J=9.9 Hz), 7.72 (1H, s), 5.12 (2H, s), 4.98 (2H, m). ESI-MS (m/z): Calcd. for C$_{18}$H$_{13}$N$_7$: 327.1; found: 328.3 (M+H).

EXAMPLE 44

6-[6-(4-Bromo-imidazol-1-yl)-[1,2,4]triazolo[4,3-b]pyridazin-3-ylmethyl]-quinoline

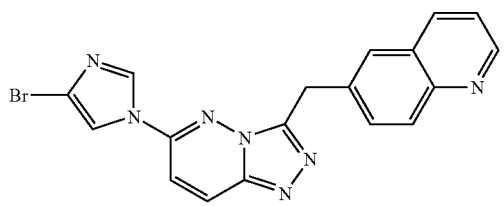

The title compound was prepared as described in Example 43. $^1$H-NMR (CD$_3$OD): δ 9.21 (2H, m), 8.72 (1H, d, J=1.5 Hz), 8.59 (1H, d, J=9.9 Hz), 8.45 (1H, m), 8.32 (1H, dd, J=1.8, 8.8 Hz), 8.27 (1H, br d, J=8.8), 8.17 (1H, d, J=1.5 Hz), 8.11 (1H, dd, J=5.7, 8.3 Hz), 8.10 (1H, d, J=9.9 Hz), 5.01 (2H, s). ESI-MS (m/z): Calcd. for C$_{18}$H$_{12}$BrN$_7$: 405.0/406.0; found: 406.3/408.3 (M+H/M+H+2).

EXAMPLE 45

4(6-Imidazol-1-yl-[1,2,4]triazolo[4,3-b]pyridazin-3-ylmethyl)-phenol

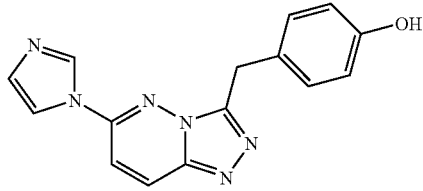

EXAMPLE 45

Step a 4-(6-Chloro-[1,2,4]triazolo[4,3-b]pyridazin-3-ylmethyl)-phenol

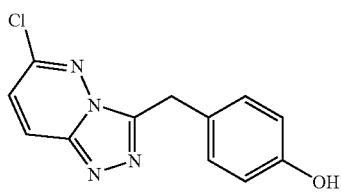

(4-Hydroxy-phenyl)-acetic acid hydrazide (log, 0.06 mol) and 3,6-dichloropyridizine (Aldrich, 8.96 g, 0.06 mol) were combined and dissolved in butanol (120 mL). The reaction mixture was heated to 100° C. overnight. The reaction mixture turned yellow and cloudy. After cooling to rt the reaction was filtered and washed with MeOH yielding the desired product (11.5 g, 36%) as a yellow brown solid. $^1$H-NMR (CD$_3$OD): δ 9.3 (1H, br s), 8.44-8.42 (1H, d, J=9.6 Hz), 7.48-7.45 (1H, d, J=9.6 Hz), 7.12-7.09 (2H, d, J=8.6 Hz), 6.70-6.68 (2H, d, J=8.6 Hz), 4.35 (2H, s).

ESI-MS (m/z): Calcd. For C$_{12}$H$_9$ClN$_4$O: 260.05; found: 261.2 (M+H).

EXAMPLE 45

Step b 4-(6-Imidazol-1-yl-[1,2,4]triazolo[4,3-b]pyridazin-3-ylmethyl)-phenol

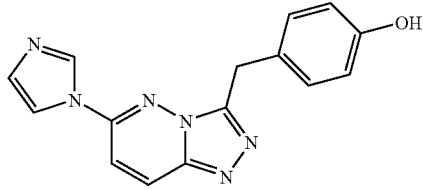

The title compound was prepared from 4-(6-Chloro-[1,2,4]triazolo[4,3-b]pyridazin-3-ylmethyl)-phenol (Example 45: step a) and imidazole as described in Example 43. $^1$H-NMR (CD$_3$OD): δ 9.78 (1H, t, J=1.3 Hz), 8.54 (1H, d, J=9.9 Hz), 8.38 (1H, t, J=1.8 Hz), 7.97 (1H, d, J=9.9 Hz), 7.83 (1H, dd, J=1.3, 1.8 Hz), 7.23 (2H, d, J=8.6 Hz), 6.72 (2H, d, J=8.6 Hz), 4.53 (s, 2H). ESI-MS (m/z): Calcd. for C$_{15}$H$_{12}$N$_6$O: 292.1; found: 293.2 (M+H).

EXAMPLE 46

4-(6-Pyrazol-1-yl-[1,2,4]triazolo[4,3-b]pyridazin-3-ylmethyl)-phenol

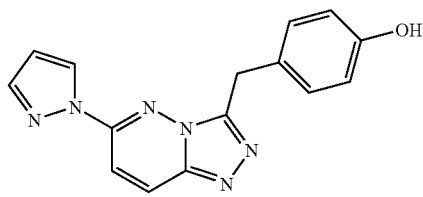

The title compound was prepared as described in Example 43. $^1$H-NMR (CDCl$_3$/CD$_3$OD): δ 8.48 (1H, dd, J=0.5, 2.8 Hz), 8.24 (1H, d, J=9.9 Hz), 8.13 (1H, d, J=9.9 Hz), 7.86 (1H, dd, J=1.3, 1.8 Hz), 7.26 (2H, d, J=8.6 Hz), 6.78 (2H, d, J=8.6 Hz), 6.65 (1H, dd, J=1.8, 2.8 Hz), 4.50 (2H, s). ESI-MS (m/z): Calcd. for C$_{15}$H$_{12}$N$_6$O: 292.1; found: 293.2 (M+H).

EXAMPLE 47

(4-Methyl-piperazin-1-yl)-[5-(3-quinolin-6-ylmethyl-[1,2,4]triazolo[4,3-b]pyridazin-6-yl)-thiophen-yl]-methanone

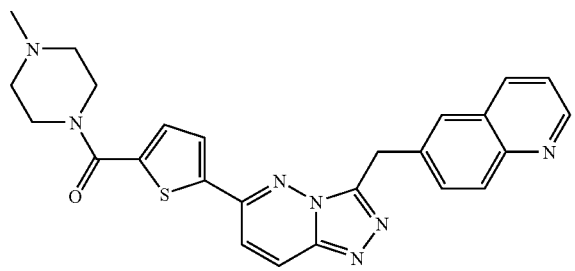

EXAMPLE 47

Step a 6-(6-Chloro-[1,2,4]triazolo[4,3-b]pyridazin-3-ylmethyl)-quinoline

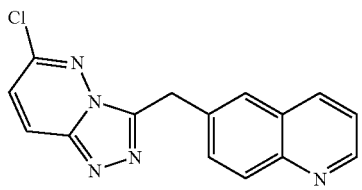

The title compound was prepared as described in Example 45. $^1$H-NMR (CDCl$_3$): δ 9.17-9.16 (1H, d, J=6.5 Hz), 8.91-8.88 (1H, d, J=9.0 Hz), 8.50-8.48 (1H, d, J=9.6 Hz), 8.28-8.25 (1H, d, J=8.5 Hz), 8.14 (1H, s), 8.06-8.03 (1H, dd, J=2.0, 8.8

Hz), 7.93-7.90 (1H, d, J=9.8 Hz), 6.72-6.70 (1H, d, J=8.0 Hz), 4.80 (2H, s). ESI-MS (m/z): Calcd. For $C_{15}H_{10}ClN_5$: 295.06; found: 296.3 (M+H).

EXAMPLE 47

Step b 5-(3-Quinolin-6-ylmethyl-[1,2,4]triazolo[4,3-b]pyridazin-6-yl)-thiophene-2-carboxylic acid ethyl ester

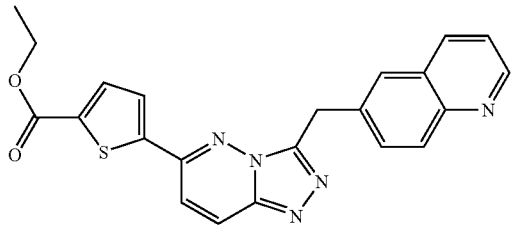

To a flask containing 6-(6-Chloro-[1,2,4]triazolo[4,3-b]pyridazin-3-ylmethyl)-quinoline as prepared in Example 47: step a (625 mg, 2.11 mmol) and Pd(PPh$_3$)$_4$ (120 mg, 0.10 mmol) under argon was added 5-ethoxycarbonylthiophenyl-2-zinc bromide (0.5M in THF, 12.7 mL, 6.35 mmol). The solution was heated to 68° C. for 3 h, during which the starting material was consumed by LC-MS. The reaction was cooled to rt and quenched by addition of methanol (5 mL) followed by 3N HCl (6 mL). Additional methanol (5 mL) and isopropanol (5 mL) was added with stirring, followed by 2N NaOH to adjust the pH~8. After stirring for 1 h, the ppt was collected to yield title compound (480 mg, 54%) contaminated with zinc salts. The material was used without further purification. $^1$H-NMR (DMSO-d$_6$): δ 8.84 (1H, dd, J=1.5, 4.0 Hz), 8.42 (1H, d, J=9.9 Hz), 8.30 (1H, m), 8.07 (1H, d, J=4.0 Hz), 7.97 (3H, m), 7.84 (1H, d, J=8.1 Hz), 7.77 (1H, dd, J=2.0, 8.8 Hz), 7.49 (1H, dd, J=4.3, 8.3 Hz), 4.75 (2H, s), 4.33 (2H, q, J=7.1 Hz), 1.33 (2H, t, J=7.1 Hz). ESI-MS (m/z): Calcd. for $C_{22}H_{17}N_5O_2S$: 415.1 found: 416.2 (M+H).

EXAMPLE 47

Step c (4-Methyl-piperazin-1-yl)-[5-(3-quinolin-6-ylmethyl-[1,2,4]triazolo[4,3-b]pyridazin-6-yl)-thiophen-yl]-methanone

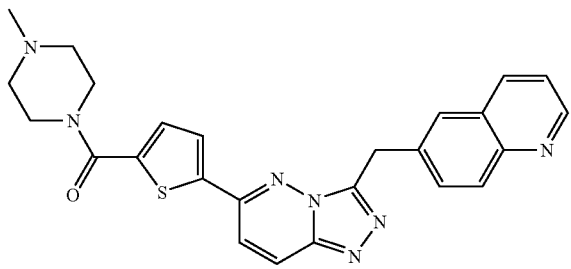

To a suspension of 5-(3-Quinolin-6-ylmethyl-[1,2,4]triazolo[4,3-b]pyridazin-6-yl)-thiophene-2-carboxylic acid ethyl ester as prepared in Example 47: step a (100 mg, 0.24 mmol) in THF (4 mL) and MeOH (2 mL) was added 2N NaOH (0.25 mL, 0.5 mmol) turning the mixture dark but more homogeneous. After stirring for 2 h, 1N HCl was added to bring the pH~2. The solvents were removed in vacuo and the residue dried on high vacuum. To the residue was added HBTU (114 mg, 0.3 mmol) and HOBt (70 mg, 0.5 mmol) followed by DMF (3 mL). DIEA (265 uL, 1.5 mmol) was added to the stirred suspension improving homogeneity. After stirring for 30 min, 1-methylpiperazine (110 μL, 1 mmol) was added and the reaction was stirred for 1 h. Water (1 mL) was added and the volatile components were removed in vacuo. The residue was purified by RP-HPLC (5-35% B over 45 min). The product-TFA salt was thrice dissolved in 1:1 MeOH/2N HCl (15 mL) and concentrated to yield the product-hydrochloride salt (41 mg, 36%) as a light-yellow solid. $^1$H-NMR (CD$_3$OD): δ 9.28 (1H, dd, J=1.3, 8.3 Hz), 9.25 (1H, dd, J=1.5, 5.6 Hz), 8.68 (1H, d, J=9.9 Hz), 8.59 (1H, d, J=9.9 Hz), 8.55 (1H, m), 8.37 (2H, m), 8.16 (1H, dd, J=5.3, 8.3 Hz), 8.12 (1H, d, J=4.0 Hz), 7.60 (1H, d, J=4.0 Hz), 5.10 (2H, s), 4.57 (2H, m), 3.62 (4H, m), 3.30 (2H, m), 2.99 (3H, s). ESI-MS (m/z): Calcd. for $C_{25}H_{23}N_7OS$: 469.2; found: 470.2 (M+H).

EXAMPLE 48

5-[3-(4-Hydroxy-benzyl)-[1,2,4]triazolo[4,3-b]pyridazin-6-yl]-thiophene-2-carboxylic acid ethyl ester

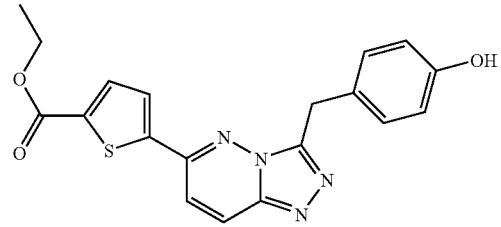

The title compound was prepared as described in Example 47. $^1$H-NMR (CDCl$_3$/CD$_3$OD): δ 8.18 (1H, d, J=9.9 Hz), 7.84 (1H, d, J=4.0 Hz), 7.82 (1H, d, J=4.0 Hz), 7.79 (1H, d, J=9.9 Hz), 7.33 (2H, d, J=8.6 Hz), 6.78 (2H, d, J=8.6 Hz), 4.51 (2H, s), 4.40 (1H, q, J=7.7 Hz), 1.46 (1H, t, J=7.7 Hz). ESI-MS (m/z): Calcd. for $C_{19}H_{16}N_4O_3S$: 380.1; found: 381.2 (M+H).

EXAMPLE 49

5-[3-(4-Hydroxy-benzyl)-[1,2,4]triazolo[4,3-b]pyridazin-6-yl]-thiophene-2-carboxylic acid (3-dimethylamino-propyl)-amide

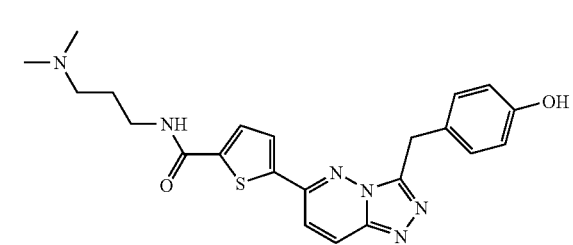

The title compound was prepared as described in Example 47. $^1$H-NMR (CD$_3$OD): δ 8.59 (1H, d, J=9.9 Hz), 8.52 (1H, d, J=9.9 Hz), 8.12 (1H, d, J=4.0 Hz), 7.90 (1H, d, J=4.0 Hz), 7.36 (2H, d, J=8.6 Hz), 6.80 (2H, d, J=8.6 Hz), 4.63 (2H, s), 3.54 (2H t, J=6.6 Hz), 3.27 (2H, m), 2.95 (s, 6H), 2.12 (2H, m). ESI-MS (m/z): Calcd. for $C_{22}H_{24}N_6O_2S$: 436.2; found: 437.2 (M+H).

EXAMPLE 50

{5-[3-(2,3-Dihydro-benzofuran-5-ylmethyl)-[1,2,4]triazolo[4,3-b]pyridazin-6-yl]-thiophen-2-yl}-(4-methyl-piperazin-1-yl)-methanone

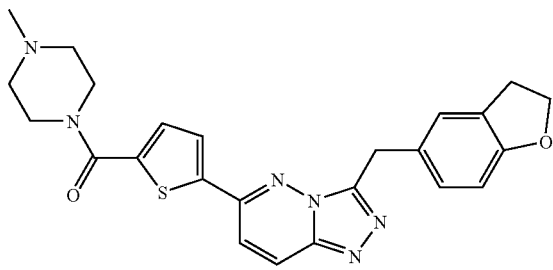

EXAMPLE 50

Step a

5-[3-(2,3-Dihydro-benzofuran-5-ylmethyl)-[1,2,4]triazolo[4,3-b]pyridazin-6-yl]-thiophene-2-carboxylic acid ethyl ester

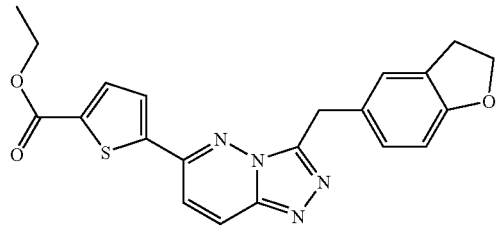

The title compound was prepared as described in Example 47. $^1$H-NMR (CDCl$_3$): δ 8.12 (1H, d, J=9.6 Hz), 7.81 (1H, d, J=4.0 Hz), 7.62 (1H, d, J=4.0 Hz), 7.46 (1H, d, J=9.6 Hz), 7.37 (1H, m), 7.25 (1H, m), 6.72 (1H, d, J=8.0 Hz), 4.52 (m, 4H), 4.43 (2H, q, J=7.1 Hz), 3.17 (2H, m), 1.44 (3H, t, J=7.1 Hz). ESI-MS (m/z): Calcd. for C$_{21}$H$_{18}$N$_4$O$_3$S: 406.1; found: 407.2 (M+H).

EXAMPLE 50

Step b

{5-[3-(2,3-Dihydro-benzofuran-5-ylmethyl)-[1,2,4]triazolo[4,3-b]pyridazin-6-yl]-thiophen-2-yl}-(4-methyl-piperazin-1-yl)-methanone

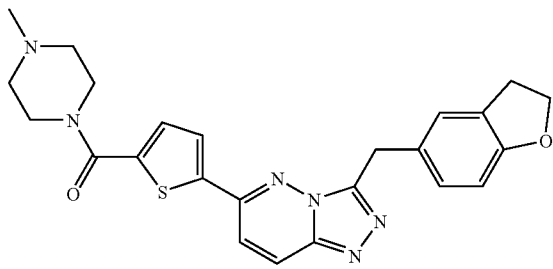

The title compound was prepared as described in Example 47. $^1$H-NMR (CDCl$_3$): δ 8.07 (1H, d, J=9.9 Hz), 7.57 (1H, d, J=3.8 Hz), 7.45 (1H, d, J=9.9 Hz), 7.34 (1H, m), 7.29 (1H, d, J=3.8 Hz), 7.25 (1H, dd, J=1.8, 8.1 Hz), 6.71 (1H, d, J=8.1 Hz), 4.51 (2H, t, J=8.6 Hz), 4.50 (2H, s), 3.80 (4H, t, J=4.9 Hz), 3.17 (2H, t, J=8.6 Hz), 2.50 (4H, t, J=4.9 Hz), 2.36 (3H, s). ESI-MS (m/z): Calcd. for C$_{24}$H$_{24}$N$_6$O$_2$S: 460.2; found: 461.2 (M+H).

EXAMPLE 51

5-[3-(2,3-Dihydro-benzofuran-5-ylmethyl)-[1,2,4]triazolo[4,3-b]pyridazin-6-yl]-thiophene-2-carboxylic acid bis-(2-methoxy-ethyl)-amide

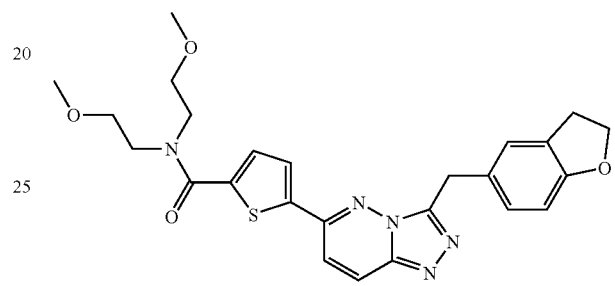

The title compound was prepared as described in Example 47. $^1$H-NMR (CHCl$_3$/CD$_3$OD): δ 8.13 (1H, d, J=9.9 Hz), 7.69 (1H, d, J=4.0 Hz), 7.66 (1H, d, J=9.9 Hz), 7.56 (1H, d, J=4.0 Hz), 7.33 (1H, m), 7.24 (1H, dd, J=1.8, 8.1 Hz), 6.71 (1H, d, J=8.3 Hz), 4.53 (2H, t, J=8.8 Hz), 4.51 (2H, s), 3.83 (4H, m), 3.68 (4H, m), 3.41 (6H, s), 3.19 (2H, t, J=8.8 Hz).

ESI-MS (m/z): Calcd. for C$_{25}$H$_{27}$N$_5$O$_4$S: 493.2; found: 494.3 (M+H).

EXAMPLE 52

5-[3-(2,3-Dihydro-benzofuran-5-ylmethyl)-[1,2,4]triazolo[4,3-b]pyridazin-6-yl]-thiophene-2-carboxylic acid (2-morpholin-4-yl-ethyl)-amide

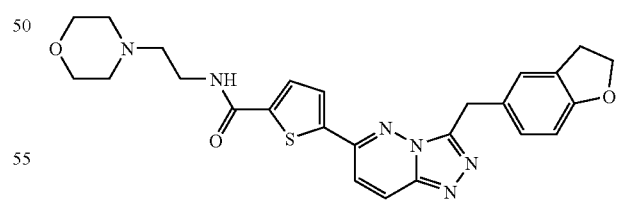

The title compound was prepared as described in Example 47. $^1$H-NMR (CDCl$_3$/CD$_3$OD): δ 8.24 (1H, d, J=9.9 Hz), 7.89 (1H, d, J=3.8 Hz), 7.85 (1H, d, J=4.0 Hz), 7.76 (1H, d, J=4.0 Hz), 7.34 (1H, m), 7.21 (1H, dd, J=1.8, 8.1 Hz), 6.70 (1H, d, J=8.4 Hz), 4.52 (2H, t, J=8.6 Hz), 4.51 (2H, s), 4.12 (2H, m), 3.91 (2H m), 3.84 (2H, t, J=6.0 Hz), 3.70 (2H, m), 3.48 (2H, t, J=6.0 Hz), 3.27 (2H, m), 3.20 (2H, t, J=8.6 Hz). ESI-MS (m/z): Calcd. for C$_{25}$H$_{26}$N$_6$O$_3$S: 490.2; found: 491.3 (M+H).

EXAMPLE 53

5-[3-(2,3-Dihydro-benzofuran-5-ylmethyl)-[1,2,4]triazolo[4,3-b]pyridazin-6-yl]-thiophene-2-carboxylic acid (3-methyl-butyl)-amide

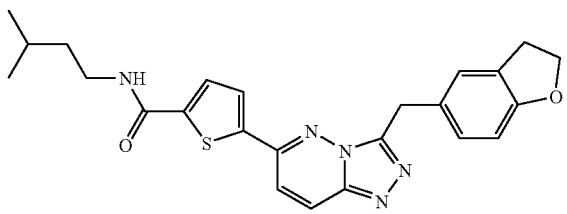

The title compound was prepared as described in Example 47. $^1$H-NMR (CDCl$_3$/CD$_3$OD): δ 8.58 (1H, d, J=8.8 Hz), 8.28 (1H, d, J=8.8 Hz), 7.94 (1H, d, J=2.8 Hz), 7.76 (1H, d, J=2.8 Hz), 7.36 (1H, m), 7.22 (1H, br d, J=8.1 Hz), 6.70 (1H, d, J=8.1 Hz), 4.59 (2H, s), 4.54 (2H, t, J=8.8 Hz), 4.55 (2H, m), 3.22 (2H, t, J=8.6 Hz), 1.71 (1H, septet, J=6.6 Hz), 1.56 (2H, m), 0.98 (6H, d, J=6.6 Hz). ESI-MS (m/z): Calcd. for C$_{24}$H$_{25}$N$_5$O$_2$S: 447.2; found: 448.3 (M+H).

EXAMPLE 54

(1,1-Dioxo-1λ6thiomorpholin-4-yl)-[5-(3-quinolin-6-ylmethyl-[1,2,4]triazolo[4,3-b]pyridazin-6-yl)-thiophen-2-yl]-methanone

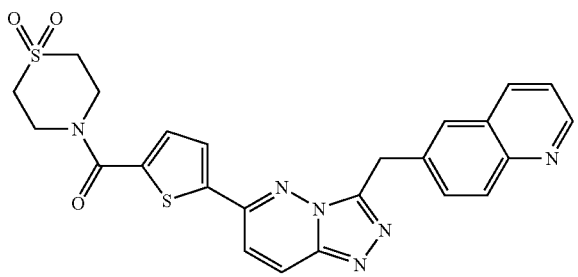

The title compound was prepared as described in Example 47. $^1$H-NMR (CD$_3$OD): δ 9.24 (2H, m), 8.62 (1H, d, J=9.6 Hz), 8.53 (2H, m), 8.34 (2H, m), 8.16 (1H, dd, J=5.3, 8.3 Hz), 8.09 (1H, d, J=4.0 Hz), 7.58 (1H, d, J=4.0 Hz), 5.08 (2H, s), 4.19 (4H, m), 3.29 (4H, m).

ESI-MS (m/z): Calcd. for C$_{24}$H$_{20}$N$_6$O$_3$S$_2$: 504.1; found: 505.2 (M+H).

EXAMPLE 55

(4-Isopropyl-piperazin-1-yl)-[5-(3-quinolin-6-ylmethyl-[1,2,4]triazolo[4,3-b]pyridazin-6-yl)-thiophen-2-yl]-methanone

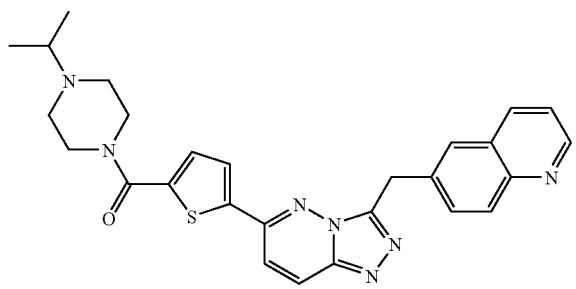

The title compound was prepared as described in Example 47. $^1$H-NMR (CD$_3$OD): δ 9.28 (2H, m), 8.67 (1H, d, J=9.9 Hz), 8.59 (1H, d, J=9.9 Hz), 8.57 (1H, m), 8.38 (2H, m), 8.18 (1H, dd, J=5.4, 8.4 Hz), 8.11 (1H, d, J=4.0 Hz), 7.58 (1H, d, J=4.0 Hz), 5.12 (2H, s), 4.64 (2H, m), 3.65 (5H, m), 3.33 (2H, m), 1.47 (6H, d, J=6.3 Hz). ESI-MS (m/z): Calcd. for C$_{27}$H$_{27}$N$_7$OS: 497.2; found: 498.3 (M+H).

EXAMPLE 56

(4-Methanesulfonyl-piperazin-1-yl)-[5-(3-quinolin-6-ylmethyl-[1,2,4]triazolo[4,3-b]pyridazin-6-yl)-thiophen-2-yl]-methanone

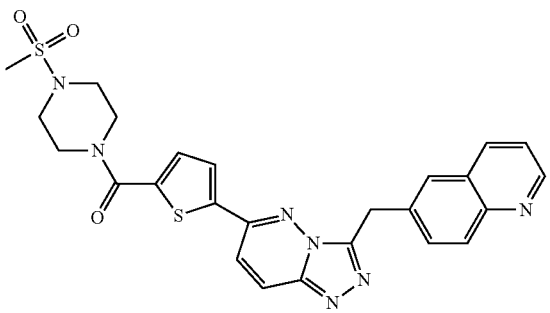

The title compound was prepared as described in 47. $^1$H-NMR (CD$_3$OD): δ 9.26 (2H, m), 8.53 (2H, m), 8.37 (1H, m), 8.32 (2H, m), 8.13 (1H, m), 8.05 (2H, s), 7.53 (1H, m), 5.05 (2H, s), 3.91 (4H, m), 3.37 (4H, m), 2.92 (2H, m). ESI-MS (m/z): Calcd. for C$_{25}$H$_{23}$N$_7$O$_3$S$_2$: 533.1; found: 534.2 (M+H).

EXAMPLE 57

6-[Difluoro-(6-thiophen-2-yl-[1,2,4]triazolo[4,3-b]pyridazin-3-yl)-methyl]-quinoline

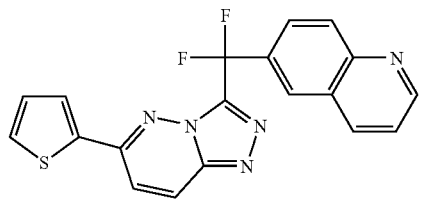

EXAMPLE 57

Step a

Oxo-quinolin-6-yl-acetic acid methyl ester

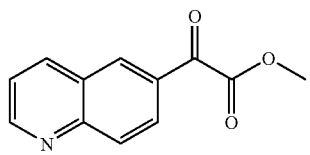

To the solution of methyl 6-quinolineacetate (1.2 g, 6 mmol) in dioxane (30 mL) was added Selenium dioxide (1.65 g, 15 mmol). The mixture was heated to reflux for 3 days, cooled to room temperature, filtered through Celite and concentrated. The residue was purified by chromatography (methylene chloride to 5% ethyl acetate in chloride) to a white solid (0.75 g, 58%). $^1$H-NMR (CDCl$_3$): δ 9.07-9.06 (1H, q, J=1.7, 2.5 Hz), 8.62-8.61 (1H, d, J=1.7 Hz), 8.32-8.31 (2H, m), 8.22-8.20 (1H, d, J=8.8 Hz), 7.54-7.51 (1H, q, J=8.8 Hz), 4.05 (3H, s).

EXAMPLE 57

Step b

Difluoro-quinolin-6-yl-acetic acid methyl ester

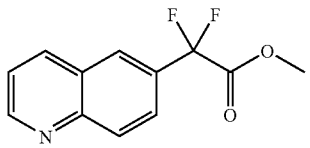

To a solution of oxa-quinolin-6-yl-acetic acid methyl ester (0.72 g, 3.3 mmol) in methylene chloride (20 mL) was added (dimethylamino)sulfur trifluoride (mL, 41 mmol) at 0° C. The mixture was stirred at room temperature for 2 days, poured into ice, extracted with methylene chloride (50 mL×3). The methylene chloride solution was washed with brine, dried over $Na_2SO_4$, filtered and concentrated. The residue was purified by chromatography (0-10% ethyl acetate in methylene chloride) to give a white solid (0.68 g, 87%). $^1$H-NMR ($CDCl_3$): δ 9.02-9.01 (1H, dd, J=1.7, 2.5 Hz), 8.26-8.23 (1H, d, J=8.0 Hz), 8.21-8.19 (1H, d, J=8.8 Hz), 8.13-8.12 (1H, s), 7.91-7.89 (1H, dd, J=2.0, 2.0 Hz), 7.51-7.48 (1H, q, J=4.0 Hz), 3.8 (3H, s).

EXAMPLE 57

Step c

Difluoro-quinolin-6-yl-acetic acid hydrazide

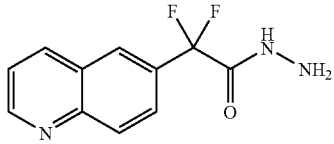

To a solution of difluoro-quinolin-6-acetic acid methyl acetate (670 mg, 2.83 mmol) in methanol (20 mL) was added anhydrous hydrazine (2 mL). The mixture heated to reflux for 2 h, cooled to room temperature, concentrated and dried in high vacuum to give a light orange solid (680 mg, 100%). $^1$H-NMR (DMSO): δ 9.02-9.01 (1H, dd, J=1.7 Hz), 8.56-8.54 (1H, d, J=9.3 Hz), 8.28 (1H, s), 8.17-8.15 (1 H, d, J=8.8 Hz), 7.91-7.88 (1H, dd, J=2.0, 2.0 Hz), 7.66-7.63 (1H, q, J=4.0 Hz).

EXAMPLE 57

Step d

6-[Difluoro-(6-thiophen-2-yl-[1,2,4]triazolo[4,3-b]pyridazin-3-yl)-methyl]-quinoline

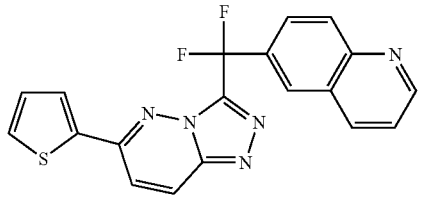

The title compound was prepared as described in Example 1: step b. $^1$H-NMR ($CDCl_3$): δ 9.00-8.98 (1H, dd, J=1.7, 4.0 Hz), 8.36 (1H, s), 8.29-8.22 (2H, m), 8.15-8.10 (2H, m), 7.68-7.67 (1H, dd, J=3.7, 1.2 Hz), 7.59-7.57 (2H, m), 7.50-7.46 (1H, q, J=4.2 Hz), 7.18-7.16 (1H, t, J=3.7 Hz). ESI-MS (m/z): Calcd. For $C_{19}H_{11}F_2N_5S$: 397.07; found: 380.3 (M+H).

EXAMPLE 58

3-[Difluoro-(4-methoxy-phenyl)-methyl]-6-thiophen-2-yl-[1,2,4]triazolo[4,3-b]pyridazine

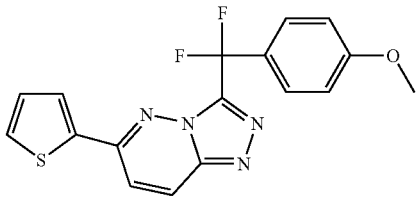

The title compound was prepared as described in Example 57. $^1$H-NMR ($CDCl_3$): δ 8.14-8.12 (1H, d, J=9.8 Hz), 7.75-7.73 (2H, d, J=9.0 Hz), 7.69-7.86 (1H, dd, J=3.5, 1.0 Hz), 7.59-7.56 (2H, t), 7.19-7.17 (1H, d, J=3.7 Hz), 7.00-6.97 (2H, d, J=9.0 Hz), 3.83 (3H, s). ESI-MS (m/z): Calcd. For $C_{17}H_{12}F_2N_4OS$: 358.07; found: 359.2 (M+H).

EXAMPLE 59

6-[Difluoro-(6-pyridin-3-yl-[1,2,4]triazolo[4,3-b]pyridazin-3-yl)-methyl]-quinoline

The title compound was prepared as described in Example 57. $^1$H-NMR (DMSO): δ 9.17 (1H, s), 8.97 (1H, d, J=4.3 Hz), 8.77 (1H, m), 8.32-8.39 (4H, m), 8.23 (1H, d, J=8.9 Hz), 8.08 (1H, dd, 8.9, 2.0 Hz), 7.85 (1H, J=9.8 Hz), 7.58 (1H, m). ESI-MS (m/z): Calcd. For $C_{20}H_{11}F_2N_6$: 374.11; found: 375.3 (M+H).

EXAMPLE 60

6-[Difluoro-(6-pyridin-4-yl-[1,2,4]triazolo[4,3-b]pyridazin-3-yl)-methyl]-quinoline

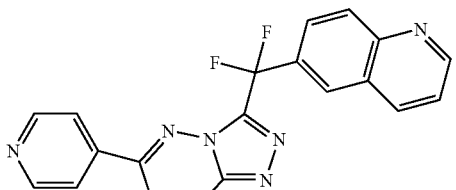

The title compound was prepared as described in Example 57. $^1$H-NMR (DMSO): δ 9.27 (1H, d, J=3.7 Hz), 9.03 (2H, d, J=5.7 Hz), 8.00 (1H, d, J=5.8 Hz), 8.84 (1H, d, J=9.8 Hz), 8.76 (1H, s), 8.46 (1H, d, J=9.2 Hz), 8.38 (3H, m), 8.28 (1H, d, J=9.1 Hz), 7.96 (1H, dd, 8.2, 4.7 Hz). ESI-MS (m/z): Calcd. For $C_{20}H_{11}F_2N_6$: 374.11; found: 375.3 (M+H).

EXAMPLE 61

6-{Difluoro-[6-(1-methyl-1H-pyrazol-4-yl)-[1,2,4]triazolo[4,3-b]pyridazin-3-yl]-methyl}-quinoline

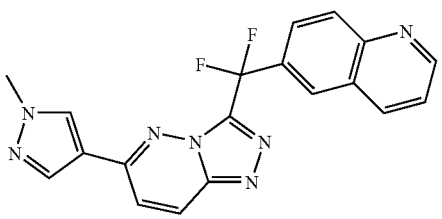

EXAMPLE 61

Step a 6-iodoquinoline

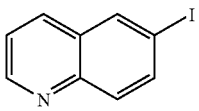

Sodium iodide (4.32 g, 28.8 mmol), Copper (I) iodide (137 mg, 0.72 mmol) and N,N'-Dimethyl-cyclohexane-1,2-diamine (0.227 mL, 1.44 mmol) and 6-Bromoquinoline (3 g, 14.4 mmol) in dioxane (15 mL) were charged in a 25 mL microwave tube. The tube was flushed with Nitrogen and sealed with a Teflon septum and Nitrogen was bubbled in the solution for 10 minutes, allowing the gas to escape through a needle. After the removal of the needle, the reaction mixture was stirred at 110° C. for 15 hours. Then, the green suspension was allowed to reach room temperature, poured into ice-water and extracted with dichloromethane. The organic layer was collected, dried (MgSO$_4$), filtered and concentrated in vacuum. The crude mixture was chromatographed over silica gel with CH$_2$Cl$_2$ 100% and CH$_2$Cl$_2$/MeOH:95/5 to yield 3.56 g (97%) of 6-Iodoquinoline as a light yellow solid.
$^1$H-NMR (DMSO): δ 8.93 (1H, dd, J=1.5, 4.1 Hz), 8.47 (1H, d, J=2.0 Hz), 8.33 (1H, d, J=8.6 Hz), 8.02 (1H, dd, J=2.0, 8.6 Hz), 7.80 (1H, d, J=8.6 Hz), 7.56 (1H, dd, J=4.1, 8.6 Hz).

EXAMPLE 61

Step b difluoro-quinolin-6-yl-acid ethyl ester

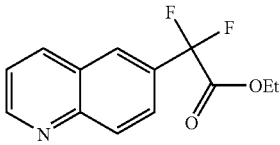

To a suspension of 6-Iodoquinoline (10.2 g, 40 mmol) and Copper (O) (nanopowder, 5.59 g, 88 mmol) in dry DMSO (97 mL) was added 8.93 g (44 mmol) of ethyl bromodifluoroacetate. The reaction mixture was stirred under nitrogen at 55° C. for 15 hours. The reaction was allowed to reach room temperature and the mixture was poured over a solution of ammonium chloride. Ethyl acetate was added and the resulting mixture filtered over Celite. The organic layer was collected, dried (MgSO$_4$), filtered and concentrated in vacuum. The crude mixture was chromatographied over silica gel with CH$_2$Cl$_2$ 100% and CH$_2$Cl$_2$/MeOH:95/5 to yield 5.07 g of Difluoro-quinolin-6-yl-acetic acid ethyl ester as light yellow oil (50%).
$^1$H-NMR (CDCl$_3$): δ 9.1 (1H, m), 8.27 (1H, m), 8.20 (2H, m), 8.15 (1H, m), 7.91 (1H, m), 7.52 (1H, m), 4.33 (2H, q, J=7.1 Hz), 1.31 (3H, t, J=7.1 Hz).

EXAMPLE 61

Step c difluoro-quinolin-6-yl-acetic acid hydrazide

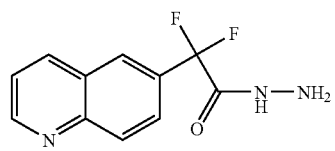

To a solution of difluoro-quinolin-6-yl-acetic acid ethyl ester (5.5 g, 21.9 mmol) in methanol (85 mL) was added hydrate hydrazine (5.3 mL, 109.5 mmol). The mixture was heated to 45° C. for 10 min., cooled to room temperature, concentrated, and taken up in dichloromethane. The organic layer was dried over MgSO$_4$, filtered and concentrated in vacuo to give a light orange solid (4.4 g, 85%).

EXAMPLE 61

Step d 3-chloro-6-(1-methyl-1H-pyrazol-4-yl)-pyridazine

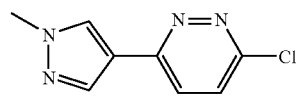

A flask was charged with 3,6-dichloropyridazine (Aldrich, 23.91 g, 160.5 mmol), 1-Methyl-4-(4,4,5,5-tetramethyl-[1,3,2]dioxaborolan-2-yl)-1H-pyrazole (20 g, 96 mmol), 2.0 M Na$_2$CO$_3$ (96 mL) and dioxane (65 mL). Nitrogen was bubbled through the reaction for 60 seconds followed by the addition of Dichlorobis(triphenylphosphine)palladium (0) (6.75 g, 9.6 mmol). The reaction was heated to 80° C. overnight followed by aqueous work up using AcOEt and a solution of K$_2$CO$_3$. After filtration over celite, the organic layer was dried (MgSO$_4$) and concentrated in vacuo. A first fraction of compound (10.2 g) was obtained by crystallization in the solvent (dichloromethane). The filtrate was purified by column chromatography (CH$_2$Cl$_2$ 100% and CH$_2$Cl$_2$/MeOH: 95/5). The two fractions were gathered and washed with diisopropylether to give the title compound as a yellow solid (12.7 g, 68%).

EXAMPLE 61

Step e 6-(Difluoro-[6-(1methyl-1H-pyrazol-4-yl)-[1,2,4]triazolo[4,3-b]pyridazin-3-yl]-methyl)-quinoline

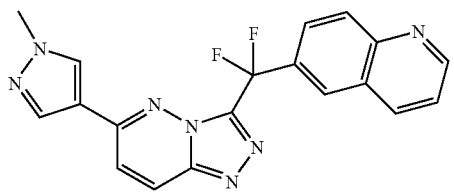

A mixture of 3-chloro-6-(1-methyl-1H-pyrazol-4-yl)-pyridazine (step d) (4.57 g, 23.6 mmol) and difluoro-quinolin-6-yl-acetic acid hydrazide (step c) (5.60 g, 23.6 mmol) in n-butanol (125 mL) was heated to 130° C. overnight. The mixture was cooled to room temperature, followed by aqueous work up using AcOEt and a solution of $K_2CO_3$. The organic layer was dried ($MgSO_4$) and concentrated in vacuo. The residue was purified by flash column chromatography (first chromatography: $CH_2Cl_2$ 100% and $CH_2Cl_2$/MeOH: 88/12 followed by another column with toluene/iPrOH/$NH_4OH$: 85/15/2) to give the title compound (5.5 g, 62%). M.p=199.7° C.

EXAMPLE 61

Synthesis of the Hydrochloride Salt

To 1 g (2.65 mmol) of 6-(difluoro-[6-(1-methyl-1H-pyrazol-4-yl)-[1,2,4]triazolo[4,3-b]pyridazin-3-yl]-methyl)-quinoline in MeOH (5 mL) is added dropwise 2 mL of HCl in isopropanol (5 to 6N). The precipitate is filtered and dried under vacuum to yield 1.01 g of the hydrochloride salt ($C_{19}H_{13}F_2N_7$, 1.30HCl, 0.60$H_2O$).
$^1$H NMR (DMSO): δ 9.26 (1H, d, J=4.5 Hz), 9.16 (1H, d, J=8.0 Hz), 8.70 (1H, s), 8.58-8.48 (2 H, m), 8.27 (1 H, d, J=9.1 Hz), 8.09 (1 H, s), 7.97 (1 H, dd, J=8.3 Hz, 4.8 Hz), 7.85 (1 H, d, J=10 Hz) 3.93 (3 H, s). Anal ($C_{19}H_{13}F_2N_7$, 1.30HCl, 0.60 $H_2O$) Calcd C, 52.41; H, 3.59; N, 22.52. Found C, 52.19; H, 3.72; N, 22.53.

Alternatively, the title compound can be prepared as described in Example 57. $^1$H-NMR (DMSO): δ 9.30 (1H, d, J=4.1 Hz), 9.16 (1H, d, J=8.4 Hz), 8.80 (1H, s), 8.51 (3H, m), 8.33 (1H, d, J=8.6 Hz), 8.09 (1H, s), 8.04 (1H, m), 7.86 (1H, d, J=9.7 Hz), 3.93 (3H, s). ESI-MS (m/z): Calcd. For $C_{19}H_{13}F_2N_7$: 377.36; found: 378.4 (M+H).

EXAMPLE 62

3-(2,3-Dihydro-benzofuran-5-ylmethyl)-6-(1-methyl-1H-pyrazol-4-yl)-[1,2,4]triazolo[4,3-b]pyridazine

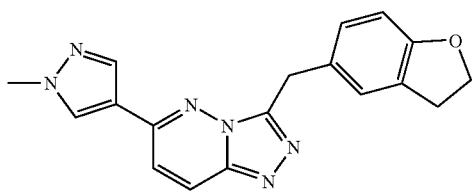

The title compound was prepared as described in Example 47. $^1$H-NMR (DMSO): δ 8.78 (1H, s), 8.33 (1H, d, J=8.6 Hz), 8.09 (1H, s), 7.86 (1H, d, J=9.7 Hz), 7.08 (1H, d, J=9.6 Hz), 6.87 (1H, m), 6.64 (1H, d, J=8.3 Hz), 5.11 (2H, s), 4.53 (2H, t, J=8.8 Hz), 3.92 (3H, s), 3.20 (2H, t, J=8.6 Hz), ESI-MS (m/z): Calcd. For $C_{18}H_{16}N_6O$: 332.14; found: 333.3 (M+H).

EXAMPLE 63

6-[6-(1-Methyl-1H-pyrazol-4-yl)-[1,2,4]triazolo[4,3-b]pyridazin-3-ylmethyl]-quinoline 1-oxide

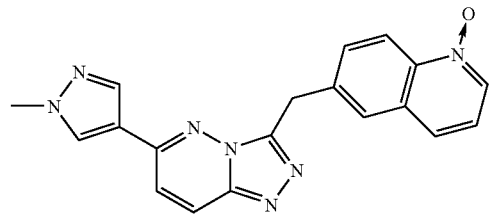

The title compound was prepared as described in Example 47. $^1$H-NMR (CDCl$_3$): δ 8.71 (1H, d, J=8.8 Hz), 8.48 (1H, d, J=6.0 Hz), 8.06 (1H, d, J=9.5 Hz), 7.98 (1H, s), 7.90 (3H, m), 7.66 (1H, d, J=8.5 Hz), 7.30 (2H, m), 4.78 (2H, s), 4.01 (3H, s).

ESI-MS (m/z): Calcd. For $C_{19}H_{15}N_7O$: 357.13; found: 358.20 (M+H).

EXAMPLE 64

6-(6-Pyrimidin-5-yl-[1,2,4]triazolo[4,3-b]pyridazin-3-ylmethyl)-quinoline

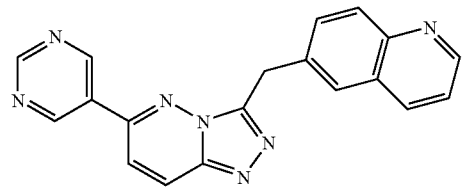

The title compound was prepared as described in Example 47. $^1$H-NMR (DMSO): δ 9.50 (1H, s), 9.38 (1H, s), 8.86 (1H, dd, J=5.6, 1.8 Hz), 8.57 (1H, d, J=9.5 Hz), 8.33 (1H, d, J=8.6 Hz), 8.07 (1H, d, J=9.7 Hz), 8.00 (2H, m), 7.84 (1H, dd, J=8.9, 2.0 Hz), 7.71 (1H, q, J=4.4 Hz), 4.86 (2H, s). ESI-MS (m/z): Calcd. For $C_{19}H_{13}N_7$: 339.12; found: 340.30 (M+H).

EXAMPLE 65

6-(6-Quinolin-3-yl-[1,2,4]triazolo[4,3-b]pyridazin-3-ylmethyl)-quinoline

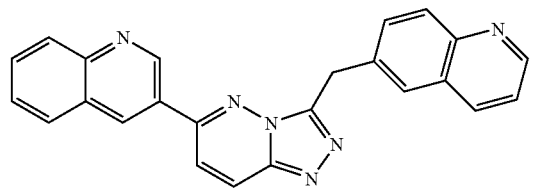

The title compound was prepared as described in Example 47. $^1$H-NMR (DMSO): δ 9.60 (1H, d, J=2.2 Hz), 9.13 (1H, d, J=2.3 Hz), 8.86 (1H, d, J=4.1 Hz), 8.56 (1H, d, J=9.6 Hz), 8.35 (1H, d, J=8.6 Hz), 8.12 (3H, m), 8.04 (2H, m), 7.91 (2H, m), 7.74 (1H, t, J=8.1 Hz), 7.51 (1H, q, J=4.2 Hz), 4.89 (2H, s). ESI-MS (m/z): Calcd. For $C_{24}H_{16}N_6$: 388.14; found: 389.30 (M+H).

EXAMPLE 66

6-[Difluoro-(6-quinolin-3-yl-[1,2,4]triazolo[4,3-b]pyridazin-3-yl)-methyl]-quinoline

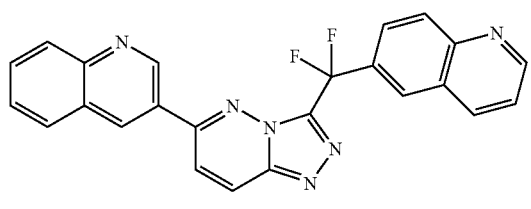

The title compound was prepared as described in Example 57. ¹H-NMR (DMSO): δ 9.52 (1H, d, J=2.2 Hz), 9.01 (1H, d, J=4.2 Hz), 8.64 (1H, d, J=2.1 Hz), 8.36 (2H, d, J=8.6 Hz), 8.30 (2H, m), 8.23 (1H, m), 8.11 (1H, m), 7.95 (1H, d, J=7.6 Hz), 7.85 (2H, m), 7.69 (1H, m), 7.50 (1H, q, J=4.1 Hz). ESI-MS (m/z): Calcd. For $C_{24}H_{14}F_2N_6$: 424.12; found: 425.30 (M+H).

EXAMPLE 67

2-Chloro-6-(6-pyridin-3-yl-[1,2,4]triazolo[4,3-b]pyridazin-3-ylmethyl)-quinoline

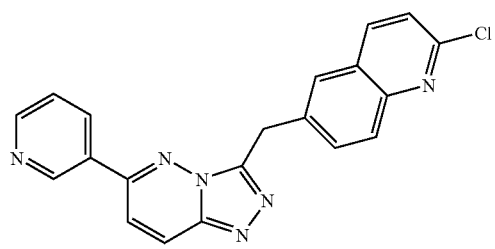

EXAMPLE 67

Step a (1-Hydroxy-quinolin-6-yl)-acetic acid methyl ester

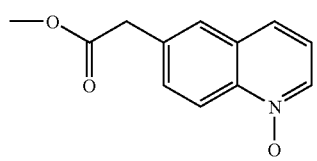

m-Perchlorobenzoic acid (6.85 g, 39.8 mmol) was added to a solution of commercially available quinolin-6-yl-acetic acid methyl ester (5.00 g, 24.8 mmol) in 1,2-dimethoxyethane at room temperature and stirred for 2 hours. Water was added and the solution was basified to pH 9-10 with saturated potassium carbonate and the product was extracted with ethyl acetate to give quantitative yield of (1-hydroxy-quinolin-6-yl)-acetic acid methyl ester. ¹H NMR (400 MHz, CDCl₃) δ 7.99 (d, 1H, J=8.4 Hz), 7.93 (d, 1H, J=8.4 Hz), 7.65 (m, 1H), 7.60 (m, 1H), 7.32 (d, 1H, J=8.8 Hz), 7.19 (s, 1H), 3.74 (s, 2H), 3.65 (s, 3H).

EXAMPLE 67

Step b (2-Chloro-quinolin-6-yl)-acetic acid methyl ester

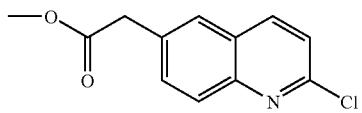

(1-Hydroxy-quinolin-6-yl)-acetic acid methyl ester (1.0 g, 4.61 mmol) was refluxed for 25 minutes in phosphorous oxychloride (30 mL). The excess phosphorous oxychloride was evaporated, saturated sodium bicarbonate was added and the crude mixture was extracted several times with ethyl acetate. The product was purified via silica gel column chromatography in hexane:ethyl acetate (1:1) to give 0.219 g (20%) of (2-chloro-quinolin-6-yl)-acetic acid methyl ester. ¹H NMR (400 MHz, CDCl₃) δ 7.99 (d, 1H, J=8.4 Hz), 7.93 (d, 1H, J=8.8 Hz), 7.63 (m, 1H), 7.60 (dd, 1H, J=2.0, 8.4 Hz), 7.30 (d, 1H, J=8.8 Hz), 3.73 (s, 2H), 3.64 (s, 3H).

EXAMPLE 67

Step c (2-Chloro-quinolin-6-yl)-acetic acid hydrazide

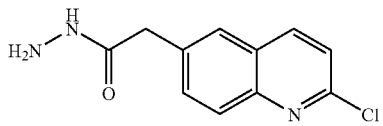

(2-Chloro-quinolin-6-yl)-acetic acid methyl ester (0.160 g, 0.679 mmol), hydrazine (0.218 g, 6.79 mmol) and methanol (3 mL) were stirred at room temperature. The reaction was evaporated to give (2-chloro-quinolin-6-yl)-acetic acid hydrazide. This compound was not purified and was used directly in the next step. ¹H NMR (400 MHz, DMSO-d₆) δ 9.39 (m, 1H), 8.43 (d, 1H, J=9.2 Hz), 7.91 (m, 2H), 7.75 (m, 1H), 7.58 (m, 1H), 4.30 (bs, 2H), 3.57 (s, 2H).

EXAMPLE 67

Step d

2-Chloro-6-(6-pyridin-3-yl-[1,2,4]triazolo[4,3-b]pyridazin-3-ylmethyl)-quinoline

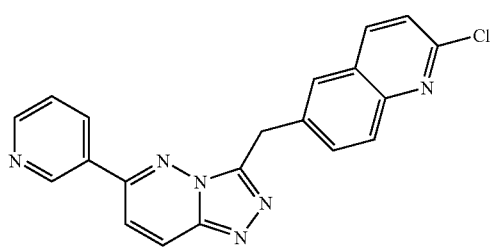

(2-Chloro-quinolin-6-yl)-acetic acid hydrazide (0.030 g, 0.127 mmol) and 3-chloro-6-pyridin-3-yl-pyridazine (0.024 g, 0.127 mmol) were heated to reflux in butanol (0.5 mL) for several hours. The reaction was cooled to room temperature and filtered. The filtrate was purified via reverse phase HPLC on a C18 column eluting with acetonitrile in water (0.1% TFA) to give 0.017 g (35%) of 2-chloro-6-(6-pyridin-3-yl-[1,2,4]triazolo[4,3-b]pyridazin-3-ylmethyl)-quinoline. $^1$H NMR (400 MHz, CD$_3$OD) δ 9.38 (m, 1H), 8.88 (d, 1H, J=5.2 Hz), 8.85 (m, 1H), 8.42 (d, 1H, J=9.6 Hz), 8.31 (d, 1H, J=8.8 Hz), 8.06 (s, 1H), 8.03 (m, 1H), 7.92 (m, 3H), 7.50 (d, 1H, J=8.8 Hz), 4.93 (s, 2H). Mass spectrum (LCMS, ESI pos.): Calcd for C$_{20}$H$_{13}$ClN$_6$; found: 373.3, 375.3 (M+H).

EXAMPLE 68

3-(4-Methoxy-benzyl)-6-(6-pyridin-3-yl-[1,2,4]triazolo[4,3-b]pyridazin-3-ylmethyl)-3H quinazolin-4-one

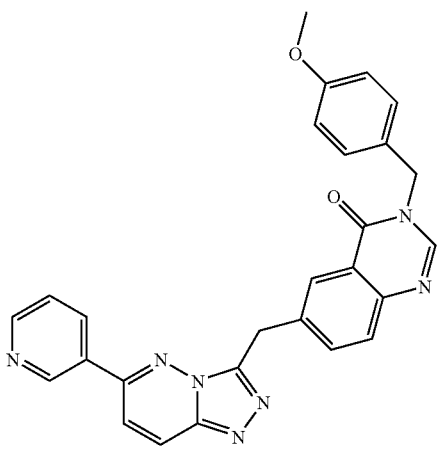

EXAMPLE 68

Step a

6-Iodo-3H-quinazolin-4-one

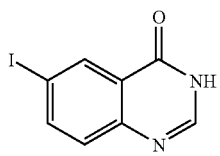

A solution of 2-amino-5-iodo-benzoic acid (5.00 g, 19.0 mmol) and formamide (3.43 g, 76.0 mmol) were heated to 150° C. for 4 hours and then cooled to room temperature. Water was added and the solution was filtered and washed with water several times to give 3.6 g (70%) of 6-iodo-1H-quinazolin-4-one. $^1$H NMR (400 MHz, DMSO-d$_6$) δ 12.39 (s, 1H), 8.37 (s, 1H), 8.11 (s, 1H), 8.09 (dd, 1H, J=2.0, 8.8 Hz), 7.45 (d, 1H, J=8.8 Hz).

EXAMPLE 68

Step b

6-Iodo-3-(4-methoxy-benzyl)-3H-quinazolin-4-one

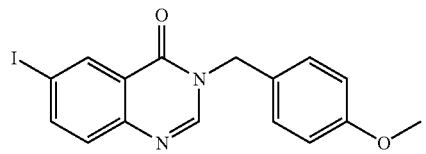

6-Iodo-1H-quinazolin-4-one (0.50 g, 1.84 mmol) was added to a solution of sodium hydride (0.110 g, 2.76 mmol) in THF (10 mL) and stirred at room temperature for one hour. 1-Chloromethyl-4-methoxy-benzene (0.345 g, 2.21 mmol) was added and the reaction was stirred for several hours. Water was added and the crude product was extracted from ethyl acetate and evaporated in vacuo. The product was purified via silica gel column chromatography in hexane:ethyl acetate (4:1) to give 0.69 g (96%) of 6-iodo-3-(4-methoxy-benzyl)-3H-quinazolin-4-one. $^1$H NMR (400 MHz, CDCl$_3$) δ 8.57 (d, 1H, J=2.0 Hz), 8.01 (s, 1H), 7.90 (dd, 1H, J=2.0, 8.8 Hz), 7.33 (d, 1H, J=8.8 Hz), 7.22 (d, 2H, J=8.0 Hz), 6.80 (d, 2H, J=8.8 Hz), 5.03 (s, 2H), 3.70 (s, 3H).

EXAMPLE 68

Step c

2-[3-(4-Methoxy-benzyl)-4-oxo-3,4-dihydro-quinazolin-6-yl]-malonic acid diethyl ester

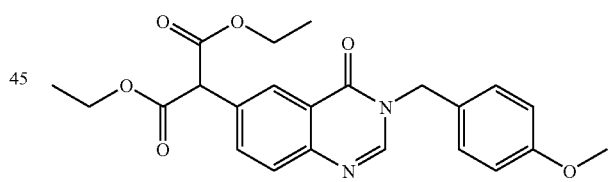

A solution of 6-iodo-3-(4-methoxy-benzyl)-3H-quinazolin-4-one (0.69 g, 1.75 mmol), malonic acid diethyl ester (0.56 g, 3.49 mmol), copper iodide (0.016 g, 0.090 mmol), biphenyl-2-ol (0.029 g, 0.175 mmol) and cesium carbonate (0.86 g, 2.63 mmol) in THF (10 mL) was heated to 70° C. in a sealed tube for 24 hours. The solution was then cooled to room temperature, saturated sodium bicarbonate was added and the crude product was extracted from ethyl acetate. The product was purified via silica gel column chromatography in hexane:ethyl acetate (1:1) to give 0.51 g (69%) of 2-[3-(4-methoxy-benzyl)-4-oxo-3,4-dihydro-quinazolin-6-yl]-malonic acid diethyl ester. $^1$H NMR (400 MHz, CDCl$_3$) δ 8.21 (m, 1H), 8.05 (s, 1H), 7.80 (dd, 1H, J=2.0, 8.4 Hz), 7.62 (d, 1H, J=8.4 Hz), 7.22 (d, 2H, J=8.8 Hz), 6.78 (d, 2H, J=8.8 Hz), 5.05 (s, 2H), 4.69 (s, 1H), 4.15 (m, 4H), 3.70 (s, 3H), 1.19 (m, 6H).

EXAMPLE 68

Step d

[3-(4-Methoxy-benzyl)-4-oxo-3,4-dihydro-quinazolin-6-yl]-acetic acid methyl ester

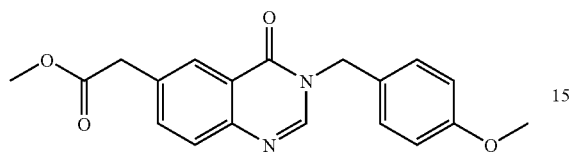

Sodium hydroxide [2N] (0.59 mL) was added to a solution of 2-[3-(4-methoxy-benzyl)-4-oxo-3,4-dihydro-quinazolin-6-yl]-malonic acid diethyl ester (0.250 g, 0.590 mmol) in methanol (5 mL) and stirred at room temperature for several hours. The crude reaction was then evaporated in vacuo, 1N HCl was added and the product was extracted with ethyl acetate to give 0.141 g of [3-(4-methoxy-benzyl)-4-oxo-3,4-dihydro-quinazolin-6-yl]-acetic acid methyl ester. This was dissolved in a mixture of toluene/methanol [8/1] (3 mL) and trimethylsilyldiazomethane [2.0M] (0.22 mL) was added at room temperature and stirred until bubbling has stopped. The reaction was then evaporated in vacuo and purified via silica gel column chromatography in hexane:ethyl acetate (1:1) to give 0.119 g (60%) of [3-(4-methoxy-benzyl)-4-oxo-3,4-dihydro-quinazolin-6-yl]-acetic acid methyl ester. Mass spectrum (LCMS, ESI pos.): Calcd for $C_{19}H_{18}N_2O_4$; found: 339.1, 340.1 (M+H).

EXAMPLE 68

Step e

[3-(4-Methoxy-benzyl)-4-oxo-3,4-dihydro-quinazolin-6-yl]-acetic acid hydrazide

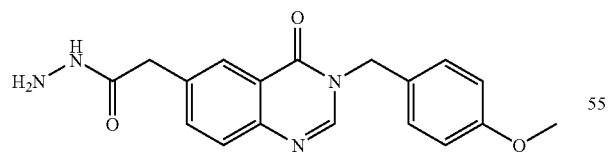

[3-(4-Methoxy-benzyl)-4-oxo-3,4-dihydro-quinazolin-6-yl]-acetic acid methyl ester (0.050 g, 0.148 mmol) and hydrazine (0.047 g, 0.148 mmol) were stirred at 50° C. in methanol (5 mL) for several hours. The reaction was then cooled to room temperature and filtered to give 0.030 g (60%) of [3-(4-methoxy-benzyl)-4-oxo-3,4-dihydro-quinazolin-6-yl]-acetic acid hydrazide. $^1$H NMR (400 MHz, CD$_3$OD) δ 10.09 (s, 1H), 9.33 (s, 1H), 8.85 (m, 1H), 8.53 (d, 1H, J=2.0, 8.4 Hz), 8.42 (d, 1H, J=8.4 Hz), 8.14 (d, 2H, J=8.4 Hz), 7.70 (d, 2H, J=8.4 Hz), 5.93 (s, 2H), 5.04 (bs, 2H), 4.52 (s, 3H), 4.31 (s, 2H).

EXAMPLE 68

Step f 3-(4-Methoxy-benzyl)-6-(6-pyridin-3-yl-[1,2,4]triazolo[4,3-b]pyridazin-3-ylmethyl)-3H quinazolin-4-one

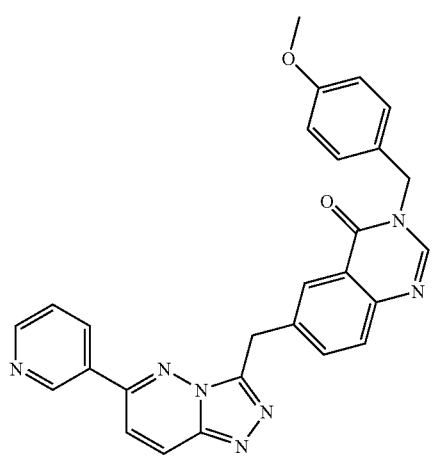

[3-(4-Methoxy-benzyl)-4-oxo-3,4-dihydro-quinazolin-6-yl]-acetic acid hydrazide (0.024 g, 0.071 mmol) and 3-chloro-6-pyridin-3-yl-pyridazine (0.012 g, 0.063 mmol) were heated to 130° C. in butanol (0.5 mL) for several hours. The compound was purified via reverse phase HPLC on a C18 column eluting with acetonitrile in water (0.1% TFA) to give 0.016 g (53%) of 3-(4-methoxy-benzyl)-6-(6-pyridin-3-yl [1,2,4]triazolo[4,3-b]pyridazin-3-ylmethyl)-3H quinazolin-4-one. $^1$H NMR (400 MHz, CDCl$_3$) δ 9.08 (m, 1H), 8.71 (dd, 1H, J=4.8, 1.6 Hz), 8.39 (m, 1H), 8.25 (m, 1H, 8.13 (d, 1H, J=9.6 Hz), 7.99 (s, 1H), 7.77 (dd, 1H, J=8.4, 2.0 Hz), 7.58 (d, 1H, J=8.4 Hz), 7.48 (d, 1H, J=9.6 Hz), 7.41 (m, 1H), 7.21 (d, 2H, J=8.4 Hz), 6.77 (d, 2H, J=8.8 Hz), 5.05 (s, 2H), 5.05 (s, 2H), 4.71 (s, 2H), 3.70 (s, 3H). Mass spectrum (LCMS, ESI pos.): Calcd for $C_{27}H_{21}N_7O_2$; found: 476.1, 477.2 (M+H).

EXAMPLE 69

6-(6-Pyridin-3-yl-[1,2,4]triazolo[4,3-b]pyridazin-3-ylmethyl)-3H-quinazolin-4-one

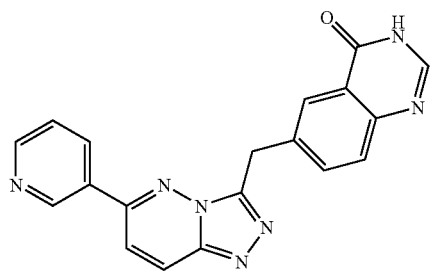

3-(4-Methoxy-benzyl)-6-(6-pyridin-3-yl-[1,2,4]triazolo[4,3-b]pyridazin-3-ylmethyl)-3H quinazolin-4-one (0.010 mg, 0.021 mmol) was treated with trifluoroacetic acid (1 mL) and anisole (0.1 mL) and heated to 90° C. for 18 hours. The compound was purified via reverse phase HPLC on a C18 column eluting with acetonitrile in water (0.1% TFA) to give 0.0026 g (35%) of 6-(6-pyridin-3-yl-[1,2,4]triazolo[4,3-b]pyridazin-3-ylmethyl)-3H-quinazolin-4-one. $^1$H NMR (400 MHz, DMSO-d$_6$) δ 9.32 (m, 1H), 8.79 (m, 1H), 8.53 (m, 2H), 8.20 (m, 1H), 8.10 (s, 1H), 8.03 (d, 1H, J=10.0 Hz), 7.89 (d, 1H, J=8.4 Hz), 7.66 (m, 2H), 4.80 (s, 2H). Mass spectrum (LCMS, ESI pos.): Calcd for C$_{19}$H$_{13}$N$_7$O; found: 356.3, 357.3 (M+H).

EXAMPLE 70

6-[6-(1-Methyl-1H-pyrazol-4-yl)-[1,2,4]triazolo[4,3-b]pyridazin-3-ylmethyl]-quinazoline

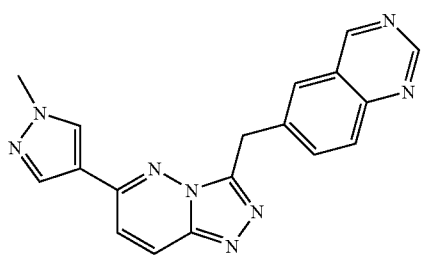

EXAMPLE 70

Step a

2-Quinazolin-6-yl-malonic acid diethyl ester

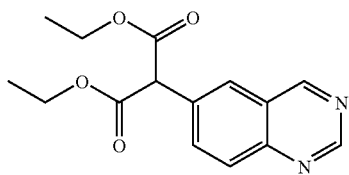

A solution of 6-iodo-quinazoline (0.500 g, 1.95 mmol), malonic acid diethyl ester (0.93 g, 5.81 mmol), copper iodide (0.019 g, 0.097 mmol), biphenyl-2-ol (0.033 g, 0.195 mmol) and cesium carbonate (0.953 g, 2.93 mmol) in THF (5 mL) was heated to 70° C. in a sealed tube for 24 hours. The solution was then cooled to room temperature, saturated ammonium chloride was added and the crude product was extracted from ethyl acetate. The product was purified via silica gel column chromatography in hexane:ethyl acetate (1:1) to give 0.39 g (80%) of 2-quinazolin-6-yl-malonic acid diethyl ester. $^1$H NMR (400 MHz, CDCl$_3$) δ 9.37 (bs, 2H), 7.96 (m, 3H), 4.78 (s, 1H), 4.18 (m, 4H), 1.19 (m, 6H).

EXAMPLE 70

Step b

Quinazolin-6-yl-acetic acid

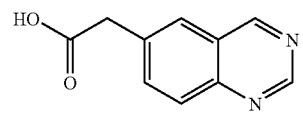

Sodium hydroxide [2M] (0.77 mL) was added to a solution of 2-quinazolin-6-yl-malonic acid diethyl ester (0.20 g, 0.77 mmol) in methanol (10 mL) and stirred at room temperature for several hours. The reaction was evaporated, ethyl acetate was added and then 1N HCl was added dropwise until the compound went into the organic layer. The organic layer was evaporated to give 0.123 g (85%) of quinazolin-6-yl-acetic acid. $^1$H NMR (400 MHz, DMSO-d$_6$) δ 9.56 (s, 1H), 9.26 (s, 1H), 7.95 (m, 3H), 3.85 (s, 2H).

EXAMPLE 70

Step c

Quinazolin-6-yl-acetic acid hydrazide

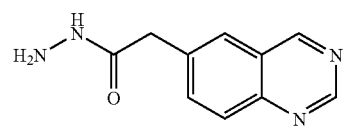

A solution of quinazolin-6-yl-acetic acid (0.025 g, 0.133 mmol), thionyl chloride (0.1 mL) and methanol (2 mL) was heated to 60° C. for 6 hours. The reaction was cooled to room temperature and evaporated several times with dichloromethane to give quinazolin-6-yl-acetic acid methyl ester. This was dissolved in a solution of methanol (2 mL) and hydrazine (0.061 mL) and stirred at room temperature for several hours. The reaction was evaporated in vacuo to give quinazolin-6-yl-acetic acid hydrazide. $^1$H NMR (400 MHz, DMSO-d$_6$) δ 9.56 (s, 1H), 9.33 (bs, 1H), 9.26 (s, 1H), 7.96 (m, 3H), 4.25 (bs, 2H), 3.84 (s, 2H).

EXAMPLE 70

Step d

6-[6-(1-Methyl-1H-pyrazol-4-yl)-[1,2,4]triazolo[4,3-b]pyridazin-3-ylmethyl]-quinazoline

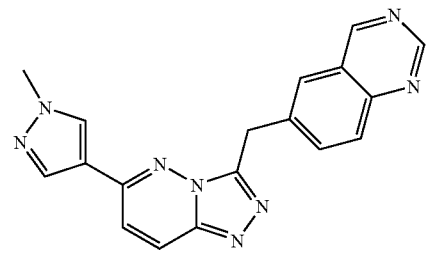

Quinazolin-6-yl-acetic acid hydrazide (0.032 g, 0.158 mmol) and 3-chloro-6-(1-methyl-1H-pyrazol-4-yl)-pyridazine (0.031 g, 0.158 mmol) were heated to 165° C. in butanol (2 mL) for five hours. The reaction was cooled to room temperature, evaporated in vacuo and purified via silica gel column chromatography eluting with 5% methanol in dichloromethane to give 0.00311 g (7%) of 6-[6-(1-methyl-1H-pyrazol-4-yl)-[1,2,4]triazolo[4,3-b]pyridazin-3-ylmethyl]-quinazoline. $^1$H NMR (400 MHz, CD$_3$OD) δ 8.45 (s, 1H), 8.29 (s, 1H), 8.06 (d, 2H, J=9.6 Hz), 7.60 (d, 2H, J=9.6 Hz), 7.55 (m, 1H), 7.17 (d, 1H, J=8.0 Hz), 6.08 (s, 1H), 4.58 (m, 2H), 3.89 (s, 3H). Mass spectrum (LCMS, ESI pos.): Calcd for C$_{18}$H$_{14}$N$_8$; found: 343.3 (M+H).

EXAMPLE 71

6-[6-(1-Methyl-1H-pyrazol-4-yl)-[1,2,4]triazolo[4,3-b]pyridazin-3-ylmethyl]-quinoxaline

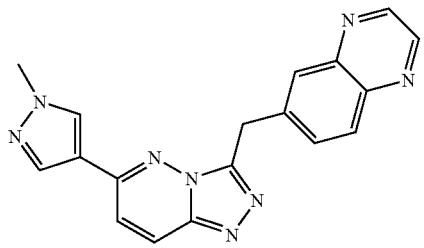

EXAMPLE 71

Step a

6-Iodo-quinoxaline

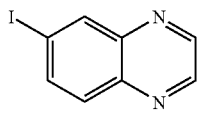

A solution of 4-iodo-benzene-1,2-diamine (0.46 g, 1.96 mmol), ethanedial [40% in water] (2.25 mL), acetic acid (1 mL) and ethanol (20 mL) were heated to 100° C. for several hours and then cooled to room temperature. Water was added and the crude product was extracted with ethyl acetate. The product was purified via silica gel column chromatography with hexane:ethyl acetate (1:1) to give 0.323 g (64%) of 6-iodo-quinoxaline. $^1$H NMR (400 MHz, CDCl$_3$) δ 8.77 (dd, 2H, J=2.0, 8.8 Hz), 8.46 (d, 1H, 2.0 Hz), 7.96 (dd, 1H, J=2.0, 8.8 Hz), 7.75 (d, 1H, J=8.8 Hz).

EXAMPLE 71

Step b

Quinoxalin-6-yl-acetic acid

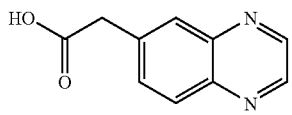

A solution of 6-iodo-quinoxaline (0.323 g, 1.26 mmol), malonic acid diethyl ester (0.404 g, 2.52 mmol), copper iodide (0.012 g, 0.063 mmol), biphenyl-2-ol (0.021 g, 0.126 mmol) and cesium carbonate (0.616 g, 1.89 mmol) in THF (5 mL) was heated to 70° C. in a sealed tube for 24 hours. The solution was then cooled to room temperature, water was added and the crude product was extracted from ethyl acetate. The product was purified via silica gel column chromatography in hexane:ethyl acetate (1:1) to give 2-quinoxalin-6-yl-malonic acid diethyl ester. 2-quinoxalin-6-yl-malonic acid diethyl ester (0.066 g, 0.229 mmol) was added to a solution of sodium hydroxide [2N] (0.229 mL) in methanol (2 mL) and stirred for several hours at room temperature. The reaction was then evaporated in vacuo, 1N HCl was added and the product was extracted with ethyl acetate to give 0.030 g (70%) of quinoxalin-6-yl-acetic acid. $^1$H NMR (400 MHz, DMSO-d$_6$) δ 12.6 (bs, 1H), 8.93 (dd, 2H, J=2.0, 6.0 Hz), 8.05 (d, 1H, 8.8 Hz), 7.99 (m, 1H), 7.79 (dd, 1H, J=2.0, 8.8 Hz), 3.89 (s, 2H).

EXAMPLE 71

Step c

Quinoxalin-6-yl-acetic acid hydrazide

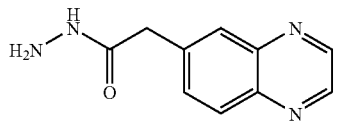

Trimethylsilyldiazomethane [2.0M in hexanes] (0.08 mL) was added dropwise to a solution of quinoxalin-6-yl-acetic acid (0.030 g, 0.159 mmol) in toluene/methanol [8/1] (0.5 mL) and stirred until the bubbling stopped. The reaction was then evaporated and the crude product was purified via silica gel column chromatography in hexane:ethyl:acetate (1:1) to give 0.013 g of quinoxalin-6-yl-acetic acid methyl ester. This was added to a solution of hydrazine (0.10 mL) in methanol and stirred at room temperature overnight. The reaction mixture was evaporated in vacuo to give 0.019 g of quinoxalin-6-yl-acetic acid hydrazide. $^1$H NMR (400 MHz, DMSO-d$_6$) δ 9.77 (bs, 1H), 9.35 (m, 2H), 8.46 (d, 1H, J=8.8 Hz), 8.39 (m, 1H), 8.19 (dd, 1H, J=2.0, 8.8 Hz), 4.68 (bs, 2H), 4.07 (s, 2H).

EXAMPLE 71

Step d

6-[6-(1-Methyl-1H-pyrazol-4-yl)-[1,2,4]triazolo[4,3-b]pyridazin-3-ylmethyl]-quinoxaline

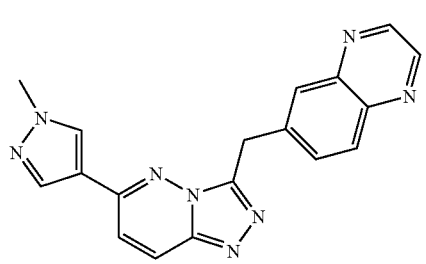

Quinoxalin-6-yl-acetic acid hydrazide (0.019 g, 0.094 mmol) and 3-chloro-6-(1-methyl-1H-pyrazol-4-yl)-pyridazine (0.018 g, 0.094 mmol) were heated to 125° C. in butanol (2 mL) for four hours. The reaction was cooled to room temperature, evaporated in vacuo and purified via silica gel column chromatography eluting with 5% methanol in dichloromethane to give 0.0029 g (15%) of 6-[6-(1-methyl-1H-pyrazol-4-yl)-[1,2,4]triazolo[4,3b]pyridazin-3-ylmethyl]-quinoxaline. $^1$H NMR (400 MHz, CD$_3$OD) δ 8.77 (m, 2H), 8.16 (s, 1H), 8.09 (m, 1H), 8.07 (d, 1H, J=10.0 Hz), 8.00 (m, 2H), 7.85 (dd, 1H, J=8.8, 2.0 Hz), 7.56 (d, 1H, J=9.6 Hz), 4.79 (s, 2H), 3.94 (s, 3H). Mass spectrum (LCMS, ESI pos.): Calcd for C$_{18}$H$_{14}$N$_8$; found: 343.3, 344.3 (M+H).

EXAMPLE 72

6-(6-Benzo[b]thiophen-2-yl-[1,2,4]triazolo[4,3-b]pyridazin-3-ylmethyl)-quinoline

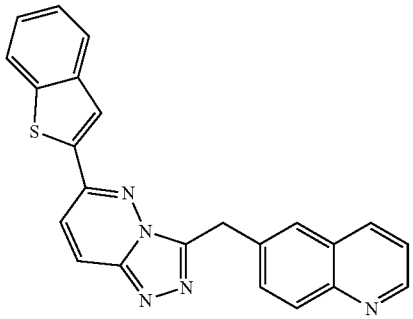

The title compound was prepared as described in Example 47. $^1$H-NMR (CDCl$_3$): δ 9.20-9.13 (1H, dd), 8.69-8.67 (1H, d, J=8.6 Hz), 8.50-8.48 (1H, d, J=8.5 Hz), 8.26-8.23 (2H, m), 8.17-8.15 (1H, d, J=9.8 Hz), 7.95-7.93 (1H, d, J=7.3 Hz), 7.80-7.77 (1H, q, J=5.0 Hz), 7.69-7.67 (1H, d, J=9.6 Hz), 7.51-7.42 (2H, m), 4.90 (2H, s). ESI-MS (m/z): Calcd. For C$_{23}$H$_{15}$N$_5$S: 393.47; found: 394.3.

EXAMPLE 73

6-[6-(1H-Pyrazol-4-yl)-[1,2,4]triazolo[4,3-b]pyridazin-3-ylmethyl]-quinolin-1-ol

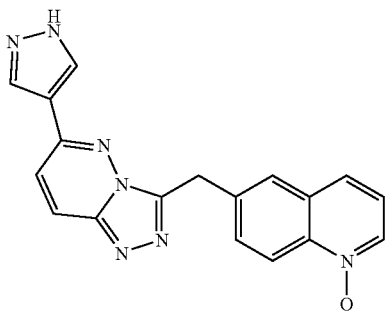

The title compound was prepared as described in Example 47. $^1$H-NMR (CDCl$_3$): δ 8.92-8.90 (1H, dd), 8.54-8.53 (1H, d, J=7.4 Hz), 8.16-8.14 (1H, d, J=8.8 Hz), 8.06 (1H, m), 8.02-7.97 (2H, m), 7.66-7.60 (2H, m), 7.53-7.48 (2H, m), 7.08-7.05 (1H, m), 7.51-7.42 (2H, m), 4.72 (2H, s). ESI-MS (m/z): Calcd. For C$_{18}$H$_{13}$N$_7$O: 343.34; found: 345.2.

EXAMPLE 74

6-[6-(5-Methyl-4,5-dihydro-thiophen-2-yl)-[1,2,4]triazolo[4,3-b]pyridazin-3-ylmethyl]-quinoline

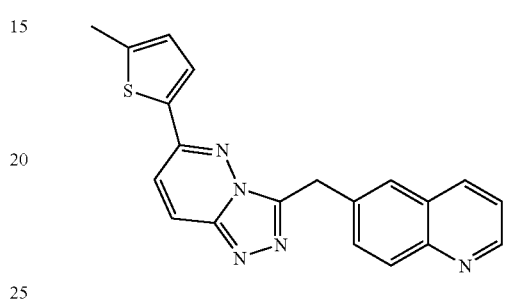

The title compound was prepared as described in Example 47. $^1$H-NMR (CDCl$_3$): δ 9.07-8.98 (2H, m), 8.27 (1H, s), 8.16-7.98 (3H, m), 7.75-7.73 (1H, d, J=8.8 Hz), 7.60-7.59 (1H, d, J=3.8 Hz), 6.79-6.77 (1H, m), 4.06-4.02 (1H, t, J=6.5 Hz), 3.91 (1H, s), 3.21-3.20 (3H, m), 2.45 (3H, s). ESI-MS (m/z): Calcd. For C$_{20}$H$_{17}$N$_5$S: 359.12; found: 358.2.

EXAMPLE 75

3-[4(3-Quinolin-6-ylmethyl-[1,2,4]triazolo[4,3-b]pyridazin-6-yl)-pyrazol-1-yl]-propan-1-ol

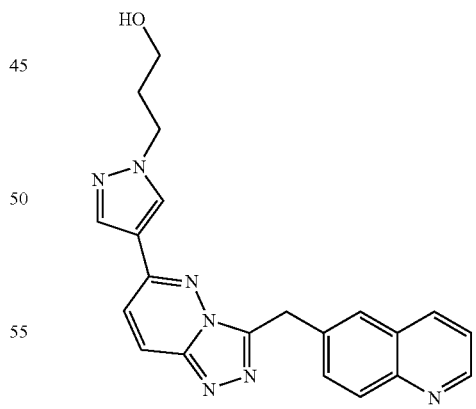

The title compound was prepared as described in Example 47. $^1$H-NMR (CDCl$_3$): δ 8.94-8.92 (1H, d, J=6.3 Hz), 8.61-8.59 (1H, d, J=8.9 Hz), 8.20-8.17 (1H, d, J=8.3 Hz), 8.05-7.93 (5H, m), 7.71-7.67 (1H, m), 7.36-7.33 (1H, d, J=9.6 Hz), 4.72 (2H, s), 4.22-4.20 (2H, m), 3.45-3.42 (2H, m), 1.95-1.95 (2H, m). ESI-MS (m/z): Calcd. For C$_{21}$H$_{19}$N$_7$O: 385.17; found: 386.31.

EXAMPLE 76

6-[6-(1H-Pyrazol-4-yl)-[1,2,4]triazolo[4,3-b]pyridazin-3-ylmethyl]-quinoline

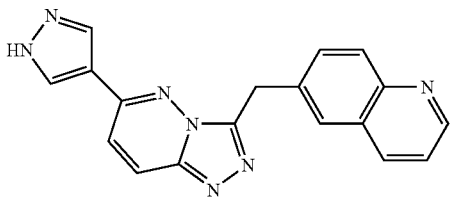

The title compound was prepared as described in Example 47. $^1$H-NMR (CDCl$_3$): δ 9.05-9.02 (1H, d, J=6.3 Hz), 8.60-8.57 (1H, d, J=7.5 Hz), 8.27-8.06 (4H, m), 7.75-7.73 (1H, d, J=9.0 Hz), 7.59-7.56 (1H, d, J=9.8 Hz), 7.50-7.48 (1H, d, J=9.8 Hz), 4.85 (2H, s). ESI-MS (m/z): Calcd. For C$_{18}$H$_{13}$N$_7$: 327.12; found: 328.32.

EXAMPLE 77

6-[6-(5-Chloro-4,5-dihydro-thiophen-2-yl)-[1,2,4]triazolo[4,3-b]pyridazin-3-ylmethyl]-quinoline

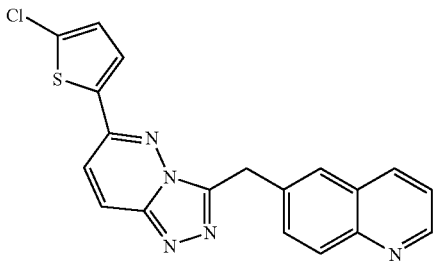

The title compound was prepared as described in Example 47. $^1$H-NMR (CDCl$_3$): δ 9.18-9.11 (2H, m), 8.38 (1H, s), 8.28-8.22 (3H, m), 8.06-8.04 (1H, q, J=5.3 Hz), 7.91-7.89 (1H, d, J=9.0 Hz), 7.80-7.79 (1H, d, J=4.2 Hz), 7.14-7.13 (1H, d, J=4.0 Hz), 4.94 (2H, s). ESI-MS (m/z): Calcd. For C$_{19}$H$_{14}$ClN$_5$S: 377.05; found: 378.3.

EXAMPLE 78

6-[6-(3H-Benzotriazol-5-yl)-[1,2,4]triazolo[4,3-b]pyridazin-3-ylmethyl]-quinoline

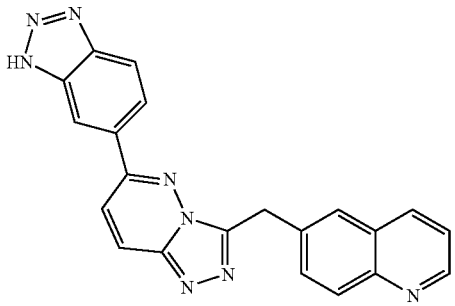

The title compound was prepared as described in Example 47. $^1$H-NMR (CDCl$_3$): δ 9.02 (1H, s), 8.61-8.60 (1H, d, J=3.7 Hz), 8.22-8.19 (1H, d, J=8.0 Hz), 8.13-8.11 (1H, d, J=9.6 Hz), 7.78 (1H, s), 7.70-7.68 (1H, d, J=8.5 Hz), 7.55-7.57 (1H, d, J=9.6 Hz), 7.47-7.44 (1H, q, J=4.5 Hz), 7.40-7.37 (1H, d, J=10.4 Hz), 4.67 (2H, s).

ESI-MS (m/z): Calcd. For C$_{21}$H$_{14}$N$_8$: 378.13; found: 379.3.

EXAMPLE 79

6-[6-(2-Methyl-3H-benzoimidazol-5-yl)-[1,2,4]triazolo[4,3-b]pyridazin-3-ylmethyl]-quinoline

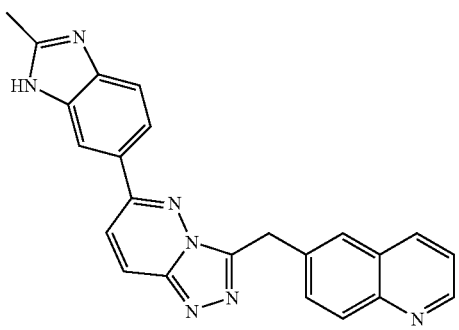

The title compound was prepared as described in Example 47. $^1$H-NMR (CDCl$_3$): δ 9.15 (1H, s), 8.76-75 (1H, d, J=3.7 Hz), 8.45-8.42 (1H, d, J=8.0 Hz), 8.30-8.27 (1H, d, J=9.6 Hz), 7.84-7.81 (1H, d, J=9.6 Hz), 7.69 (1H, s), 7.54-7.52 (1H, d, J=9.6 Hz), 7.43-7.40 (1H, d, J=8.3 Hz), 4.78 (2H, s), 2.66 (3H, s). ESI-MS (m/z): Calcd. For C$_{23}$H$_{17}$N$_7$: 391.15; found: 392.3.

EXAMPLE 80

6-[6-(1H-Indol-2-yl)-[1,2,4]triazolo[4,3-b]pyridazin-3-ylmethyl]-quinoline

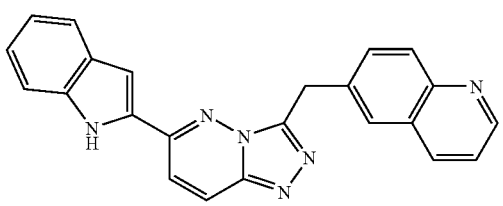

The title compound was prepared as described in Example 1. $^1$H-NMR (DMSO-d$_6$): δ 11.94 (1H, s), 9.21 (1H, m), 9.04 (1H, d, J=8.9 Hz), 8.43 (1H, s), 8.40 (1H, d, J=9.8 Hz), 8.32 (1H, d, J=8.5 Hz), 8.26 (1H, m), 8.04 (1H, d, J=9.7 Hz), 8.00 (1H, dd, J=8.4 Hz, 5.0 Hz), 7.67 (1H, d, J=7.8 Hz), 7.59 (1H, d, J=8.1 Hz), 7.53 (1H, d, J=1.2 Hz), 7.27 (1H, t, J=7.6 Hz), 7.09 (1H, t, J=7.7 Hz), 4.97 (2H, s). ESI-MS (m/z): Calcd. For C$_{23}$H$_{16}$N$_6$: 376.1; found: 377.3 (M+H).

EXAMPLE 81

6-(6-Benzofuran-2-yl-[1,2,4]triazolo[4,3-b]pyridazin-3-ylmethyl)-quinoline

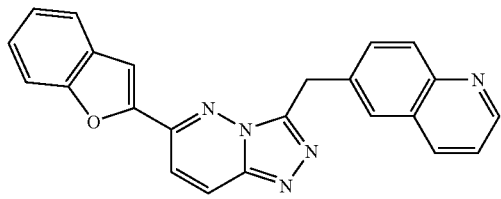

The title compound was prepared as described in Example 1. $^1$H-NMR (DMSO-d$_6$): δ 9.07 (1H, m), 8.75 (1H, m), 8.49 (1H, d, J=9.9 Hz), 8.17 (2H, m), 8.06 (2H, m), 8.00 (1H, d, J=9.9 Hz), 7.80 (3H, m), 7.51 (1H, m), 7.38 (1H, t, J=7.1 Hz), 4.88 (2H, s).

ESI-MS (m/z): Calcd. For C$_{23}$H$_{15}$N$_5$O: 377.1; found: 378.3 (M+H).

EXAMPLE 82

3-(2-Methyl-benzothiazol-6-ylmethyl)-6-(1-methyl-1H-pyrazol-4-yl)-[1,2,4]triazolo[4,3-b]pyridazine

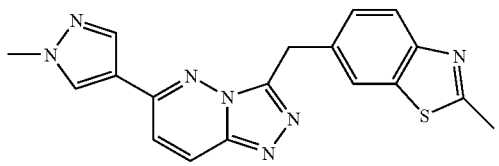

The title compound was prepared as described in Example 1. $^1$H NMR (CDCl$_3$/CD$_3$OD) δ 8.07 (1H, d, J=9.8 Hz), 8.03 (2H, m), 7.90 (1H, m), 7.86 (1H, d, J=8.3 Hz), 7.55 (1H, dd, J=8.3 Hz, 1.8 Hz), 7.39 (1H, d, J=9.7 Hz), 4.70 (2H, s), 4.02 (3H, s), 2.81 (3H, s). ESI-MS (m/z): Calcd. For C$_{18}$H$_{15}$N$_7$S: 361.1; found: 362.3 (M+H).

EXAMPLE 83

5-(3-Quinolin-6-ylmethyl-[1,2,4]triazolo[4,3-b]pyridazin-6-yl)-nicotinonitrile

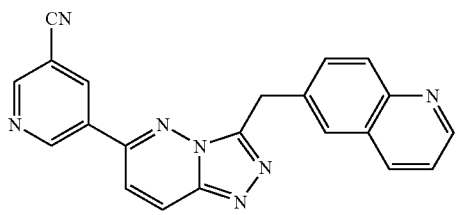

The title compound was prepared as described in Example 1. $^1$H NMR (CDCl$_3$/CD$_3$OD) δ 9.39 (1H, d, J=2.2 Hz), 9.05 (1H, d, J=1.8 Hz), 8.83 (1H, dd, J=4.3 Hz, 1.5 Hz), 8.58 (1H, t, J=2.0 Hz), 8.34 (1H, d, J=9.6 Hz), 8.21 (1H, m), 8.05 (1H, d, J=8.8 Hz), 7.93 (1H, d, J=1.7 Hz), 7.80 (1H, dd, J=8.9 Hz, 2.0 Hz), 7.71 (1H, d, J=9.9 Hz), 7.47 (1H, dd, J=8.3 Hz, 4.5 Hz), 4.88 (2H, s). ESI-MS (m/z): Calcd. For C$_{21}$H$_{13}$N$_7$: 363.1; found: 364.3 (M+H).

EXAMPLE 84

6-[6-(1H-Indol-5-yl)-[1,2,4]triazolo[4,3-b]pyridazin-3-ylmethyl]-quinoline

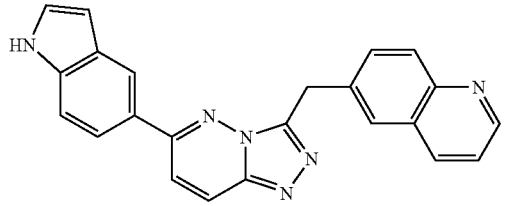

The title compound was prepared as described in Example 1. $^1$H-NMR (DMSO-d$_6$): δ 11.50 (1H, s), 9.25 (1H, d, J=4.0 Hz), 9.12 (1H, d, J=8.3 Hz), 8.39 (4H, m), 8.23 (1H, dd, J=8.8 Hz, 1.9 Hz), 8.08 (1H, d, J=9.9 Hz), 8.04 (1H, dd, J=8.3 Hz, 5.2 Hz), 7.87 (1H, dd, J=8.6 Hz, 1.5 Hz), 7.55 (1H, d, J=8.6 Hz), 7.47 (1H, t, J=2.7 Hz), 6.58 (1H, s), 4.94 (2H, s). ESI-MS (m/z): Calcd. For C$_{23}$H$_{16}$N$_6$: 376.1; found: 377.3 (M+H).

EXAMPLE 85

6-[6-(1-Methyl-1H-indol-5-yl)-[1,2,4]triazolo[4,3-b]pyridazin-3-ylmethyl]-quinoline

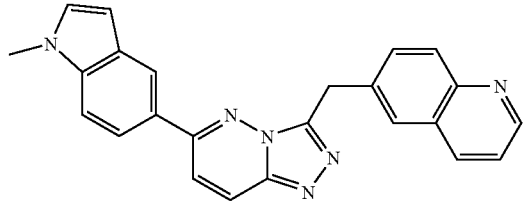

The product of the preceding example (0.074 g, 0.197 mmol) was dissolved in dry N,N-dimethylformamide (10 mL) under argon, treated with 60% sodium hydride in mineral oil (0.014 g, 0.350 mmol), and stirred at ambient temperature for 20 mins. The reaction was treated with iodomethane (0.020 mL, 0.320 mmol) via syringe, stirred another 18 h, diluted with water, and extracted three times with dichloromethane and twice with ethyl acetate. The combined organic layers were washed with brine, dried over Na$_2$SO$_4$, filtered, and the filtrate evaporated in vacuo giving an amber solid. This was dissolved in hot anhydrous acetonitrile (10 mL), treated dropwise with 0.53 N HCl/MeCN (0.75 mL, 0.40 mmol) with shaking, and cooled to 0° C. The suspension was filtered over a fine glass frit and the solids washed twice with ether and dried under high vacuum giving the title compound as an orange solid. $^1$H-NMR (DMSO-d$_6$): δ 9.24 (1H, d, J=4.1 Hz), 9.10 (1H, d, J=8.3 Hz), 8.38 (4H, m), 8.22 (1H, d, J=8.6 Hz), 8.09 (1H, d, J=10.1 Hz), 8.04 (1H, m), 7.93 (1H, d, J=8.5 Hz), 7.61 (1H, d, J=8.8 Hz), 7.45 (1H, s), 6.58 (1H, s), 4.94 (2H, s), 3.85 (3H, s). ESI-MS (m/z): Calcd. For C$_{24}$H$_{18}$N$_6$: 390.1; found: 391.3 (M+H).

EXAMPLE 86

6-{Difluoro-[6-(2-methyl-pyridin-4-yl)-[1,2,4]triazolo[4,3-b]pyridazin-3-yl]-methyl}-quinoline

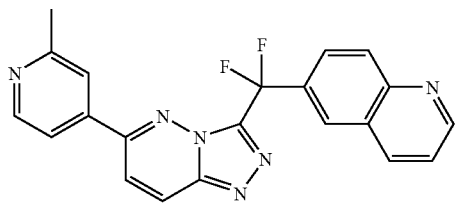

The title compound was prepared as described in Example 1. $^1$H-NMR (DMSO-$d_6$): δ 9.15 (1H, bs), 8.86 (2H, m), 8.80 (1H, d, J=10.6 Hz), 8.67 (1H, s), 8.33 (1H, d, J=7.9 Hz), 8.28 (1H, d, J=10.1 Hz), 8.20 (3H, m), 7.83 (1H, m), 2.75 (3H, s). ESI-MS (m/z): Calcd. For $C_{21}H_{14}N_6F_2$: 388.4; found: 389.3 (M+H). Alternatively, the Peppsi-iPr catalyst with KOtBu and isopropyl alcohol may be used in place of Pd(PPh$_3$)$_4$ with Na$_2$CO$_3$ in dioxane.

EXAMPLE 87

6-[6-(2-Methyl-pyridin-4-yl)-[1,2,4]triazolo[4,3-b]pyridazin-3-ylmethyl]-quinoline

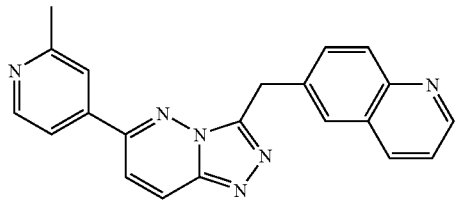

The title compound was prepared as described in Example 1. $^1$H-NMR (CDCl$_3$): δ 8.88 (1H, dd, J=4.3 Hz, 1.8 Hz), 8.70 (1H, d, J=4.6 Hz), 8.21 (1H, d, J=9.5 Hz), 8.11 (1H, m), 8.08 (1H, d, J=8.5 Hz), 7.89 (1H, d, J=1.8 Hz), 7.84 (1H, dd, J=8.6 Hz, 2.0 Hz), 7.61 (1H, s), 7.58 (1H, m), 7.52 (1H, d, J=9.8 Hz), 7.39 (1H, dd, J=8.3 Hz, 4.3 Hz), 4.86 (2H, s), 2.68 (3H, s). ESI-MS (m/z): Calcd. For $C_{21}H_{16}N_6$: 352.1; found: 353.3 (M+H).

EXAMPLE 88

5-(3-Quinolin-6-ylmethyl-[1,2,4]triazolo[4,3-b]pyridazin-6-yl)-pyridin-2-ylamine

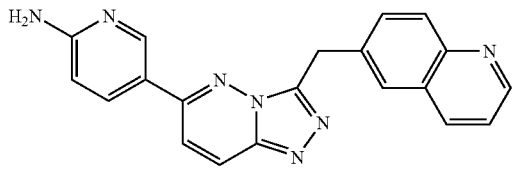

The title compound was prepared as described in Example 1. $^1$H-NMR (DMSO-$d_6$): δ 8.85 (1H, dd, J=4.4 Hz, 1.8 Hz), 8.68 (1H, d, J=2.0 Hz), 8.32 (1H, m), 8.30 (1H, d, J=9.9 Hz), 8.09 (1H, dd, J=8.8 Hz, 2.6 Hz), 7.97 (2H, m), 7.86 (1H, d, J=9.9 Hz), 7.80 (1H, dd, J=8.6 Hz, 2.1 Hz), 7.50 (1H, dd, J=8.3 Hz, 4.1 Hz), 6.64 (2H, bs), 6.57 (1H, d, J=8.6 Hz), 4.77 (2H, s). ESI-MS (m/z): Calcd. For $C_{20}H_{15}N_7$: 353.1; found: 354.3 (M+H).

EXAMPLE 89

6-[6-(6-Methoxy-pyridin-3-yl)-[1,2,4]triazolo[4,3-b]pyridazin-3-ylmethyl]-quinoline

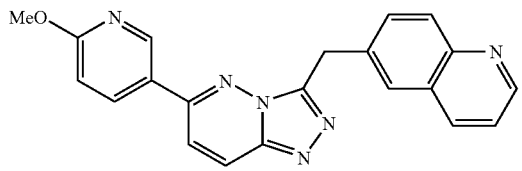

The title compound was prepared as described in Example 1. $^1$H NMR (CDCl$_3$/CD$_3$OD) δ 8.87 (1H, dd, J=4.0 Hz, 1.8 Hz), 8.74 (1H, d, J=2.0 Hz), 8.15 (1H, d, J=9.9 Hz), 8.14 (1H, dd, J=8.8 Hz, 2.5 Hz), 8.10 (1H, m), 8.06 (1H, d, J=8.9 Hz), 7.87 (1H, m), 7.84 (1H, m), 7.49 (1H, d, J=9.8 Hz), 7.37 (1H, dd, J=8.2 Hz, 4.1 Hz), 6.90 (1H, d, J=8.8 Hz), 4.82 (2H, s), 4.03 (3H, s). ESI-MS (m/z): Calcd. For $C_{21}H_{16}N_6O$: 368.1; found: 369.3 (M+H).

EXAMPLE 90

5-(3-Quinolin-6-ylmethyl-[1,2,4]triazolo[4,3-b]pyridazin-6-yl)-1H-pyridin-2-one

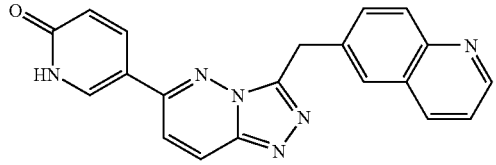

The product of the preceding example (0.063 g, 0.171 mmol) was dissolved in dry dichloromethane (5 mL) under argon, treated with 1N boron tribromide in dichloromethane (1.25 mL, 1.25 mmol), and stirred at ambient temperature for 18 h. The reaction was not complete by TLC, so it was heated to 50° C. under reflux condenser for 20 h, cooled to ambient temperature, and quenched with saturated aqueous NaHCO$_3$. The aqueous layer was extracted several times with dichloromethane and ethyl acetate, and the combined organic layers were washed with water and brine, dried over Na$_2$SO$_4$, and filtered. The evaporated filtrate was then purified by preparative TLC on silica gel (20% MeOH/CH$_2$Cl$_2$) giving the title compound as a light yellow solid. $^1$H NMR (CDCl$_3$/CD$_3$OD) δ 8.82 (1H, dd, J=4.3 Hz, 2.6 Hz), 8.19 (1H, d, J=8.3 Hz), 8.15 (1H, d, J=9.9 Hz), 8.14 (1H, dd, J=9.6 Hz, 2.7 Hz), 8.05 (1H, d, J=8.6 Hz), 8.01 (1H, d, J=2.7 Hz), 7.88 (1H, s), 7.83 (1H, dd, J=8.6 Hz, 1.8 Hz), 7.51 (1H, d, J=9.6 Hz), 7.45 (1H, dd, J=8.3 Hz, 4.3 Hz), 6.71 (1H, d, J=9.9 Hz), 4.81 (2H, s). ESI-MS (m/z): Calcd. For C$_{20}$H$_{14}$N$_6$O: 354.1; found: 355.4 (M+H).

EXAMPLE 91

5-(6-Pyridin-3-yl-[1,2,4]triazolo[4,3-b]pyridazin-3-ylmethyl)-quinoline

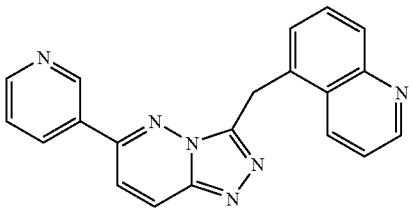

The title compound was prepared as described in Example 1. $^1$H NMR (CDCl$_3$/CD$_3$OD) δ 9.16 (1H, d, J=1.6 Hz), 8.92 (2H, m), 8.80 (1H, dd, J=4.8 Hz, 1.6 Hz), 8.18 (1H, d, J=9.6 Hz), 8.16 (1H, m), 8.05 (1H, d, J=8.3 Hz), 7.76 (1H, m), 7.69 (1H, dd, J=8.3 Hz, 7.0 Hz), 7.51 (1H, d, J=9.6 Hz), 7.49 (2H, m), 5.09 (2H, s). ESI-MS (m/z): Calcd. For C$_{20}$H$_{14}$N$_6$: 338.1; found: 339.3 (M+H).

EXAMPLE 92

3-(2-Methyl-benzothiazol-6-ylmethyl)-6-pyridin-3-yl-[1,2,4]triazolo[4,3-b]pyridazine

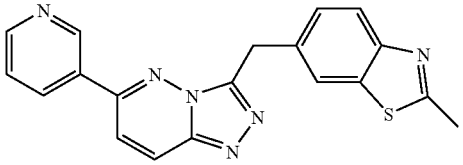

The title compound was prepared as described in Example 1. $^1$H NMR (CDCl$_3$/CD$_3$OD) δ 9.17 (1H, d, J=1.7 Hz), 8.77 (1H, dd, J=4.9 Hz, 1.3 Hz), 8.30 (1H, dd, J=6 Hz, 2 Hz), 8.25 (1H, d, J=9.5 Hz), 7.92 (1H, d, J=1.3 Hz), 7.87 (1H, d, J=8.3 Hz), 7.67 (1H, d, J=9.9 Hz), 7.57 (2H, m), 4.77 (2H, s), 2.81 (3H, s).

ESI-MS (m/z): Calcd. For C$_{19}$H$_{14}$N$_6$S: 358.1; found: 359.2 (M+H).

EXAMPLE 93

6-[6-(1-Methyl-1H-pyrazol-4-yl)-[1,2,4]triazolo[4,3-b]pyridazin-3-ylmethyl]-benzothiazol-2-ylamine

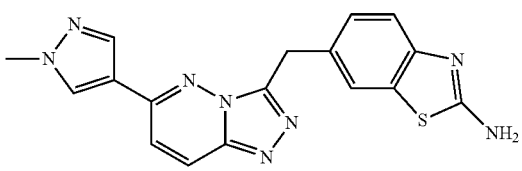

The title compound was prepared as described in Example 1. $^1$H-NMR (DMSO-d$_6$): δ 8.67 (2H, bs), 8.54 (1H, s), 8.31 (1H, d, J=9.9 Hz), 8.18 (1H, s), 7.82 (1H, d, J=1.1 Hz), 7.67 (1H, d, J=9.9 Hz), 7.37 (2H, m), 4.55 (2H, s), 3.94 (3H, s). ESI-MS (m/z): Calcd. For C$_{17}$H$_{14}$N$_8$S: 362.1; found: 363.2 (M+H).

EXAMPLE 94

Dimethyl-{6-[6-(1-methyl-1H-pyrazol-4-yl)-[1,2,4]triazolo[4,3-b]pyridazin-3-ylmethyl]-benzothiazol-2-yl}-amine

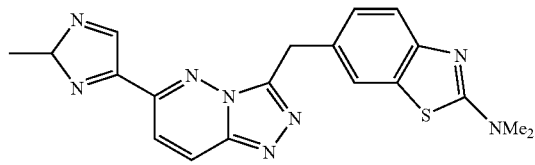

The product of the preceding example (0.046 g, 0.127 mmol) was dissolved in dry N,N-dimethylformamide (5 mL) under argon, treated with 60% sodium hydride in mineral oil (0.013 g, 0.325 mmol) and iodomethane (0.040 mL, 0.642 mmol), and stirred at ambient temperature for 4 h. The reaction was concentrated to dryness in vacuo, dissolved in 10% MeOH/CH$_2$Cl$_2$, filtered, and the filtrate purified twice by preparative TLC on silica gel (first with 10%, then 5% MeOH/CH$_2$Cl$_2$) giving the title compound as a yellow solid. $^1$H NMR (CDCl$_3$) δ 8.02 (1H, d, J=9.6 Hz), 7.98 (1H, m), 7.91 (1H, s), 7.67 (1H, d, J=1.8 Hz), 7.48 (1H, d, J=8.4 Hz), 7.38 (1H, m), 7.23 (1H, d, J=9.6 Hz), 4.61 (2H, s), 4.01 (3H, s), 3.17 (6H, s). ESI-MS (m/z): Calcd. For C$_{19}$H$_{18}$N$_8$S: 390.1; found: 391.3 (M+H).

EXAMPLE 95

6-[6-(2-Chloro-pyridin-4-yl)-[1,2,4]triazolo[4,3-b]pyridazin-3-ylmethyl]-quinoline

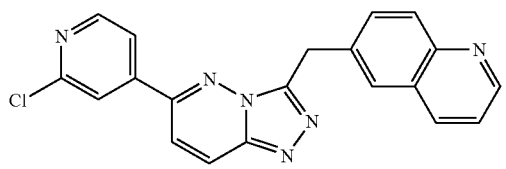

The title compound was prepared as described in Example 1. $^1$H-NMR (DMSO-d$_6$): δ 8.44 (1H, dd, J=4.3 Hz, 1.5 Hz), 8.59 (1H, d, J=4.6 Hz), 8.30 (1H, d, J=9.8 Hz), 8.20 (1H, m), 8.06 (1H, d, J=8.5 Hz), 7.93 (1H, m), 7.88 (1H, m), 7.82 (1H, dd, J=8.8 Hz, 2.0 Hz), 7.77 (1H, dd, J=5.3 Hz, 1.5 Hz), 7.63 (1H, d, J=9.5 Hz), 7.45 (1H, dd, J=8.4 Hz, 4.3 Hz), 4.87 (2H, s). ESI-MS (m/z): Calcd. For C$_{20}$H$_{13}$N$_6$Cl: 372.1; found: 373.4 (M+H).

EXAMPLE 96

5-(3-Quinolin-6-ylmethyl-[1,2,4]triazolo[4,3-b]pyridazin-6-yl)-pyridine-2-carbonitrile

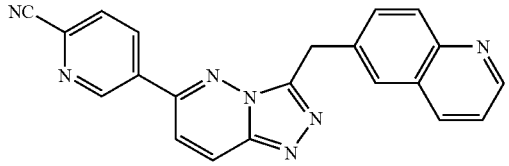

The title compound was prepared as described in Example 1. ¹H NMR (CDCl₃/CD₃OD) δ 9.31 (1H, d, J=2.3 Hz), 8.83 (1H, dd, J=4.5 Hz, 1.6 Hz), 8.42 (1H, dd, J=8.2 Hz, 4.2 Hz), 8.33 (1H, d, J=9.6 Hz), 8.19 (1H, m), 8.05 (1H, d, J=8.7 Hz), 7.94 (1H, d, J=8.1 Hz), 7.89 (1H, d, J=1.6 Hz), 7.81 (1H, dd, J=8.7 Hz, 1.9 Hz), 7.69 (1H, d, J=9.7 Hz), 7.45 (1H, dd, J=8.4 Hz, 4.3 Hz), 4.87 (s, 2H).

ESI-MS (m/z): Calcd. For C₂₁H₁₃N₇: 363.1; found: 364.3 (M+H).

EXAMPLE 97

{5-[3-(Difluoro-quinolin-6-yl-methyl)-[1,2,4]triazolo[4,3-b]pyridazin-6-yl] thiophen-2-yl}-(4-methyl-piperazin-1-yl)-methanone

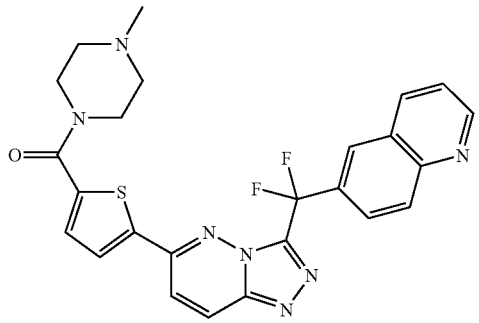

EXAMPLE 97

Step a 5-(6-Chloro-pyridazin-3-yl)-thiophene-2-carboxylic acid ethyl ester

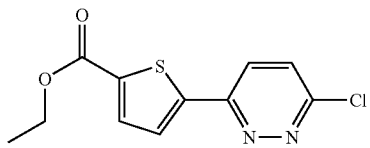

To a dry flask containing 3,6-dichloro-pyridazine (2.8 g, 18.8 mmol) and 5-ethoxycarbonylthiophenyl-2-zinc bromide (0.5 M in THF, 16 ml, 8 mmol) in 100 mL dry dioxane was added Pd(PPh₃)₄ (450 mg, 0.39 mmol). The resulting solution was heated to 60° C. for overnight under N₂, allowed to cool to 20° C. The reaction was quenched by addition of 15 mL methanol followed by addition of 3NHCl (10 mL). The mixture was kept stirring at 20° C. for 1 more hour. Saturated NaHCO₃ was added to neutralize the mixture. After aqueous work up, the mixture was extracted by CH₂Cl₂, dried over Na₂SO₄ and concentrated in vacuum. The residue was purified by column to give 5-(6-chloro-pyridazin-3-yl)-thiophene-2-carboxylic acid ethyl ester (1.4 g, 65%). ¹H NMR (CDCl₃) δ7.81 (d, J=3.9 Hz, 1H), 7.77 (d, J=9.1 Hz, 1H), 7.63 (d, J=3.9 Hz, 1H), 7.55 (d, J=9.1 Hz, 1H), 4.38 (q, 2H), 1.40 (t, 3H); MS (ES) m/z 269(M+H⁺).

EXAMPLE 97

Step b

5-[3-(Difluoro-quinolin-6-yl-methyl)-[1,2,4]triazolo[4,3-b]pyridazin-6-yl]-thiophene-2-carboxylic acid

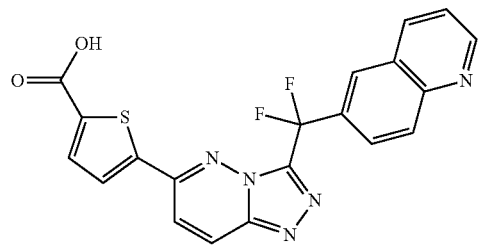

A mixture of the 5-(6-Chloro-pyridazin-3-yl)-thiophene-2-carboxylic acid ethyl ester prepared in step a (54 mg, 0.20 mmol), difluoro-quinolin-6-yl-acetic acid hydrazide (Example 57: Step c) (71 mg, 0.30 mmol) and n-butanol (3 mL) were combined in a sealed tube and heated in a 130° C. oil bath for 4.5 hours. The mixture was cooled to room temperature, diluted with dichloromethane (30 mL) and washed with saturated NaHCO₃ (1×). The aqueous layer was extracted with dichloromethane (2×). The combined organic layers was dried over MgSO₄, filtered, evaporated in vacuo and the crude product chromatographed to provide the intermediate ethyl ester (62.4 mg) 68% yield. The ethyl ester was dissolved in a 2:1 tetrahydrofuran/methanol (3 mL) mixture and treated with 2N NaOH (0.14 mL). The mixture was stirred for 3 hours at 20° C., evaporated in vacuo, diluted with water (10 mL), and acidified with 6 N HCl to pH 2. The solid precipitates were collected and dried to afford the product 97a (60 mg, 100%). ¹H NMR (400 MHz, DMSO-d₆) δ 9.03 (m, 1H); 8.64 (d, J=9.8 Hz, 1H), 8.59 (d, J=9.0 Hz, 1H), 8.49 (s, 1H), 8.20-8.17 (m, 2H), 8.12 (d, J=4.0 Hz, 1H), 8.03 (dd, J=9.2, 2.1 Hz, 1H), 7.79 (d, J=4.3 Hz, 1H), 7.65 (dd, J=8.3, 4.2 Hz, 1H); MS (m/z): 424 (MH⁺)

EXAMPLE 97

Step c

[5-[3-(Difluoro-quinolin-6-yl-methyl)-[1,2,4]triazolo[4,3-b]pyridazin-6-yl]-thiophen-2-yl]-(4-methyl-piperazin-1-yl)-methanone

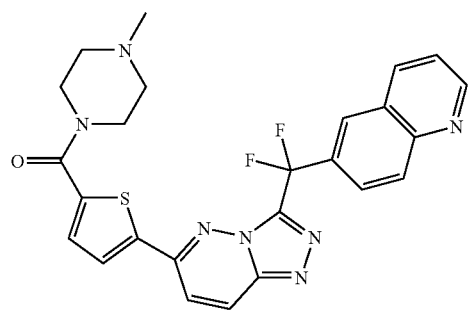

To a solution of the compound prepared in step b (50 mg, 0.12 mmol) in dry DMF 5 mL were added HATU (0.112 g, 0.29 mmol), HOBt (0.023 g, 0.17 mmol) and DIEA (0.1 mL, 0.57 mmol) respectively. The resulting mixture was stirred at RT for 30 minutes and N-Methylpiperazine was added. Stirring was continued for an additional hour and water (20 mL) was added. Dichloromethane (20 mL) was added and layers separated. The $CH_2Cl_2$ layer was dried over $MgSO_4$, evaporated in vacuo and chromatographed ($CH_2Cl_2$/MeOH with 0.1% $Et_3N$) to provide the compound as a tan solid. $^1H$ NMR (400 MHz, $CD_3OD$) δ 8.97 (m, 1H), 8.57 (d, J=7.9 Hz, 1H), 8.49 (s, 1H), 8.35 (d, J=9.8 Hz, 1H), 8.19 (d, J=9.2 Hz, 1H), 8.07 (dd, J=9.1, 1.9 Hz, 1H), 8.01 (d, J=9.6 Hz, 1H), 7.88 (d, J=3.7 Hz, 1H), 7.66 (dd, J=4.4, 4.3 Hz, 1H), 7.44 (d, J=3.8 Hz, 1H), 3.86 (m, 4H), 2.82 (m, 4H), 2.57 (s, 3H); MS (m/z): 506 (MH$^+$).

EXAMPLE 98

{5-[3-(Difluoro-quinolin-6-yl-methyl)-[1,2,4]triazolo[4,3-b]pyridazin-6-yl]-thiophen-2-yl}-(4-methanesulfonyl-piperazin-1-yl)-methanone

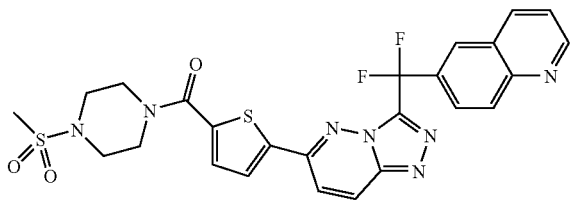

To a solution of the compound prepared in Example 97b (1.0 g, 2.3 mmol in dry $CH_2Cl_2$ (100 ml) were added 1-methanesulfonyl-piperazine (460 mg, 2.8 mmol), EDC (560 mg, 2.8 mmol), DMAP (340 mg, 2.8 mmol) respectively. The resulting mixture was stirred at 20° C. for overnight. After aqueous work up, the organic layer was separated, washed with brine, dried over $Na_2SO_4$. The solvent was removed in vacuum. The residue was purified by column to give the desired product as a white solid (680 mg, 51%). $^1H$ NMR ($CDCl_3$) δ 9.03 (s, 1H), 8.31 (d, J=11.2 Hz 1H), 8.11 (m, 4H) 7.61 (d, J=3.8 Hz, 1H), 7.57 (d, J=9.8 Hz, 1H) 7.49 (m, 1H), 7.31 (d, J=3.8 Hz, 1H) 3.90 (m, 4H), 3.34 (m, 4H), 2.86 (s, 3H); MS (ES) m/z 570.2 (M+H$^+$).

EXAMPLE 99

6-{Difluoro-[6-(1-methanesulfonyl-1H-pyrazol-4-yl)-[1,2,4]triazolo[4,3-b]pyridazin-3-yl]-methyl}-quinoline

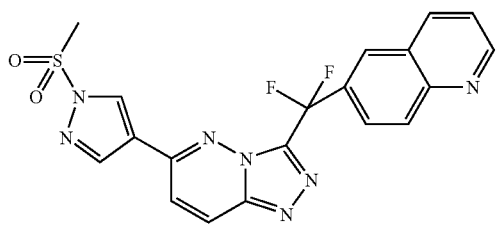

EXAMPLE 99

Step a 4-(6-Chloro-pyridazin-3-yl)-pyrazole-1-carboxylic acid tert-butyl ester

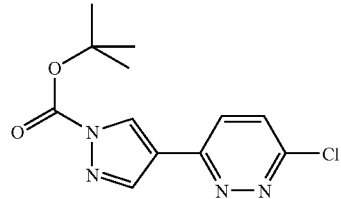

A mixture of 3,6-dichloro-pyridazine (1.06 g, 6.98 mmol) and 4-(4,4,5,5-tetramethyl-1,3,2-dioxaborolan-2-yl)-pyrazole-1-carboxylic acid tert-butyl ester (1.47 g, 5.0 mmol) in 2.0 M potassium carbonate (10 mL, 20 mmol) and 1,4-dioxane (40 mL) was degassed by house vacuum for 15 min followed by bubbling with argon for ~10 min, Peppsi-ipr (340 mg, 0.5 mmol) was then added. After flushing with argon for another ~10 min, the mixture was heated at 70° C. for 4 h and allowed to cool to room temperature. The solid was removed by filtration through Celite, and the filtrate was separated. The aqueous solution was extracted with $CH_2Cl_2$ and the combined organic phases were dried over $Na_2SO_4$, concentrated, and purified by column to provide 0.65 g desired product (46%). $^1H$ NMR (DMSO) δ 9.08 (s, 1H), 8.47 (s, 1H), 8.31 (d, J=9.0 Hz, 1H), 8.01 (d, J=9.0 Hz, 1H), 1.59 (s, 3H); MS (ES) m/z 280.8(M+H$^+$).

EXAMPLE 99

Step b

6-[Difluoro-[6-(1H-pyrazol-4-yl)-[1,2,4]triazolo[4,3-b]pyridazin-3-yl]-methyl]-quinoline

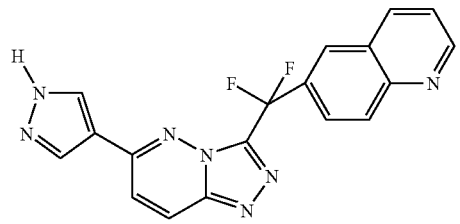

A 100 ml flask containing a mixture of 3-chloro-6-(pyrazole-1-carboxylic acid tert-butyl ester)-pyridazine (140 mg, 0.5 mmol), difluoro-quinolin-6-yl-acetic acid hydrazide (130 mg, 0.55 mmol) and catalytic amount of 3N HCl in 40 mL isopropanol was heated to 80° C. for overnight. The reaction mixture was neutralized by $NaHCO_3$ and extracted by $CH_2Cl_2$. The solvent was removed in vacuo and the residue was purified by flash chromatography to give 110 mg (61%) desired product. $^1H$ NMR ($CDCl_3$) δ 10.2(bs, 1H), 8.83 (d, J=9.23 Hz, 1H), 8.42 (m, 1H), 8.19-8.31 (m, 4H), 7.77 (d, J=9.0 Hz, 1H), 7.60 (d, J=9.0 Hz, 1H), 7.45-7.57 (m, 2H); MS (ES) m/z 364.0 (M+H$^+$).

EXAMPLE 99

Step c

6-[Difluoro-[6-(1-methanesulfonyl-1H-pyrazol-4-yl)-[1,2,4]triazolo[4,3-b]pyridazin-3-yl]-methyl]-quinoline

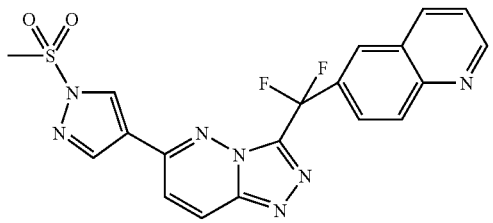

To a 50 mL dry flask containing 6-{difluoro-[6-(1H-pyrazol-3-yl)-[1,2,4]triazolo[4,3-b]pyridazin-3-yl]-methyl}-quinoline (110 mg, 0.303 mmol), triethylamine (120 mg, 1.2 mmol) in CH$_2$Cl$_2$ (6 mL) was added methanesulfonyl chloride (138 mg, 1.21 mmol). The reaction mixture was stirred at 0° C. for 90 min, until TLC showed the reaction was completed. The mixture was then neutralized by saturated NaHCO$_3$, extracted by CH$_2$Cl$_2$, dried over Na$_2$SO$_4$, concentrated by vacuo and purified by column to give 113 mg (85%) of the target compound. $^1$H NMR (CDCl$_3$) δ 9.02 (dd, J=4.3, 1.3 Hz, 1H) 8.44 (d, J=9.4 Hz, 1H), 8.23-8.30 (m, 5H), 8.03 (d, J=6.4 Hz, 1H), 7.51 (dd, J=9.7, 4.0 Hz, 1H), 7.43 (d, J=9.8 Hz, 1H), 3.45 (s, 3H); MS (ES) m/z 442.1 (M+H$^+$).

EXAMPLE 100

6-{[6-(2-Ethynyl-pyridin-4-yl)-[1,2,4]triazolo[4,3-b]pyridazin-3-yl]-difluoro-methyl}-quinoline

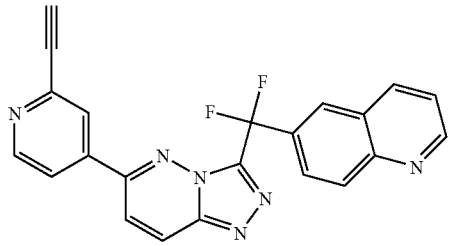

EXAMPLE 100

Step a

3-Chloro-6-(2-chloro-pyridin-4-yl)-pyridazine

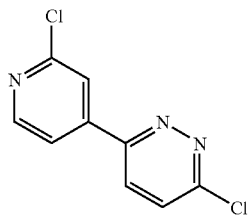

A mixture of 3,6-dichloro-pyridazine (1.04 g, 6.98 mmol) and 2-chloropyridine boronic acid (1.00 g, 6.37 mmol) in 2.0 M potassium carbonate (10 mL, 20 mmol) and 1,4-dioxane (20 mL) was bubbled with argon for ~10 min, bis(triphenylphosphine) palladium (II) dichloride (236 mg, 0.336 mmol) was then added. After flushing with argon for another ~10 min, the mixture was heated at 80° C. for 18 h and allowed to cool to room temperature. The solid was removed by filtration through Celite, and the filtrate was separated. The aqueous solution was extracted with CH$_2$Cl$_2$ and the combined organic phases were dried, concentrated, and purified by column to provide 296 mg (21%) of 100a as a solid: $^1$H NMR (400 MHz, CDCl$_3$) δ 8.58 (d, J=5.1 Hz, 1 H), 8.00 (m, 1 H), 7.90 (dd, J=5.5, 1.6 Hz, 1 H), 7.89 (d, J=9.0 Hz, 1 H), 7.68 (d, J=9.0 Hz, 1 H); MS (ES) m/z: 226/228 (M+H$^+$).

EXAMPLE 100

Step b

6-{[6-(2-Chloro-pyridin-4-yl)-[1,2,4]triazolo[4,3-b]pyridazin-3-yl]-difluoro-methyl}-quinoline

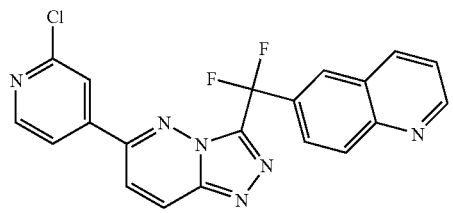

A pressure tube containing a mixture of 3-chloro-6-(2-chloro-pyridin-4-yl)-pyridazine (200 mg, 0.884 mmol) and difluoro-quinolin-6-yl-acetic acid hydrazide (314 mg, 1.32 mmol) in butanol (7 mL) was flushed with argon and then sealed. After heating at 102° C. for 64 h, the solvent was removed in vacuo and the residue was purified by flash chromatography to give 134 mg (37%) of 100b: $^1$H NMR (400 MHz, CDCl$_3$) δ 9.04 (m, 1 H), 8.62 (d, J=5.1 Hz, 1 H), 8.37-8.33 (m, 4 H), 8.07 (dd, J=9.0, 2.0 Hz, 1 H), 7.83 (m, 1 H), 7.75 (dd, J=5.1, 1.6 Hz, 1 H), 7.67 (d, J=9.8 Hz, 1 H), 7.58 (m, 1 H); MS (ES) m/z: 409/411 (M+H$^+$).

EXAMPLE 100

Step c

6-{[6-(2-Ethynyl-pyridin-4-yl)-[1,2,4]triazolo[4,3-b]pyridazin-3-yl]-difluoro-methyl}-quinoline A mixture of 100b (60 mg, 0.15 mmol) in DMF (0.7 mL) and Et$_2$NH (0.45 mL) was degassed with argon for ~5 min, and triphenylphosphine (8 mg, 0.031 mmol), CuI (3 mg, 0.016 mmol) and bis(triphenylphosphine)palladium (II) dichloride (10 mg, 0.014 mmol) were then added. The degassing was continued for about 5 min and trimethylsilylacetylene was added. The mixture was microwaved at 120° C. for 50 min and concentrated in vacuo. The residue was purified by chromatography to give 10 mg (14%) of 6-{difluoro-[6-(2-trimethylsilanylethynyl-pyridin-4-yl)-[1,2,4]triazolo[4,3-b]pyridazin-3-yl]-methyl}-quinoline.

The above product (10 mg, 0.021 mmol) in THF (1.2 mL) was treated with 0.1 M NaOH (0.2 mL, 0.02 mmol) for 1 h and concentrated. The residue was partitioned between CH$_2$Cl$_2$ and water. The organic layer was dried, concentrated, and chromatographed to provide 8 mg (94%) of 100: $^1$H NMR (400 MHz, CDCl$_3$) δ 8.96 (d, J=4.3 Hz, 1 H), 8.74 (d, J=5.1 Hz, 1 H), 8.29-8.19 (m, 4 H), 8.00-7.98 (m, 1 H), 7.92 (s, 1 H), 7.72 (dd, J=5.1, 1.6 Hz, 1 H), 7.62 (d, J=9.8 Hz, 1 H), 7.45 (dd, J=8.2, 4.3 Hz, 1 H), 3.26 (s, 1 H); MS (ES) m/z: 399 (M+H$^+$).

EXAMPLE 101

4-[3-(Difluoro-quinolin-6-yl-methyl)-[1,2,4]triazolo[4,3-b]pyridazin-6-yl]-pyridine-2-carbonitrile

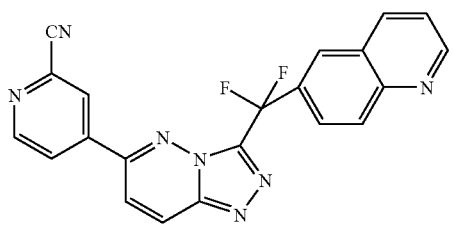

A mixture of 6-{[6-(2-Chloro-pyridin-4-yl)-[1,2,4]triazolo[4,3-b]pyridazin-3-yl]-difluoro-methyl}-quinoline (see Example 100b) (50 mg, 0.122 mmol) in DMF (4 mL) and Zn(CN)$_2$ (43 mg, 0.367 mmol) was degassed with house vacuum for ~5 min, and tetrakis(triphenylphosphine)palladium (13.4 mg, 0.012 mmol) were then added. The mixture was microwaved at 190° C. for 20 min. Following the aqueous work up, solvent was removed by vacuo. The target compound, 211 mg (41%), was obtained by column purification. $^1$H NMR (CDCl$_3$) δ 9.04 (dd, J=4.2, 1.6 Hz, 1H), 8.95 (d, J=5.12 Hz, 1H), 8.41 (d, J=9.8 Hz, 1H), 8.22-8.35 (m, 4H), 8.00-8.05 (m, 2H), 7.70 (d, J=9.8 Hz, 1H), 7.54 (dd, J=8.2, 3.8 Hz, 1H); MS (ES) m/z 400.3 (M+H$^+$).

EXAMPLE 102

{5-[3-(Benzofuran-5-yl-difluoro-methyl)-[1,2,4]triazolo[4,3-b]pyridazin-6-yl]-thiophen-2-yl}-(4-methyl-piperazin-1-yl)-methanone

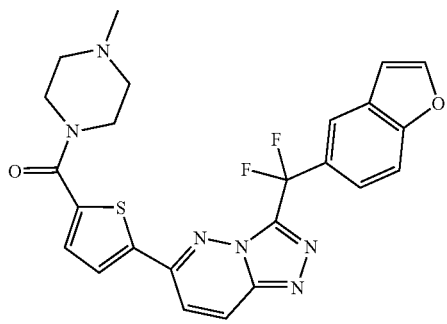

EXAMPLE 102

Step a (2,3-Dihydro-benzofuran-5-yl)-oxo-acetic acid ethyl ester

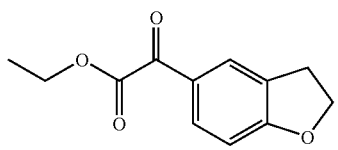

Solid AlCl$_3$ (5.55 g, 0.042 M) was added portionwise to a cold (0° C.) solution of dihydrobenzofuran (5.0 g, 0.042 M) and ethyl oxalyl chloride (4.5 mL, 0.042 M) in dry dichloromethane (80 mL). After complete addition the dark solution was warmed up to RT and stirred for 2 hr. The resulting reaction mixture was slowly poured into a concentrated HCl/ice water solution (5 mL/200 mL). The aqueous mixture was stirred for 20 minutes and dichloromethane (150 mL) was added. Layers were separated. The aqueous layer was extracted with dichloromethane (1×). The combined CH$_2$Cl$_2$ extracts were dried over MgSO$_4$, filtered, evaporated in vacuo and the crude oil purified by chromatography (Hexane/EtOAc) to provide the desired product as an oil (4.8 g) 54%. $^1$H NMR (400 MHz, CDCl$_3$) δ7.88 (s, 1H), 7.86 (d, J=8.3 Hz, 1H), 6.85 (d, J=8.8 Hz, 1H), 4.72 (t, J=9 Hz, 2H), 4.45 (q, J=7.2 Hz, 2H), 3.28 (t, J=9.2 Hz, 2H), 1.42 (t, J=7.2 Hz, 3H). MS (m/z): 221 (MH$^+$).

EXAMPLE 102

Step b

Benzofuran-5-yl-oxo-acetic acid ethyl ester

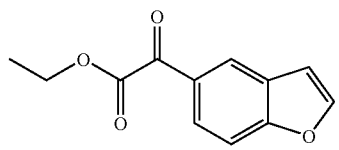

N-Bromosuccinimide (3.88 g, 0.022 M) was slowly added to a solution of the compound prepared in step a (4.8 g, 0.022 M) and benzoyl peroxide (0.030 g, 0.12 mmol) in carbon tetrachloride (80 mL). The mixture was stirred at reflux for 3 hours, cooled to RT, evaporated to dryness and chromatographed (Heptane/EtOAc) to afford the product as an oil (3.8 g) 100%. $^1$H NMR (400 MHz, CDCl$_3$) δ 8.32 (s, 1H) 8.02 (dd, J=8.7, 1.8 Hz, 1H), 7.73 (d, J=2.1 Hz, 1H), 7.61 (d, J=8.8 Hz, 1H), 6.88 (s, 1H), 4.48 (q, J=7.3 Hz, 2H), 1.46 (t, J=7.1 Hz, 3H). MS (m/z): 219 (MH$^+$).

EXAMPLE 102

Step c

Benzofuran-5-yl-difluoro-acetic acid ethyl ester

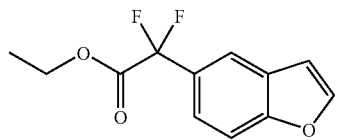

To a cold solution (0° C.) of the compound prepared in Step b (0.895 g, 4.1 mmol) in dichoromethane (10 mL) was slowly added (diethylamino)sulfur trifluoride (DAST) (5 g, 31.0 mmol). The mixture was warmed to RT and stirring was continued for 24 hr. The reaction mixture was then poured into ice water (100 mL) and extracted with CH$_2$Cl$_2$ (2×100 mL). The combined CH$_2$Cl$_2$ extracts was dried over MgSO$_4$, filtered, evaporated in vacuo and chromatographed (Hexane/CH$_2$Cl$_2$) to provide the desired product (0.8 g, 79%). $^1$H NMR (400 MHz, CDCl$_3$) δ 7.88 (s, 1H), 7.70 (d, J=1.8 Hz, 1H), 7.56 (m, 2H), 6.83 (d, J=1.7 Hz, 1H), 4.32 (q, J=6.8 Hz, 2H), 1.31 (t, J=6.8 Hz, 3H); MS (m/z): 241 (MH$^+$).

EXAMPLE 102

Step d

Benzofuran-5-yl-difluoro-acetic acid hydrazide

A mixture of the compound prepared in step c (127 mg, 0.53 mmol) and hydrazine (0.28 mL, 8.9 mmol) in dry methanol (3 mL) was stirred at reflux for 3 hr, cooled to RT and evaporated in vacuo to afford a semisolid product (0.12 g) 99%. $^1$H NMR (400 MHz, DMSO-$d_6$) δ 8.12 (s, 1H), 7.90 (s, 1H), 7.76 (d, J=9.1 Hz, 1H), 7.52 (dd, J=8.5, 1.5 Hz, 1H), 7.09 (d, J=1.3 Hz, 1H)

EXAMPLE 102

Step e

5-[3-(Benzofuran-5-yl-difluoro-methyl)-[1,2,4]triazolo[4,3-b]pyridazin-6-yl]-thiophene-2-carboxylic acid ethyl ester

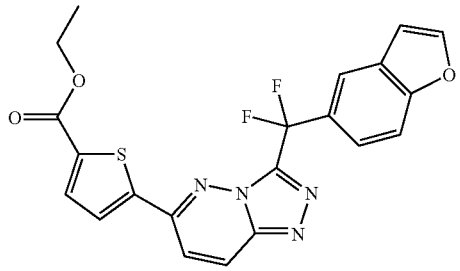

To a mixture of the compound prepared in step d (0.115 g, 0.51 mmol) and the compound prepared in Example 97a (165 mg 0.61 mmol) in n-butanol (3 mL) was added one drop of 3N HCl. The mixture was heated in a 130° C. oil bath for 3 hours, cooled to RT, diluted with dichloromethane (20 mL) and washed with saturated NaHCO$_3$ (1×). The CH$_2$Cl$_2$ extract was dried over MgSO$_4$, filtered and evaporated in vacuo. The crude residual semisolid was purified by chromatography to provide the desired product (35 mg) 16%. $^1$H NMR (400 MHz, DMSO-$d_6$) δ 8.20 (d, J=9.8 Hz, 1H), 8.19 (m, 4H), 7.88 (d, J=3.8 Hz, 1H), 7.78 (d, J=9.0 Hz, 1H), 7.63 (J=9.1 Hz, 1H), 7.09 (s, 1H), 4.38 (q, J=7.6 Hz, 2H), 1.37 (t, J=6.9 Hz, 3H). MS (m/z): 441 (MH$^+$).

EXAMPLE 102

Step f

{5-[3-(Benzofuran-5-yl-difluoro-methyl)-[1,2,4]triazolo[4,3-b]pyridazin-6-yl]-thiophen-2-yl}-(4-methyl-piperazin-1-yl)-methanone

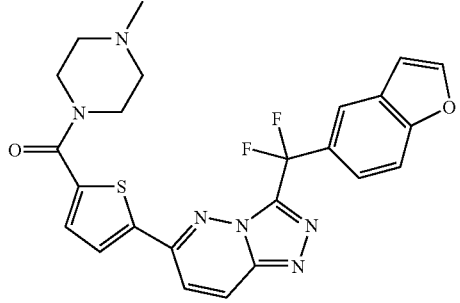

The compound prepared in step e was dissolved in a 2:1 THF/methanol (3 mL) mixture and treated with 2N NaOH (0.15 mL). The mixture was stirred for 3 hours at RT, evaporated in vacuo, diluted with water (10 mL), and acidified with 6 N HCl to pH 2. The white solid precipitates were collected, dried under reduced pressure, dissolved in DMF (2 mL) and treated with HATU (0.0.62 g, 0.16 mmol), HOBt (0.013 g, 0.09 mmol) and DIEA (0.06 mL, 0.32 mmol) respectively. The resulting mixture was stirred at RT for 30 minutes and N-Methylpiperazine (0.014 mL, 0.14 mmol) was added. Stirring was continued for an additional hour and water (20 mL) was added. Dichloromethane (20 mL) was added and layers separated. The CH$_2$Cl$_2$ layer was dried over MgSO$_4$, evaporated in vacuo and chromatographed (CH$_2$Cl$_2$/0-10% MeOH) to yield a solid product. Recrystallization for EtOAc afforded the title compound as an off-white solid. $^1$H NMR (400 MHz, DMSO-d6) δ 8.60 (d, J=9.8, 1H), 8.17-8.07 (m, 4H), 7.79 (d, J=9.1 Hz, 1H), 7.65 (dd, J=8.5, 2.1 Hz, 1H), 7.50 (d, J=3.9 Hz, 1H), 7.08 (s, 1H), 3.67 (m, 4H), 3.34 (m, 4H), 2.32 (s, 3H); MS (m/z): 495 (MH$^+$).

EXAMPLE 103

(5-{3-[(2,3-Dihydro-benzofuran-5-yl)-difluoro-methyl]-[1,2,4]triazolo[4,3-b]pyridazin-6-yl}-thiophen-2-yl)-(4-methyl-piperazin-1-yl)-methanone

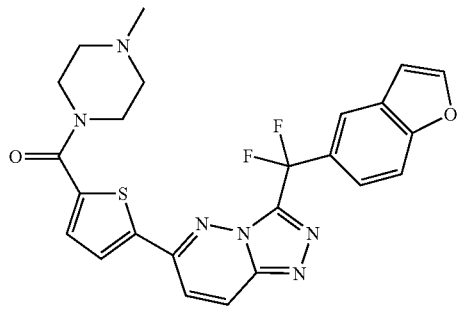

EXAMPLE 103

Step a (2,3-Dihydro-benzofuran-5-yl)-difluoro-acetic acid ethyl ester

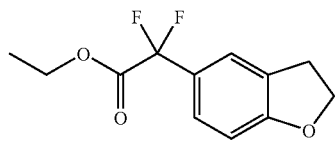

To a cold solution (0° C.) of the compound prepared in step a of Example 102 (1.0 g, 4.54 mmol) in dichoromethane (20 mL) was slowly added (diethylamino)sulfur trifluoride (DAST) (5 g, 31.0 mmol). The mixture was warmed to RT and stirring was continued for 24 hr. The reaction mixture was then poured into ice water (80 mL) and extracted with CH$_2$Cl$_2$ (2×100 mL). The combined CH$_2$Cl$_2$ extracts was dried over MgSO$_4$, filtered, evaporated in vacuo and chromatographed (Hexane/EtOAc) to provide the desired product. $^1$H NMR (400 MHz, CDCl$_3$) δ 7.42 (s, 1H), 7.36 (dd, J=8.5, 1.9 Hz, 1H), 6.81 (d, J=8.9 Hz, 1H), 4.62 (t, J=8.3 Hz, 2H), 4.30 (t, J=7.4 Hz, 2H), 3.24 (t, J=8.9 Hz, 1H), 1.31 (t, J=7.1 Hz, 1H).

EXAMPLE 103

Step b

5-[3-[(2,3-Dihydro-benzofuran-5-yl)-difluoro-methyl]-[1,2,4]triazolo[4,3-b]pyridazin-6-yl]-thiophene-2-carboxylic acid ethyl ester

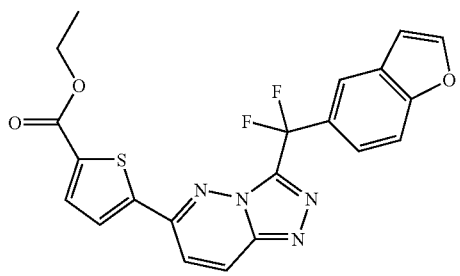

A solution of the compound prepared in step a (0.30 g, 1.24 mmol) in $CH_3OH$ (10 mL) was treated with hydrazine (0.58 mL, 18.6 mmol). The resulting mixture was stirred at reflux for 2.5 hr, cooled to RT and evaporated to dryness. The residue (0.28 g, 1.22 mmol) was combined with the compound prepared in step a of Example 97 (0.66 g, 2.4 mmol) in n-butanol (5 mL), heated in a 130° C. oil bath for 3 hours, cooled to RT, diluted with dichloromethane (20 mL) and washed with saturated $NaHCO_3$ (1×). The $CH_2Cl_2$ extract was dried over $MgSO_4$, filtered, evaporated in vacuo and chromatographed ($CH_2Cl_2$/0-10% MeOH) to provide the desired product (78 mg) 14%. $^1H$ NMR (400 MHz, DMSO-$d_6$) δ 8.62 (d, J=9.74 Hz, 1H), 8.19 (dd, J=9.8, 3.7 Hz, 2H), 7.90 (d, J=3.8 Hz, 1H), 7.64 (s, 1H), 7.37 (d, J=9.9 Hz, 1H), 6.88 (d, J=8.5 Hz, 1H), 4.61 (t, J=8.7 Hz, 2H), 4.36 (q, J=7.2 Hz, 2H), 3.28 (t, J=8.3 Hz, 2H), 1.34 (t, J=7.2 Hz). MS (m/z): 443 (MH$^+$)

EXAMPLE 103

Step c (5-{3-[(2,3-Dihydro-benzofuran-5-yl)-difluoro-methyl]-[1,2,4]triazolo[4,3-b]pyridazin-6-yl}-thiophen-2-yl)-(4-methyl-piperazin-1-yl)-methanone

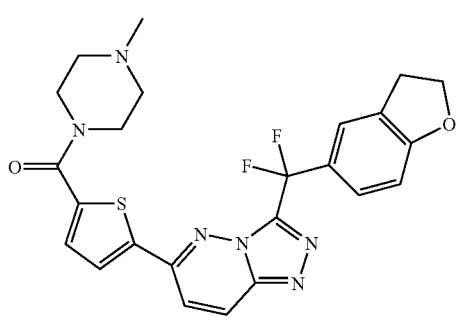

The compound prepared in step b was dissolved in a 2:1 THF/methanol (3 mL) mixture and treated with 2N NaOH (0.15 mL). The mixture was stirred for 3 hours at RT, evaporated in vacuo, diluted with water (10 mL), and acidified with 6 N HCl to pH 2. The white solid precipitates were collected, dried under reduced pressure, dissolved in DMF (3 mL) and treated with HATU (0.12 g, 0.31 mmol), HOBt (24 mg, 0.18 mmol) and DIEA (0.1 mL, 1.04 mmol) respectively. The resulting mixture was stirred at RT for 30 minutes and N-methylpiperazine (0.027 mL, 0.24 mmol) was added. Stirring was continued for an additional hour and water (20 mL) was added. dichloromethane (20 mL) was added and layers separated. The $CH_2Cl_2$ layer was dried over $MgSO_4$ and evaporated in vacuo. The residue was purified by reverse phase HPLC (Varian Prostar HPLC, Pursuit prep column, $CH_3CN$/$H_2O$ containing 0.1% TFA). The final compound was filtered through a $HCO_3$ cartridge and dried under reduced pressure to provide the title compound.

$^1H$ NMR (400 MHz, DMSO-$d_6$) δ 8.58 (d, J=9.7 Hz, 1H), 8.16 (d, J=9.6 Hz, 1H), 8.08 (d, J=3.7 Hz, 1H) 7.58 (s, 1H), 7.49 (d, J=3.9 Hz, 1H), 7.41 (d, J=8.6 Hz, 1H), 6.88 (d, J=7.8 Hz, 1H), 4.59 (t, J=8.5 Hz, 2H) 3.65 (m, 4H), 3.25 (t, J=8.9 Hz, 2H), 2.36 (m, 4H), 2.22 (s, 3H); MS (m/z): 497 (MH$^+$)

EXAMPLE 104

6-{Difluoro-[6-(2-propyl-thiazol-5-yl)-[1,2,4]triazolo[4,3-b]pyridazin-3-yl]-methyl}-quinoline

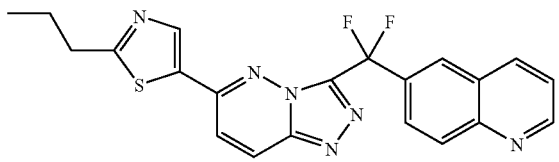

A pressure tube containing a mixture of 3-chloro-6-(2-propyl-thiazol-5-yl)-pyridazine (Example 20, step a) (36 mg, 0.15 mmol) and difluoro-quinolin-6-yl-acetic acid hydrazide (71 mg, 0.30 mmol) in butanol (2 mL) was flushed with argon and then sealed. After heating at 95° C. for 64 h, the solvent was removed in vacuo and the residue was purified by flash chromatography to give 60 mg (95%) of 8 as a light brown solid: $^1H$ NMR (400 MHz, CDCl$_3$) δ 9.03 (dd, J=4.3, 1.6 Hz, 1 H), 8.36 (m, 3 H), 8.18 (d, J=9.4 Hz, 2 H), 8.16-8.14 (m, 1 H), 7.58 (d, J=9.4 Hz, 2 H), 3.06 (t, J=7.6 Hz, 2 H), 1.93-1.88 (m, 2 H), 1.08 (t, J=7.4 Hz, 3 H); MS (ES) m/z: 423 (M+H$^+$).

Biological Activity

The following representative assays were performed in determining the biological activities of compounds within the scope of the invention. They are given to illustrate the invention in a non-limiting fashion.

EXAMPLE A

Cloning, Expression, and Purification of Recombinant c-Met Protein

This example describes the cloning, expression, and purification of the cytoplasmic domain of c-Met which has the c-Met receptor tyrosine kinase activity. The cytoplasmic domain has 435 amino acids and shows high homology with the SRC family of tyrosine kinases (Park et al., 1987, Proc Natl Acad Sci USA. 84(18):6379-83).

A cDNA for the cytoplasmic domain of Met receptor, containing the tyrosine kinase domain, was amplified by PCR. Oligonucleotides were custom synthesized by Gibco-BRL (Carlsbad, Calif.). Forward oligonucleotide metkinF2 is identical to nucleotides 3068-3097 of the nucleotide sequence listed in NM_000245, except that nucleotides between 3073 and 3078 have been altered to create a BamHI site for cloning purposes. Reverse oligonucleotide metkinR2a is identical to nucleotides 4378-4348 of the complementary sequence of that listed in NM_000245 except that nucleotides between 4372-4367 have been altered to create a XhoI site (underlined) for cloning purposes. The oligonucleotides were used as PCR primers to amplify Met receptor cytoplasmic domain cDNA from Quick Clone placental cDNA (Clontech; Palo Alto, Calif.). Amplification was performed using Taq DNA polymerase (Gibco-BRL; Carlsbad, Calif.), 1.25 mM each dNTP, 200 nM each oligo, in a 50 µl volume. The thermocycle profile was 30 cycles of each containing 94° C. for 30 seconds, 60° C. for 30 seconds, and 72° C. for 1 minute, on a Perkin Elmer 9600 thermocycler.

The amplified cDNA for the cytoplasmic domain of Met receptor was cloned onto an expression vector. The PCR product was digested with BamHI (New England Biolabs; Beverly, Mass.) and XhoI (New England Biolabs). A digested 1.3 kb product was isolated and purified from a 1% agarose gel using Gene Clean (Qbiogene; Irvine, Calif.). Vector pFastBacHTa (Gibco-BRL) was digested with BamHI and XhoI (New England Biolabs) and the 4.7 kb linear fragment was purified from a 1% agarose gel using Gene Clean (Bio101). The 1.3 kb Met cDNA fragment was ligated to pFastBacHTa vector at 4° C. for 16 hours with T4 DNA ligase (New England Biolabs) in a final volume of 10 µl. Cloning the Met cytoplasmic domain cDNA clone into the BamHI site of pFastBacHTa placed the cDNA in-frame with the His-6 tag of the vector to allow for expression of an N-terminal His-tagged protein. Half the ligation mix (5 µL) was used to transform 50 µl DH5α competent E. coli cells (Gibco-BRL). The transformation mix was plated onto LB agarose plates containing 100 µg/ml ampicillin and incubated for 16 hours at 37° C. Colonies were picked from these plates and grown in LB broth containing 100 µg/ml ampicillin for 16 hours. Plasmid DNA was isolated using Qiagen plasmid DNA purification reagents (Qiagen; Valencia, Calif.) and clones screened by digest with BamHI/XhoI. Three clones which had the appropriate size fragment released from the digest were submitted to ACGT, Inc for DNA sequence analysis.

One clone, pFastBacHTmetkin-15, contained no mutations in the cloned c-Met cytoplasmic domain and was used to generate a recombinant baculovirus for expression. Recombinant baculovirus was generated using the Gibco BRL Bac-To-Bac system following the protocol specified by the manufacturer. Briefly, DH10Bac cells were transformed with pFastBacHTmetkin-15, clones were selected, viral DNA isolated, and screened by PCR for Met cDNA insert. Sf9 insect cells were transfected with the recombinant baculovirus DNA. Media containing PO viral stock was collected and used for 2 subsequent rounds of viral amplification.

Multiple concentrations of amplified viral stock were used to infect Sf9 cells. Cells were harvested 24, 48, and 72 hours post transfection. Infected Sf9 cells were lysed in 50 mM Tris-HCl pH 8.0, 150 mM NaCl, 150 mM imidazole, 1.0 mM PMSF, 0.5% NP40, 3.5 µg/ml leupeptin, 3.5 µg/ml aprotinin and total protein concentration determined in a BCA assay (Pierce; Rockford, Ill.). Cell lysates were separated on a 4-15% SDS-PAGE then transferred to nitrocellulose membrane for immunoblot analysis. Nitocellulose blots were probed with an anti-His6 antibody to confirm expression of the His-tagged met kinase protein. Optimal viral concentration to Sf9 cell ratio was determined by examination of lysates collected from different infection conditions. Maximal protein recovery occurred 48 hours post infection.

A small-scale expression/purification of the His-tagged cytoplasmic domain of Met receptor was performed. Sf9 insect cells transfected with the recombinant baculovirus that expresses the His-tagged cytoplasmic domain of Met receptor were lysed in buffer containing 50 mM Tris-HCl pH 8.0, 150 mM NaCl, 150 mM imidazole, 1.0 mM PMSF, 0.5% NP40, 3.5 µg/ml leupeptin, 3.5 µg/ml aprotinin. The lysate was incubated with 5 ml of a 50% solution of Ni-agarose beads (Qiagen) in PBS for 2 hours rotating at 4° C. to capture the His-tagged protein. The lysate containing His-tagged protein bound to Ni-agarose beads was loaded onto a 10 ml column. Ni-agarose beads were allowed to pack and supernatant allowed to flow through. The packed column was then washed with 60 ml of wash buffer (same as lysis buffer). 5 ml of elution buffer (50 mM Tris-HCl pH 8, 150 mM NaCl, 150 mM imidazole, 1.0 mM PMSF) was added to the column and 10 fractions (0.5 ml volume each) were collected. Small aliquots of each fraction were separated by 4-15% SDS-PAGE and either transferred to nitrocellulose for immunoblot analysis or processed for Coomassie stain (Bio-Safe Safe Coomassie, Bio-Rad). The major protein band on the Coomassie stain gel has the appropriate size for His6-MetKin (52 kD), corresponding to the His-tagged protein detected by immunoblot. Protein concentration as estimated from the Coomassie stain gel was approximately 2 mg/ml.

Recombinant viral stock was transferred to the contract lab, Pan Vera (Madison, Wis.) for large-scale expression and purification of His6-MetKin in quantities sufficient for High Throughput Screening. A 60 L scale up and 4 step purification scheme yielded 98.4 mg of protein that is more than 95% pure.

EXAMPLE B

Delfia Autophosphorylation Kinase Assay on the c-Met

A DELFIA time resolved fluorescence assay was developed for screening of compounds that decreases the autophosphorylation thus the kinase activity of c-Met. The DELFIA assay is non-radioactive. The autophosphorylation of the c-Met is measured by an anti-phosphotyrosine antibody coupled to an Europium tag.

A major advantage of this format is that it allowed for the development of an autophosphorylation assay using Ni-chelate plates which bind the hexa-his tag on the recombinant Met kinase. The autophosphorylation assay allows one to use a known substrate, Met kinase itself, for the phosphorylation. The DELFIA Met autophosphorylation assay is very sensitive with a signal to noise ratio in excess of 50:1.

The assay procedure for screening is as follows. The purified His6 tagged cytoplasmic domain of c-Met was diluted to a concentration of 500 ng/ml in enzyme dilution buffer (50 mM Tris-HCl, pH8.0, 0.1% BSA) and dispensed to assay plates at a volume of 50 µl per well. Black opaque HisGrab Nickel coated 96 well plates (Pierce, Rockford, Ill.) were selected for use. Next, 2.5 µl of compound in 40% DMSO was added to test wells, 2.5 µl of 40% DMSO only was added to the negative control wells. The autophosphorylation reaction was initiated upon the addition of 50 µl of reaction buffer, 50 mM Tris-HCl, pH 8.0, 10 mM $MgCl_2$, 0.1 mM $Na_3VO_4$, 1 mM DTT, 1 µM ATP. Plates were incubated at room temperature for 1 hour followed by 2 washes with 200 µl/well of PBS. Europium conjugated anti-phosphotyrosine antibody, Eu-PY20 from Perkin Elmer was diluted to 50 ng/ml in Delfia AB buffer (Perkin Elmer, Boston, Mass.), added to the 96 well assay plates at a volume of 100 µl/well, and incubated at room temperature for 2 hours. Assay plates were then washed 4 times each with 200 μl/well of Delfia wash buffer (Perkin Elmer). After the final wash 150 μl of Delfia Enhancement solution (Perkin Elmer) was added to each well of the assay plate and incubated at room temperature for 1 hour. Plates were read on an LJL Analyst instrument (Molecular Devices; Sunnyvale, Calif.) with filter settings of 360 excitation, 620 emission, and 410 dichroic. $IC_{50}$ values were calculated using Graphpad Prism software (Graphpad Software; San Diego, Calif.).

EXAMPLE C

A Cell Based ELISA Assay for c-Met Phosphorylation

A cell based ELISA assay was developed to evaluate the ability of compounds to inhibit HGF stimulated c-Met phosphorylation in cells.

S114 cells were seeded to a 96 well tissue culture treated dish at a concentration of $5 \times 10^4$ per well. After a 16-20 hour incubation, culture medium was removed and replaced with serum free medium supplemented with 0.5% BSA. Test compound was then added and incubated with the cells for 60 minutes, followed by the addition of 1 μl HGF at 2.5 μg/μl for 15 minutes. Cells were then lysed with the addition of 25 μl of ice cold 3×RIPA buffer (50 mM Tris HCl, pH 7.5, 1% Triton, 1% IGEPAL, 0.25% deoxycholic acid, 150 mM NaCl, 1 mM sodium orthovanidate, 1 mM sodium fluoride, and 1 tablet protease cocktail inhibitor (Boheringer Mannheim, cat. #1697498). Cell lysates were then transferred to NUNC Maxisorp plates coated with anti-c-Met receptor antibody AF276 (R&D Systems). Lysates were incubated with the antibody-coated plates for 1 hour at room temperature. Plates were washed with Delfia wash buffer (Perkin Elmer, Boston, Mass.) and 100 μl of 0.25 ug/ml europium conjugated PT66 anti-phosphotyrosine antibody (Perkin Elmer, Boston, Mass.). Following another 1 hour incubation at room temperature the plates were washed three times with Delfia wash buffer (Perkin Elmer). After the final wash, 150 ml of Delfia enhancer solution (Perkin Elmer) was added and allowed to incubate for 60 minutes. Plates were read on an LJL Analyst instrument (Molecular Devices; Sunnyvale, Calif.) with filter settings of 360 excitation, 620 emission, and 410 dichroic. $IC_{50}$ values were calculated using Graphpad Prism software (Graphpad Software; San Diego, Calif.).

EXAMPLE D

HepG2 Cellular Scatter Assay

Introduction

Human Growth Factor (HGF) and its receptor (c-Met) are involved in cellular motility. Indeed HGF was also identified as Scatter Factor (SF), based on its powerful motility effect on certain cell types. Cellular motility is critical for pathological processes of oncologic disease, most importantly, the establishment of metastatic lesions distant from the primary tumor and formation of new blood vessels (angiogenesis). One therapeutic hypothesis is that this movement of cell types may be blunted or eliminated by the use of c-Met kinase inhibitors. (See: Jiang, W. C, Martin, T. A., Parr, C., Davies, G., Matsumoto, K. and Nakamura, T. Critical Reviews in Oncology/Hematology 53 (2005) 35-69. and references cited therein.) It should also be noted that cellular motility, especially with regard to angiogenesis, is important in other disease states.

Methods

Cellular scatter was measured with a Real-Time Cell Electronic Sensing system (RT-CES), from ACEA Biosciences Inc. (San Diego, Calif.). The RT-CES system uses specialized RT-ACE microtiter plates (cat:RCD96, ACEA Biosciences Inc.) to non-invasively quantify cellular status in real-time. The interaction of cells with the surface of the plates, which are integrated with microelectronic sensor arrays, leads to the generation of a cell-electrode impedance response. A higher impedance value indicates more cell attachment and thus less cellular scatter.

50 μl of Assay Media (MEM supplemented with 10% FBS, 2 mM L-glutamine, 1.5 g/L sodium bicarbonate, 1 mM sodium pyruvate, and 0.1 mM non-essential amino acids) was added into 96-well RT-ACE plates and recorded for 30 min on the RT-CES. 50 μl of HepG2 cells (cat: HB-8065, ATCC) were added into each well (50 μl@104 cells/ml=5000 cells/well). The plate was read in RT-CES and incubated for 20-24 hours. After the 20-24 hours incubation, 50 μl of Assay Media containing different concentrations of testing compounds was added into each well and incubated for 1 hour. Finally, 50 μl of Assay Media containing 160 ng/ml of HGF was added into each well (40 ng/ml in 200 μl). The plate was incubated and read in the RT-CES for 20-24 hours, with a record time every 15 minutes. The positive control was HGF without compounds and negative control was no-HGF without compound. All determinations were performed in duplicate wells and $IC_{50}$ values were calculated using GraphPad Prism software (GraphPad Software; San Diego, Calif.).

EXAMPLE E

U87MG Glioblastoma Tumor Xenograft Model

Introduction

The U87MG glioblsatoma cell line (Piedmont Research Center LLC) expresses the c-Met receptor and responds to Human Growth Factor (HGF). This study investigated whether treatment with an inhibitor of c-Met is efficacious against the U87MG glioblastoma tumor xenograft model. This study utilized a tumor growth inhibition (TGI) assay to test per os (p.o.) compound monotherapy in groups of fifteen nude mice. A control group was treated with vehicle, 20% Hydroxypropyl Beta-Cyclodextrin (HPBCD). All treatments began on Day 1 (D1) in mice bearing established subcutaneous (s.c.) U87MG tumors.

Methods and Materials

Mice

Female athymic nude mice (Harlan) were 10-11 weeks old with a BW range of 18.1-25.0 g on D1 of the study. The animals were fed ad libitum water (reverse osmosis, 1 ppm Cl) and NIH 31 Modified and Irradiated Lab Diet® consisting of 18.0% crude protein, 5.0% crude fat, and 5.0% crude fiber. The mice were housed on irradiated ALPHA-dri® Bed-o-cobs® Laboratory Animal Bedding in static microisolators on a 12-hour light cycle at 21-22° C. (70-72° F.) and 40-60% humidity. All animals were housed in a Laboratory Animal Medicine facility that is fully accredited by the American Association for Assessment and Accreditation of Laboratory Animal Care (AAALAC). All procedures involving animals were conducted in compliance with the NIH *Guide for the Care and Use of Laboratory Animals* and all protocols were approved by an Internal Animal Care and Use Committee (IACUC).

Tumor Implantation

Xenografts were initiated from U87MG human glioblastoma tumor fragments maintained by serial transplantation in athymic nude mice. Each test mouse received a subcutaneous U87MG tumor fragment (1 mm$^3$) implanted in the right flank, and the growth of tumors was monitored as the average size approached 200 mm$^3$. Twelve days later, on Day 1 of the study, the animals were sorted into 4 groups (n=12-15 mice/group) with individual tumor volumes ranging from 172-352 mm$^3$ and group mean tumor volumes of 216 mm$^3$. Tumor volume was calculated using the formula:

$$\text{Tumor Volume} = \frac{w^2 \times l}{2}$$

where w=width and l=length in mm of the tumor. Tumor weight may be estimated with the assumption that 1 mg is equivalent to 1 mm$^3$ of tumor volume.

Drug Treatment

Dosing solutions of compounds of the present invention were prepared fresh weekly in a vehicle consisting of 20% Hydroxypropyl Beta-Cyclodextrin (HPBCD) in water. In all groups, the dosing volume of 0.2 mL/20-g mouse was scaled to the body weight of each animal. Doses were given to allow for the HCl salt form of the compound.

Tumor Growth Inhibition (TGI) Analysis

TGI was calculated from the difference between the median tumor volumes of vehicle-treated and drug-treated mice, expressed as a percentage of the median tumor volume of the vehicle-treated control group, by the following relation:

$$\% \, TGI = \left( \frac{\text{Median Tumor } Volume_{control} - \text{Median Tumor } Volume_{drug\text{-}treated}}{\text{Median Tumor } Volume_{control}} \right) \times 100$$

The MTV (n) is defined as the median tumor volume (MTV) for the number of animals, n, remaining in the study on that day.

Toxicity

Animals were weighed daily for the first five days of the study and then twice weekly. The mice were examined frequently for overt signs of any adverse, drug-related side effects, and clinical signs of toxicity were recorded when observed. Acceptable toxicity is defined as a group mean body-weight (BW) loss of less than 20% during the study, and not more than one treatment-related (TR) death among ten animals. A death is classified as TR if it is attributable to treatment side effects as evidenced by clinical signs and/or necropsy, or due to unknown causes during the dosing period or within 10 days of the last dose. A death is classified as non treatment-related (NTR) if there is no evidence that the death was related to drug side effects. A death is classified as non treatment-related unknown (NTRu) if the cause of death is unknown.

Statistical and Graphical Analyses

The Mann-Whitney U-test, for analysis of medians, was used to determine the statistical significance of the difference between the MTVs. Prism 3.03 (GraphPad) for Windows was used for the statistical analyses and graphic presentations. Tumor growth was plotted as the median tumor volume, versus time, for each group in the study. In addition, final tumor volume and final percent tumor growth inhibition (% TGI) were also represented on the graph or on a separate bar graph. (*=p<0.05, =p<0.01, *=p<0.001). Results of the U87MG tumor growth study are shown in FIG. 1, FIG. 2, and FIG. 3.

FIG. 1: Example 1 was administered orally (p.o.) at doses of 30 and 50 mg/kg twice a day (b.i.d), for 21 consecutive days. Both doses produced statistically significant, dose-dependent inhibition of growth of U87MG tumors grown subcutaneously in athymic nude mice. On the last day of treatment (Day 21), the 30 and 50 mg/kg doses decreased mean tumor volume by 66% (p<0.001) and 97% (p<0.001), respectively, compared to the mean tumor volume of the vehicle-treated group. Tumor regression was observed at the 50 mg/kg dose.

Figure 2:
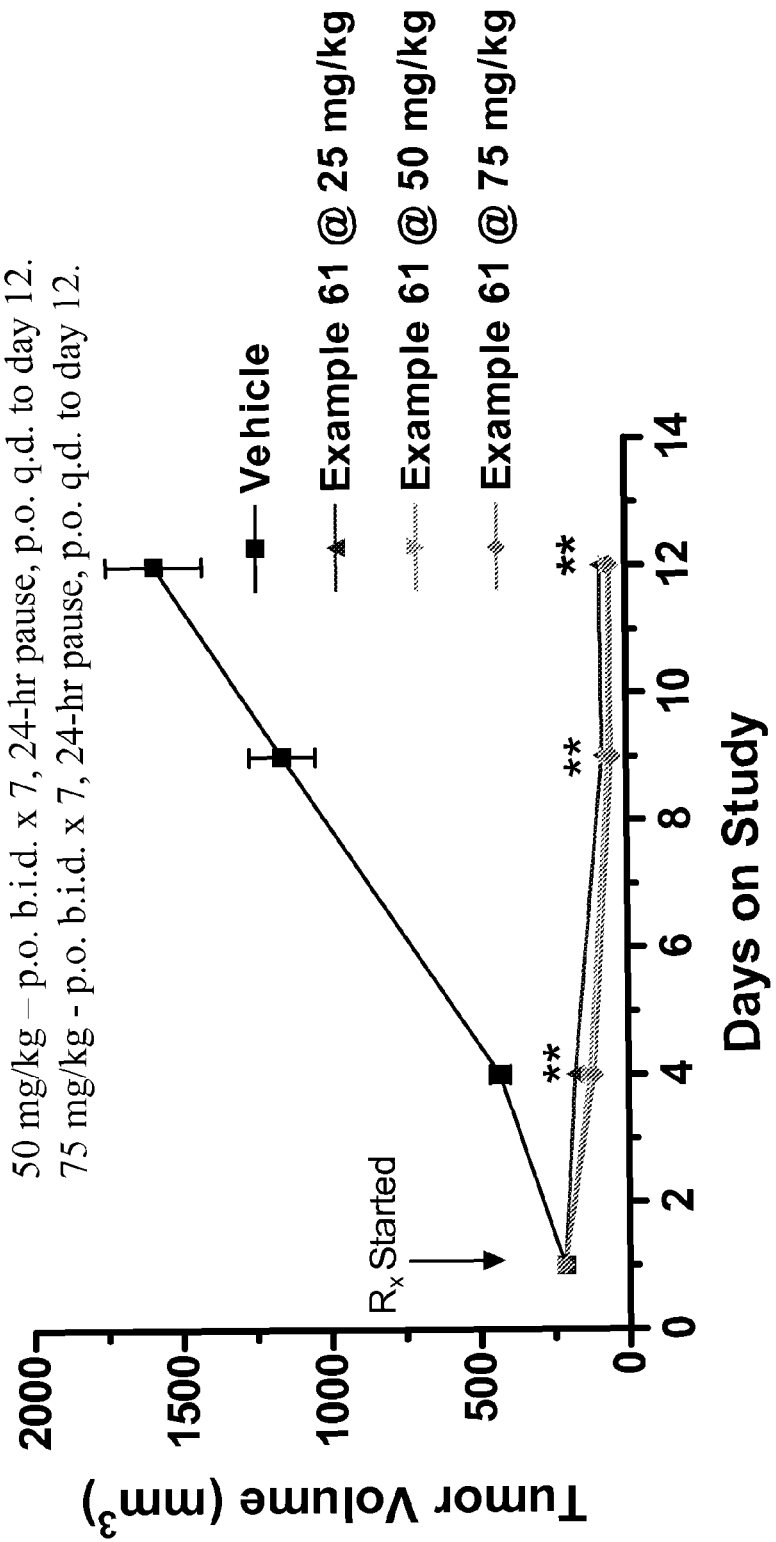
FIG. 2 shows the effects of oral administration of compounds of the present invention (Example Compound No. 61) on tumor growth inhibition (TGI) in U87MG glioblastoma tumors in nude mice. All treatments began on Day 1 in mice bearing established subcutaneous U87MG tumors. Tumor growth is plotted as the median tumor volume ($mm^3$), versus time (Days), for each group in the study. At the end of the 12-day study, final TGI % was calculated from the difference between the median tumor volumes of vehicle-treated and drug-treated mice, expressed as a percentage of the median tumor volume of the vehicle-treated control group. (*=$p<0.05$, =$p<0.01$, *=$p<0.001$)

FIG. 2: Example 61 was administered p.o. at doses of 25, 50, and 75 mg/kg. All doses produced statistically significant, tumor growth inhibition of U87MG tumors grown subcutaneously in athymic nude mice (p<0.01). Tumor regression was also observed with all three doses. The 25 mg/kg dose was administered once a day (q.d.) on day 1 and b.i.d. to day 12. The 50 mg/kg dose was administered b.i.d. for 7 days, with a 24-hr pause, then q.d. to day 12. Like the 50 mg/kg dose, the 75 mg/kg dose was administered b.i.d. for 7 days, with a 24-hr pause, then q.d. to day 12.

Figure 3:
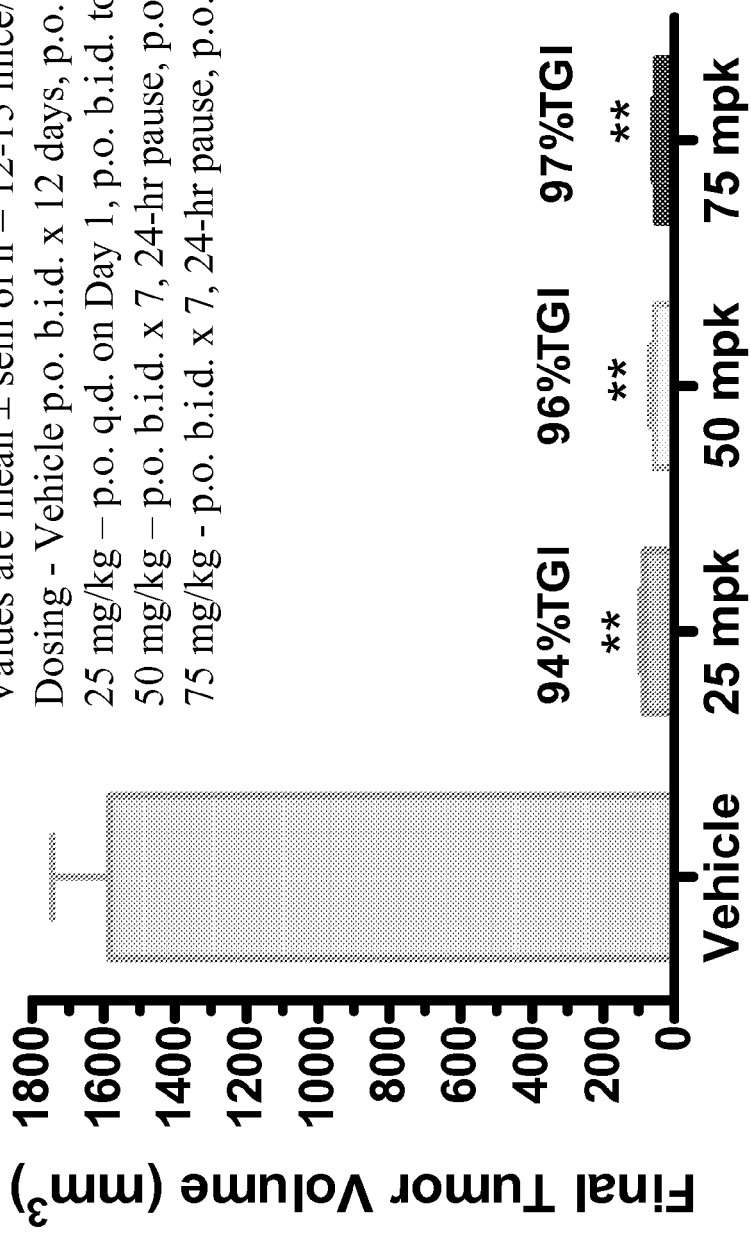
FIG. 3 shows the effects of oral administration of compounds of the present invention (Example Compound No. 61) on tumor growth inhibition (TGI) in U87MG glioblastoma tumors in nude mice. All treatments began on Day 1 in mice bearing established subcutaneous U87MG tumors. At the end of the 12-day study, final TGI % was calculated from the difference between the median tumor volumes of vehicle-treated and drug-treated mice, expressed as a percentage of the median tumor volume of the vehicle-treated control group. (*=$p<0.05$, =$p<0.01$, *=$p<0.001$)

FIG. 3: Example 61 was administered p.o. at doses of 25, 50, and 75 mg/kg. On the last day of treatment (Day 12), mean tumor volume was decreased by 94% (p<0.01), 96% (p<0.01) and 97% (p<0.01) at doses of 25, 50, and 75 mg/kg, respectively. The 25 mg/kg dose was administered once a day (q.d.) on day 1 and b.i.d. to day 12. The 50 mg/kg dose was administered b.i.d. for 7 days, with a 24-hr pause, then q.d. to day 12. Like the 50 mg/kg dose, the 75 mg/kg dose was administered b.i.d. for 7 days, with a 24-hr pause, then q.d. to day 12.

EXAMPLE F

S114 Tumor Model

Methods

Mice

Female athymic nude mice (CD-1, nu/nu, 9-10 weeks old) were obtained from Charles River Laboratories (Wilmington, Mass.) and were maintained according to NIH standards. All mice were group housed (5 mice/cage) under clean-room conditions in sterile micro-isolator cages on a 12-hour light/dark cycle in a room maintained at 21-22° C. and 40-50% humidity. Mice were fed irradiated standard rodent diet and water ad libitum. All animals were housed in a Laboratory Animal Medicine facility that is fully accredited by the American Association for Assessment and Accreditation of Laboratory Animal Care (AAALAC). All procedures involving animals were conducted in compliance with the NIH *Guide for the Care and Use of Laboratory Animals* and all protocols were approved by an Internal Animal Care and Use Committee (IACUC).

S114 Tumors

The murine NIH 3T3 derived cell line S114, which has been engineered to over-express both Human Growth Factor (HGF) and the human c-Met receptor, was propagated in DMEM media (Life Technologies, Bethesda, Md.). Immediately prior to injection, cells were washed counted and resuspended in PBS. Female athymic nude mice weighing no less than 20-21 grams were inoculated subcutaneously in the left inguinal region of the thigh with 5×10$^6$ cells in a delivery volume of 0.1 mL. Tumors were allowed to grow to for five days.

Drug Treatment

Mice were dosed orally at 100 mg/kg compound in 20% HPBCD or with vehicle (20% HPBCD, control group). Dosing was continued for 4 consecutive days. Compounds of the present invention were prepared fresh daily as a clear solution in 20% HPβCD and administered as described above. Body weight was measured at the end of the study and a loss of body weight >10% was used as an indication of lack of compound tolerability. Unacceptable toxicity was defined as body weight loss >20% during the study. Mice were closely examined daily at each dose for overt clinical signs of adverse, drug-related side effects. No significant change in body weight or behavior was noted in the study.

Analysis

On the day of study termination, a final tumor volume and final body weight were obtained on each animal. Mice were euthanized using 100% $CO^2$ and tumors were immediately excised intact and weighed, with final tumor wet weight (grams) serving as a primary efficacy endpoint. Prism 3.03 (GraphPad) for Windows was used for the statistical analyses and graphic presentations. Results of the S114 tumor study are shown in FIG. 4.

Figure 4:
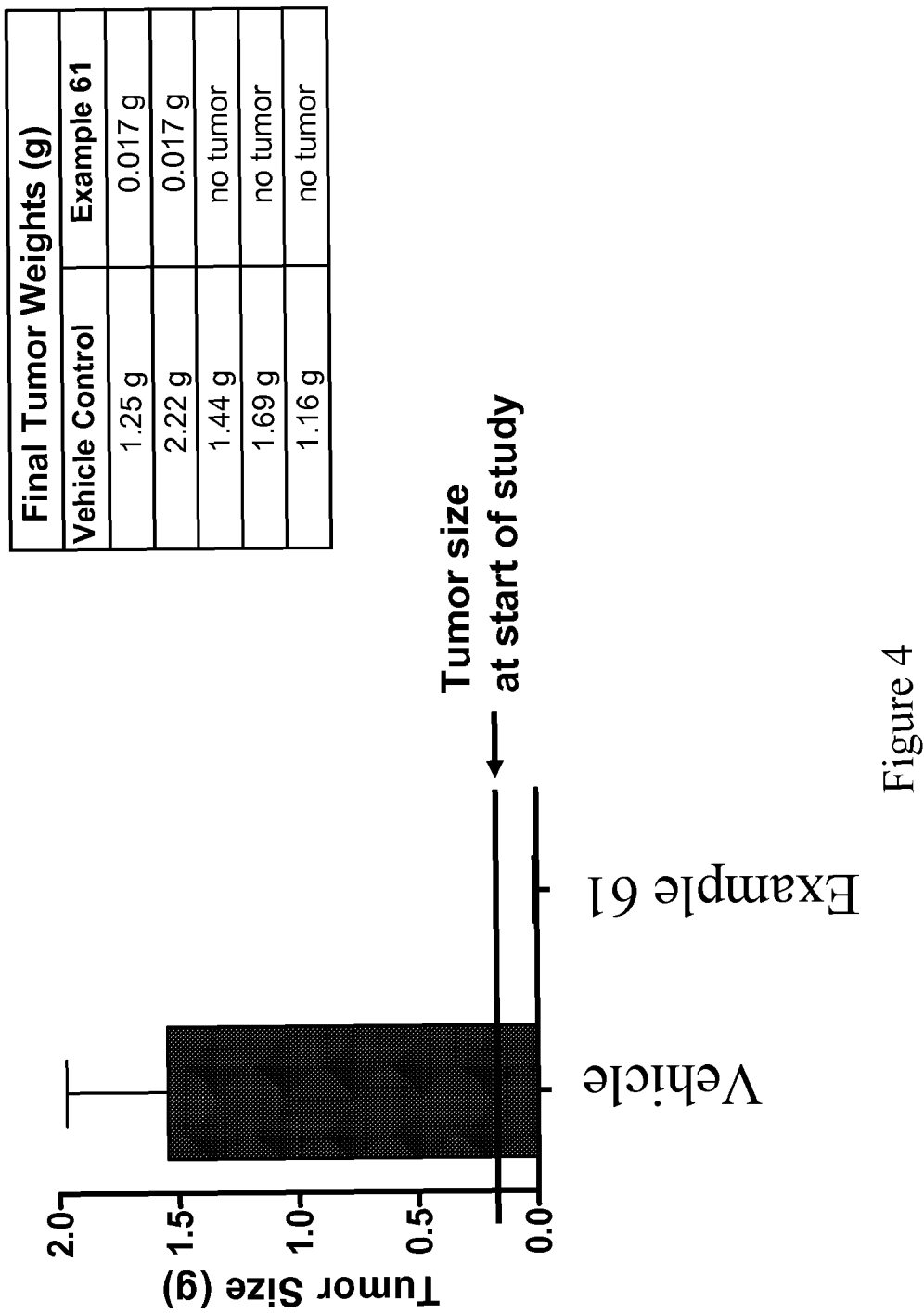
FIG. 4 shows the effects of oral administration of compounds of the present invention (Example Compound No. 61) on the growth of S114 tumors. Female athymic nude mice were inoculated subcutaneously in the left inguinal region of the thigh with $5\times10^6$ S114 cells in a delivery volume of 0.1 mL. Tumors were allowed to grow to for five days. Mice were dosed orally at 100 mg/kg compound in 20% HPBCD or with vehicle (20% HPBCD, control group). Dosing was continued for 4 consecutive days. On the day of study termination, tumors were immediately excised intact and weighed, with final tumor wet weight (grams) serving as a primary efficacy endpoint.

FIG. 4: Example 61 was administered p.o. at a dose of 100 mg/kg q.d., for four consecutive days. The S114 tumors regressed in all five mice treated with Example 61. Furthermore, tumors in three of the five mice regressed to non-palpable, non-detectable tumors by the end of the study.

Biological Data

The activity of representative compounds of the present invention is presented in the chart below. All activities are in µM and data is accepted as valid if the 95% confidence intervals calculated by Graphpad prism are within 2 fold of the $IC_{50}$.

| Example # | c-Met Cell ELISA IC-50 (µM) | cMet Delfia autophos IC-50 (µM) |
|---|---|---|
| 1 | 0.014 | 0.003 |
| 2 | no data | no data |
| 3 | 1.03 | 0.016 |
| 4 | 0.313 | 0.07 |
| 5 | 1.93 | 0.015 |
| 6 | 0.112 | 0.008 |
| 7 | 2.15 | 0.111 |
| 8 | no data | 0.243 |
| 9 | 0.048 | 0.0016 |
| 10 | no data | 0.217 |
| 11 | 0.086 | 0.006 |
| 12 | no data | 0.056 |
| 13 | 0.215 | 0.015 |
| 14 | no data | >10 |
| 15 | 0.088 | 0.002 |
| 16 | 0.2948 | 0.009 |
| 17 | 0.01 | 0.004 |
| 18 | 0.086 | 0.01 |
| 19 | no data | 0.172 |
| 20 | 0.007 | 0.001 |
| 21 | no data | 0.023 |
| 22 | 0.009 | 0.015 |
| 23 | 0.113 | 0.041 |
| 24 | no data | 1.78 |
| 25 | 0.483 | 0.041 |
| 26 | no data | 0.413 |
| 27 | no data | 8.21 |
| 28 | no data | 1.9 |
| 29 | no data | 0.086 |
| 30 | no data | 0.57 |
| 31 | 2.4 | 0.077 |
| 32 | no data | 0.305 |
| 33 | 9.9 | 0.096 |
| 34 | no data | 1.19 |
| 35 | 0.075 | 0.009 |
| 36 | no data | 2.7 |
| 37 | 0.346 | 0.016 |
| 38 | 0.002 | 0.00045 |
| 39 | 0.001 | 0.002 |
| 40 | no data | 1.08 |
| 41 | no data | 0.056 |
| 42 | 0.406 | 0.013 |
| 43 | 0.14 | 0.011 |
| 44 | 0.143 | 0.002 |
| 45 | no data | 0.07 |
| 46 | no data | 0.227 |
| 47 | 0.001 | 0.0004 |
| 48 | 0.014 | 0.002 |
| 49 | 0.343 | 0.0021 |
| 50 | 0.012 | 0.002 |
| 51 | 0.008 | 0.0002 |
| 52 | 0.04 | 0.003 |
| 53 | 0.035 | 0.004 |
| 54 | 0.006 | N/A |
| 55 | 0.001 | 0.001 |
| 56 | 0.023 | 0.0009 |
| 57 | no data | 0.0003 |
| 58 | 0.314 | 0.095 |
| 59 | 0.008 | 0.003 |
| 60 | 0.012 | 0.001 |
| 61 | 0.002 | 0.001 |
| 62 | 0.27 | 0.02 |
| 63 | no data | 0.6 |
| 64 | 0.17 | 0.017 |
| 65 | 0.002 | 0.0003 |
| 66 | 0.005 | 0.0009 |
| 67 | no data | 0.9 |
| 68 | 0.03 | 0.002 |
| 69 | >1 | 0.017 |
| 70 | 0.14 | 0.025 |
| 71 | 0.099 | 0.02 |
| 72 | 0.0002 | 0.0003 |
| 73 | 0.0005 | 0.0001 |
| 74 | 0.0006 | 0.0001 |
| 75 | 0.06 | 0.0008 |
| 76 | 0.18 | 0.004 |
| 77 | 0.002 | 0.0015 |
| 78 | no data | 0.32 |
| 79 | 3.3 | 0.03 |
| 80 | no data | no data |
| 81 | no data | no data |
| 82 | no data | 0.017 |
| 83 | no data | 0.014 |
| 84 | 0.0009 | no data |
| 85 | 0.26 | 0.053 |
| 86 | 0.034 | 0.0028 |
| 87 | 0.004 | 0.0006 |
| 88 | 0.05 | 0.002 |
| 89 | 0.23 | 0.004 |
| 90 | 0.54 | 0.003 |
| 91 | no data | 1.05 |
| 92 | 0.01 | 0.004 |
| 93 | 0.13 | 0.004 |
| 94 | 0.64 | 0.03 |
| 95 | 0.009 | 0.001 |
| 96 | 0.16 | 0.012 |
| 97 | 0.003 | 0.003 |
| 98 | 0.004 | 0.002 |
| 99 | 0.034 | 0.002 |
| 100 | 0.140 | 0.005 |
| 100b | 0.034 | 0.002 |
| 101 | 0.120 | 0.001 |
| 102 | 0.079 | 0.003 |
| 103 | 0.210 | 0.004 |
| 104 | 0.037 | 0.002 |

| Example # | HepG2 IC50 (µM) |
|---|---|
| 60 | 0.287 |
| 61 | 0.106 |
| 86 | 0.715 |
| 99 | 1.102 |
| 97 | 1.165 |

-continued

| Example # | HepG2 IC50 (µM) |
|---|---|
| 98 | 0.064 |
| 104 | 0.543 |

Methods of Treatment/Prevention

In another aspect of this invention, compounds of the invention can be used to inhibit tyrosine kinase activity or expression, including c-Met activity, reduce kinase activity or expression, including c-Met activity, and modulate expression of c-Met in a cell or a subject, or to treat disorders related to c-Met kinase activity or expression in a subject. Inhibition of c-Met activity is believed to indirectly modulate c-Met expression.

In one embodiment to this aspect, the present invention provides a method for reducing or inhibiting the kinase activity of c-Met, and modulate expression of c-Met in a cell comprising the step of contacting the cell with a compound of Formula I. The present invention also provides a method for reducing or inhibiting the kinase activity of c-Met, and modulate expression of c-Met in a subject comprising the step of administering a compound of Formula I to the subject. The present invention further provides a method of inhibiting cell proliferation in a cell comprising the step of contacting the cell with a compound of Formula I.

The kinase activity or expression of c-Met in a cell or a subject can be determined by procedures well known in the art, such as the c-Met kinase assay described herein. Inhibition of c-Met kinase activity in cells can also be measured by determining the level of c-Met phosphorylation using an ELISA assay format such as the one described here or by Western Blotting.

The term "subject" as used herein, refers to an animal, preferably a mammal, most preferably a human, who has been the object of treatment, observation or experiment.

The term "contacting" as used herein, refers to the addition of compound to cells such that compound is taken up by the cell.

In other embodiments to this aspect, the present invention provides both prophylactic and therapeutic methods for treating a subject at risk of (or susceptible to) developing a cell proliferative disorder or a disorder related to c-Met. Such disorders include pre-existing conditions related to c-Met expression (or over expression) and/or c-Met mutation.

In one example, the invention provides methods for preventing in a subject a cell proliferative disorder or a disorder related to c-Met, comprising administering to the subject a prophylactically effective amount of a pharmaceutical composition comprising the compound of Formula I and a pharmaceutically acceptable carrier. Administration of said prophylactic agent can occur prior to the manifestation of symptoms characteristic of the cell proliferative disorder or disorder related to c-Met, such that a disease or disorder is prevented or, alternatively, delayed in its progression.

In another example, the invention pertains to methods of treating in a subject a cell proliferative disorder or a disorder related to c-Met comprising administering to the subject a therapeutically effective amount of a pharmaceutical composition comprising the compound of Formula I and a pharmaceutically acceptable carrier. Administration of said therapeutic agent can occur concurrently with the manifestation of symptoms characteristic of the disorder, such that said therapeutic agent serves as a therapy to compensate for the cell proliferative disorder or disorders related to c-Met.

In another example, the invention pertains to methods of modulating in a subject a cell proliferative disorder or a disorder related to c-Met, such that modulation of the level of c-Met expression or of c-Met activity may act to ameliorate the cell proliferative disorder or a disorder related to c-Met, comprising administering to the subject a therapeutically effective amount of a pharmaceutical composition comprising the compound of Formula I and a pharmaceutically acceptable carrier.

The term "prophylactically effective amount" refers to an amount of an active compound or pharmaceutical agent that inhibits or delays in a subject the onset of a disorder as being sought by a researcher, veterinarian, medical doctor or other clinician.

The term "therapeutically effective amount" as used herein, refers to an amount of active compound or pharmaceutical agent that elicits the biological or medicinal response in a subject that is being sought by a researcher, veterinarian, medical doctor or other clinician, which includes alleviation of the symptoms of the disease or disorder being treated.

Methods are known in the art for determining therapeutically and prophylactically effective doses for the instant pharmaceutical composition.

As used herein, the term "composition" is intended to encompass a product comprising the specified ingredients in the specified amounts, as well as any product which results, directly or indirectly, from combinations of the specified ingredients in the specified amounts.

As used herein, the terms "disorders related to c-Met", or "disorders related to c-Met receptor tyrosine kinase" shall include diseases associated with or implicating c-Met activity, for example, the overactivity of c-Met, and conditions that accompany with these diseases. The term "overactivity of c-Met" refers to either 1) c-Met expression in cells which normally do not express c-Met; 2) c-Met activity by cells which normally do not possess active c-Met; 3) increased c-Met expression leading to unwanted cell proliferation; or 4) mutations leading to constitutive activation of c-Met. Examples of "disorders related to c-Met" include disorders resulting from over stimulation of c-Met due to abnormally high amount of c-Met or mutations in c-Met, or disorders resulting from abnormally high amount of c-Met activity due to abnormally high amount of c-Met or mutations in c-Met.

It is known that overactivity of c-Met has been implicated in the pathogenesis of a number of diseases, such as cell proliferative disorders, neoplastic disorders and cancers.

The term "cell proliferative disorders" refers to unwanted cell proliferation of one or more subset of cells in a multicellular organism resulting in harm (i.e., discomfort or decreased life expectancy) to the multicellular organisms. Cell proliferative disorders can occur in different types of animals and humans. Cell proliferative disorders include neoplastic disorders (as used herein, a "neoplastic disorder" refers to a tumor resulting from abnormal or uncontrolled cellular growth) and other cell proliferative disorders.

Examples of cell proliferative disorders related to c-Met, include tumors and cancers—for instance, hereditary and sporadic human papillary renal carcinomas, breast cancer, colorectal cancer, gastric carcinoma, glioma, ovarian cancer, hepatocellular carcinoma, head and neck squamous cell carcinomas, testicular carcinoma, basal cell carcinoma, liver carcinoma, sarcoma, malignant pleural mesothelioma, melanoma, multiple myeloma, osteosarcoma, pancreatic cancer, prostate cancer, synovial sarcoma, thyroid carcinoma, non-small cell lung cancer (NSCLC) and small cell lung cancer, transitional cell carcinoma of urinary bladder, testicular carcinoma, basal cell carcinoma, liver carcinoma—including leukemias, lymphomas, and myelomas—for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM), myeloid sarcoma, non-Hodgkin's lymphoma and Hodgkin's disease (also called Hodgkin's lymphoma)—and diseases associated with the formation of new vasculature, such as rheumatoid, arthritis, and retinopathy.

Other cell proliferative disorders in which overactivity of c-Met has been implicated in their pathogenesis include cancers in which c-Met activity contributes to the invasive/metastatic phenotype, including cancers in which c-Met is not overexpressed or otherwise altered.

In a further embodiment to this aspect, the invention encompasses a combination therapy for treating or inhibiting the onset of a cell proliferative disorder or a disorder related to c-Met in a subject. The combination therapy comprises administering to the subject a therapeutically or prophylactically effective amount of a compound of Formula I, and one or more other anti-cell proliferation therapy including chemotherapy, radiation therapy, gene therapy and immunotherapy.

In an embodiment of the present invention, the compound of the present invention may be administered in combination with chemotherapy. As used herein, chemotherapy refers to a therapy involving a chemotherapeutic agent. A variety of chemotherapeutic agents may be used in the combined treatment methods disclosed herein. Chemotherapeutic agents contemplated as exemplary, include, but are not limited to: platinum compounds (e.g., cisplatin, carboplatin, oxaliplatin); taxane compounds (e.g., paclitaxcel, docetaxol); campotothecin compounds (irinotecan, topotecan); vinca alkaloids (e.g., vincristine, vinblastine, vinorelbine); anti-tumor nucleoside derivatives (e.g., 5-fluorouracil, leucovorin, gemcitabine, capecitabine) alkylating agents (e.g., cyclophosphamide, carmustine, lomustine, thiotepa); epipodophyllotoxins/podophyllotoxins (e.g. etoposide, teniposide); aromatase inhibitors (e.g., anastrozole, letrozole, exemestane); anti-estrogen compounds (e.g., tamoxifen, fulvestrant), antifolates (e.g., premetrexed disodium); hypomethylating agents (e.g., azacitidine); biologics (e.g., gemtuzamab, cetuximab, rituximab, pertuzumab, trastuzumab, bevacizumab, erlotinib); antibiotics/anthracylines (e.g. idarubicin, actinomycin D, bleomycin, daunorubicin, doxorubicin, mitomycin C, dactinomycin, caminomycin, daunomycin); antimetabolites (e.g., clofarabine, aminopterin, cytosine arabinoside, methotrexate); tubulin-binding agents (e.g. combretastatin, colchicine, nocodazole); topoisomerase inhibitors (e.g., camptothecin); differentiating agents (e.g., retinoids, vitamin D and retinoic acid); retinoic acid metabolism blocking agents (RAMBA) (e.g., accutane); kinase inhibitors (e.g., flavoperidol, imatinib mesylate, gefitinib); farnesyltransferase inhibitors (e.g., tipifamib); histone deacetylase inhibitors; inhibitors of the ubiquitin-proteasome pathway (e.g., bortezomib, Yondelis).

Further useful agents include verapamil, a calcium antagonist found to be useful in combination with antineoplastic agents to establish chemosensitivity in tumor cells resistant to accepted chemotherapeutic agents and to potentiate the efficacy of such compounds in drug-sensitive malignancies. See Simpson W G, The calcium channel blocker verapamil and cancer chemotherapy. Cell Calcium. 1985 December; 6(6): 449-67. Additionally, yet to emerge chemotherapeutic agents are contemplated as being useful in combination with the compound of the present invention.

In another embodiment of the present invention, the compound of the present invention may be administered in combination with radiation therapy. As used herein, "radiation therapy" refers to a therapy comprising exposing the subject in need thereof to radiation. Such therapy is known to those skilled in the art. The appropriate scheme of radiation therapy will be similar to those already employed in clinical therapies wherein the radiation therapy is used alone or in combination with other chemotherapeutics.

In another embodiment of the present invention, the compound of the present invention may be administered in combination with a gene therapy. As used herein, "gene therapy" refers to a therapy targeting on particular genes involved in tumor development. Possible gene therapy strategies include the restoration of defective cancer-inhibitory genes, cell transduction or transfection with antisense DNA corresponding to genes coding for growth factors and their receptors, RNA-based strategies such as ribozymes, RNA decoys, antisense messenger RNAs and small interfering RNA (siRNA) molecules and the so-called 'suicide genes'.

In other embodiments of this invention, the compound of the present invention may be administered in combination with an immunotherapy. As used herein, "immunotherapy" refers to a therapy targeting particular protein involved in tumor development via antibodies specific to such protein. For example, monoclonal antibodies against vascular endothelial growth factor have been used in treating cancers.

Where a second pharmaceutical is used in addition to a compound of the present invention, the two pharmaceuticals may be administered simultaneously (e.g. in separate or unitary compositions) sequentially in either order, at approximately the same time, or on separate dosing schedules. In the latter case, the two compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular chemotherapeutic agent being administered in conjunction with the compound of the present invention, their route of administration, the particular tumor being treated and the particular host being treated.

As will be understood by those of ordinary skill in the art, the appropriate doses of chemotherapeutic agents will be generally similar to or less than those already employed in clinical therapies wherein the chemotherapeutics are administered alone or in combination with other chemotherapeutics.

The optimum method and order of administration and the dosage amounts and regime can be readily determined by those skilled in the art using conventional methods and in view of the information set out herein.

By way of example only, platinum compounds are advantageously administered in a dosage of 1 to 500 mg per square meter ($mg/m^2$) of body surface area, for example 50 to 400 $mg/m^2$, particularly for cisplatin in a dosage of about 75 $mg/m^2$ and for carboplatin in about 300 $mg/m^2$ per course of treatment. Cisplatin is not absorbed orally and must therefore be delivered via injection intravenously, subcutaneously, intratumorally or intraperitoneally.

By way of example only, taxane compounds are advantageously administered in a dosage of 50 to 400 mg per square meter ($mg/m^2$) of body surface area, for example 75 to 250 mg/m², particularly for paclitaxel in a dosage of about 175 to 250 mg/m² and for docetaxel in about 75 to 150 mg/m² per course of treatment.

By way of example only, camptothecin compounds are advantageously administered in a dosage of 0.1 to 400 mg per square meter (mg/m²) of body surface area, for example 1 to 300 mg/m², particularly for irinotecan in a dosage of about 100 to 350 mg/m² and for topotecan in about 1 to 2 mg/m² per course of treatment.

By way of example only, vinca alkaloids may be advantageously administered in a dosage of 2 to 30 mg per square meter (mg/m²) of body surface area, particularly for vinblastine in a dosage of about 3 to 12 mg/m², for vincristine in a dosage of about 1 to 2 mg/m², and for vinorelbine in dosage of about 10 to 30 mg/m² per course of treatment.

By way of example only, anti-tumor nucleoside derivatives may be advantageously administered in a dosage of 200 to 2500 mg per square meter (mg/m²) of body surface area, for example 700 to 1500 mg/m². 5-fluorouracil (5-FU) is commonly used via intravenous administration with doses ranging from 200 to 500 mg/m² (preferably from 3 to 15 mg/kg/day). Gemcitabine is advantageously administered in a dosage of about 800 to 1200 mg/m² and capecitabine is advantageously administered in about 1000 to 2500 mg/m² per course of treatment.

By way of example only, alkylating agents may be advantageously administered in a dosage of 100 to 500 mg per square meter (mg/m²) of body surface area, for example 120 to 200 mg/m², particularly for cyclophosphamide in a dosage of about 100 to 500 mg/m², for chlorambucil in a dosage of about 0.1 to 0.2 mg/kg of body weight, for carmustine in a dosage of about 150 to 200 mg/m², and for lomustine in a dosage of about 100 to 150 mg/m² per course of treatment.

By way of example only, podophyllotoxin derivatives may be advantageously administered in a dosage of 30 to 300 mg per square meter (mg/m²) of body surface area, for example 50 to 250 mg/m², particularly for etoposide in a dosage of about 35 to 100 mg/m² and for teniposide in about 50 to 250 mg/m² per course of treatment.

By way of example only, anthracycline derivatives may be advantageously administered in a dosage of 10 to 75 mg per square meter (mg/m²) of body surface area, for example 15 to 60 mg/m², particularly for doxorubicin in a dosage of about 40 to 75 mg/m², for daunorubicin in a dosage of about 25 to 45 mg/m², and for idarubicin in a dosage of about 10 to 15 mg/m² per course of treatment.

By way of example only, anti-estrogen compounds may be advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

By way of example only, biologics may be advantageously administered in a dosage of about 1 to 5 mg per square meter (mg/m²) of body surface area, or as known in the art, if different. For example, trastuzumab is advantageously administered in a dosage of 1 to 5 mg/m² particularly 2 to 4 mg/m² per course of treatment.

Dosages may be administered, for example once, twice or more per course of treatment, which may be repeated for example every 7, 14, 21 or 28 days.

The compounds of the present invention can be administered to a subject systemically, for example, intravenously, orally, subcutaneously, intramuscular, intradermal, or parenterally. The compounds of the present invention can also be administered to a subject locally. Non-limiting examples of local delivery systems include the use of intraluminal medical devices that include intravascular drug delivery catheters, wires, pharmacological stents and endoluminal paving.

The compounds of the present invention can further be administered to a subject in combination with a targeting agent to achieve high local concentration of the compound at the target site. In addition, the compounds of the present invention may be Formulated for fast-release or slow-release with the objective of maintaining the drugs or agents in contact with target tissues for a period ranging from hours to weeks.

The present invention also provides a pharmaceutical composition comprising a compound of Formula I in association with a pharmaceutically acceptable carrier. The pharmaceutical composition may contain between about 0.1 mg and 1000 mg, preferably about 100 to 500 mg, of the compound, and may be constituted into any form suitable for the mode of administration selected.

The phrases "pharmaceutically acceptable" refer to molecular entities and compositions that do not produce an adverse, allergic or other untoward reaction when administered to an animal, or a human, as appropriate. Veterinary uses are equally included within the invention and "pharmaceutically acceptable" Formulations include Formulations for both clinical and/or veterinary use.

Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release Formulations), granules, and powders, and liquid forms, such as solutions, syrups, elixirs, emulsions, and suspensions. Forms useful for parenteral administration include sterile solutions, emulsions and suspensions.

The pharmaceutical composition of the present invention also includes a pharmaceutical composition for slow release of a compound of the present invention. The composition includes a slow release carrier (typically, a polymeric carrier) and a compound of the present invention.

Slow release biodegradable carriers are well known in the art. These are materials that may form particles that capture therein an active compound(s) and slowly degrade/dissolve under a suitable environment (e.g., aqueous, acidic, basic, etc) and thereby degrade/dissolve in body fluids and release the active compound(s) therein.

The particles are preferably nanoparticles (i.e., in the range of about 1 to 500 nm in diameter, preferably about 50-200 nm in diameter, and most preferably about 100 nm in diameter).

The present invention also provides methods to prepare the pharmaceutical compositions of this invention. The compound of Formula I, as the active ingredient, is intimately admixed with a pharmaceutical carrier according to conventional pharmaceutical compounding techniques, which carrier may take a wide variety of forms depending on the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. In preparation for slow release, a slow release carrier, typically a polymeric carrier, and a compound of the present invention are first dissolved or dispersed in an organic solvent. The obtained organic solution is then added into an aqueous solution to obtain an oil-in-water-type emulsion. Preferably, the aqueous solution includes surface-active agent(s). Subsequently, the organic solvent is evaporated from the oil-in-water-type emulsion to obtain a colloidal suspension of particles containing the slow release carrier and the compound of the present invention.

The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, from about 0.01 mg to 200 mg/kg of body weight per day. Preferably, the range is from about 0.03 to about 100 mg/kg of body weight per day, most preferably, from about 0.05 to about 10 mg/kg of body weight per day. The compounds may be administered on a regimen of 1 to 5 times per day. The dosages, however, may be varied depending upon the requirement of the patients, the severity of the condition being treated and the compound being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preFormulation composition containing a homogeneous mixture of a compound of the present invention, or a pharmaceutically acceptable salt thereof. When referring to these preFormulation compositions as homogeneous, it is meant that the active ingredient is dispersed evenly throughout the composition so that the composition may be readily subdivided into equally effective dosage forms such as tablets, pills and capsules. This solid preFormulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, acetyl alcohol and cellulose acetate.

The liquid forms in which the compound of Formula I may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. The liquid forms in suitably flavored suspending or dispersing agents may also include the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

Advantageously, compounds of Formula I may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The daily dosage of the products of the present invention may be varied over a wide range from 1 to 5000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 200 mg/kg of body weight per day. Particularly, the range is from about 0.03 to about 15 mg/kg of body weight per day, and more particularly, from about 0.05 to about 10 mg/kg of body weight per day. The compound of the present invention may be administered on a regimen up to four or more times per day, preferably of 1 to 2 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The compounds of the present invention can also be administered in the form of liposome delivery systems, such as small unilamellar vesicles, large unilamellar vesicles, and multilamellar vesicles. Liposomes can be formed from a variety of lipids, including but not limited to amphipathic lipids such as phosphatidylcholines, sphingomyelins, phosphatidylethanolamines, phophatidylcholines, cardiolipins, phosphatidylserines, phosphatidylglycerols, phosphatidic acids, phosphatidylinositols, diacyl trimethylammonium propanes, diacyl dimethylammonium propanes, and stearylamine, neutral lipids such as triglycerides, and combinations thereof. They may either contain cholesterol or may be cholesterol-free.

The compounds of the present invention can also be administered locally. Any delivery device, such as intravascular drug delivery catheters, wires, pharmacological stents and endoluminal paving, may be utilized. The delivery system for such a device may comprise a local infusion catheter that delivers the compound at a rate controlled by the administer.

The present invention provides a drug delivery device comprising an intraluminal medical device, preferably a stent, and a therapeutic dosage of a compound of the invention.

The term "stent" refers to any device capable of being delivered by a catheter. A stent is routinely used to prevent vascular closure due to physical anomalies such as unwanted inward growth of vascular tissue due to surgical trauma. It often has a tubular, expanding lattice-type structure appropriate to be left inside the lumen of a duct to relieve an obstruction. The stent has a lumen wall-contacting surface and a lumen-exposed surface. The lumen-wall contacting surface is the outside surface of the tube and the lumen-exposed surface is the inner surface of the tube. The stent can be polymeric, metallic or polymeric and metallic, and it can optionally be biodegradable.

Commonly, stents are inserted into the lumen in a non-expanded form and are then expanded autonomously, or with the aid of a second device in situ. A typical method of expansion occurs through the use of a catheter-mounted angioplasty balloon which is inflated within the stenosed vessel or body passageway in order to shear and disrupt the obstructions associated with the wall components of the vessel and to obtain an enlarged lumen. Self-expanding stents as described in U.S. Pat. No. 6,776,796 (Falotico et al.) may also be utilized. The combination of a stent with drugs, agents or compounds that prevent inflammation and proliferation, may provide the most efficacious treatment for post-angioplastry restenosis.

Compounds of the invention can be incorporated into or affixed to the stent in a number of ways and in utilizing any number of biocompatible materials. In one exemplary embodiment, the compound is directly incorporated into a polymeric matrix, such as the polymer polypyrrole, and subsequently coated onto the outer surface of the stent. The compound elutes from the matrix by diffusion through the polymer. Stents and methods for coating drugs on stents are discussed in detail in the art. In another exemplary embodiment, the stent is first coated with as a base layer comprising a solution of the compound, ethylene-co-vinylacetate, and polybutylmethacrylate. Then, the stent is further coated with an outer layer comprising only polybutylmethacrylate. The outlayer acts as a diffusion barrier to prevent the compound from eluting too quickly and entering the surrounding tissues. The thickness of the outer layer or topcoat determines the rate at which the compound elutes from the matrix. Stents and methods for coating are discussed in detail in WIPO publication WO9632907, U.S. Publication No. 2002/0016625 and references disclosed therein.

The solution of the compound of the invention and the biocompatible materials/polymers may be incorporated into or onto a stent in a number of ways. For example, the solution may be sprayed onto the stent or the stent may be dipped into the solution. In a preferred embodiment, the solution is sprayed onto the stent and then allowed to dry. In another exemplary embodiment, the solution may be electrically charged to one polarity and the stent electrically changed to the opposite polarity. In this manner, the solution and stent will be attracted to one another. In using this type of spraying process, waste may be reduced and more control over the thickness of the coat may be achieved. Compound is preferably only affixed to the outer surface of the stent that makes contact with one tissue. However, for some compounds, the entire stent may be coated. The combination of the dose of compound applied to the stent and the polymer coating that controls the release of the drug is important in the effectiveness of the drug. The compound preferably remains on the stent for at least three days up to approximately six months and more, preferably between seven and thirty days.

Any number of non-erodible biocompatible polymers may be utilized in conjunction with the compounds of the invention. It is important to note that different polymers may be utilized for different stents. For example, the above-described ethylene-co-vinylacetate and polybutylmethacrylate matrix works well with stainless steel stents. Other polymers may be utilized more effectively with stents formed from other materials, including materials that exhibit superelastic properties such as alloys of nickel and titanium.

Restesosis is responsible for a significant morbidity and mortality following coronary angioplasty. Restenosis occurs through a combination of four processes including elastic recoil, thrombus formation, intima hyperplasia and extracellular matrix remodeling. Several growth factors have been recently identified to play a part in these processes leading to restenosis. See Schiele T M et. al., 2004, "Vascular restenosis—striving for therapy." Expert Opin Pharmacother. 5(11): 2221-32. Vascular smooth muscle cells (VSMC) express c-Met receptor. Exposure to hepatocyte growth factor, the ligand for c-Met, stimulates these cells to exhibit a migratory phenotype. See Taher et. al., Hepatocyte growth factor triggers signaling cascades mediating vascular smooth muscle cell migration. *Biochem Biophys Res Commun*. (2002) 298 (1):80-6; Morishita R, Aoki M, Yo Y, Ogihara T. Hepatocyte growth factor as cardiovascular hormone: role of HGF in the pathogenesis of cardiovascular disease. Endocr J. (2002) June; 49(3):273-84. Since VSMC migration from the media to the intima of arteries plays a role in the development of atherosclerosis and restenosis, antagonists of c-Met kinase activity are believed to present a viable therapeutic strategy in the treatment of these diseases.

Accordingly, the present invention provides a method for the treatment of disorders related to c-Met, including restenosis, intimal hyperplasia or inflammation, in blood vessel walls, comprising the controlled delivery, by release from an intraluminal medical device, such as a stent, of a compound of the invention in therapeutically effective amounts.

Methods for introducing a stent into a lumen of a body are well known and the compound-coated stents of this invention are preferably introduced using a catheter. As will be appreciated by those of ordinary skill in the art, methods will vary slightly based on the location of stent implantation. For coronary stent implantation, the balloon catheter bearing the stent is inserted into the coronary artery and the stent is positioned at the desired site. The balloon is inflated, expanding the stent. As the stent expands, the stent contacts the lumen wall. Once the stent is positioned, the balloon is deflated and removed. The stent remains in place with the lumen-contacting surface bearing the compound directly contacting the lumen wall surface. Stent implantation may be accompanied by anticoagulation therapy as needed.

Optimum conditions for delivery of the compounds for use in the stent of the invention may vary with the different local delivery systems used, as well as the properties and concentrations of the compounds used. Conditions that may be optimized include, for example, the concentrations of the compounds, the delivery volume, the delivery rate, the depth of penetration of the vessel wall, the proximal inflation pressure, the amount and size of perforations and the fit of the drug delivery catheter balloon. Conditions may be optimized for inhibition of smooth muscle cell proliferation at the site of injury such that significant arterial blockage due to restenosis does not occur, as measured, for example, by the proliferative ability of the smooth muscle cells, or by changes in the vascular resistance or lumen diameter. Optimum conditions can be determined based on data from animal model studies using routine computational methods.

Another alternative method for administering compounds of this invention may be by conjugating the compound to a targeting agent which directs the conjugate to its intended site of action, i.e., to vascular endothelial cells, or to tumor cells. Both antibody and non-antibody targeting agents may be used. Because of the specific interaction between the targeting agent and its corresponding binding partner, a compound of the present invention can be administered with high local concentrations at or near a target site and thus treats the disorder at the target site more effectively.

The antibody targeting agents include antibodies or antigen-binding fragments thereof, that bind to a targetable or accessible component of a tumor cell, tumor vasculature, or tumor stroma. The "targetable or accessible component" of a tumor cell, tumor vasculature or tumor stroma, is preferably a surface-expressed, surface-accessible or surface-localized component. The antibody targeting agents also include antibodies or antigen-binding fragments thereof, that bind to an intracellular component that is released from a necrotic tumor cell. Preferably such antibodies are monoclonal antibodies, or antigen-binding fragments thereof, that bind to insoluble intracellular antigen(s) present in cells that may be induced to be permeable, or in cell ghosts of substantially all neoplastic and normal cells, but are not present or accessible on the exterior of normal living cells of a mammal. In the present invention, the targetable or accessible component might be the c-Met receptor as it is accessible and expressed on or near the target tissues.

As used herein, the term "antibody" is intended to refer broadly to any immunologic binding agent such as IgG, IgM, IgA, IgE, F(ab')2, a univalent fragment such as Fab', Fab, Dab, as well as engineered antibodies such as recombinant antibodies, humanized antibodies, bispecific antibodies, and the like. The antibody can be either the polyclonal or the monoclonal, although the monoclonal is preferred. There is a very broad array of antibodies known in the art that have immunological specificity for the cell surface of virtually any solid tumor type (see a Summary Table on monoclonal antibodies for solid tumors in U.S. Pat. No. 5,855,866 to Thorpe et al). Methods are known to those skilled in the art to produce and isolate antibodies against tumor (U.S. Pat. No. 5,855,866 to Thorpe et al., and U.S. Pat. No. 6,34,2219 to Thorpe et al.).

Techniques for conjugating therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985). Similar techniques can also be applied to attach compounds of the invention to non-antibody targeting agents.

Those skilled in the art will know, or be able to determine, methods of forming conjugates with non-antibody targeting agents, such as small molecules, oligopeptides, polysaccharides, or other polyanionic compounds.

Although any linking moiety that is reasonably stable in blood, can be used to link the compounds of the present invention to the targeting agent, biologically-releasable bonds and/or selectively cleavable spacers or linkers are preferred. "Biologically-releasable bonds" and "selectively cleavable spacers or linkers" still have reasonable stability in the circulation, but are releasable, cleavable or hydrolysable only or preferentially under certain conditions, i.e., within a certain environment, or in contact with a particular agent. Such bonds include, for example, disulfide and trisulfide bonds and acid-labile bonds, as described in U.S. Pat. Nos. 5,474,765 and 5,762,918 and enzyme-sensitive bonds, including peptide bonds, esters, amides, phosphodiesters and glycosides as described in U.S. Pat. Nos. 5,474,765 and 5,762,918. Such selective-release design features facilitate sustained release of the compounds from the conjugates at the intended target site.

The present invention provides a pharmaceutical composition comprising an effective amount of a compound of the present invention conjugated to a targeting agent and a pharmaceutically acceptable carrier.

The present invention further provides a method of treating of a disorder related to c-Met, particularly a tumor, comprising administering to a subject a therapeutically effective amount of a compound of Formula I conjugated to a targeting agent.

When proteins such as antibodies or growth factors, or polysaccharides are used as targeting agents, they are preferably administered in the form of injectable compositions. The injectable antibody solution will be administered into a vein, artery or into the spinal fluid over the course of from 2 minutes to about 45 minutes, preferably from 10 to 20 minutes. In certain cases, intradermal and intracavitary administration are advantageous for tumors restricted to areas close to particular regions of the skin and/or to particular body cavities. In addition, intrathecal administrations may be used for tumors located in the brain.

Therapeutically effective dose of the compound of the present invention conjugated to a targeting agent depends on the individual, the disease type, the disease state, the method of administration and other clinical variables. The effective dosages are readily determinable using data from an animal model. Experimental animals bearing solid tumors are frequently used to optimize appropriate therapeutic doses prior to translating to a clinical environment. Such models are known to be very reliable in predicting effective anti-cancer strategies. For example, mice bearing solid tumors, are widely used in pre-clinical testing to determine working ranges of therapeutic agents that give beneficial anti-tumor effects with minimal toxicity.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of Formula I:

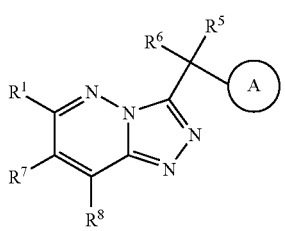

Formula I and N-Oxides, prodrugs, pharmaceutically acceptable salts and stereochemical isomers thereof, wherein:
$R^1$ is pyridine or benzopyridine optionally substituted with one, two or three $R_a$ substituents;
  wherein $R_a$ is —$NH_2$, halogen, alkoxy, alkylether, alkylthio, alkylsulfonyl, phenylsulfonyl, heteroarylsulfonyl, heterocyclylsulfonyl, —$SO_2NH_2$, alkylsulfonamide, alkyl, aminoalkyl, alkylamino, phenyl, heteroaryl, cyano, alkenyl, alkynyl, cycloalkyl, heterocyclyl, —$CO_2$-alkyl, —C(O)—$R_b$, —$C_{(1-4)}$alkyl-morpholinyl, —$C_{(1-4)}$alkyl-piperidinyl, —$C_{(1-4)}$alkyl-piperazinyl, —$C_{(1-4)}$alkyl—N'-methyl piperazinyl, —$C_{(1-4)}$alkyl-$R_b$, —C(O)NH—$C_{(1-4)}$alkyl-$R_b$, or —C(O)N$R_cR_d$;
    wherein $R_b$ is heterocyclyl, alkylsulfonyl, —$SO_2NH_2$, alkylsulfonamide, —OH, —Oalkyl, —$NH_2$, —NHalkyl, or —N(alkyl)$_2$;
  $R_c$ and $R_d$ are independently selected from: H, phenyl, heteroaryl, or $C_{1-6}$ alkyl, wherein said $C_{1-6}$alkyl may optionally be substituted with one substituent selected from: —N(CH$_3$)$_2$, morpholinyl, piperidinyl, piperazinyl, N-methyl piperazinyl, alkylsulfonyl, —$SO_2NH_2$, alkylsulfonamide, hydroxyl, and alkoxy;
  or $R_c$ and $R_d$ together may form a 5 to 7 membered heterocyclic ring, optionally containing a second heteromoiety selected from O, NH, N(alkyl), SO, SO$_2$, or S; wherein said $R_c$—$R_d$ heterocyclic ring is optionally substituted with alkyl, —SO$_2$alkyl, or —C(O)alkyl;
A is a ring selected from the group consisting of: phenyl, mono or bicyclic heteroaryl, 3-(4-Methoxy-benzyl)-3H-quinazolin-4-on-6-yl, quinazolin-4-on-6-yl, and benzo-fused heterocyclyl; wherein said phenyl, heteroaryl, or benzo-fused heterocyclyl are optionally substituted with one to three substituents independently selected from the group consisting of: —OH, alkyl, phenyl, heteroaryl, alkoxy, —CN, halogen, nitro, —NH$_2$, —N(CH$_3$)$_2$, —NHC(O)NHC$_{1-6}$alkyl, and —NHC(O)C$_{1-6}$alkyl;
$R^5$ and $R^6$ are independently F;
or $R^5$ and $R^6$ can together form a $C_{3-5}$ cycloalkyl ring, an aziridinyl ring, or, an epoxidyl ring; and
$R^7$ and $R^8$ are H, halogen or $C_{1-6}$ alkyl.

2. A compound of claim 1, wherein
$R^1$ is pyridine or benzopyridine is optionally substituted with one, two or three $R_a$ substituents;
$R^7$ and $R^8$ are H.

3. A compound of claim 2, wherein
$R_c$ and $R_d$ are independently selected from: H, phenyl, heteroaryl, or $C_{1-6}$ alkyl, wherein said $C_{1-6}$alkyl may optionally be substituted with one substituent selected from:
—N(CH$_3$)$_2$, morpholinyl, piperidinyl, piperazinyl, N-methyl piperazinyl, alkylsulfonyl, —SO$_2$NH$_2$, alkylsulfonamide, hydroxyl, and alkoxy; or $R_c$ and $R_d$ together may form a 5 to 7 membered heterocyclic ring selected from the group consisting of: piperidinyl, morpholinyl, and piperazinyl, wherein said piperazinyl is optionally substituted with alkyl, —SO$_2$alkyl, or —C(O)alkyl.

4. A compound of claim 3, wherein
A is a ring selected from the group consisting of: phenyl, mono or bicyclic heteroaryl, 3-(4-Methoxy-benzyl)-3H-quinazolin-4-on-6-yl, quinazolin-4-on-6-yl, and benzo-fused heterocyclyl; wherein said phenyl, heteroaryl, or benzo-fused heterocyclyl are optionally substituted with one substituent independently selected from the group consisting of:
—OH, alkyl, phenyl, heteroaryl, alkoxy, —CN, halogen, nitro, —NH$_2$, —N(CH$_3$)$_2$, —NHC(O)NHC$_{1-6}$alkyl, and —NHC(O)C$_{1-6}$alkyl.

5. A compound of claim 4, wherein
A is a ring selected from the group consisting of: 2,3 dihydrobenzofuran-5-yl, quinolin-6-yl, quinolin-6-yl-N-Oxide, 2-amino benzothiazol-6-yl, 4-methoxyphenyl, 3-(4-Methoxy-benzyl)-3H-quinazolin-4-on-6-yl, quinazolin-4-on-6-yl, and 4-hydroxy phenyl.

6. A compound of claim 5, wherein
$R^1$ is pyridine or benzopyridine optionally substituted with one $R_a$ substituent.

7. A compound of claim 6, wherein
$R^1$ is thiazol-2-yl, pyridin-2-on-5-yl, or pyridyl, wherein said thiophen-2-yl, thiazol-2-yl, pyrazolyl, imidazolyl, and pyridyl may be optionally substituted with one $R_a$ substituent.

8. A compound selected from the group consisting of:

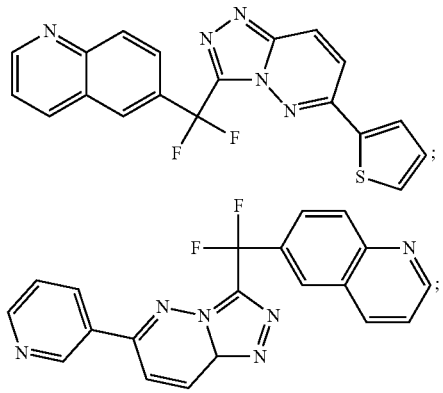

-continued

[chemical structures]

and N-Oxides, prodrugs, pharmaceutically acceptable salts and stereochemical isomers thereof.

9. A compound selected from the group consisting of:

[chemical structures]

and N-Oxides, prodrugs, pharmaceutically acceptable salts and stereochemical isomers thereof 10. A compound which is

[chemical structure]

and N-Oxides, prodrugs, pharmaceutically acceptable salts and stereochemical isomers thereof 11. A pharmaceutical composition comprising a compound of claim 1 and a pharmaceutically acceptable carrier.

12. A process for the preparation of a compound of claim 1, said process comprising reacting a compound of Formula IV:

IV

[chemical structure]

with a compound of Formula V:

wherein X is Cl or I or Br, and Y is zincate.

13. A process for the preparation of a compound of claim 1, said process comprising reacting a compound of Formula III:

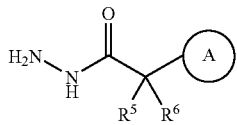

with a compound of Formula VI:

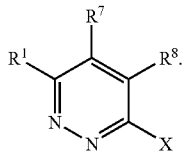

wherein X is Cl or I or Br.

14. A pharmaceutical composition comprising a product made by the process of claim 13 and a pharmaceutically acceptable carrier.

15. A pharmaceutical composition comprising a product made by the process of claim 12 and a pharmaceutically acceptable carrier.

* * * * *

UNITED STATES PATENT AND TRADEMARK OFFICE
CERTIFICATE OF CORRECTION

PATENT NO. : 8,173,654 B2  
APPLICATION NO. : 12/187524  
DATED : May 8, 2012  
INVENTOR(S) : Lu et al.

Page 1 of 1

It is certified that error appears in the above-identified patent and that said Letters Patent is hereby corrected as shown below:

In the Claims

Column 170, Claim 10

Line 40, delete " 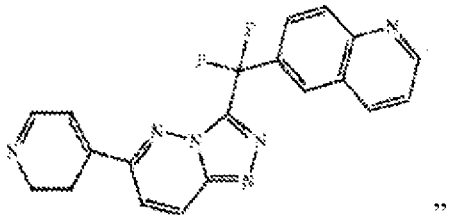 "

And insert -- 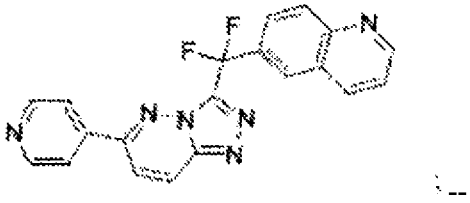 --

Signed and Sealed this  
Thirty-first Day of December, 2013

Margaret A. Focarino  
*Commissioner for Patents of the United States Patent and Trademark Office*